(12) United States Patent
Allan

(10) Patent No.: US 7,691,379 B2
(45) Date of Patent: *Apr. 6, 2010

(54) ANTI-IL-9 ANTIBODY FORMULATIONS

(75) Inventor: Christian B. Allan, Brookeville, MD (US)

(73) Assignee: Medimmune, LLC, Gaithersburg, MD (US)

( * ) Notice: Subject to any disclaimer, the term of this patent is extended or adjusted under 35 U.S.C. 154(b) by 186 days.

This patent is subject to a terminal disclaimer.

(21) Appl. No.: 11/105,268

(22) Filed: Apr. 12, 2005

(65) Prior Publication Data

US 2005/0260204 A1 Nov. 24, 2005

Related U.S. Application Data

(60) Provisional application No. 60/561,845, filed on Apr. 12, 2004.

(51) Int. Cl.
*A61K 39/395* (2006.01)
*C07K 16/00* (2006.01)

(52) U.S. Cl. ............................... 424/145.1; 530/388.23

(58) Field of Classification Search .................. None
See application file for complete search history.

(56) References Cited

U.S. PATENT DOCUMENTS

| | | | |
|---|---|---|---|
| 4,597,966 | A | 7/1986 | Zolton et al. |
| 5,824,307 | A | 10/1998 | Johnson |
| 6,656,467 | B2 | 12/2003 | Young et al. |
| 6,818,216 | B2 | 11/2004 | Young et al. |
| 6,855,493 | B2 | 2/2005 | Young et al. |
| 2002/0168360 | A1 | 11/2002 | Dingivan et al. |
| 2003/0190311 | A1 | 10/2003 | Dall'Acqua et al. |
| 2003/0219439 | A1 | 11/2003 | Reed et al. |
| 2004/0005544 | A1 | 1/2004 | Fouchier et al. |
| 2004/0091486 | A1 | 5/2004 | Kinch et al. |
| 2005/0002934 | A1 | 1/2005 | Reed et al. |
| 2005/0147607 | A1 | 7/2005 | Reed |

FOREIGN PATENT DOCUMENTS

| | | |
|---|---|---|
| WO | WO 00/78815 | 12/2000 |
| WO | WO 02/43660 | 6/2002 |
| WO | WO 02/069904 | 9/2002 |
| WO | WO 02/070007 | 9/2002 |
| WO | WO 02/098370 | 12/2002 |
| WO | WO 02/102974 | 12/2002 |
| WO | WO 03/075741 | 9/2003 |
| WO | WO 03/075957 | 9/2003 |
| WO | WO 03/094859 | 11/2003 |

OTHER PUBLICATIONS

U.S. Appl. No. 60/561,845, filed Apr. 12, 2004, Allan.
U.S. Appl. No. 60/477,801, filed Jun. 10, 2003, Reed.
U.S. Appl. No. 60/462,307, filed Apr. 11, 2003, Reed.
U.S. Appl. No. 60/398,475, filed Jul. 25, 2002, Young et al.
U.S. Appl. No. 60/388,920, filed Sep. 14, 2002, Oliver et al.
U.S. Appl. No. 60/388,921, filed Jun. 14, 2002, Oliver et al.
U.S. Appl. No. 60/379,368, filed May 10, 2002, Kinch et al.
U.S. Appl. No. 60/371,728, filed Apr. 12, 2002, Reed et al.
U.S. Appl. No. 60/371,683, filed Apr. 12, 2002, Reed et al.
U.S. Appl. No. 09/724,531, filed Nov. 28, 2000, Young et al.
Johnson et al., 1997, "Development of a humanized monoclonal antibody (MEDI-493) with potent in vitro and in vivo activity against respiratory syncytial virus," J. Infect. Dis. 176(5):1215-1224.
Kikawa et al., 2002, "Regulation of the EphA2 kinase by the low molecular weight tyrosine phosphatase induces transformation," J. Biol. Chem. 277(42):39274-39279 (10271-111-888).
Van Snick et al., 1989, "Cloning and characterization of a cDNA for a new mouse T cell growth factor (P40)," J. Exp. Med. 169(1):363-368.
Yang et al., 1989, "Expression cloning of cDNA encoding a novel human hematopoietic growth factor: human homologue of murine T-cell growth factor P40," Blood 74(6):1880-1884.
Zhang et al., 1998, "Crystal structure of a human low molecular weight phosphotyrosyl phosphatase. Implications for substrate specificity," J. Biol. Chem. 273(34):21714-21720 (10271-111-888).
Cheng et al., 2002, "Anti-interleukin-9 antibody treatment inhibits airway inflammation and hyperreactivity in mouse asthma model," Am. J. Respir. Crit. Care Med. 166(3):409-16.
U.S. Appl. No. 60/462,259, filed Apr. 2003, Reed et al.
U.S. Appl. No. 60/477,797, filed Jun. 2003, Reed et al.

*Primary Examiner*—Robert Landsman
*Assistant Examiner*—Bruce D. Hissong

(57) ABSTRACT

The present invention provides liquid formulations of antibodies or antibody fragments that immunospecifically bind to an IL-9 polypeptide, which formulations exhibit stability, low to undetectable levels of aggregation, and very little to no loss of the biological activities of the antibodies or antibody fragments, even during long periods of storage. In particular, the present invention provides liquid formulations of antibodies or fragments thereof that immunospecifically bind to an IL-9 polypeptide, which formulations are substantially free of surfactants, sugars, sugar alcohols, amino acids other than histidine (preferably with pKa values of less than 5 and above 7), and/or other common excipients. Furthermore, the invention provides methods of preventing, treating or ameliorating a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, utilizing the liquid formulations of the present invention.

81 Claims, 18 Drawing Sheets

Figure 16:
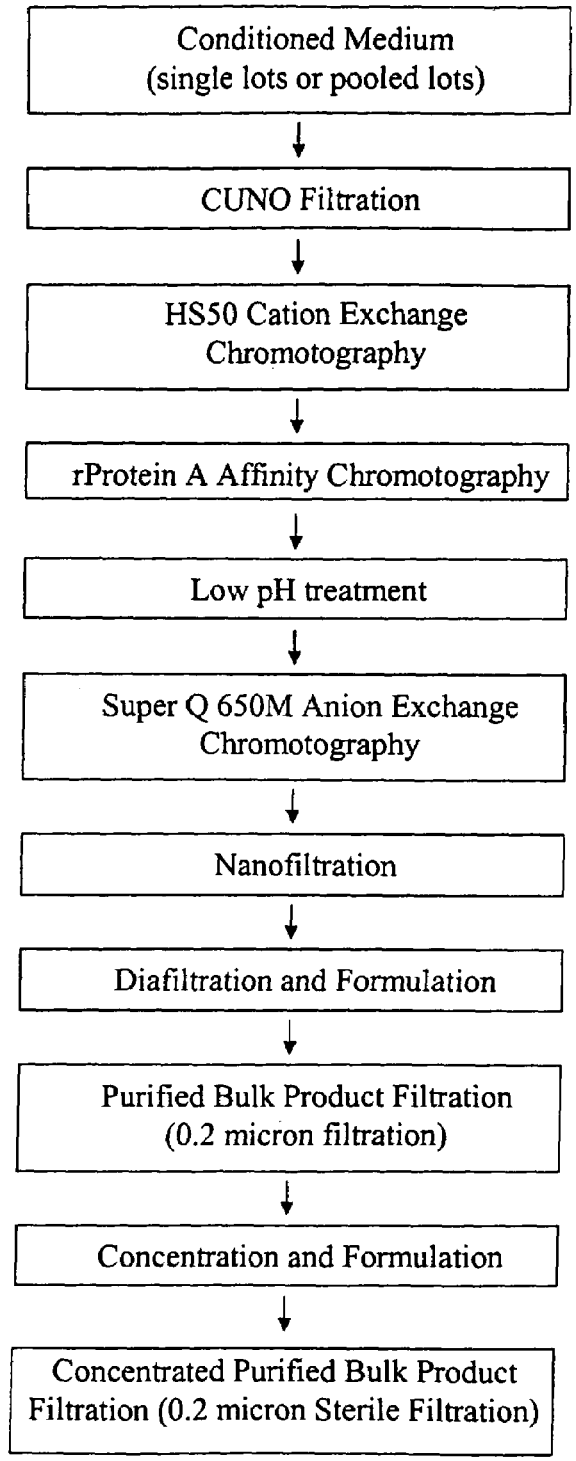

QVQLVQSGAEVKKPGASVKVSCKAS<u>GYTFTGYWIE</u>WVRQAPGQGLEWMG<u>EI
LPGSGTTNYNEKFKG</u>RVTMTRDTSTSTVYMELSSLRSEDTAVYYCAR<u>ADYYGS
DYVKFDY</u>WGQGTLVTVSS

FIG. 1A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QHFYSYPLT</u>FGGGTKVEIK

FIG. 1B

QVQLVQSGAEVKKPGASVKVSCKAS<u>GYTFTGYWIE</u>WVRQAPGQGLEWMG<u>E
WLPGSGTTNYNEKFKG</u>RVTMTRDTSTSTVYMELSSLRSEDTAVYYCAR<u>ADYY
GSDYVKFDY</u>WGQGTLVTVSS

FIG. 2A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QHFYSYPLT</u>FGGGTKVEIK

FIG. 2B

QVQLVQSGAEVKKPGASVKVSCKAS<u>GYTFTYYWIE</u>WVRQAPGQGLEWMG<u>EWL
PGSGTTNYNEKFKG</u>RVTMTRDTSTSTVYMELSSLRSEDTAVYYCAR<u>ADYYGSD
HVKFDY</u>WGQGTLVTVSS

FIG. 3A

DIQMTQSPSSLSASVGDRVTITC<u>LASQHVGTHVT</u>WYQQKPGKAPKLLIY<u>GTSY
RYS</u>GVPSRFSGSGSGTDFTLTISSLQPEDFATYYC<u>QHFYDYPLT</u>FGGGTKVEIK

FIG. 3B

QVQLVQSGAEVKKPGASVKVSCKAS<u>GYTFTGYWIE</u>WVRQAPGQGLEWMG<u>E
WLPGSGTTNYNEKFKG</u>RVTMTRDTSTSTVYMELSSLRSEDTAVYYCAR<u>ADYY
GSDHVKFDY</u>WGQGTLVTVSS

FIG. 4A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QHFYEYPLT</u>FGGGTKVEIK

FIG. 4B

QVQLVQSGAEVKKPGSSVKVSCKAS<u>GGTFSGYWIE</u>WVRQAPGQGLEWMG<u>EI
LPGSGTTNYNEKFKG</u>RVTITADESTSTAYMELSSLRSEDTAVYYCAR<u>ADYYGS
DYVKFDY</u>WGQGTLVTVSS

FIG. 5A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QQFYEYPLT</u>FGGGTKVEIK

FIG. 5B

QVQLVQSGAEVKKPGSSVKVSCKAS<u>GGTFSGYWIE</u>WVRQAPGQGLEWMG<u>EI
LPGSGTTNPNEKFK</u>GRVTITADESTSTAYMELSSLRSEDTAVYYCAR<u>ADYYGS
DYVKFDY</u>WGQGTLVTVSS

FIG. 6A

DIQMTQSPSSLSASVGDRVTITC<u>KASQHVGTHVT</u>WYQQKPGKAPKLLIY<u>STSY
RY</u>SGVPSRFSGSGSGTDFTLTISSLQPEDFATYYC<u>QQFYEYPLT</u>FGGGTKVEIK

FIG. 6B

QVQLVQSGAEVKKPGSSVKVSCKAS<u>GGTFSGYWIE</u>WVRQAPGQGLEWMG<u>EI
LPGSGTTNYNEKFKG</u>RVTITADESTSTAYMELSSLRSEDTAVYYCAR<u>ADYYGS
DYVKFDY</u>WGQGTLVTVSS

FIG. 7A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 7B

QVQLVQSGAEVKKPGSSVKVSCKAS<u>GGTFSYYWIE</u>WVRQAPGQGLEWMGE<u>I
LPGSGTTNPNEKFK</u>GRVTITADESTSTAYMELSSLRSEDTAVYYCAR<u>ADYYGS
DYVKFDY</u>WGQGTLVTVSS

FIG. 8A

DIQMTQSPSSLSASVGDRVTITC<u>KASQHVITHVT</u>WYQQKPGKAPKLLIY<u>GTS
YSYS</u>GVPSRFSGSGSGTDFTLTISSLQPEDFATYYC<u>QQFYEYPLT</u>FGGGTKVEIK

FIG. 8B

```
  1 CAGGTGCAG CTGGTGCAG TCTGGGGCT GAGGTGAAG AAGCCTGGG
 46 TCCTCAGTG AAGGTTTCC TGCAAGGCA TCTGGAGGC ACCTTCAGC
 91 TATTACTGG ATAGAGTGG GTGCGACAG GCCCCTGGA CAAGGGCTT
136 GAGTGGATG GGAGAGATT TTACCTGGA AGTGGTACT ACTAACCCG
181 AATGAGAAG TTCAAGGGC AGAGTCACC ATTACCGCG GACGAATCC
226 ACGAGCACA GCCTACATG GAGCTGAGC AGCCTGAGA TCTGAGGAC
271 ACGGCCGTG TATTACTGT GCGAGAGCG GATTACTAC GGTAGTGAT
316 TACGTCAAG TTTGACTAC TGGGGCCAA GGAACCCTG GTCACCGTC
361 TCCTCA
```

Fig. 9A

```
  1 GACATCCAG ATGACCCAG TCTCCATCC TCCCTGTCT GCATCTGTA
 46 GGAGACAGA GTCACCATC ACTTGCAAG GCAAGTCAG CATGTGATT
 91 ACTCATGTA ACCTGGTAT CAGCAGAAA CCAGGGAAA GCCCCTAAG
136 CTCCTGATC TATGGGACA TCCTACAGC TACAGTGGG GTCCCATCA
181 AGGTTCAGT GGCAGTGGA TCTGGGACA GATTTCACT CTCACCATC
226 AGCAGTCTG CAACCTGAA GATTTTGCA ACTTATTAC TGTCAGCAA
271 TTTTACGAG TATCCTCTC ACGTTCGGC GGAGGGACC AAGGTGGAG
316 ATCAAA
```

Fig. 9B

QVQLVQSGAEVKKPGSSVKVSCKAS<u>GGTFSGYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 10A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 10B

QVQLVQSGAEVKKPGSSVKVSCKAS<u>GGTFSYYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 11A

DIQMTQSPSSLSASVGDRVTITC<u>KASQHVITHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 11B

```
1    ccgctgtcaa gatgcttctg gccatggtcc ttacctctgc cctgctcctg tgctccgtgg
61   caggccaggg gtgtccaacc ttggcgggga tcctggacat caacttcctc atcaacaaga
121  tgcaggaaga tccagcttcc aagtgccact gcagtgctaa tgtgaccagt tgtctctgtt
181  tgggcattcc ctctgacaac tgcaccagac catgcttcag tgagagactg tctcagatga
241  ccaataccac catgcaaaca agatacccac tgattttcag tcgggtgaaa aaatcagttg
301  aagtactaaa gaacaacaag tgtccatatt tttcctgtga acagccatgc aaccaaacca
361  cggcaggcaa cgcgctgaca tttctgaaga gtcttctgga aattttccag aaagaaaaga
421  tgagagggat gagaggcaag atatgaagat gaaatattat ttatcctatt tattaaattt
481  aaaaagcttt ctctttaagt tgctacaatt taaaaatcaa gtaagctact ctaaatcagt
541  atcagttgtg attatttgtt taacattgta tgtctttatt ttgaaataaa t
```

FIG. 12

```
  1 mllamvltsa lllcsvagqg cptlagildi nflinkmqed paskchcsan vtsclclgip
 61 sdnctrpcfs erlsqmtntt mqtryplifs rvkksvevlk nnkcpyfsce qpcnqttagn
121 altflkslle ifqkekmrgm rgki
```

FIG. 13A

```
  1 maellasags acswdfprap psfpppaasr gglggtrsfr phrgaesprp grdrdgvrvp
 61 massrcpapr gcrclpgasl awlgtvllll adwvllrtal prifsllvpt alpllrvwav
121 glsrwavlwl gacgvlratv gsksenagaq gwlaalkpla aalglalpgl alfreliswg
181 apgsadstrl lhwgshptaf vvsyaaalpa aalwhklgsl wvpggqggsg npvrrllgcl
241 gsetrrlslf lvlvvlsslg emaipfftgr ltdwilqdgs adtftrnltl msiltiasav
301 lefvgdgiyn ntmghvhshl qgevfgavlr qeteffqqnq tgnimsrvte dtstlsdsls
361 enlslflwyl vrglcllgim lwgsvsltmv tlitlpllfl lpkkvgkwyq llevqvresl
421 akssqvaiea lsamptvrsf aneegeaqkf reklqeiktl nqkeavayav nswttsisgm
481 llkvgilyig gqlvtsgavs sgnlvtfvly qmqftqavev llsiyprvqk avgssekife
541 yldrtprcpp sglltplhle glvqfqdvsf aypnrpdvlv lqgltftlrp gevtalvgpn
601 gsgkstvaal lqnlyqptgg qllldgkplp qyehrylhrq vaavgqepqv fgrslqenia
661 ygltqkptme eitaaavksg ahsfisglpq gydtevdeag sqlsggqrqa valaralirk
721 pcvlilddat saldansqlq veqllyespe rysrsvllit qhlslveqad hilfleggai
781 reggthqqlm ekkgcywamv qapadape
```

FIG. 13B

```
  1 mvltsalllc svagqgcptl agildinfli nkmqedpask chcsanvtsc lclgipsdnc
 61 trpcfserls qmtnttmqtr yplifsrvkk svevlknnkc pyfsceqpcn qttagnaltf
121 lkslleifqk ekmrgmrgki
```

FIG. 13C

```
   1 agcagctctg taatgcgctt gtggtttcag atgtgggcgg cctgtgtgaa cctgtcgtgc
  61 aaagctcacg tcaccaactg ctgcagttat ctcctgaatc aggctgaggg tctttgctgt
 121 gcacccagag atagttgggt gacaaatcac ctccaggttg gggatgcctc agacttgtga
 181 tgggactggg cagatgcatc tgggaaggct ggaccttgga gagtgaggcc ctgaggcgag
 241 acatgggcac ctggctcctg gcctgcatct gcatctgcac ctgtgtctgc ttgggagtct
 301 ctgtcacagg ggaaggacaa gggccaaggt ctagaacctt cacctgcctc accaacaaca
 361 ttctcaggat cgattgccac tggtctgccc cagagctggg acagggctcc agccctggc
 421 tcctcttcac cagcaaccag gctcctggcg gcacacataa gtgcatcttg cggggcagtg
 481 agtgcaccgt cgtgctgcca cctgaggcag tgctcgtgcc atctgacaat ttcaccatca
 541 ctttccacca ctgcatgtct gggagggagc aggtcagcct ggtgacccg gagtacctgc
 601 cccggagaca cgttaagctg gacccgccct ctgacttgca gagcaacatc agttctggcc
 661 actgcatcct gacctggagc atcagtcctg ccttggagcc aatgaccaca cttctcagct
 721 atgagctggc cttcaagaag caggaagagg cctgggagca ggcccagcac agggatcaca
 781 ttgtcggggt gacctggctt atacttgaag cctttgagct ggaccctggc tttatccatg
 841 aggccaggct gcgtgtccag atggccacac tggaggatga tgtggtagag gaggagcgtt
 901 atacaggcca gtggagtgag tggagccagc ctgtgtgctt ccaggctccc cagagacaag
 961 gccctctgat cccaccctgg gggtggccag gcaacaccct tgttgctgtg tccatctttc
1021 tcctgctgac tggcccgacc tacctcctgt tcaagctgtc gcccagggtg aagagaatct
1081 tctaccagaa cgtgccctct ccagcgatgt tcttccagcc cctctacagt gtacacaatg
1141 ggaacttcca gacttggatg ggggcccacg gggccggtgt gctgttgagc caggactgtg
1201 ctggcaccc acagggagcc ttggagccct gcgtccagga ggccactgca ctgctcactt
1261 gtggccagc gcgtccttgg aaatctgtgg ccctggagga ggaacaggag ggccctggga
1321 ccaggctccc ggggaacctg agctcagagg atgtgctgcc agcagggtgt acggagtgga
1381 gggtacagac gcttgcctat ctgccacagg aggactgggc ccccacgtcc ctgactaggc
1441 cggctccccc agactcagag ggcagcagga gcagcagcag cagcagcagc agcaacaaca
1501 acaactactg tgccttgggc tgctatgggg gatggcacct ctcagccctc ccaggaaaca
1561 cacagagctc tgggcccatc ccagccctgg cctgtggcct ttcttgtgac catcagggcc
1621 tggagaccca gcaaggagtt gcctgggtgc tggctggtca ctgccagagg cctgggctgc
1681 atgaggacct ccagggcatg ttgctccctt ctgtcctcag caaggctcgg tcctggacat
1741 tctaggtccc tgactcgcca gatgcatcat gtccatttgt ggaaaatgga ctgaagtttc
1801 tggagccctt gtctgagact gaacctcctg agaaggggcc cctagcagcg gtcagaggtc
1861 ctgtctggat ggaggctgga ggctcccccc tcaaccctc tgctcagtgc ctgtggggag
1921 cagcctctac cctcagcatc ctgccacaa gttcttcctt ccattgtccc ttttctttat
1981 ccctgacctc tctgagaagt ggggtgtggt ctctcagctg ttctgccctc atacccttaa
2041 agggccagcc tgggccagt ggacacaggt aagcaccat gaccacctgg tgtgacctct
2101 ctgtgcctta ctgaggcacc tttctagaga ttaaaggggg cttgatggct gttaaaaaaa
2161 aaaaaaaaa a
```

FIG. 14A

```
   1 agcagctctg taatgcgctt gtggtttcag atgtgggcgg cctgtgtgaa cctgtcgtgc
  61 aaagctcacg tcaccaactg ctgcagttat ctcctgaatc aggctgaggg tctttgctgt
 121 gcacccagag atagttgggt gacaaatcac ctccaggttg gggatgcctc agacttgtga
 181 tgggactggg cagatgcatc tgggaagtaa ctgctgcaag aacggacaga cactgctgca
 241 gagaacttgc cacggtgttt catgctgtgg ctggtggttc caggctgcac gctccattct
 301 aggaaagggg ccctcagccc agtcccttgc aggctggacc ttggagagtg aggccctgag
 361 gcgagacatg ggcacctggc tcctggcctg catctgcatc tgcacctgtg tctgcttggg
 421 agtctctgtc acaggggaag gacaagggcc aaggtctaga accttcacct gcctcaccaa
 481 caacattctc aggatcgatt gccactggtc tgccccagag ctgggacagg gctccagccc
 541 ctggctcctc ttcaccaggc tcctggcggc acacataagt gcatcttgcg gggcagtgag
 601 tgcaccgtcg tgctgccacc tgaggcagtg ctcgtgccat ctgacaattt caccatcact
 661 ttccaccact gcatgtctgg gagggagcag gtcagcctgg tggacccgga gtacctgccc
 721 cggagacacg agcaacatca gttctggcca ctgcatcctg acctggagca tcagtcctgc
 781 cttggagcca atgaccacac ttctcagcta tgagctggcc ttcaagaagc aggaagaggc
 841 ctgggagcag gccagcaca gggatcacat tgtcggggtg acctggctta tacttgaagc
 901 ctttgagctg gaccctggct ttatccatga ggcaggctg cgtgtccaga tggccacact
 961 ggaggatgat gtggtagagg aggagcgtta tacaggccag tggagtgagt ggagccagcc
1021 tgtgtgcttc caggctcccc agagacaagg ccctctgatc ccaccctggg ggtggccagg
1081 caacacccctt gttgctgtgt ccatctttct cctgctgact ggcccgacct acctcctgtt
1141 caagctgtcg cccagacttg gatgggggcc cacggggccg gtgtgctgtt gagccaggac
1201 tgtgctggca ccccacaggg agccttggag ccctgcgtcc aggaggccac tgcactgctc
1261 acttgtggcc cagcgcgtcc ttggaaatct gtggccctgg aggaggaaca ggagggccct
1321 gggaccaggc tcccggggaa cctgagctca gaggatgtgc tgccagcagg gtgtacggag
1381 tggagggtac agacgcttgc ctatctgcca caggaggact gggcccccac gtccctgact
1441 aggccggctc ccccagactc agagggcagc aggagcagca gcagcagcag cagcagcaac
1501 aacaacaact actgtgcctt gggctgctat ggggatggc acctctcagc cctcccagga
1561 aacacacaga gctctgggcc catcccagcc ctggcctgtg gcctttcttg tgaccatcag
1621 ggcctggaga cccagcaagg agttgcctgg gtgctggctg tcactgcca gaggcctggg
1681 ctgcatgagg acctccaggg catgttgctc ccttctgtcc tcagcaaggc tcggtcctgg
1741 acattctagg tccctgactc gccagatgca tcatgtccat tttgggaaaa tggactgaag
1801 tttctggagc ccttgtctga gactgaacct cctgagaagg ggccctagc agcggtcaga
1861 ggtcctgtct ggatggaggc tgaggctcc ccctcaacc cctctgctca gtgcctgtgg
1921 ggagcagcct ctaccctcag catcctggcc acaagttctt ccttccattg tccctttct
1981 ttatccctga cctctctgag aagtggggtg tggtctctca gctgttctgc cctcataccc
2041 ttaaagggcc agcctgggcc cagtggacac aggtaaggca ccatgaccac ctggtgtgac
2101 ctctctgtgc cttactgagg cacctttcta gagattaaaa ggggcttgat ggctgttaaa
2161 aaaaaaaaaa aaaaa
```

FIG. 14B

```
   1 gaagagcaag cgccatgttg aagccatcat taccattcac atccctctta ttcctgcagc
  61 tgcccctgct gggagtgggg ctgaacacga caattctgac gcccaatggg aatgaagaca
 121 ccacagctga tttcttcctg accactatgc ccactgactc cctcagtgtt tccactctgc
 181 ccctcccaga ggttcagtgt tttgtgttca atgtcgagta catgaattgc acttggaaca
 241 gcagctctga gccccagcct accaacctca ctctgcatta ttggtacaag aactcggata
 301 atgataaagt ccagaagtgc agccactatc tattctctga agaaatcact tctggctgtc
 361 agttgcaaaa aaaggagatc cacctctacc aaacatttgt tgttcagctc caggacccac
 421 gggaacccag gagacaggcc acacagatgc taaaactgca gaatctggtg atccctggg
 481 ctccagagaa cctaacactt cacaaactga gtgaatccca gctagaactg aactggaaca
 541 acagattctt gaaccactgt ttggagcact tggtgcagta ccggactgac tgggaccaca
 601 gctggactga acaatcagtg gattatagac ataagttctc cttgcctagt gtggatgggc
 661 agaaacgcta cacgtttcgt gttcggagcc gctttaaccc actctgtgga agtgctcagc
 721 attggagtga atggagccac ccaatccact gggggagcaa tacttcaaaa gagaatcctt
 781 tcctgtttgc attggaagcc gtggttatct ctgttggctc catgggattg attatcagcc
 841 ttctctgtgt gtatttctgg ctggaacgga cgatgccccg aattccacc ctgaagaacc
 901 tagaggatct tgttactgaa taccacggga acttttcggc ctggagtggt gtgtctaagg
 961 gactggctga gagtctgcag ccagactaca gtaacgact ctgcctcgtc agtgagattc
1021 ccccaaaagg aggggcctt ggggagggc ctggggcctc cccatgcaac cagcatagcc
1081 cctactgggc cccccatgt tacaccctaa agcctgaaac ctgaacccca atcctctgac
1141 agaagaaccc cagggtcctg tagccctaag tggtactaac tttccttcat tcaacccacc
1201 tgcgtctcat actcacctca ccccactgtg gctgatttgg aattttgtgc ccccatgtaa
1261 gcacccttc atttggcatt ccccacttga gaattaccct tttgccccga acatgttttt
1321 cttctccctc agtctggccc ttccttttcg caggattctt cctcctccc tctttccctc
1381 ccttcctctt tccatctacc ctccgattgt tcctgaaccg atgagaaata aagtttctgt
1441 tgataatcat c
```

FIG. 14C

```
  1 mglgrciweg wtlesealrr dmgtwllaci cictcvclgv svtgegqgpr srtftcltnn
 61 ilridchwsa pelgqgsspw llftsnqapg gthkcilrgs ectvvlppea vlvpsdnfti
121 tfhhcmsgre qvslvdpeyl prrhvkldpp sdlqsnissg hciltwsisp alepmttlls
181 yelafkkqee aweqaqhrdh ivgvtwlile afeldpgfih earlrvqmat leddvveeer
241 ytgqwsewsq pvcfqapqrq gplippwgwp gntlvavsif llltgptyll fklsprvkri
301 fyqnvpspam ffqplysvhn gnfqtwmgah gagvllsqdc agtpqgalep cvqeatallt
361 cgparpwksv aleeeqegpg trlpgnlsse dvlpagctew rvqtlaylpq edwaptsltr
421 pappdsegsr ssssssssnn nnycalgcyg gwhlsalpgn tqssgpipal acglscdhqg
481 letqqgvawv laghcqrpgl hedlqgmllp svlskarswt f
```

FIG. 15A

```
  1 mhlgsnccku gqtllqrtch gvsccgwwfq aarsilgkgp saqslagwtl esealrrdmg
 61 twllacicic tcvclgvsvt gegqgprsrt ftcltnnilr idchwsapel gqgsspwllf
121 trllaahisa scgavsapsc chlrqcschl tispslstta clggsrsaww trstcpgdts
181 nissghcilt wsispalepm ttllsyelaf kkqeeaweqa qhrdhivgvt wlileafeld
241 pgfihearlr vqmatleddv veeerytgqw sewsqpvcfq apqrqgplip pwgwpgntlv
301 avsiflltg ptyllfklsp rlgwgptgpv cc
```

FIG. 15B

```
  1 mlkpslpfts llflqlpllg vglnttiltp ngnedttadf flttmptdsl svstlplpev
 61 qcfvfnveym nctwnsssep qptnltlhyw yknsdndkvq kcshylfsee itsgcqlqkk
121 eihlyqtfvv qlqdpreprr qatqmlklqn lvipwapenl tlhklsesql elnwnnrfln
181 hclehlvqyr tdwdhswteq svdyrhkfsl psvdgqkryt frvrsrfnpl cgsaqhwsew
241 shpihwgsnt skenpflfal eavvisvgsm gliisllcvy fwlertmpri ptlknledlv
301 teyhgnfsaw sgvskglaes lqpdyserlc lvseippkgg algegpgasp cnqhspywap
361 pcytlkpet
```

FIG. 15C

```
                             SEQUENCE LISTING

<160> NUMBER OF SEQ ID NOS: 65

<210> SEQ ID NO 1
<211> LENGTH: 10
<212> TYPE: PRT
<213> ORGANISM: Homo sapiens

<400> SEQUENCE: 1

Gly Tyr Thr Phe Thr Gly Tyr Trp Ile Glu
1               5                   10

<210> SEQ ID NO 2
<211> LENGTH: 17
<212> TYPE: PRT
<213> ORGANISM: Homo sapiens

<400> SEQUENCE: 2

Glu Ile Leu Pro Gly Ser Gly Thr Thr Asn Tyr Asn Glu Lys Phe Lys
1               5                   10                  15

Gly

<210> SEQ ID NO 3
<211> LENGTH: 13
<212> TYPE: PRT
<213> ORGANISM: Homo sapiens

<400> SEQUENCE: 3

Ala Asp Tyr Tyr Gly Ser Asp Tyr Val Lys Phe Asp Tyr
1               5                   10

<210> SEQ ID NO 4
<211> LENGTH: 11
<212> TYPE: PRT
<213> ORGANISM: Homo sapiens

<400> SEQUENCE: 4

Lys Ala Ser Gln His Val Gly Thr His Val Thr
1               5                   10

<210> SEQ ID NO 5
<211> LENGTH: 7
<212> TYPE: PRT
<213> ORGANISM: Homo sapiens

<400> SEQUENCE: 5

Ser Thr Ser Tyr Arg Tyr Ser
1               5

<210> SEQ ID NO 6
<211> LENGTH: 9
<212> TYPE: PRT
<213> ORGANISM: Homo sapiens

<400> SEQUENCE: 6

Gln His Phe Tyr Ser Tyr Pro Leu Thr
1               5

<210> SEQ ID NO 7
```

```
<211> LENGTH: 118
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Ser Cys Lys Ala Ser Gly Tyr Thr Phe Thr Gly Tyr Trp
            20                  25                  30

Ile Glu Trp Val Arg Gln Ala Pro Gly Gln Leu Glu Trp Met Gly Glu
        35                  40                  45

Ile Leu Pro Gly Ser Thr Thr Asn Tyr Asn Glu Lys Phe Lys Gly Arg
    50                  55                  60

Val Thr Met Thr Arg Asp Thr Ser Thr Ser Thr Val Tyr Met Glu Leu
65                  70                  75                  80

Ser Ser Leu Arg Ser Glu Asp Thr Ala Val Tyr Tyr Cys Ala Arg Ala
                85                  90                  95

Asp Tyr Tyr Gly Ser Asp Tyr Val Lys Phe Asp Tyr Trp Gly Gln Gly
            100                 105                 110

Thr Leu Val Thr Ser Ser
        115

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Val Gly Thr His
            20                  25                  30

Val Thr Trp Tyr Gln Gln Lys Pro Gly Lys Ala Pro Lys Leu Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Ser Tyr Pro Leu
                85                  90                  95

Thr Phe Gly Gly Gly Thr Lys Val Glu Ile Lys
            100                 105

<210> SEQ ID NO 9
<211> LENGTH: 124
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Trp Leu Pro Gly Ser Gly Thr Thr Asn Tyr Asn Asn Glu Lys
    50                  55                  60
```

```
Phe Lys Gly Arg Val Thr Met Thr Arg Asp Thr Ser Ser Thr Ser Thr
 65                  70                  75                  80

Val Tyr Met Glu Leu Ser Ser Leu Arg Ser Glu Asp Thr Ala Val Tyr
                 85                  90                  95

Tyr Cys Ala Arg Ala Asp Tyr Tyr Gly Ser Asp Tyr Val Lys Phe Asp
            100                 105                 110

Tyr Trp Gly Gln Gly Thr Leu Val Thr Val Ser Ser
        115                 120
```

<210> SEQ ID NO 10
<211> LENGTH: 17
<212> TYPE: PRT
<213> ORGANISM: Homo sapiens

<400> SEQUENCE: 10

```
Glu Trp Leu Pro Gly Ser Gly Thr Thr Asn Tyr Asn Glu Lys Phe Lys
 1               5                  10                  15

Gly
```

<210> SEQ ID NO 11
<211> LENGTH: 10
<212> TYPE: PRT
<213> ORGANISM: Homo sapiens

<400> SEQUENCE: 11

```
Gly Tyr Thr Phe Thr Tyr Tyr Trp Ile Glu
 1               5                  10
```

<210> SEQ ID NO 12
<211> LENGTH: 13
<212> TYPE: PRT
<213> ORGANISM: Homo sapiens

<400> SEQUENCE: 12

```
Ala Asp Tyr Tyr Gly Ser Asp His Val Lys Phe Asp Tyr
 1               5                  10
```

<210> SEQ ID NO 13
<211> LENGTH: 11
<212> TYPE: PRT
<213> ORGANISM: Homo sapiens

<400> SEQUENCE: 13

```
Leu Ala Ser Gln His Val Gly Thr His Val Thr
 1               5                  10
```

<210> SEQ ID NO 14
<211> LENGTH: 7
<212> TYPE: PRT
<213> ORGANISM: Homo sapiens

<400> SEQUENCE: 14

```
Gly Thr Ser Tyr Arg Tyr Ser
 1               5
```

<210> SEQ ID NO 15
<211> LENGTH: 120
<212> TYPE: PRT
<213> ORGANISM: Homo sapiens

<400> SEQUENCE: 15

```
Gln Val Gln Leu Val Gln Ser Gly Ala Glu Val Lys Lys Pro Gly Ala
 1               5                  10                  15
```

```
Ser Val Lys Val Ser Cys Lys Ala Ser Gly Tyr Thr Phe Thr Tyr Tyr
            20                  25                  30

Trp Ile Glu Trp Val Arg Gln Ala Pro Gly Gln Gly Leu Glu Trp Met
            35                  40                  45

Glu Trp Leu Pro Gly Ser Gly Thr Thr Asn Tyr Asn Glu Lys Phe Lys
            50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Asp Tyr Tyr Gly Ser Asp His Val Lys Phe Asp Tyr Trp Gly
                100                 105                 110

Gln Thr Leu Val Thr Val Ser Ser
            115                 120

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln His Val Gly Thr His
            20                  25                  30

Val Thr Trp Tyr Gln Gln Lys Pro Gly Lys Ala Pro Lys Leu Leu Ile
            35                  40                  45

Tyr Gly Thr Ser Tyr Arg Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Asp Tyr Pro Leu
                85                  90                  95

Thr Phe Gly Gly Gly Thr Lys Val Glu Ile Lys
                100                 105

<210> SEQ ID NO 17
<211> LENGTH: 120
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
            35                  40                  45

Gly Glu Trp Leu Pro Gly Ser Gly Thr Thr Asn Tyr Asn Glu Lys Phe
            50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Asp Tyr Tyr Gly Ser Asp His Lys Phe Asp Tyr Trp Gly
                100                 105                 110
```

Gln Gly Thr Leu Thr Val Ser Ser
         115                 120

<210> SEQ ID NO 18
<211> LENGTH: 107
<212> TYPE: PRT
<213> ORGANISM: Homo sapiens

<400> SEQUENCE: 18

Asp Gln Ile Met Thr Gln Ser Pro Ser Ser Leu Ser Ala Ser Val Gly
1               5                   10                  15

Asp Arg Val Thr Ile Thr Cys Lys Ala Ser Gln His Val Gly Thr His
            20                  25                  30

Val Thr Trp Thr Tyr Gln Gln Lys Pro Gly Lys Ala Pro Lys Leu Leu
        35                  40                  45

Ile Tyr Gly Thr Ser Tyr Arg Tyr Ser Gly Val Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Glu Tyr Pro Leu
                85                  90                  95

Thr Phe Gly Gly Gly Thr Lys Val Glu Ile Lys
            100                 105

<210> SEQ ID NO 19
<211> LENGTH: 10
<212> TYPE: PRT
<213> ORGANISM: Homo sapiens

<400> SEQUENCE: 19

Gly Gly Thr Phe Ser Gly Tyr Trp Ile Glu
1               5                   10

<210> SEQ ID NO 20
<211> LENGTH: 9
<212> TYPE: PRT
<213> ORGANISM: Homo sapiens

<400> SEQUENCE: 20

Gln Gln Phe Tyr Glu Tyr Pro Leu Thr
1               5

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1               5                   10                  15

Ser Val Lys Ser Cys Lys Ala Gly Gly Thr Phe Ser Gly Tyr Trp Ile
            20                  25                  30

Glu Trp Val Arg Gln Ala Pro Gly Gln Gly Leu Glu Trp Met Gly Glu
        35                  40                  45

Ile Leu Pro Gly Ser Gly Thr Thr Asn Tyr Asn Glu Lys Phe Lys Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg

```
                      85                  90                  95

Ala Asp Tyr Tyr Gly Ser Asp Tyr Val Lys Phe Asp Tyr Trp Gly Gln
            100                 105                 110

Thr Leu Val Thr Val Ser Ser
        115

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Val Gly Asp
1               5                   10                  15

Arg Val Thr Ile Thr Cys Lys Ala Ser Gln His Val Gly Thr His Val
            20                  25                  30

Thr Trp Tyr Gln Gln Lys Pro Gly Lys Ala Pro Lys Lys Leu Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Pro Leu Thr
                85                  90                  95

Gly Phe Gly Gly Gly Thr Lys Val Ile Glu Lys
            100                 105

<210> SEQ ID NO 23
<211> LENGTH: 121
<212> TYPE: PRT
<213> ORGANISM: Homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Trp Ile Glu Glu Val Arg Gln Ala Pro Gly Gln Gly Leu Glu Trp Met
        35                  40                  45

Gly Glu Ile Leu Pro Gly Ser Gly Thr Thr Asn Pro Asn Glu Lys Phe
    50                  55                  60

Lys Gly Arg Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Asp Tyr Tyr Gly Ser Asp Tyr Val Lys Phe Asp Tyr Trp Gly
            100                 105                 110

Gln Gly Thr Leu Val Thr Val Ser Ser
        115                 120

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15
```

-continued

Asp Arg Val Thr Ile Thr Cys Lys Ala Ser Gln His Val Gly Thr His
            20                  25                  30

Val Thr Trp Tyr Gln Gln Lys Pro Gly Lys Ala Pro Lys Leu Leu Ile
        35                  40                  45

Tyr Ser Thr Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Glu Pro Leu
                 85                  90                  95

Thr Phe Gly Gly Gly Thr Lys Val Glu Ile Lys
            100                 105

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Lys Ala Ser Ser Gln His Val Gly Thr
            20                  25                  30

His Val Thr Trp Tyr Gln Gln Lys Pro Gly Lys Ala Pro Lys Leu Leu
        35                  40                  45

Ile Tyr Gly Thr Ser Tyr Arg Tyr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Phe Tyr Glu Tyr Pro
                 85                  90                  95

Leu Thr Phe Gly Gly Gly Thr Val Glu Ile Lys
            100                 105

<210> SEQ ID NO 26
<211> LENGTH: 10
<212> TYPE: PRT
<213> ORGANISM: Homo sapiens

<400> SEQUENCE: 26

Gly Gly Thr Phe Ser Tyr Tyr Trp Ile Glu
 1               5                  10

<210> SEQ ID NO 27
<211> LENGTH: 62
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Tyr Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Thr Thr Asn Pro Asn Glu
 50                  55                  60

```
<210> SEQ ID NO 28
<211> LENGTH: 107
<212> TYPE: PRT
<213> ORGANISM: Homo sapiens

<400> SEQUENCE: 28

Asp Ile Gln Met Met Thr Gln Ser Pro Ser Ser Leu Ala Ser Val Gly
1               5                   10                  15

Asp Arg Val Thr Ile Thr Cys Lys Ala Ser Gln His Val Ile Thr His
            20                  25                  30

Val Thr Trp Tyr Gln Gln Lys Pro Gly Lys Ala Pro Lys Leu Leu Ile
        35                  40                  45

Tyr Gly Thr Ser Tyr Ser Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Tyr Pro Leu
                85                  90                  95

Thr Phe Gly Gly Gly Thr Lys Val Glu Ile Lys
            100                 105

<210> SEQ ID NO 29
<211> LENGTH: 122
<212> TYPE: PRT
<213> ORGANISM: Homo sapiens

<400> SEQUENCE: 29

Gln Val Gln Leu Val Gln Ser Asx Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Thr Thr Asn Pro Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asp Tyr Tyr Gly Ser Asp Tyr Val Lys Phe Asp Tyr Trp
            100                 105                 110

Gly Gln Gly Thr Leu Val Thr Val Ser Ser
        115                 120

<210> SEQ ID NO 30
<211> LENGTH: 105
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Thr Ile Thr Cys Lys Ala Ser Gln His Val Gly Thr His Val
            20                  25                  30

Thr Trp Tyr Gln Lys Pro Gly Lys Ala Pro Lys Leu Leu Ile Tyr Gly
        35                  40                  45

Thr Ser Tyr Arg Tyr Ser Gly Val Pro Ser Arg Phe Ser Gly Ser Gly
```

```
                50                  55                  60
Ser Gly Thr Asp Phe Thr Leu Thr Ile Ser Ser Leu Gln Pro Glu Asp
 65                  70                  75                  80

Phe Ala Thr Tyr Tyr Cys Gln Gln Phe Tyr Glu Tyr Pro Leu Thr Phe
                 85                  90                  95

Gly Gly Gly Thr Lys Val Glu Ile Lys
            100                 105

<210> SEQ ID NO 31
<211> LENGTH: 127
<212> TYPE: PRT
<213> ORGANISM: Homo sapiens

<400> SEQUENCE: 31

Gln Val Gln Leu Val Gln Ser Gly Ala Glu Val Lys Lys Pro Gly Ser
 1               5                  10                  15

Ser Val Lys Lys Pro Gly Ser Ser Val Lys Ser Cys Lys Ala Ser Gly
                20                  25                  30

Gly Thr Phe Ser Tyr Tyr Trp Ile Glu Trp Val Arg Gln Ala Pro Gly
             35                  40                  45

Gln Gly Leu Glu Trp Met Gly Glu Ile Leu Pro Gly Ser Gly Thr Thr
         50                  55                  60

Asn Pro His Glu Lys Phe Lys Gly Arg Val Thr Ile Thr Ala Asp Glu
 65                  70                  75                  80

Ser Thr Ser Thr Ala Tyr Met Glu Leu Ser Ser Leu Arg Ser Glu Asp
                 85                  90                  95

Thr Ala Val Tyr Tyr Cys Ala Arg Ala Asp Tyr Tyr Gly Ser Asp Tyr
                100                 105                 110

Val Lys Phe Asp Tyr Trp Gly Gln Gly Thr Leu Val Thr Ser Ser
            115                 120                 125

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln His Val Ile Thr His
                20                  25                  30

Val Thr Trp Tyr Gln Gln Lys Pro Gly Lys Ala Pro Lys Leu Leu Ile
             35                  40                  45

Tyr Gly Thr Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Glu Tyr Pro Leu
                 85                  90                  95

Thr Phe Gly Gly Gly Thr Lys Val Glu Ile Lys
                100                 105

<210> SEQ ID NO 33
<211> LENGTH: 25
<212> TYPE: PRT
<213> ORGANISM: Homo sapiens

<400> SEQUENCE: 33
```

-continued

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Gln Gly Leu Glu Trp Met Gly
1               5                   10

<210> SEQ ID NO 35
<211> LENGTH: 32
<212> TYPE: PRT
<213> ORGANISM: Homo sapiens

<400> SEQUENCE: 35

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 36
<211> LENGTH: 11
<212> TYPE: PRT
<213> ORGANISM: Homo sapiens

<400> SEQUENCE: 36

Trp Gly Gln Gly Thr Leu Val Thr Val Ser Ser
1               5                   10

<210> SEQ ID NO 37
<211> LENGTH: 25
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 38
<211> LENGTH: 32
<212> TYPE: PRT
<213> ORGANISM: Homo sapiens

<400> SEQUENCE: 38

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 39
<211> LENGTH: 23
<212> TYPE: PRT
<213> ORGANISM: Homo sapiens

<400> SEQUENCE: 39

-continued

```
Asp Ile Gln Met Thr Gln Ser Pro Ser Ser Leu Ser Ala Ser Val Gly
1               5                  10                  15

Asp Arg Val Thr Ile Thr Cys
            20

<210> SEQ ID NO 40
<211> LENGTH: 15
<212> TYPE: PRT
<213> ORGANISM: Homo sapiens

<400> SEQUENCE: 40

Trp Tyr Gln Gln Lys Pro Gly Lys Ala Pro Lys Leu Leu Ile Tyr
1               5                  10                  15

<210> SEQ ID NO 41
<211> LENGTH: 32
<212> TYPE: PRT
<213> ORGANISM: Homo sapiens

<400> SEQUENCE: 41

Gly Val Pro Ser Arg Phe Ser Gly Ser Gly Ser Gly Thr Asp Phe Thr
1               5                  10                  15

Leu Thr Ile Ser Ser Leu Gln Pro Glu Asp Phe Ala Thr Tyr Tyr Cys
            20                  25                  30

<210> SEQ ID NO 42
<211> LENGTH: 10
<212> TYPE: PRT
<213> ORGANISM: Homo sapiens

<400> SEQUENCE: 42

Phe Gly Gly Gly Thr Lys Val Glu Ile Lys
1               5                  10

<210> SEQ ID NO 43
<211> LENGTH: 366
<212> TYPE: DNA
<213> ORGANISM: Homo sapiens

<400> SEQUENCE: 43
caggtgcagc tggtgcagtc tggggctgag gtgaagaagc ctgggtcctc agtgaaggtt      60
tcctgcaagg catctggagg caccttcagc tattactgga tagagtgggt gcgacaggcc     120
cctggacaag gcttgagtg gatgggagag attttacctg gaagtggtac tactaacccg      180
aatgagaagt tcaagggcag agtcaccatt accgcggacg aatccacgag cacagcctac     240
atggagctga gcagcctgag atctgaggac acggccgtgt attactgtgc gagagcggat     300
tactacggta gtgattacgt caagtttgac tactggggcc aaggaaccct ggtcaccgtc     360
tcctca                                                                366

<210> SEQ ID NO 44
<211> LENGTH: 30
<212> TYPE: DNA
<213> ORGANISM: Homo sapiens

<400> SEQUENCE: 44
ggaggcacct tcagctatta ctggatagag                                       30

<210> SEQ ID NO 45
<211> LENGTH: 51
<212> TYPE: DNA
<213> ORGANISM: Homo sapiens
```

<400> SEQUENCE: 45
gagattttac ctggaagtgg tactactaac ccgaatgaga agttcaaggg c    51

<210> SEQ ID NO 46
<211> LENGTH: 39
<212> TYPE: DNA
<213> ORGANISM: Homo sapiens

<400> SEQUENCE: 46
gcggattact acggtagtga ttacgtcaag tttgactac    39

<210> SEQ ID NO 47
<211> LENGTH: 321
<212> TYPE: DNA
<213> ORGANISM: Homo sapiens

<400> SEQUENCE: 47
gacatccaga tgacccagtc tccatcctcc ctgtctgcat ctgtaggaga cagagtcacc    60
atcacttgca aggcaagtca gcatgtgatt actcatgtaa cctggtatca gcagaaacca    120
gggaaagccc ctaagctcct gatctatggg acatcctaca gctacagtgg ggtcccatca    180
aggttcagtg gcagtggatc tgggacagat ttcactctca ccatcagcag tctgcaacct    240
gaagattttg caacttatta ctgtcagcaa ttttacgagt atcctctcac gttcggcgga    300
gggaccaagg tggagatcaa a    321

<210> SEQ ID NO 48
<211> LENGTH: 33
<212> TYPE: DNA
<213> ORGANISM: Homo sapiens

<400> SEQUENCE: 48
aaggcaagtc agcatgtgat tactcatgta acc    33

<210> SEQ ID NO 49
<211> LENGTH: 15
<212> TYPE: DNA
<213> ORGANISM: Homo sapiens

<400> SEQUENCE: 49
gggacatcct acagc    15

<210> SEQ ID NO 50
<211> LENGTH: 27
<212> TYPE: DNA
<213> ORGANISM: Homo sapiens

<400> SEQUENCE: 50
cagcaatttt acgagtatcc tctcacg    27

<210> SEQ ID NO 51
<211> LENGTH: 591
<212> TYPE: DNA
<213> ORGANISM: Homo sapiens

<400> SEQUENCE: 51
ccgctgtcaa gatgcttctg gccatggtcc ttacctctgc cctgctcctg tgctccgtgg    60
caggccaggg gtgtccaacc ttggcgggga tcctggacat caacttcctc atcaacaaga    120
tgcaggaaga tccagcttcc aagtgccact gcagtgctaa tgtgaccagt gtgtctctgtt    180

```
tgggcattcc ctctgacaac tgcaccagac catgcttcag tgagagactg tctcagatga    240
ccaataccac catgcaaaca agatacccac tgattttcag tcgggtgaaa aaatcagttg    300
aagtactaaa gaacaacaag tgtccatatt tttcctgtga acagccatgc aaccaaacca    360
cggcaggcaa cgcgctgaca tttctgaaga gtcttctgga aattttccag aaagaaaaga    420
tgagagggat gagaggcaag atatgaagat gaaatattat ttatcctatt tattaaattt    480
aaaaagcttt ctctttaagt tgctacaatt taaaaatcaa gtaagctact ctaaatcagt    540
atcagttgtg attatttgtt taacattgta tgtctttatt ttgaaataaa t             591
```

```
<210> SEQ ID NO 52
<211> LENGTH: 144
<212> TYPE: PRT
<213> ORGANISM: Homo sapiens

<400> SEQUENCE: 52
```

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

```
<210> SEQ ID NO 53
<211> LENGTH: 808
<212> TYPE: PRT
<213> ORGANISM: Homo sapiens

<400> SEQUENCE: 53
```

Met Ala Glu Leu Leu Ala Ser Ala Gly Ser Ala Cys Ser Trp Asp Phe
1               5                   10                  15

Pro Arg Ala Pro Pro Ser Phe Pro Pro Ala Ala Ser Arg Gly Gly
            20                  25                  30

Leu Gly Gly Thr Arg Ser Phe Arg Pro His Arg Gly Ala Glu Ser Pro
        35                  40                  45

Arg Pro Gly Arg Asp Arg Asp Gly Val Arg Val Pro Met Ala Ser Ser
    50                  55                  60

Arg Cys Pro Ala Pro Arg Gly Cys Arg Cys Leu Pro Gly Ala Ser Leu
65                  70                  75                  80

Ala Trp Leu Gly Thr Val Leu Leu Leu Ala Asp Trp Val Leu Leu
                85                  90                  95

Arg Thr Ala Leu Pro Arg Ile Phe Ser Leu Leu Val Pro Thr Ala Leu
            100                 105                 110

Pro Leu Leu Arg Val Trp Ala Val Gly Leu Ser Arg Trp Ala Val Leu

-continued

```
            115                 120                 125
Trp Leu Gly Ala Cys Gly Val Leu Arg Ala Thr Val Gly Ser Lys Ser
        130                 135                 140
Glu Asn Ala Gly Ala Gln Gly Trp Leu Ala Ala Leu Lys Pro Leu Ala
145                 150                 155                 160
Ala Ala Leu Gly Leu Ala Leu Pro Gly Leu Ala Leu Phe Arg Glu Leu
                165                 170                 175
Ile Ser Trp Gly Ala Pro Gly Ser Ala Asp Ser Thr Arg Leu Leu His
            180                 185                 190
Trp Gly Ser His Pro Thr Ala Phe Val Val Ser Tyr Ala Ala Ala Leu
            195                 200                 205
Pro Ala Ala Ala Leu Trp His Lys Leu Gly Ser Leu Trp Val Pro Gly
        210                 215                 220
Gly Gln Gly Gly Ser Gly Asn Pro Val Arg Arg Leu Leu Gly Cys Leu
225                 230                 235                 240
Gly Ser Glu Thr Arg Arg Leu Ser Leu Phe Leu Val Leu Val Val Leu
                245                 250                 255
Ser Ser Leu Gly Glu Met Ala Ile Pro Phe Phe Thr Gly Arg Leu Thr
            260                 265                 270
Asp Trp Ile Leu Gln Asp Gly Ser Ala Asp Thr Phe Thr Arg Asn Leu
        275                 280                 285
Thr Leu Met Ser Ile Leu Thr Ile Ala Ser Ala Val Leu Glu Phe Val
        290                 295                 300
Gly Asp Gly Ile Tyr Asn Asn Thr Met Gly His Val His Ser His Leu
305                 310                 315                 320
Gln Gly Glu Val Phe Gly Ala Val Leu Arg Gln Glu Thr Glu Phe Phe
                325                 330                 335
Gln Gln Asn Gln Thr Gly Asn Ile Met Ser Arg Val Thr Glu Asp Thr
            340                 345                 350
Ser Thr Leu Ser Asp Ser Leu Ser Glu Asn Leu Ser Leu Phe Leu Trp
            355                 360                 365
Tyr Leu Val Arg Gly Leu Cys Leu Leu Gly Ile Met Leu Trp Gly Ser
        370                 375                 380
Val Ser Leu Thr Met Val Thr Leu Ile Thr Leu Pro Leu Leu Phe Leu
385                 390                 395                 400
Leu Pro Lys Lys Val Gly Lys Trp Tyr Gln Leu Leu Glu Val Gln Val
                405                 410                 415
Arg Glu Ser Leu Ala Lys Ser Ser Gln Val Ala Ile Glu Ala Leu Ser
            420                 425                 430
Ala Met Pro Thr Val Arg Ser Phe Ala Asn Glu Glu Gly Glu Ala Gln
            435                 440                 445
Lys Phe Arg Glu Lys Leu Gln Glu Ile Lys Thr Leu Asn Gln Lys Glu
        450                 455                 460
Ala Val Ala Tyr Ala Val Asn Ser Trp Thr Thr Ser Ile Ser Gly Met
465                 470                 475                 480
Leu Leu Lys Val Gly Ile Leu Tyr Ile Gly Gly Gln Leu Val Thr Ser
                485                 490                 495
Gly Ala Val Ser Ser Gly Asn Leu Val Thr Phe Val Leu Tyr Gln Met
            500                 505                 510
Gln Phe Thr Gln Ala Val Glu Val Leu Leu Ser Ile Tyr Pro Arg Val
        515                 520                 525
Gln Lys Ala Val Gly Ser Ser Glu Lys Ile Phe Glu Tyr Leu Asp Arg
    530                 535                 540
```

```
Thr Pro Arg Cys Pro Pro Ser Gly Leu Leu Thr Pro Leu His Leu Glu
545                 550                 555                 560

Gly Leu Val Gln Phe Gln Asp Val Ser Phe Ala Tyr Pro Asn Arg Pro
                565                 570                 575

Asp Val Leu Val Leu Gln Gly Leu Thr Phe Thr Leu Arg Pro Gly Glu
            580                 585                 590

Val Thr Ala Leu Val Gly Pro Asn Gly Ser Gly Lys Ser Thr Val Ala
        595                 600                 605

Ala Leu Leu Gln Asn Leu Tyr Gln Pro Thr Gly Gly Gln Leu Leu Leu
    610                 615                 620

Asp Gly Lys Pro Leu Pro Gln Tyr Glu His Arg Tyr Leu His Arg Gln
625                 630                 635                 640

Val Ala Ala Val Gly Gln Glu Pro Gln Val Phe Gly Arg Ser Leu Gln
                645                 650                 655

Glu Asn Ile Ala Tyr Gly Leu Thr Gln Lys Pro Thr Met Glu Glu Ile
                660                 665                 670

Thr Ala Ala Val Lys Ser Gly Ala His Ser Phe Ile Ser Gly Leu
675                 680                 685

Pro Gln Gly Tyr Asp Thr Glu Val Asp Glu Ala Gly Ser Gln Leu Ser
690                 695                 700

Gly Gly Gln Arg Gln Ala Val Ala Leu Ala Arg Ala Leu Ile Arg Lys
705                 710                 715                 720

Pro Cys Val Leu Ile Leu Asp Asp Ala Thr Ser Ala Leu Asp Ala Asn
                725                 730                 735

Ser Gln Leu Gln Val Glu Gln Leu Leu Tyr Glu Ser Pro Glu Arg Tyr
                740                 745                 750

Ser Arg Ser Val Leu Leu Ile Thr Gln His Leu Ser Leu Val Glu Gln
            755                 760                 765

Ala Asp His Ile Leu Phe Leu Glu Gly Gly Ala Ile Arg Glu Gly Gly
        770                 775                 780

Thr His Gln Gln Leu Met Glu Lys Lys Gly Cys Tyr Trp Ala Met Val
785                 790                 795                 800

Gln Ala Pro Ala Asp Ala Pro Glu
                805

<210> SEQ ID NO 54
<211> LENGTH: 140
<212> TYPE: PRT
<213> ORGANISM: Homo sapiens

<400> SEQUENCE: 54

Met Val Leu Thr Ser Ala Leu Leu Leu Cys Ser Val Ala Gly Gln Gly
1               5                   10                  15

Cys Pro Thr Leu Ala Gly Ile Leu Asp Ile Asn Phe Leu Ile Asn Lys
            20                  25                  30

Met Gln Glu Asp Pro Ala Ser Lys Cys His Cys Ser Ala Asn Val Thr
        35                  40                  45

Ser Cys Leu Cys Leu Gly Ile Pro Ser Asp Asn Cys Thr Arg Pro Cys
    50                  55                  60

Phe Ser Glu Arg Leu Ser Gln Met Thr Asn Thr Thr Met Gln Thr Arg
65                  70                  75                  80

Tyr Pro Leu Ile Phe Ser Arg Val Lys Lys Ser Val Glu Val Leu Lys
                85                  90                  95

Asn Asn Lys Cys Pro Tyr Phe Ser Cys Glu Gln Pro Cys Asn Gln Thr
```

```
              100                 105                 110
Thr Ala Gly Asn Ala Leu Thr Phe Leu Lys Ser Leu Leu Glu Ile Phe
        115                 120                 125

Gln Lys Glu Lys Met Arg Gly Met Arg Gly Lys Ile
    130                 135                 140

<210> SEQ ID NO 55
<211> LENGTH: 2171
<212> TYPE: DNA
<213> ORGANISM: Homo sapiens

<400> SEQUENCE: 55
agcagctctg taatgcgctt gtggtttcag atgtgggcgg cctgtgtgaa cctgtcgtgc      60
aaagctcacg tcaccaactg ctgcagttat ctcctgaatc aggctgaggg tctttgctgt     120
gcacccagag atagttgggt gacaaatcac ctccaggttg ggatgcctc agacttgtga      180 tgggactggg cagatgcatc tgggaaggct ggaccttgga gagtgaggcc ctgaggcgag     240
acatgggcac ctggctcctg gcctgcatct gcatctgcac ctgtgtctgc ttgggagtct     300
ctgtcacagg ggaaggacaa gggccaaggt ctagaacctt cacctgcctc accaacaaca     360
ttctcaggat cgattgccac tggtctgccc cagagctggg acagggctcc agcccctggc     420
tcctcttcac cagcaaccag gctcctgcg cacacataa gtgcatcttg cggggcagtg       480
agtgcaccgt cgtgctgcca cctgaggcag tgctcgtgcc atctgacaat tcaccatca     540 ctttccacca ctgcatgtct gggagggagc aggtcagcct ggtggacccg gagtacctgc     600
cccggagaca cgttaagctg gacccgccct ctgacttgca gagcaacatc agttctggcc     660
actgcatcct gacctggagc atcagtcctg ccttggagcc aatgaccaca cttctcagct     720
atgagctggc cttcaagaag caggaagagg cctgggagca ggcccagcac agggatcaca     780
ttgtcggggt gacctggctt atacttgaag ccttttgagct ggaccctggc tttatccatg     840
aggccaggct gcgtgtccag atggccacac tggaggatga tgtggtagag gaggagcgtt     900
atacaggcca gtggagtgag tggagccagc ctgtgtgctt ccaggctccc cagagacaag     960
gccctctgat cccacccctgg gggtggccag gcaacaccct tgttgctgtg tccatctttc    1020
tcctgctgac tggcccgacc tacctcctgt tcaagctgtc gcccagggtg aagagaatct    1080
tctaccagaa cgtgccctct ccagcgatgt tcttccagcc cctctacagt gtacacaatg    1140
ggaacttcca gacttggatg ggggcccacg gggccggtgt gctgttgagc caggactgtg    1200
ctggcacccc acagggagcc ttggagccct gcgtccagga ggccactgca ctgctcactt    1260
gtggcccagc gcgtccttgg aaatctgtgg ccctggagga ggaacaggag ggccctggga    1320
ccaggctccc ggggaacctg agctcagagg atgtgctgcc agcagggtgt acggagtgga    1380
gggtacagac gcttgcctat ctgccacagg aggactgggc ccccacgtcc ctgactaggc    1440
cggctccccc agactcagag ggcagcagga gcagcagcag cagcagcagc agcaacaaca    1500
acaactactg tgccttgggc tgctatgggg gatggcacct ctcagccctc ccaggaaaca    1560
cacagagctc tgggcccatc ccagccctgg cctgtgcct tcttgtgac catcagggcc      1620 tggagaccca gcaaggagtt gcctgggtgc tggctggtca ctgccagagg cctgggctgc    1680
atgaggacct ccagggcatg ttgctcccctt ctgtcctcag caaggctcgg tcctggacat    1740
tctaggtccc tgactcgcca gatgcatcat gtccattttg ggaaaatgga ctgaagtttc    1800
tggagccctt gtctgagact gaacctcctg agaaggggcc cctagcagcg gtcagaggtc    1860
ctgtctggat ggaggctgga ggctccccccc tcaacccctc tgctcagtgc ctgtggggag    1920
```

```
cagcctctac cctcagcatc ctggccacaa gttcttcctt ccattgtccc ttttctttat   1980
ccctgacctc tctgagaagt ggggtgtggt ctctcagctg ttctgccctc ataccttaa    2040 agggccagcc tgggcccagt ggacacaggt aaggcaccat gaccacctgg tgtgacctct   2100
ctgtgcctta ctgaggcacc tttctagaga ttaaaagggg cttgatggct gttaaaaaaa   2160
aaaaaaaaaa a                                                        2171

<210> SEQ ID NO 56
<211> LENGTH: 2175
<212> TYPE: DNA
<213> ORGANISM: Homo sapiens

<400> SEQUENCE: 56
agcagctctg taatgcgctt gtggtttcag atgtgggcgg cctgtgtgaa cctgtcgtgc     60
aaagctcacg tcaccaactg ctgcagttat ctcctgaatc aggctgaggg tctttgctgt    120
gcacccagag atagttgggt gacaaatcac ctccaggttg gggatgcctc agacttgtga    180
tgggactggg cagatgcatc tgggaagtaa ctgctgcaag aacgacagac cactgctgca    240
gagaacttgc cacggtgttt catgctgtgg ctggtggttc caggctgcac gctccattct    300
aggaaagggg ccctcagccc agtcccttgc aggctggacc ttggagagtg aggccctgag    360
gcgagacatg ggcacctggc tcctggcctg catctgcatc tgcacctgtg tctgcttggg    420
agtctctgtc acaggggaag gacaagggcc aaggtctaga accttcacct gcctcaccaa    480
caacattctc aggatcgatt gccactggtc tgccccagag ctgggacagg gctccagccc    540
ctggctcctc ttcaccaggc tcctggcggc acacataagt gcatcttgcg gggcagtgag    600
tgcaccgtcg tgctgccacc tgaggcagtg ctcgtgccat ctgacaattt caccatcact    660
ttccaccact gcatgtctgg gagggagcag gtcagcctgg tggacccgga gtacctgccc    720
cggagacacg agcaacatca gttctggcca ctgcatcctg acctggagca tcagtcctgc    780
cttggagcca atgaccacac ttctcagcta tgagctggcc ttcaagaagc aggaagaggc    840
ctgggagcag gccagcaca gggatcacat tgtcggggtg acctggctta tacttgaagc    900 cttttgagctg gaccctggct ttatccatga ggccaggctg cgtgtccaga tggccacact    960
ggaggatgat gtggtagagg aggagcgtta tacaggccag tggagtgagt ggagccagcc   1020
tgtgtgcttc caggctcccc agagacaagg ccctctgatc ccaccctggg ggtggccagg   1080
caacacccct tgttgctgtgt ccatctttct cctgctgact ggcccgacct acctcctgtt   1140
caagctgtcg cccagacttg gatggggccc cacggggccg gtgtgctgtt gagccaggac   1200
tgtgctggca ccccacaggg agccttggag ccctgcgtcc aggaggccac tgcactgctc   1260
acttgtggcc cagcgcgtcc ttggaaatct gtggccctgg aggaggaaca ggagggccct   1320
gggaccaggc tcccggggaa cctgagctca gaggatgtgc tgccagcagg gtgtacggag   1380
tggagggtac agacgcttgc ctatctgcca caggaggact gggcccccac gtccctgact   1440
aggccggctc cccagactc agagggcagc aggagcagca gcagcagcag cagcagcaac   1500
aacaacaact actgtgcctt gggctgctat ggggatggc acctctcagc cctcccagga   1560
aacacacaga gctctgggcc catcccagcc ctggcctgtg gcctttcttg tgaccatcag   1620
ggcctggaga cccagcaagg agttgcctgg gtgctggctg gtcactgcca gaggcctggg   1680
ctgcatgagg acctccaggg catgttgctc ccttctgtcc tcagcaaggc tcggtcctgg   1740
acattctagg tccctgactc gccagatgca tcatgtccat tttgggaaaa tggactgaag   1800
```

| | |
|---|---:|
| tttctggagc ccttgtctga gactgaacct cctgagaagg ggcccctagc agcggtcaga | 1860 |
| ggtcctgtct ggatggaggc tggaggctcc cccctcaacc cctctgctca gtgcctgtgg | 1920 |
| ggagcagcct ctaccctcag catcctggcc acaagttctt ccttccattg tcccttttct | 1980 |
| ttatccctga cctctctgag aagtggggtg tggtctctca gctgttctgc cctcataccc | 2040 |
| ttaaagggcc agcctgggcc cagtggacac aggtaaggca ccatgaccac ctggtgtgac | 2100 |
| ctctctgtgc cttactgagg cacctttcta gagattaaaa ggggcttgat ggctgttaaa | 2160 |
| aaaaaaaaaa aaaaa | 2175 |

<210> SEQ ID NO 57
<211> LENGTH: 1451
<212> TYPE: DNA
<213> ORGANISM: Homo sapiens

<400> SEQUENCE: 57

| | |
|---|---:|
| gaagagcaag cgccatgttg aagccatcat taccattcac atccctctta ttcctgcagc | 60 |
| tgcccctgct gggagtgggg ctgaacacga caattctgac gcccaatggg aatgaagaca | 120 |
| ccacagctga tttcttcctg accactatgc ccactgactc cctcagtgtt ccactctgc | 180 |
| ccctcccaga ggttcagtgt tttgtgttca atgtcgagta catgaattgc acttggaaca | 240 |
| gcagctctga gccccagcct accaacctca ctctgcatta ttggtacaag aactcggata | 300 |
| atgataaagt ccagaagtgc agccactatc tattctctga agaaatcact tctggctgtc | 360 |
| agttgcaaaa aaaggagatc cacctctacc aaacatttgt tgttcagctc caggacccac | 420 |
| gggaacccag gagacaggcc acacagatgc taaaactgca gaatctggtg atcccctggg | 480 |
| ctccagagaa cctaacactt cacaaactga gtgaatccca gctagaactg aactggaaca | 540 |
| acagattctt gaaccactgt ttggagcact ggtgcagta ccggactgac tgggaccaca | 600 |
| gctggactga acaatcagtg gattatagac ataagttctc cttgcctagt gtggatgggc | 660 |
| agaaacgcta cacgtttcgt gttcggagcc gctttaaccc actctgtgga agtgctcagc | 720 |
| attggagtga atggagccac ccaatccact gggggagcaa tacttcaaaa gagaatcctt | 780 |
| tcctgttgc attggaagcc gtggttatct ctgttggctc catgggattg attatcagcc | 840 |
| ttctctgtgt gtatttctgg ctggaacgga cgatgccccg aattcccacc ctgaagaacc | 900 |
| tagaggatct tgttactgaa taccgggga acttttcggc ctggagtggt gtgtctaagg | 960 |
| gactggctga gagtctgcag ccagactaca gtgaacgact ctgcctcgtc agtgagattc | 1020 |
| ccccaaaagg aggggccctt ggggaggggc ctggggcctc ccatgcaac cagcatagcc | 1080 |
| cctactgggc cccccatgt tacacccctaa agcctgaaac ctgaacccca atcctctgac | 1140 |
| agaagaaccc cagggtcctg tagccctaag tggtactaac tttccttcat tcaacccacc | 1200 |
| tgcgtctcat actcacctca ccccactgtg gctgatttgg aattttgtgc cccatgtaa | 1260 |
| gcacccccttc atttggcatt ccccacttga gaattaccct tttgccccga acatgttttt | 1320 |
| cttctccctc agtctggccc ttccttttcg caggattctt cctccctccc tctttccctc | 1380 |
| ccttcctctt tccatctacc ctccgattgt tcctgaaccg atgagaaata aagtttctgt | 1440 |
| tgataatcat c | 1451 |

<210> SEQ ID NO 58
<211> LENGTH: 521
<212> TYPE: PRT
<213> ORGANISM: Homo sapiens

<400> SEQUENCE: 58

```
Met Gly Leu Gly Arg Cys Ile Trp Glu Gly Trp Thr Leu Glu Ser Glu
1               5                   10                  15

Ala Leu Arg Arg Asp Met Gly Thr Trp Leu Ala Cys Ile Cys Ile
            20                  25                  30

Cys Thr Cys Val Cys Leu Gly Val Ser Val Thr Gly Glu Gly Gln Gly
        35                  40                  45

Pro Arg Ser Arg Thr Phe Thr Cys Leu Thr Asn Asn Ile Leu Arg Ile
    50                  55                  60

Asp Cys His Trp Ser Ala Pro Glu Leu Gly Gln Gly Ser Ser Pro Trp
65                  70                  75                  80

Leu Leu Phe Thr Ser Asn Gln Ala Pro Gly Gly Thr His Lys Cys Ile
                85                  90                  95

Leu Arg Gly Ser Glu Cys Thr Val Val Leu Pro Pro Glu Ala Val Leu
            100                 105                 110

Val Pro Ser Asp Asn Phe Thr Ile Thr Phe His His Cys Met Ser Gly
            115                 120                 125

Arg Glu Gln Val Ser Leu Val Asp Pro Glu Tyr Leu Pro Arg Arg His
    130                 135                 140

Val Lys Leu Asp Pro Pro Ser Asp Leu Gln Ser Asn Ile Ser Ser Gly
145                 150                 155                 160

His Cys Ile Leu Thr Trp Ser Ile Ser Pro Ala Leu Glu Pro Met Thr
                165                 170                 175

Thr Leu Leu Ser Tyr Glu Leu Ala Phe Lys Lys Gln Glu Glu Ala Trp
            180                 185                 190

Glu Gln Ala Gln His Arg Asp His Ile Val Gly Val Thr Trp Leu Ile
        195                 200                 205

Leu Glu Ala Phe Glu Leu Asp Pro Gly Phe Ile His Glu Ala Arg Leu
    210                 215                 220

Arg Val Gln Met Ala Thr Leu Glu Asp Val Val Glu Glu Glu Arg
225                 230                 235                 240

Tyr Thr Gly Gln Trp Ser Glu Trp Ser Gln Pro Val Cys Phe Gln Ala
            245                 250                 255

Pro Gln Arg Gln Gly Pro Leu Ile Pro Pro Trp Gly Trp Pro Gly Asn
        260                 265                 270

Thr Leu Val Ala Val Ser Ile Phe Leu Leu Leu Thr Gly Pro Thr Tyr
    275                 280                 285

Leu Leu Phe Lys Leu Ser Pro Arg Val Lys Arg Ile Phe Tyr Gln Asn
    290                 295                 300

Val Pro Ser Pro Ala Met Phe Phe Gln Pro Leu Tyr Ser Val His Asn
305                 310                 315                 320

Gly Asn Phe Gln Thr Trp Met Gly Ala His Gly Ala Gly Val Leu Leu
            325                 330                 335

Ser Gln Asp Cys Ala Gly Thr Pro Gln Gly Ala Leu Glu Pro Cys Val
            340                 345                 350

Gln Glu Ala Thr Ala Leu Leu Thr Cys Gly Pro Ala Arg Pro Trp Lys
        355                 360                 365

Ser Val Ala Leu Glu Glu Glu Gln Glu Gly Pro Gly Thr Arg Leu Pro
    370                 375                 380

Gly Asn Leu Ser Ser Glu Asp Val Leu Pro Ala Gly Cys Thr Glu Trp
385                 390                 395                 400

Arg Val Gln Thr Leu Ala Tyr Leu Pro Gln Glu Asp Trp Ala Pro Thr
            405                 410                 415
```

-continued

```
Ser Leu Thr Arg Pro Ala Pro Asp Ser Glu Gly Ser Arg Ser Ser
            420                 425                 430

Ser Ser Ser Ser Ser Ser Asn Asn Asn Asn Tyr Cys Ala Leu Gly Cys
        435                 440                 445

Tyr Gly Gly Trp His Leu Ser Ala Leu Pro Gly Asn Thr Gln Ser Ser
    450                 455                 460

Gly Pro Ile Pro Ala Leu Ala Cys Gly Leu Ser Cys Asp His Gln Gly
465                 470                 475                 480

Leu Glu Thr Gln Gln Gly Val Ala Trp Val Leu Ala Gly His Cys Gln
                485                 490                 495

Arg Pro Gly Leu His Glu Asp Leu Gln Gly Met Leu Leu Pro Ser Val
            500                 505                 510

Leu Ser Lys Ala Arg Ser Trp Thr Phe
        515                 520

<210> SEQ ID NO 59
<211> LENGTH: 332
<212> TYPE: PRT
<213> ORGANISM: Homo sapiens

<400> SEQUENCE: 59

Met His Leu Gly Ser Asn Cys Cys Lys Asn Gly Gln Thr Leu Leu Gln
1               5                   10                  15

Arg Thr Cys His Gly Val Ser Cys Cys Gly Trp Trp Phe Gln Ala Ala
            20                  25                  30

Arg Ser Ile Leu Gly Lys Gly Pro Ser Ala Gln Ser Leu Ala Gly Trp
        35                  40                  45

Thr Leu Glu Ser Glu Ala Leu Arg Arg Asp Met Gly Thr Trp Leu Leu
    50                  55                  60

Ala Cys Ile Cys Ile Cys Thr Cys Val Cys Leu Gly Val Ser Val Thr
65                  70                  75                  80

Gly Glu Gly Gln Gly Pro Arg Ser Arg Thr Phe Thr Cys Leu Thr Asn
                85                  90                  95

Asn Ile Leu Arg Ile Asp Cys His Trp Ser Ala Pro Glu Leu Gly Gln
            100                 105                 110

Gly Ser Ser Pro Trp Leu Leu Phe Thr Arg Leu Leu Ala Ala His Ile
        115                 120                 125

Ser Ala Ser Cys Gly Ala Val Ser Ala Pro Ser Cys Cys His Leu Arg
    130                 135                 140

Gln Cys Ser Cys His Leu Thr Ile Ser Pro Ser Leu Ser Thr Thr Ala
145                 150                 155                 160

Cys Leu Gly Gly Ser Arg Ser Ala Trp Trp Thr Arg Ser Thr Cys Pro
                165                 170                 175

Gly Asp Thr Ser Asn Ile Ser Ser Gly His Cys Ile Leu Thr Trp Ser
            180                 185                 190

Ile Ser Pro Ala Leu Glu Pro Met Thr Thr Leu Leu Ser Tyr Glu Leu
        195                 200                 205

Ala Phe Lys Lys Gln Glu Glu Ala Trp Glu Gln Ala Gln His Arg Asp
    210                 215                 220

His Ile Val Gly Val Thr Trp Leu Ile Leu Glu Ala Phe Glu Leu Asp
225                 230                 235                 240

Pro Gly Phe Ile His Glu Ala Arg Leu Arg Val Gln Met Ala Thr Leu
                245                 250                 255

Glu Asp Asp Val Val Glu Glu Arg Tyr Thr Gly Gln Trp Ser Glu
            260                 265                 270
```

-continued

Trp Ser Gln Pro Val Cys Phe Gln Ala Pro Gln Arg Gln Gly Pro Leu
           275                 280                 285

Ile Pro Pro Trp Gly Trp Pro Gly Asn Thr Leu Val Ala Val Ser Ile
    290                 295                 300

Phe Leu Leu Leu Thr Gly Pro Thr Tyr Leu Leu Phe Lys Leu Ser Pro
305                 310                 315                 320

Arg Leu Gly Trp Gly Pro Thr Gly Pro Val Cys Cys
                325                 330

<210> SEQ ID NO 60
<211> LENGTH: 369
<212> TYPE: PRT
<213> ORGANISM: Homo sapiens

<400> SEQUENCE: 60

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser

```
                305                 310                 315                 320
Leu Gln Pro Asp Tyr Ser Glu Arg Leu Cys Leu Val Ser Glu Ile Pro
                    325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 61
<211> LENGTH: 17
<212> TYPE: PRT
<213> ORGANISM: Homo sapiens

<400> SEQUENCE: 61

Glu Ile Leu Pro Gly Ser Gly Thr Thr Asn Pro Asn Glu Lys Phe Lys
1               5                   10                  15
Gly

<210> SEQ ID NO 62
<211> LENGTH: 11
<212> TYPE: PRT
<213> ORGANISM: Homo sapiens

<400> SEQUENCE: 62

Lys Ala Ser Gln His Val Ile Thr His Val Thr
1               5                   10

<210> SEQ ID NO 63
<211> LENGTH: 7
<212> TYPE: PRT
<213> ORGANISM: Homo sapiens

<400> SEQUENCE: 63

Gly Thr Ser Tyr Ser Tyr Ser
1               5

<210> SEQ ID NO 64
<211> LENGTH: 9
<212> TYPE: PRT
<213> ORGANISM: Homo sapiens

<400> SEQUENCE: 64

Gln His Phe Tyr Asp Tyr Pro Leu Thr
1               5

<210> SEQ ID NO 65
<211> LENGTH: 9
<212> TYPE: PRT
<213> ORGANISM: Homo sapiens

<400> SEQUENCE: 65

Gln His Phe Tyr Glu Tyr Pro Leu Thr
1               5
```

ANTI-IL-9 ANTIBODY FORMULATIONS

This application claims the benefit of U.S. Provisional Application No. 60/561,845, filed Apr. 12, 2004, which is incorporated by reference herein in its entirety.

1. INTRODUCTION

The present invention relates to high concentration liquid formulations of antibodies or fragments thereof that immunospecifically bind to an IL-9 polypeptide, which formulations exhibit stability, low to undetectable levels of antibody fragmentation, low to undetectable levels of aggregation, and very little to no loss of the biological activities of the antibodies, even during long periods of storage. In particular, the present invention relates to liquid formulations of antibodies (including antibody fragments thereof) that immunospecifically bind to an IL-9 polypeptide, which formulations are substantially free of surfactants, sugars, sugar alcohols and/or amino acids other than histidine. The present invention also relates to methods of preventing, treating, managing or ameliorating symptoms associated with an inflammatory disorder (e.g., asthma), or a respiratory infection, utilizing high concentration liquid formulations of antibodies or (including antibody fragments thereof) that immunospecifically bind to an IL-9 polypeptide.

2. BACKGROUND OF THE INVENTION

Currently, many antibodies are provided as lyophilized formulations. Lyophilized formulations of antibodies have a number of limitations, including a prolonged process for lyophilization and resulting high cost for manufacturing. In addition, a lyophilized formulation has to be reconstituted aseptically and accurately by healthcare practitioners prior to administering to patients. The reconstitution step itself requires certain specific procedures: (1) a sterile diluent (i.e., water for intravenous administration and 5% dextrose in water for intramuscular administration) is added to the vial containing lyophilized antibody, slowly and aseptically, and the vial must be swirled very gently for 30 seconds to avoid foaming; (2) the reconstituted antibody may need to stand at room temperature for a minimum of 20 minutes until the solution clarifies; and (3) the reconstituted preparation must be administered within six (6) hours after the reconstitution. Such reconstitution procedure is cumbersome and the time limitation after the reconstitution can cause a great inconvenience in administering the formulation to patients, leading to significant waste, if not reconstituted properly or if the reconstituted dose is not used within six (6) hours and must be discarded.

Thus, a need exists for liquid formulations of antibodies, in particular, anti-IL-9 antibodies, at a concentration comparable to or higher than the reconstituted lyophilized formulations so that there is no need to reconstitute the formulation prior to administration. This allows healthcare practitioners much quicker and easier administration of antibodies to a patient.

Prior liquid antibody preparations have short shelf lives and may lose biological activity of the antibodies resulting from chemical and physical instabilities during the storage. Chemical instability may be caused by deamidation, racemization, hydrolysis, oxidation, beta elimination or disulfide exchange, and physical instability may be caused by antibody denaturation, aggregation, precipitation or adsorption. Among those, aggregation, deamidation and oxidation are known to be the most common causes of the antibody degradation (Wang et al., 1988, *J. of Parenteral Science & Technology* 42(Suppl):S4-S26; Cleland et al., 1993, *Critical Reviews in Therapeutic Drug Carrier Systems* 10(4):307-377). Thus, there is a need for a stable liquid formulation of antibodies, in particular, stable liquid anti-IL-9 antibodies.

3. SUMMARY OF INVENTION

The present invention is based, in part, on the development of high concentration liquid formulations of antibodies (including antibody fragments thereof) that immunospecifically bind to an IL-9 polypeptide, which formulations exhibit, in the absence of surfactants, sugars, sugar alcohols, and amino acids other than histidine (preferably, free of amino acids with pKa values of less than 5 and above 7), stability, low to undetectable levels of antibody fragmentation and/or aggregation, and very little to no loss of the biological activities of the antibodies (including antibody fragments thereof) during manufacture, preparation, transportation, and storage. The liquid formulations of the present invention facilitate the administration of antibodies (including antibody fragments thereof) that immunospecifically bind to an IL-9 polypeptide for the prevention, treatment, management and amelioration of diseases or disorders associated with or characterized by aberrant expression and/or activity of an IL-9 polypeptide, diseases or disorders associated with or characterized by aberrant expression and/or activity of the IL-9 receptor ("IL-9R") or one or more subunits thereof, autoimmune diseases, inflammatory diseases, proliferative diseases, or infections (preferably, respiratory infections), or one or more symptoms thereof (e.g., wheezing). Examples of autoimmune diseases include, but are not limited to: diabetes, Hashimoto's disease, autoimmune adrenal insufficiency, pure red cell anemia, multiple sclerosis, rheumatoid carditis, systemic lupus erythematosus, rheumatoid arthritis, chronic inflammation, Sjogren's syndrome polymyositis, dermatomyositis and scleroderma. Examples of inflammatory disorders include, but are not limited to, asthma and allergic reactions (Types I-IV). Examples of respiratory infections include, but are not limited to, infections of the upper and lower respiratory tracts, including viral infections, bacterial infections and/or fungal infections. Examples of viral infections include parainfluenza virus infection, influenza virus infection, metapenumovirus infection, or respiratory syncytial virus (RSV) infection. The antibody formulations of the invention may also be used to treat subjects that have or previously had bronchopulmonary dysplasia, congenital heart disease, cysteic fibrosis or acquired or congenital immunodeficiency. In particular, the liquid formulations of the present invention enable a healthcare professional to quickly administer a sterile dosage of an antibody (including antibody fragment thereof) that immunospecifically binds to an IL-9 polypeptide without having to accurately and sterilely reconstitute the antibody (including antibody fragment thereof) prior to administration.

The present invention provides liquid formulations substantially free of surfactants, said formulations preferably comprising histidine at a concentration in the range from about 5 to about 25 mM or higher (preferably at a concentration of 10 mM), NaCl at a concentration in the range from about 100 to about 200 mM (preferably at a concentration of 150 mM) and antibodies (including antibody fragments thereof) that immunospecifically bind to an IL-9 polypeptide at a concentration of 50 mg/ml or higher (although, in certain embodiments, the concentration of the antibody is lower than 50 mg/ml). The present invention also provides liquid formulations substantially free of surfactants, sugars, sugar alcohols, and/or amino acids (preferably, free of amino acids with a pKa value of less than 5 and above 7, particularly amino acids other than histidine), said formulations having a pH ranging from about 5.0 to about 7.0, preferably about pH 6.0, and comprising histidine, and a concentration of 50 mg/ml or higher of antibodies (including antibody fragments thereof) that immunospecifically bind to an IL-9 polypeptide. The liquid formulations of the present invention may further comprise one or more excipients such as a saccharide, an amino acid (e.g., arginine, lysine, and methionine) and a polyol. In a preferred embodiment, a liquid formulation of the present invention comprises histidine and a concentration of 95 mg/ml or higher of antibodies (including antibody fragments thereof) that immunospecifically bind to an IL-9 polypeptide, and said formulation is substantially free of surfactants, sugars, sugar alcohols, and/or amino acids other than histidine.

The present invention encompasses stable liquid formulations of 4D4, 4D4H2-1 D11, 4D4com-XF-9, 4D4com-2F9, 7F3, 71A10, 7F3 22D3, 7F3com-2H2, 7F3com-3H5, or 7F3com-3D4 (for amino acid sequences, see U.S. patent application Ser. No. 60/477,797, filed Jun. 10, 2003, and U.S. patent application Ser. No. 10/823,253 to be filed concurrently herewith on Apr. 12, 2004, entitled "Recombinant IL-9 Antibodies and Uses Thereof," both of which are incorporated by reference herein in their entireties) which exhibit low to undetectable levels of antibody aggregation and/or fragmentation with very little to no loss of the biological activities of 4D4, 4D4H2-1 D11, 4D4com-XF-9, 4D4com-2F9, 7F3, 71A10, 7F3 22D3, 7F3com-2H2, 7F3com-3H5, or 7F3com-3D4 during manufacture, preparation, transportation, and long periods of storage. The present invention also encompasses stable liquid formulations of antibodies that immunospecifically bind to an IL-9 polypeptide and have increased in vivo half-lives relative to known antibodies such as, e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4, said formulations exhibiting low to undetectable levels of antibody aggregation and/or fragmentation, and very little to no loss of the biological activities of the antibodies (including antibody fragments thereof). The present invention also encompasses stable liquid formulations of antibodies that immunospecifically bind to an IL-9 polypeptide, said antibodies (including antibody fragments thereof) comprising a variable heavy (VH) and/or variable light (VL) domain having the amino acid sequence of the VH and/or VL domain of 4D4, 4D4H2-1 D11, 4D4com-XF-9, 4D4com-2F9, 7F3, 71A10, 7F3 22D3, 7F3com-2H2, 7F3com-3H5, or 7F3com-3D4, said formulations exhibiting low to undetectable levels of antibody aggregation and/or fragmentation, and very little to no loss of the biological activities of the antibodies (including antibody fragments thereof). The present invention further encompasses stable liquid formulations of antibodies (including antibody fragments thereof) that immunospecifically bind to an IL-9 polypeptide, said antibodies (including antibody fragments thereof) comprising one or more VH complementarity determining regions (CDRs) and/or one or more VL CDRs having the amino acid sequence of one or more VH CDRs and/or VL CDRs listed in Table 1, infra, said formulations exhibiting low to undetectable levels of antibody aggregation and/or fragmentation, and very little to no loss of the biological activities of the antibodies (including antibody fragments thereof).

TABLE 1

Residues that are different between each amino acid sequence encoding the various CDRs appear in bold, underlined font.

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| 4D4 | SEQ. ID NO.: 7 | GYTFTGYWIE (SEQ. ID NO.: 1): | EILPGSGTTN YNEKFKG (SEQ. ID NO.: 2) | ADYYGSDYV KEDY (SEQ. ID NO.: 3) | SEQ. ID NO.: 8 | KASQHVGTH VT (SEQ. ID NO.: 4) | STSYRYS (SEQ. ID NO.: 5) | QHFYSYPLT (SEQ. ID NO.: 6) |
| 4D4 H2-1 D11 | SEQ. ID NO.: 9 | GYTFTGYWIE (SEQ. ID NO.: 1) | EWLPGSGTT NYNEKFKG (SEQ. ID NO.: 10) | ADYYGSDYV KFDY (SEQ. ID NO.: 3) | SEQ. ID NO.: 8 | KASQHVGTH VT (SEQ. ID NO.: 4) | STSYRYS (SEQ. ID NO.: 5) | QHFYSYPLT (SEQ. ID NO.: 6) |
| 4D4com-XF-9 | SEQ. ID NO.: 15 | GYTFTYYWIE (SEQ. ID NO.: 11) | EWLPGSGTT NYNEKFKG (SEQ. ID NO.: 10) | ADYYGSDHV KFDY (SEQ. ID NO.: 12) | SEQ. ID NO.: 16 | LASQHVGTH VT (SEQ. ID NO.: 13) | GTSYRYS (SEQ. ID NO.: 14) | QHFYDYPLT (SEQ. ID NO.: 6) |
| 4D4com-2F9 | SEQ. ID NO.: 17 | GYTFTGYWIE (SEQ. ID NO.: 1) | EWLPGSGTT NYNEKFKG (SEQ. ID NO.: 10) | ADYYGSDHV KFDY (SEQ. ID NO.: 12) | SEQ. ID NO.: 18 | KASQHVGTH VT (SEQ. ID NO.: 4) | GTSYRYS (SEQ. ID NO.: 14) | QHFYEYPLT (SEQ. ID NO.: 6) |
| 7F3 | SEQ. ID NO.: 21 | GGTFSGYWIE (SEQ. ID NO.: 19) | EILPGSGTTN YNEKFKG (SEQ. ID NO.: 2) | ADYYGSDYV KFDY (SEQ. ID NO.: 3) | SEQ. ID NO.: 22 | KASQHVGTH VT (SEQ. ID NO.: 4) | STSYRYS (SEQ. ID NO.: 5) | QQFYEYPLT (SEQ. ID NO.: 20) |
| 71A10 | SEQ. ID NO.: 23 | GGTFSGYWIE (SEQ. ID NO.: 19) | EILPGSGTTN PNEKFKG (SEQ. ID NO.: 2) | ADYYGSDYV KEDY (SEQ. ID NO.: 3) | SEQ. ID NO.: 24 | KASQHVGTH VT (SEQ. ID NO.: 4) | STSYRYS (SEQ. ID NO.: 5) | QQFYEYPLT (SEQ. ID NO.: 20) |

TABLE 1-continued

Residues that are different between each amino acid sequence encoding the various CDRs appear in bold, underlined font.

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| 7F3 22D3 | SEQ. ID NO.: 21 | GGTFSGYWIE (SEQ. ID NO.: 19) | EILPGSGTTNYNEKFKG (SEQ. ID NO.: 2) | ADYYGSDYVKFDY (SEQ. ID NO.: 3) | SEQ. ID NO.: 25 | KASQHVGTHVT (SEQ. ID NO.: 4) | GTSYRYS (SEQ. ID NO.: 14) | QQFYEYPLT (SEQ. ID NO.: 20) |
| 7F3com-2H2 | SEQ. ID NO.: 27 | GGTFSYYWIE (SEQ. ID NO.: 26) | EILPGSGTTNPNEKFKG (SEQ. ID NO.: 2) | ADYYGSDYKFDY (SEQ. ID NO.: 3) | SEQ. ID NO.: 28 | KASQHVITHVT (SEQ. ID NO.: 4) | GTSYSYS (SEQ. ID NO.: 14) | QQFYEYPLT (SEQ. ID NO.: 20) |
| 7F3com-3H5 | SEQ. ID NO.: 29 | GGTFSGYWIE (SEQ. ID NO.: 19) | EILPGSGTTNPNEKFKG (SEQ. ID NO.: 2) | ADYYGSDYKFDY (SEQ. ID NO.: 3) | SEQ. ID NO.: 30 | KASQHVGTHVT (SEQ. ID NO.: 4) | GTSYRYS (SEQ. ID NO.: 14) | QQFYEYPLT (SEQ. ID NO.: 20) |
| 7F3com-3D4 | SEQ. ID NO.: 31 | GGTFSYYWIE (SEQ. ID NO.: 26) | EILPGSGTTNPNEKFKG (SEQ. ID NO.: 2) | ADYYGSDYVKFDY (SEQ. ID NO.: 3) | SEQ. ID NO.: 32 | KASQHVITHVT (SEQ. ID NO.: 4) | GTSYRYS (SEQ. ID NO.: 14) | QQFYEYPLT (SEQ. ID NO.: 20) |

The present invention encompasses liquid formulations of antibodies (including antibody fragments thereof) that immunospecifically bind to an IL-9 polypeptide, said formulations having stability at 38-42° C. as assessed by high performance size exclusion chromatography (HPSEC). The liquid formulations of the present invention exhibit stability, as assessed by HPSEC, at temperature ranges of 38-42° C. for at least 15 days but no more than 25 days; at temperature ranges of 20-24° C. for at least 6 months but not more than 1.5 years; and at temperature ranges of 2-8° C. (especially at 4° C.) for at least 1.5 years, at least 2 years, at least 2.5 years, or at least 3 years. The present invention also encompasses liquid formulations of antibodies (including antibody fragments thereof) that immunospecifically bind to an IL-9 polypeptide, said formulations having low to undetectable levels of antibody aggregation as measured by HPSEC. In a preferred embodiment, the liquid formulations of the present invention exhibit stability at 38-42° C. for at least 15 days and exhibit low to undetectable levels of antibody aggregation as measured by HPSEC and, further, exhibit very little to no loss of the biological activity of the antibodies (including antibody fragments thereof) of the formulation compared to the reference antibodies as measured by antibody binding assays such as, e.g., ELISAs.

The present invention provides methods for preparing liquid formulations of an antibody (including antibody fragment thereof) that immunospecifically binds to an IL-9 polypeptide, said methods comprising concentrating a fraction containing the purified antibody to a final antibody concentration ranging from about 1 mg/ml, about 5 mg/ml, about 10 mg/ml, about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 150 mg/ml, about 175 mg/ml, or about 200 mg/ml using a semipermeable membrane with an appropriate molecular weight (MW) cutoff (e.g., a 30 kD cutoff for whole antibody molecules and F(ab')$_2$ fragments; and a 10 kD cutoff for antibody fragments such as Fab fragments) and diafiltering the concentrated antibody fraction into the formulation buffer using the same membrane. The formulation buffer of the present invention comprises histidine at a concentration ranging from about 1 mM to about 100 mM, preferably from about 5 mM to about 50 mM, more preferably about 10 mM to about 25 mM. The formulation buffer of the present invention further comprises NaCl at a concentration ranging from about 10 mM to about 200 mM, from about 50 to about 200 mM, from about 100 to about 150 mM, more preferably about 150 mM. The pH of the formulation may range from about 5.0 to about 7.0, preferably 5.5 to about 6.5, more preferably about 5.8 to about 6.2, and most preferably about 6.0. To obtain an appropriate pH for a particular antibody, it is preferable that histidine (and glycine, if added) is first dissolved in water to obtain a buffer solution with higher pH than the desired pH and then the pH is brought down to the desired level by the addition of HCl. This way, the formation of inorganic salts (e.g., the formation of NaCl when, e.g., histidine hydrochloride is used as the source of histidine and the pH is raised to the desired level by the addition of NaOH) can be avoided.

The liquid formulations of the present invention may be sterilized by sterile filtration using a 0.2μ filter. Sterilized liquid formulations of the present invention may be administered to a subject for the prevention, treatment, management and amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. The liquid formulations of the present invention may be administered in combination with other therapies (e.g., prophylactic or therapeutic agents other than antibodies that immunospecifically bind to an IL-9 polypeptide, such as anti-inflammatory agents, immunomodulatory agents and anti-cancer agents).

The present invention also provides kits comprising the liquid formulations of antibodies (including antibody fragments thereof) that immunospecifically bind to an IL-9 polypeptide for use by, e.g., a healthcare professional. The present invention further provides methods of preventing, treating, managing or ameliorating a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms of any of the foregoing. The liquid formulations of the invention can be administered parenterally (e.g., intradermally, intramuscularly, intraperitoneally, intravenously and subcutaneously) orally, or intranasally to a subject to prevent, treat, manage or ameliorate a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms of any of the foregoing. The liquid formulations of the present invention can also be used to diagnose, detect or monitor disease or disorder associated with or characterized by aberrant expression and/or activity of an IL-9 polypeptide, diseases or disorders associated with or characterized by aberrant expression and/or activity of the IL-9R or one or more subunits thereof, autoimmune diseases, inflammatory diseases, proliferative diseases, or infections (preferably, respiratory infections), or one or more symptoms thereof.

3.1. Terminology

All liquid formulations of antibodies and/or antibody fragments that immunospecifically bind to an IL-9 polypeptide described above are herein collectively referred to as "liquid formulations of the invention," "antibody liquid formulations of the invention," "antibody formulations of the invention," "liquid formulations of antibodies or fragments thereof that immunospecifically bind to an IL-9 polypeptide," or "liquid formulations of anti-IL-9 antibodies."

As used herein the term "aberrant" refers to a deviation from the norm, e.g., the average healthy subject and/or a population of average healthy subjects. The term "aberrant expression," as used herein, refers to abnormal expression of a gene product (e.g., RNA, protein, polypeptide, or peptide) by a cell or subject relative to a normal, healthy cell or subject and/or a population of normal, healthy cells or subjects. Such aberrant expression may be the result of the amplification of the gene. In a specific embodiment, the term "aberrant expression" refers to abnormal expression of IL-9 and/or an IL-9R or subunit thereof by a cell or subject relative to the expression of the gene product by a normal, healthy cell or subject and/or a population of normal, healthy cells or subjects and encompasses the expression of an IL-9 and/or an IL-9R or subunit thereof gene product at an unusual location within the cell or subject, the expression of an IL-9 and/or an IL-9R or subunit thereof gene product at an altered level in the cell or subject, the expression of a mutated IL-9 and/or an IL-9R or subunit thereof gene product, or a combination thereof. The term "aberrant activity," as used herein, refers to an altered level of a gene product, the increase of an activity by a gene product, or the loss of an activity of a gene product in a cell or subject relative to a normal, healthy cell or subject and/or a population of normal healthy cells or subjects. In specific embodiments, the term "aberrant activity" refers to an IL-9 and/or IL-9R or subunit thereof activity that deviates from that normally found in a healthy cell or subject and/or a population of normal, healthy cells or subjects (e.g., an increase in IL-9's affinity for the IL-9R). Examples of IL-9 activities include, but are not limited to, the phosphorylation of the IL-9R, the activation of Jak3, the activation of MEK, the activation of STAT-1, and the activation of STAT-3.

As used herein, the term "about" in the context of a given numerate value or range refers to a value or range that is within 20%, preferably within 10%, and more preferably within 5% of the given value or range.

As used herein, the term "analog" in the context of a proteinaceous agent (e.g., proteins, polypeptides, peptides, and antibodies) refers to a proteinaceous agent that possesses a similar or identical functions as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possesses a similar or identical function as a first organic or inorganic molecule and is structurally similar to the first organic or inorganic molecule.

As used herein, the terms "antagonist" and "antagonists" refer to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of another molecule. In various embodiments, an antagonist reduces the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

The term "antibody fragment" as used herein refers to a fragment of an antibody that immunospecifically binds to an IL-9 polypeptide. Antibody fragments may be generated by any technique known to one of skill in the art. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain. Antibody fragments can be also produced by recombinant DNA technologies. Antibody fragments may be one or more complementarity determining regions (CDRs) of antibodies, or one or more antigen-binding fragments of an antibody.

As used herein, the terms "antibody" and "antibodies" refer to monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

The term "antibodies or antibody fragments that immunospecifically bind to an IL-9 polypeptide" and analogous terms as used herein refer to antibodies or antibody fragments that specifically bind to an IL-9 polypeptide or a fragment of an IL-9 polypeptide and do not specifically bind to other polypeptides. Preferably, antibodies or antibody fragments of the invention have a higher affinity to an IL-9 polypeptide or a fragment of an IL-9 polypeptide when compared to the affinity to other polypeptides or fragments of other polypeptides. The affinity of an antibody is a measure of its bonding with a specific antigen at a single antigen-antibody site, and is in essence the summation of all the attractive and repulsive forces present in the interaction between the antigen-binding site of an antibody and a particular epitope. The affinity of an antibody to a particular antigen (e.g., an IL-9 polypeptide or fragment of an IL-9 polypeptide) may be expressed by the equilibrium constant K, defined by the equation K=[Ag Ab]/[Ag][Ab], which is the affinity of the antibody-combining site where [Ag] is the concentration of free antigen, [Ab] is the concentration of free antibody and [Ag Ab] is the concentration of the antigen-antibody complex. Where the antigen and antibody react strongly together there will be very little free antigen or free antibody, and hence the equilibrium constant or affinity of the antibody will be high. High affinity antibodies are found where there is a good fit between the antigen and the antibody (for a discussion regarding antibody affinity, see Sigal and Ron ed., 1994, Immunology and Inflammation—Basic Mechanisms and Clinical Consequences, McGraw-Hill, Inc. New York at pages 56-57; and Seymour et al., 1995, Immunology—An Introduction for the Health Sciences, McGraw-Hill Book Company, Australia at pages 31-32). Preferably, antibodies or antibody fragments that immunospecifically bind to an IL-9 polypeptide or fragment thereof do not cross-react with other antigens. That is, antibodies or antibody fragments of the invention immunospecifically bind to an IL-9 polypeptide or fragment thereof with a higher energy than to other polypeptides or fragments of other polypeptides (see, e.g., Paul ed., 1989, Fundamental Immunology, $2^{nd}$ ed., Raven Press, New York at pages 332-336 for a discussion regarding antibody specificity). Antibodies or antibody fragments that immunospecifically bind to an IL-9 polypeptide can be identified, for example, by immunoassays such as radioimmunoassays (RIAs), enzyme-linked immunosorbent assays (ELISAs), and BIAcore assays (described in Section 5.7, infra) or other techniques known to those of skill in the art (see, e.g., Seymour et al., 1995, Immunology—An Introduction for the Health Sciences, McGraw-Hill Book Company, Australia at pages 33-41 for a discussion of various assays to determine antibody-antigen interactions in vivo). Preferably antibodies or antibody fragments that immunospecifically bind to an IL-9 polypeptide or fragment thereof only antagonize an IL-9 polypeptide and do not significantly antagonize other activities.

As used herein, the term "control IgG antibody" refers to an IgG antibody or other "control antibody" that does not immunospecifically bind to an IL-9 polypeptide and preferably does not cross-react with an IL-9 polypeptide.

As used herein, the term "cytokine receptor modulator" refers to an agent that modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins, and antibodies that immunospecifically bind to a cytokine receptor or a fragment of the antibody or cytokine receptor. Further, examples of cytokine receptor modulators include, but are not limited to, peptides, polypeptides (e.g., soluble cytokine receptors), fusion proteins and antibodies that immunospecifically binds to a cytokine or a fragment thereof.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl, nitryl, or amine group. An organic molecule may also be esterified, alkylated and/or phosphorylated.

As used herein, the terms "disorder" and "disease" are used interchangeably to refer to a condition in a subject in which the subject differs from a healthy, unaffected subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Certain conditions may be characterized as more than one disorder. For example, certain conditions may be characterized as both autoimmune and inflammatory disorders.

As used herein, the term "effective amount" refers to the amount of a therapy (e.g., a prophylactic or therapeutic agent) which is sufficient to reduce and/or ameliorate the severity and/or duration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, prevent the advancement of said disease or disorder, cause regression of said disease or disorder, prevent the recurrence, development, or onset of one or more symptoms associated with said disease or disorder, or enhance or improve the prophylactic or therapeutic effect(s) of another therapy (e.g., prophylactic or therapeutic agent).

As used herein, the term "epitopes" refers to fragments of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and decreased viscosity. Examples of excipients include, but are not limited to, proteins (e.g., serum albumin), amino acids (e.g., aspartic acid, glutamic acid, lysine, arginine, glycine and histidine), surfactants (e.g., SDS, polysorbate and non-ionic surfactant), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18$^{th}$ ed., Mack Publishing Co., Easton, Pa.), which is incorporated herein in its entirety.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a second, different polypeptide or protein. In another embodiment, a fragment of a protein or polypeptide retains at least one function of the protein or polypeptide. In another embodiment, a fragment of a polypeptide or protein retains at least two, three, four, or five functions of the polypeptide or protein. Preferably, a fragment of an antibody that immunospecifically binds to an IL-9 polypeptide retains the ability to immunospecifically bind to an IL-9 polypeptide. A "functional fragment" is a fragment that retains at least one function of the protein or polypeptide.

As used herein, the term "fusion protein" refers to a polypeptide or protein that comprises an amino acid sequence of a first polypeptide or protein or fragment, analog or derivative thereof, and an amino acid sequence of a heterologous polypeptide or protein (i.e., a second polypeptide or protein or fragment, analog or derivative thereof different than the first polypeptide or protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent. For example, two different proteins, polypeptides, or peptides with immunomodulatory activity may be fused together to form a fusion protein. In a preferred embodiment, fusion proteins retain or have improved activity relative to the activity of the original polypeptide or protein prior to being fused to a heterologous protein, polypeptide, or peptide.

The terms "high concentration" and "concentrated antibody" as used herein refer to a concentration of 50 mg/ml or higher, preferably 95 mg/ml or higher of an antibody (including antibody fragment thereof) that immunospecifically binds to an IL-9 polypeptide, in an antibody formulation.

As used herein, the term "host cell" includes a particular subject cell transfected or transformed with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the terms "human child" or "child" or variations thereof refer to a human between 24 months of age and 18 years of age.

As used herein, the terms "elderly human," "elderly," or variations thereof refer to a human 65 years old or older, preferably 70 years old or older.

As used herein, the terms "human infant" or "infant" or variations thereof refer to a human less than 24 months of age, preferably less than 12 months, less than 6 months, less than 3 months, less than 2 months, or less than 1 month of age.

As used herein, the terms "human infant born prematurely," "preterm infant," or "premature infant," or variations thereof refer to a human born at less than 40 weeks of gestational age, preferably less than 35 weeks gestational age, who is less than 6 months old, preferably less than 3 months old, more preferably less than 2 months old, and most preferably less than 1 month old.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95% or 98%) identical to each other typically remain hybridized to each other. Such stringent conditions are known to those skilled in the art and can be found, for example, in *Current Protocols in Molecular Biology*, John Wiley & Sons, N.Y. (1989 and updates), 6.3.1-6.3.6.

Generally, stringent conditions are selected to be about 5 to 110°C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0M sodium ion concentration (or other salts) at pH 7.0 to 8.3 and the temperature is at least about 30° C. for short probes (for example, 10 to 50 nucleotides) and at least 60° C. for long probes (for example, greater than 50 nucleotides). Stringent conditions may also be achieved with the addition of destabilizing agents, for example, formamide. For selective or specific hybridization, a positive signal is at least two times background, preferably 10 times background hybridization.

In one, non-limiting example, stringent hybridization conditions are hybridization at 6× sodium chloride/sodium citrate (SSC) at about 45° C., followed by one or more washes in 0.1×SSC, 0.2% SDS at about 68° C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.).

As used herein, the term "IL-9 polypeptide" refers to IL-9, an analog, derivative or a fragment thereof, including mature and immature forms of IL-9 (see, Van Snick et al., 1989, J. Exp. Med. 169:363-68 and Yang et al., 1989, Blood 74:1880-84, which are both incorporated by reference herein in their entireties), or a fusion protein comprising IL-9, an analog, derivative or a fragment thereof. The IL-9 polypeptide may be from any species. The nucleotide and/or amino acid sequences of IL-9 polypeptides can be found in the literature or public databases, or the nucleotide and/or amino acid sequences can be determined using cloning and sequencing techniques known to one of skill in the art. For example, the nucleotide sequence of human IL-9 can be found in the GenBank database (see, e.g., Accession No. NM_000590; FIG. 12). The amino acid sequence of human IL-9 can be found in the GenBank database (see, e.g., Accession Nos. A60480, NP_000584 and AAC17735; FIG. 13) and in U.S. Provisional Application No. 60/371,683, entitled, "Recombinant Anti-Interleukin-9 Antibodies," filed Apr. 12, 2002 (the amino acid sequence of human IL-9 on page 15 is specifically incorporated herein by reference). In a preferred embodiment, an IL-9 polypeptide is human IL-9, an analog, derivative or a fragment thereof.

As used herein, the terms "IL-9 receptor" and "IL-9R" refer to an IL-9 receptor or an analog, derivative, or fragment thereof, or a fusion protein comprising an IL-9 receptor, an analog, derivative, or a fragment thereof. As used herein, the terms "one or more subunits" and "a subunit" in the context of an IL-9R refer to the IL-9R ligand-specific alpha subunit ("IL-9Rα") and/or common $\gamma_c$ chain (also present in IL-2R, IL-4R, IL-7R, and IL-15R complexes) of the functional IL-9R or an analog, derivative, or fragment thereof. In a preferred embodiment, a functional IL-9R mediates a proliferative response in T cells treated with IL-9 as determined by any cell proliferation assay known to those skilled in the art (e.g., a [$^3$H]-thymidine incorporation assay or a hexosamimidase assay) (see, e.g., Renauld et al., 1992, Proc. Natl. Acad. Sci. USA, 89:5690-94 and Bauer et al., 1998, J. Biol. Chem. 273:9255-60, which are both incorporated by reference herein in their entireties). Preferebly, treating a T cell line expressing a functional IL-9R (e.g., TS1 RA3 cells (R&D Systems) expressing both human and murine IL-9Rα) with IL-9, results in a dose-dependent increase in T cell proliferation, as measured by any cell proliferation assay known to those skilled in the art (see, Renauld et al., 1992, Proc. Natl. Acad. Sci. USA, 89:5690-94 and Bauer et al., 1998, J. Biol.

Chem. 273:9255-60). In another preferred embodiment, a functional IL-9R, comprising the $\gamma_c$ and IL-9Rα chains, initiates a signaling cascade through the Janus kinases JAK1 and JAK3, thereby activating homo- and heterodimers of the signal transducer and activator transcription (STAT) factors STAT-1, STAT-3 and STAT-5 (see, Bauer et al., 1998, J. Biol. Chem. 273:9255-60). In another preferred embodiment, a functional IL-9R may prevent apoptosis through a mechanism involving STAT-3 and STAT-5, as determined by apoptosis assays known to those skilled in the art (see, Bauer et al., 1998, J. Biol. Chem. 273:9255-60). The IL-9R or one or more subunits thereof may be from any species. The nucleotide and/or amino acid sequences of the IL-9R and the subunits thereof can be found in the literature or in public databases, or the nucleotide and/or amino acid sequences can be determined using cloning and sequencing techniques known to one of skill in the art. For example, the nucleotide sequence of human IL-9R can be found in the GenBank database (see, e.g., Accession Nos. NM_002186, NM_176786, and NM_000206; FIG. 14). The amino acid sequence of human IL-9R can be found in the GenBank database (see, e.g., Accession Nos. NP_002177; NP_789743, and NP_000197; FIG. 15) and in U.S. Provisional Application No. 60/371,683, entitled, "Recombinant Anti-Interleukin-9 Antibodies," filed Apr. 12, 2002 (the amino acid sequence of human IL-9R on page 16 is herein specifically incorporated by reference). In a preferred embodiment, an IL-9R or one or more subunits thereof is a human IL-9R or one or more subunits thereof, an analog, derivative, or a fragment thereof.

As used herein, the term "immunomodulatory agent" and variations thereof including, but not limited to, immunomodulatory agents, immunomodulants or immunomodulatory drugs, refer to an agent that modulates a host's immune system. In a specific embodiment, an immunomodulatory agent is an agent that shifts one aspect of a subject's immune response. In certain embodiments, an immunomodulatory agent is an agent that inhibits or reduces a subject's immune system (i.e., an immunosuppressant agent). In certain other embodiments, an immunomodulatory agent is an agent that activates or increases a subject's immune system (i.e., an immunostimulatory agent). In accordance with the invention, an immunomodulatory agent used in the combination therapies of the invention does not include an antibody of the invention. Immunomodulatory agents include, but are not limited to, small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. The term "in combination" as used herein refers to the use of more than one therapies (e.g., prophylactic and/or therapeutic agents). The use of the term "in combination" does not restrict the order in which therapies (e.g., prophylactic and/or therapeutic agents) are administered to a subject with a disease or disorder (e.g., a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof). A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder (e.g., disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof).

As used herein, the term "immunospecifically binds to an antigen" and analogous terms refer to peptides, polypeptides, proteins, fusion proteins and antibodies (including antibody fragments thereof) that specifically bind to an antigen or a fragment and do not specifically bind to other antigens. A peptide, polypeptide, protein, or antibody that immunospecifically binds to an antigen may bind to other peptides, polypeptides, or proteins with lower affinity as determined by, e.g., immunoassays, BIAcore, or other assays known in the art. Antibodies (including antibody fragments thereof) that immunospecifically bind to an antigen may be cross-reactive with related antigens. Preferably, antibodies (including antibody fragments thereof) that immunospecifically bind to an antigen do not significantly cross-react with other antigens (i.e., is not detectable in routine immunological assays). An antibody binds specifically to an antigen when it binds to the antigen with higher affinity than to any cross-reactive antigen as determined using experimental techniques, such as radioimmunoassays (RIAs) and enzyme-linked immunosorbent assays (ELISAs). See, e.g., Paul, ed., 1989, Fundamental Immunology, 2nd ed., Raven Press, New York at pages 332-336 for a discussion regarding antibody specificity.

As used herein, the term "in combination" refers to the use of more than one therapy (e.g., more than one prophylactic agent and/or therapeutic agent). The use of the term "in combination" does not restrict the order in which therapies (e.g., prophylactic and/or therapeutic agents) are administered to a subject with a respiratory condition. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject with a respiratory condition.

The term "inorganic salt" as used herein refers to any compounds containing no carbon that result from replacement of part or all of the acid hydrogen or an acid by a metal or a group acting like a metal and are often used as tonicity adjusting compounds in pharmaceutical compositions and preparations of biological materials. The most common inorganic salts are NaCl, KCl, $NaH_2PO_4$, etc.

As used herein, the term "isolated" in the context of an organic or inorganic molecule (whether it be a small or large molecule), other than a proteinaceous agent or nucleic acid molecule, refers to an organic or inorganic molecule substantially free of a different organic or inorganic molecule. Preferably, an organic or inorganic molecule is 60%, 65%, 70%, 75%, 80%, 85%, 90%, 95%, or 99% free of a second, different organic or inorganic molecule. In a preferred embodiment, an organic and/or inorganic molecule is isolated.

As used herein, the term "isolated" in the context of a proteinaceous agent (e.g., a peptide, polypeptide, fusion protein, or antibody) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also preferably substantially free of culture medium, i.e., culture medium represents less than about 20%, 10%, or 5% of the volume of the proteinaceous agent preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In a specific embodiment, proteinaceous agents disclosed herein are isolated. In a preferred embodiment, an antibody of the invention is isolated. In a specific embodiment, an "isolated" antibody is purified by a multi-step purification process that comprises three chromatography steps (cation exchange, protein A and anion exchange), a nanofiltration step, and a low pH treatment step (for a detailed description, see Section 6, infra).

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, nucleic acid molecules are isolated; however, "isolated" excludes members of a population of a library of clones such as a cDNA library.

The phrase "low to undetectable levels of aggregation" as used herein refers to samples containing no more than 5%, no more than 4%, no more than 3%, no more than 2%, no more than 1% and most preferably no more than 0.5% aggregation by weight of protein as measured by high performance size exclusion chromatography (HPSEC).

The term "low to undetectable levels of fragmentation" as used herein refers to samples containing equal to or more than 80%, 85%, 90%, 95%, 98% or 99% of the total protein, for example, in a single peak as determined by HPSEC, or in two peaks (e.g., heavy- and light-chains) (or as many peaks as there are subunits) by reduced Capillary Gel Electrophoresis (rCGE), representing the non-degraded antibody or a non-degraded fragment thereof, and containing no other single peaks having more than 5%, more than 4%, more than 3%, more than 2%, more than 1%, or more than 0.5% of the total protein in each. The term "reduced Capillary Gel Electrophoresis" as used herein refers to capillary gel electrophoresis under reducing conditions sufficient to reduce disulfide bonds in an antibody.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, the term "mast cell modulator" refers to an agent which modulates the activation of a mast cell, mast cell degranulation, and/or expression of a particular protein such as a cytokine. Such an agent may directly or indirectly modulate the activation of a mast cell, degranulation of the mast cell, and/or the expression of a particular protein such as a cytokine. Non-limiting examples of mast cell modulators include, but are not limited to, small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides, or peptides), fusion proteins, antibodies, synthetic or natural inorganic molecules, synthetic or natural organic molecule, or mimetic agents which inhibit and/or reduce the expression, function, and/or activity of a stem cell factor, a mast cell protease, a cytokine (such as IL-3, IL-4, and IL-9), a cytokine receptor (such as IL-3R, IL-4R, and IL-9R), and a stem cell receptor. Other non-limiting examples of mast cell modulators include, but are not limited to small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides, or peptides), fusion proteins, antibodies, synthetic or natural inorganic molecules, synthetic or natural organic molecule, or mimetic agents which inhibit and/or reduce the expression, function and/or activity of IgE. In certain embodiments, a mast cell modulator is an agent that prevents or reduces the activation of additional mast cells following degranulation of mast cells. In other embodiments, a mast cell modulator is an agent that inhibits or reduces mast cell degranulation.

As used herein, the terms "non-responsive" and refractory" describe patients treated with a currently available therapy (e.g., prophylactic or therapeutic agent) for a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof which is not clinically adequate to relieve one or more symptoms associated with the disorder. Typically, such patients suffer from severe, persistently active disease and require additional therapy to ameliorate the symptoms associated with the disorder.

The phrase "pharmaceutically acceptable" as used herein means approved by a regulatory agency of the Federal or a state government, or listed in the U.S. Pharmacopeia, European Pharmacopia or other generally recognized pharmacopeia for use in animals, and more particularly in humans.

The term "polyol" as used herein refers to a sugar that contains many —OH groups compared to a normal saccharide.

As used herein, the terms "prevent," "preventing," and "prevention" refer to the inhibition of the development or onset of disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, or the prevention of the recurrence, onset, or development of one or more symptoms of a respiratory condition in a subject resulting from the administration of a therapy (e.g., a prophylactic or therapeutic agent), or the administration of a combination of therapies (e.g., a combination of prophylactic or therapeutic agents).

As used herein, the terms "prophylactic agent" and "prophylactic agents" refer to any agent(s) which can be used in the prevention of the onset, recurrence or development of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In certain embodiments, the term "prophylactic agent" refers to an antibody that immunospecifically binds to an IL-9 polypeptide. In certain other embodiments, the term "prophylactic agent" refers to an agent other than an antibody that immunospecifically binds to an IL-9 polypeptide. Preferably, a prophylactic agent is an agent which is known to be useful to or has been or is currently being used to the prevent or impede the onset, development, progression and/or severity of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. Prophylactic agents may be characterized as different agents based upon one or more effects that the agents have in vitro and/or in vivo. For example, a mast cell modulator may also be characterized as an immunomodulatory agent.

As used herein, the term "prophylactically effective amount" refers to the amount of a therapy (e.g., prophylactic agent) which is sufficient to result in the prevention of the development, recurrence, or onset of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, or to enhance or improve the prophylactic effect(s) of another therapy (e.g., a prophylactic agent).

As used herein, a "prophylactic protocol" refers to a regimen for dosing and timing the administration of one or more therapies (e.g., one or more prophylactic agents) that has a prophylactic effect.

A used herein, a "protocol" includes dosing schedules and dosing regimens. The protocols herein are methods of use and include prophylactic and therapeutic protocols.

The term "saccharide" as used herein refers to a class of molecules that are derivatives of polyhydric alcohols. Saccharides are commonly referred to as carbohydrates and may contain different amounts of sugar (saccharide) units, e.g., monosaccharides, disaccharides and polysaccharides.

As used herein, the phrase "side effects" encompasses unwanted and adverse effects of a prophylactic or therapeutic agent. Side effects are always unwanted, but unwanted effects are not necessarily adverse. An adverse effect from a therapy (e.g., a prophylactic or therapeutic agent) might be harmful, uncomfortable, or risky.

Side effects from administration of REMICADE™ include, but are not limited to, risk of serious infection and hypersensitivity reactions. Other side effects range from non-specific symptoms such as fever or chills, pruritus or urticaria, and cardiopulmonary reactions such as chest pain, hypotension, hypertension or dyspnea, to effects such as myalgia and/or arthralgia, rash, facial, hand or lip edema, dysphagia, sore throat, and headache. Yet other side effects include, but are not limited to, abdominal hernia, splenic infarction, splenomegaly, dizziness, upper motor neuron lesions, lupus erythematosus syndrome, rheumatoid nodules, ceruminosis, abdominal pain, diarrhea, gastric ulcers, intestinal obstruction, intestinal perforation, intestinal stenosis, nausea, pancreatitis, vomiting, back pain, bone fracture, tendon disorder or injury, cardiac failure, myocardial ischemia, lymphoma, thrombocytopenia, cellulitis, anxiety, confusion, delirium, depression, somnolence, suicide attempts, anemia, abscess, bacterial infections, and sepsis. Side effects from administration of ENBREL™ include, but are not limited to, risk of serious infection and sepsis, including fatalities. Adverse side effects range from serious infections such as pyelonephritis, bronchitis, septic arthritis, abdominal abscess, cellulitis, osteomyelitis, wound infection, pneumonia, foot abscess, leg ulcer, diarrhea, sinusitis, sepsis, headache, nausea, rhinitis, dizziness, pharyngitis, cough, asthenia, abdominal pain, rash, peripheral edema, respirator disorder, dyspepsia, sinusitis, vomiting, mouth ulcer, alopecia, and pheumonitis to other less frequent adverse effects such as heart failure, myocardial infarction, myocardia ischemia, cerebral ischemia, hyertension, hypotension, cholcystitis, pancreatitis, gastrointestinal hemorrhage, bursitis, depression, dyspnea, deep vein thrombosis, pulmonary embolism, membranous glomerulonephropathy, polymyositis, and thrombophlebitis. The side effects resulting from administration of methotrexate include, but are not limited to, serious toxic reactions, which can be fatal, such as unexpectedly severe bone marrow suppression, gastrointestinal toxicity, hepatotoxicity, fibrosis and cirrhosis after prolonged use, lung diseases, diarrhea and ulcerative stomatitis, malignant lymphomas and occasionally fatal severe skin reactions.

Side effects from chemotherapy include, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Other side effects include gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* (56th ed., 2002 and 57th ed., 2003).

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such agents.

The terms "stability" and "stable" as used herein in the context of a liquid formulation comprising an antibody (including antibody fragment thereof) that immunospecifically binds to an IL-9 polypeptide refer to the resistance of the antibody or (including antibody fragment thereof) in the formulation to degradation or fragmentation under given manufacture, preparation, transportation and storage conditions. The "stable" formulations of the invention retain biological activity under given manufacture, preparation, transportation and storage conditions. The stability of said antibody (including antibody fragment thereof) can be assessed by degrees of degradation or fragmentation, as measured by HPSEC, compared to a reference formulation. For example, a reference formulation may be a reference standard frozen at −70° C. consisting of 10 mg/ml of an antibody (including antibody fragment thereof) (e.g., 4D4, 4D4 H2-1 D11, 4D4com-XF-9, 4D4com-2F9, 7F3, 71A10, 7F3 22D3, 7F3com-2H2, 7F3com-3H5, or 7F3com-3D4) in histidine-HCl buffer, pH 6.0 that contains 150 mM NaCl, which reference formulation regularly gives a single monomer peak ($\geq$97% area) by HPSEC. Alternatively, a reference formulation may be a reference standard frozen at −70° C. consisting of 10 mg/ml of an antibody (including antibody fragment thereof) (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4) in histidine-HCl buffer at pH 6.0, which reference formulation regularly gives a single monomer peak ($\geq$97% area) by HPSEC. The overall stability of a formulation comprising an antibody (including antibody fragment thereof) that immunospecifically binds to an IL-9 polypeptide can be assessed by various immunological assays including, for example, ELISA and radioimmunoassay using isolated an IL-9 polypeptide molecules or cells expressing the same.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgus monkey, chimpanzee, and a human), and more preferably a human. In a certain embodiment, the subject is a mammal, preferably a human, with a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In another embodiment, the subject is a farm animal (e.g., a horse, pig, or cow) or a pet (e.g., a dog or cat) with a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In another embodiment, the subject is a mammal, preferably a human, at risk of developing a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof (e.g., an immunocompromised or immunosuppressed mammal). In another embodiment, the subject is not an immunocompromised or immunosuppressed mammal, preferably a human. In another embodiment, the subject is a mammal, preferably a human, with a lymphocyte count that is not under approximately 500 cells/mm$^3$. In another embodiment, the subject is a human infant or a human infant born prematurely. In another embodiment, the subject is a human child or a human adult. In another embodiment, the subject is a human child with bronchopulmonary dysplasia, congenital heart diseases, or cystic fibrosis. In another embodiment, the subject is an elderly human. In yet another embodiment, the subject is a human in an institution or group home, such as, but not limited to, a nursing home.

The term "substantially free of surfactant" as used herein refers to a formulation of an antibody (including antibody fragment thereof) that immunospecifically binds to an IL-9 polypeptide, said formulation containing less than 0.0005%, less than 0.0003%, or less than 0.0001% of surfactants.

The term "substantially free of sugars, sugar alcohols, and amino acids other than histidine" as used herein refers to a formulation of an antibody (including antibody fragment thereof) that immunospecifically binds to an IL-9 polypeptide, said formulation containing less than 0.0005%, less than 0.0003%, or less than 0.0001% of sugars, sugar alcohols, and amino acids other than histidine.

As used herein, the term "synergistic" refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a respiratory condition. The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a respiratory condition. In addition, a synergistic effect can result in improved efficacy of therapies (e.g., prophylactic or therapeutic agents) in the prevention or treatment of a respiratory condition. Finally, the synergistic effect of a combination of therapies (e.g., prophylactic or therapeutic agents) may avoid or reduce adverse or unwanted side effects associated with the use of any single therapy.

As used herein, the term "T cell receptor modulator" refers to an agent which modulates the phosphorylation of a T cell receptor, the activation of a signal transduction pathway associated with a T cell receptor and/or the expression of a particular protein associated with T cell receptor activity such as a cytokine. Such an agent may directly or indirectly modulate the phosphorylation of a T cell receptor, the activation of a signal transduction pathway associated with a T cell receptor, and/or the expression of a particular protein associated with T cell receptor activity such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically bind to a ligand for a T cell receptor or fragments thereof.

As used herein, the terms "therapeutic agent" and "therapeutic agents" refer to any agent(s) which can be used in the prevention, treatment, management, or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In certain embodiments, the term "therapeutic agent" refers to an antibody that binds to an IL-9 polypeptide. In certain other embodiments, the term "therapeutic agent" refers an agent other than an antibody that immunospecifically binds to an IL-9 polypeptide. Preferably, a therapeutic agent is an agent that is known to be useful for, or has been or is currently being used for the prevention, treatment, management, or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to the amount of a therapy (e.g., an antibody that immunospecifically binds to an IL-9 polypeptide), that is sufficient to reduce the severity of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, reduce the duration of a respiratory condition, ameliorate one or more symptoms of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, autoimmune diseases, inflammatory diseases, proliferative diseases, or infections (preferably, respiratory infections), or one or more symptoms thereof, cause regression of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, or enhance or improve the therapeutic effect(s) of another therapy.

The terms "therapies" and "therapy" can refer to any protocol(s), method(s), and/or agent(s) that can be used in the prevention, treatment, management, or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In certain embodiments, the terms "therapy" and "therapy" refer to anti-viral therapy, anti-bacterial therapy, anti-fungal therapy, biological therapy, supportive therapy, and/or other therapies useful in treatment, management, prevention, or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof known to skilled medical personnel.

As used herein, the term "therapeutic protocol" refers to a regimen for dosing and timing the administration of one or more therapies (e.g., therapeutic agents) that has a therapeutic effective.

As used herein, the terms "treat," "treatment," and "treating" refer to the reduction or amelioration of the progression, severity, and/or duration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof resulting from the administration of one or more therapies (including, but not limited to, the administration of one or more prophylactic or therapeutic agents). In certain embodiments, such terms refer to a reduction in the swelling of organs or tissues, or a reduction in the pain associated with a respiratory condition. In other embodiments, such terms refer to a reduction in the inflammation or constriction of an airway(s) associated with asthma. In other embodiments, such terms refer to a reduction in the replication of an infectious agent, or a reduction in the spread of an infectious agent to other organs or tissues in a subject or to other subjects. In other embodiments, such terms refer to the reduction of the release of inflammatory agents by mast cells, or the reduction of the biological effect of such inflammatory agents. In other embodiments, such terms refer to a reduction of the growth, formation and/or increase in the number of hyperproliferative cells (e.g., cancerous cells). In yet other embodiments, such terms refer to the eradication, removal or control of primary, regional or metastatic cancer (e.g., the minimization or delay of the spread of cancer).

The term "very little to no loss of the biological activities" as used herein refers to antibody activities, including but not limited to, specific binding abilities of antibodies (including antibody fragments thereof) to an IL-9 polypeptide as measured by various immunological assays, including, but not limited to ELISAs and radioimmunoassays. In one embodiment, the antibodies (including antibody fragments thereof) of the formulations of the invention retain approximately 50%, preferably 55%, 60%, 65%, 70%, 75%, 80%, 85%, 90%, 95% or 98% of the ability to immunospecifically bind to an IL-9 polypeptide as compared to a reference antibody (including antibody fragment thereof) (e.g., 4D4, 4D4 H2-1 D11, 4D4com-XF-9, 4D4com-2F9, 7F3, 71A10, 7F3 22D3, 7F3com-2H2, 7F3com-3H5, or 7F3com-3D4) as measured by an immunological assay known to one of skill in the art or described herein. For example, an ELISA based assay may be used to compare the ability of an antibody (including antibody fragment thereof) to immunospecifically bind to an IL-9 polypeptide to a 4D4, 4D4H2-1 D11, 4D4com-XF-9, 4D4com-2F9, 7F3, 71A10, 7F3 22D3, 7F3com-2H2, 7F3com-3H5, or 7F3com-3D4 reference standard. In this assay, referred to as the IL-9 Binding ELISA, plates are coated with an isolated IL-9 and the binding signal of a set concentration of a 4D4, 4D4 H2-1 D11, 4D4com-XF-9, 4D4com-2F9, 7F3, 71A10, 7F3 22D3, 7F3com-2H2, 7F3com-3H5, or 7F3com-3D4 reference standard is compared to the binding signal of the same concentration of a test antibody (including antibody fragment thereof). A "reference standard" as used herein refers to an antibody (including antibody fragment thereof) (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4) that is frozen at −70° C. consisting of 10 mg/ml of an antibody (including antibody fragment thereof) (e.g., 4D4, 4D4 H2-1 D11, 4D4com-XF-9, 4D4com-2F9, 7F3, 71A10, 7F3 22D3, 7F3com-2H2, 7F3com-3H5, or 7F3com-3D4) in histidine-HCl buffer, pH 6.0, and containing 150 mM NaCl, which reference formulation regularly gives a single monomer peak (≧97% area) by HPSEC. In another embodiment, the term "very little to no loss of biological activities" as used herein refers to antibody activities, including other effector activities of the antibody.

4. BRIEF DESCRIPTION OF THE FIGURES

FIGS. 1A-B show the amino acid sequences of the (A) variable heavy domain (SEQ ID NO.: 7) of 4D4 with the VH CDR1 (SEQ ID NO.: 1), the VH CDR2 (SEQ ID NO.: 2), and the VH CDR3 (SEQ ID NO.: 3) underlined, starting in order from VH CDR1 at the far left; and (B) variable light domain (SEQ ID. NO.: 8) of 4D4, with the VL CDR1 (SEQ ID NO.: 4), the VL CDR2 (SEQ ID NO.: 5), and the VL CDR3 (SEQ ID NO.: 6) underlined, starting in order from VL CDR1 at the far left.

FIGS. 2A-B show the amino acid sequences of the (A) variable heavy domain (SEQ ID NO.: 9) of 4D4H2-1 D11, with the VH CDR1 (SEQ ID NO.: 1), the VH CDR2 (SEQ ID NO.: 10), and the VH CDR3 (SEQ ID NO.: 3) underlined, starting in order from VH CDR1 at the far left; and (B) variable light domain (SEQ ID. NO.: 8) of 4D4H2-1 D11, the VL CDR1 (SEQ ID NO.: 4), the VL CDR2 (SEQ ID NO.: 5), and the VL CDR3 (SEQ ID NO.: 6) underlined, starting in order from VL CDR1 at the far left.

FIGS. 3A-B show the amino acid sequences of the (A) variable heavy domain (SEQ ID NO.: 15) of 4D4com-XF-9, with the VH CDR1 (SEQ ID NO.: 1), the VH CDR2 (SEQ ID NO.: 10), and the VH CDR3 (SEQ ID NO.: 12) underlined, starting in order from VH CDR1 at the far left; and (B) variable light domain (SEQ ID. NO.: 16) of 4D4com-XF-9, the VL CDR1 (SEQ ID NO.: 13), the VL CDR2 (SEQ ID NO.: 14), and the VL CDR3 (SEQ ID NO.: 64) underlined, starting in order from VL CDR1 at the far left.

FIGS. 4A-B show the amino acid sequences of the (A) variable heavy domain (SEQ ID NO.: 17) of 4D4com-2F9, with the VH CDR1 (SEQ ID NO.: 1), the VH CDR2 (SEQ ID NO.: 10), and the VH CDR3 (SEQ ID NO.: 12) underlined, starting in order from VH CDR1 at the far left; and (B) variable light domain (SEQ ID. NO.: 18) of 4D4com-2F9, with the VL CDR1 (SEQ ID NO.: 4), the VL CDR2 (SEQ ID NO.: 14), and the VL CDR3 (SEQ ID NO.: 65) underlined, starting in order from VL CDR1 at the far left.

FIGS. 5A-B show the amino acid sequences of the (A) variable heavy domain (SEQ ID NO.: 21) of 7F3, with the VH CDR1 (SEQ ID NO.: 19), the VH CDR2 (SEQ ID NO.: 2), and the VH CDR3 (SEQ ID NO.: 3) underlined, starting in order from VH CDR1 at the far left; and (B) variable light domain (SEQ ID. NO.: 22) of 7F3, with the VL CDR1 (SEQ ID NO.: 4), the VL CDR2 (SEQ ID NO.: 5), and the VL CDR3 (SEQ ID NO.: 20) underlined, starting in order from VL CDR1 at the far left.

FIGS. 6A-B show the amino acid sequences of the (A) variable heavy domain (SEQ ID NO.: 23) of 71A10, with the VH CDR1 (SEQ ID NO.: 19), the VH CDR2 (SEQ ID NO.: 61), and the VH CDR3 (SEQ ID NO.: 3) underlined, starting in order from VH CDR1 at the far left; and (B) variable light domain (SEQ ID. NO.: 24) of 71A10, the VL CDR1 (SEQ ID NO.: 4), the VL CDR2 (SEQ ID NO.: 5), and the VL CDR3 (SEQ ID NO.: 20) underlined, starting in order from VL CDR1 at the far left.

FIGS. 7A-B show the amino acid sequences of the (A) variable heavy domain (SEQ ID NO.: 21) of 7F3 22D3, with the VH CDR1 (SEQ ID NO.: 19), the VH CDR2 (SEQ ID NO.: 2), and the VH CDR3 (SEQ ID NO.: 3) underlined, starting in order from VH CDR1 at the far left; and (B) variable light domain (SEQ ID. NO.: 25) of 7F3 22D3, with the VL CDR1 (SEQ ID NO.: 4), the VL CDR2 (SEQ ID NO.: 14), and the VL CDR3 (SEQ ID NO.: 20) underlined, starting in order from VL CDR1 at the far left.

FIGS. 8A-B show the amino acid sequences of the (A) variable heavy domain (SEQ ID NO.: 27) of 7F3com-2H2, the VH CDR1 (SEQ ID NO.: 26), with the VH CDR2 (SEQ ID NO.: 61), and the VH CDR3 (SEQ ID NO.: 3) are underlined, starting in order from VH CDR1 at the far left; and (B) variable light domain (SEQ ID. NO.: 28) of 7F3com-2H2, the VL CDR1 (SEQ ID NO.: 62), the VL CDR2 (SEQ ID NO.: 63), and the VL CDR3 (SEQ ID NO.: 20) underlined, starting in order from VL CDR1 at the far left.

FIGS. 9A-B show the nucleotide sequences of the (A) variable heavy domain (SEQ ID NO.: 43) of 7F3com-2H2 with the VH CDR1 (SEQ ID NO.: 44), the VH CDR2 (SEQ ID NO.: 45) and the VH CDR3 (SEQ ID NO.: 46) underlined, starting in order from VH CDR1 at the far left; and (B) variable light domain (SEQ ID NO.: 47) of 7F3com-2H2 with the VL CDR1 (SEQ ID NO.: 48), the VL CDR2 (SEQ ID NO.:49), and the VL CDR3 (SEQ ID NO.: 50) underlined, starting in order from VL CDR1 at the far left.

FIGS. 10A-B show the amino acid sequences of the (A) variable heavy domain (SEQ ID NO.: 29) of 7F3com-3H5, with the VH CDR1 (SEQ ID NO.: 19), the VH CDR2 (SEQ ID NO.: 61), and the VH CDR3 (SEQ ID NO.: 3) underlined, starting in order from VH CDR1 at the far left and (B) variable light domain (SEQ ID. NO.: 30) of 7F3com-3H5, with the VL CDR1 (SEQ ID NO.: 4), the VL CDR2 (SEQ ID NO.: 14), and the VL CDR3 (SEQ ID NO.: 20) underlined, starting in order from VL CDR1 at the far left.

FIGS. 11A-B show the amino acid sequences of the (A) variable heavy domain (SEQ ID NO.: 31) of 7F3com-3D4, with the VH CDR1 (SEQ ID NO.: 26), the VH CDR2 (SEQ ID NO.: 61), and the VH CDR3 (SEQ ID NO.: 3) underlined, starting in order from VH CDR1 at the far left and (B) variable light domain (SEQ ID. NO.: 32) of 7F3com-3D4, with the VL CDR1 (SEQ ID NO.: 62), the VL CDR2 (SEQ ID NO.: 14), and the VL CDR3 (SEQ ID NO.: 20) underlined, starting in order from VL CDR1 at the far left.

FIG. 12 shows the nucleotide sequence of human IL-9 (SEQ ID NO.: 51) located in the GenBank database (Accession No. NM_000590).

FIGS. 13A-C show the amino acid sequences of human IL-9 located in the GenBank database: (A) Accession No. A60480 (SEQ ID NO.: 52); (B) Accession No. NP_000584 (SEQ ID NO.: 53); and (C)AAC17735 (SEQ ID NO.: 54).

FIGS. 14A-C show the nucleotide sequences of human IL-9R subunits found in the GenBank database. (A) Accession No. NM_002186 (SEQ ID NO.: 55) and (B) Accession No. NM_176786 (SEQ ID NO.: 56) are the nucleotide sequences of the human IL-9R alpha subunit isoform precursors. (C) Accession No. NM_000206 (SEQ ID NO.: 57) is the nucleotide sequence of the human IL-9R gamma chain.

FIGS. 15A-C show the amino acid sequences of human IL-9R found in the GenBank database. (A) Accession No. NP_002177 (SEQ ID NO.: 58) and (B) Accession No. NP_789743 (SEQ ID NO.: 59) are the amino acid sequences of the human IL-9R alpha subunit isoform precursors; and (C) Accession No. NP_000197 (SEQ ID NO: 60) is the amino acid sequence of the human IL-9R gamma chain.

FIG. 16 is a schematic diagram showing the outline for preparing purified antibodies that immunospecifically bind to an IL-9 polypeptide.

5. DETAILED DESCRIPTION OF THE INVENTION

The liquid formulations of the present invention provide a ready-to-use preparation of an antibody (including antibody fragment thereof) that immunospecifically binds to an IL-9 polypeptide for administering to a subject without having to reconstitute the preparation accurate and aseptical techniques, and waiting for a period of time until the solution clarifies before administering the formulation to the subject. In addition, such reconstituted solutions must be used within a certain period, leading to very costly waste. It simplifies the procedure of administering the formulation to a subject for a healthcare professional. Furthermore, due to its high stability during the storage, the formulations of the present invention can contain an antibody (including antibody fragment thereof) that immunospecifically binds to an IL-9 polypeptide at concentrations in the range of about 15 mg/ml to about 300 mg/ml without causing an adverse effect on the biological activities of the antibody due to protein aggregation and/or fragmentation during a prolonged storage. Such stability not only ensures the efficacy of the antibodies but also reduces possible risks of adverse effects in a subject. Furthermore, the use of fewer components in the formulation reduces the risk of contamination. In addition, the manufacturing process of the liquid formulations of the present invention is simplified and more efficient than the manufacturing process for the lyophilized version because all stages of the manufacturing of the liquid formulations are carried out in an aqueous solution, involving no drying process, such as lyophilization and freeze-drying. Accordingly, it is more cost effective as well.

5.1. Antibody Formulations

The liquid formulations of the present invention provide antibody formulations which are substantially free of surfactants, and/or other excipients such as sugars, sugar alcohols, amino acids (preferably, with a pKa value of less than 5 or higher than 7 and/or amino acids other than histidine or lysine), and yet exhibit high stability during long periods of storage. In a specific embodiment, such antibody formulations are homogeneous. In a preferred embodiment, the formulations of the invention are sterile. The formulations of the present invention comprise an aqueous carrier, histidine and NaCl buffer, and an antibody (including antibody fragment thereof) which immunospecifically binds to an IL-9 polypeptide at concentrations of about 15 mg/ml to about 300 mg/ml. In one embodiment, the formulations of the invention do not comprise other ingredients except for water or suitable solvents. In another preferred embodiment, the water is distilled. In a specific embodiment, the antibody that immunospecifically binds to an IL-9 polypeptide which is included in the liquid formulations of the invention is 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof. In another embodiment, the antibody that immunospecifically binds to an IL-9 polypeptide which is included in the liquid formulations of the invention is not 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof. In a preferred embodiment, the antibody that immunospecifically binds to an IL-9 polypeptide which is included in the liquid formulation of the invention is an antibody (including antibody fragment thereof) comprising one or more of the VH CDRs and/or one or more of the VL CDRs listed in Table 1, supra. In another embodiment, the antibody (including antibody fragment thereof) that immunospecifically binds to an IL-9 polypeptide which is included in the liquid formulations of the invention is an antibody (including antibody fragment thereof) conjugated to another moiety, including but not limited to, a heterologous polypeptide, another antibody (including antibody fragment thereof), a marker sequence, a diagnostic agent, a therapeutic agent, a radioactive metal ion, a polymer, albumin, and a solid support. In yet another embodiment, liquid formulations of the invention comprise two or more antibodies or (including antibody fragments thereof) that immunospecifically binds to an IL-9 polypeptide, wherein at least one of the antibodies (including antibody fragments thereof) is 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof.

The concentration of an antibody (including antibody fragment thereof) that immunospecifically binds to an IL-9 polypeptide which is included in the liquid formulations of the invention is at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 175 mg/ml, at least 200 mg/ml, at least 250 mg/ml, at least 275 mg/ml, or at least 300 mg/ml. In a specific embodiment, the concentration of an antibody (including antibody fragment thereof) that immunospecifically binds to an IL-9 polypeptide which is included in the liquid formulation of the invention is about 75 mg/ml, about 100 mg/ml, about 125 mg/ml, about 150 mg/ml, about 175 mg/ml, about 200 mg/ml, about 225 mg/ml, about 250 mg/ml, about 275 mg/ml, or about 300 mg/ml. In another embodiment, the concentration of an antibody (including antibody fragment thereof) that immunospecifically binds to an IL-9 polypeptide which is included in the liquid formulation of the invention is between 15-500 mg/ml, between 50-300 mg/ml, between 50-250 mg/ml, between 50-200 mg/ml, between 50-175 mg/ml, between 50-150 mg/ml, between 50-125 mg/ml, or between 50-100 mg/ml.

Preferably, the formulation is buffered by histidine (although other appropriate buffers may be used). The concentration of histidine which is included in the liquid formulations of the invention ranges from 1 mM to 100 mM, preferably 5 mM to 50 mM, and more preferably 10 mM to about 25 mM. In a specific embodiment, the concentration of histidine which is included in the liquid formulations of the invention is 5 mM, 10 mM, 15 mM, 20 mM, 25 mM, 30 mM, 35 mM, 40 mM, 45 mM, or 50 mM. Histidine can be in the form of L-histidine, D-histidine, or a mixture thereof, but L-histidine is the most preferable. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, preferably at least 99%, and most preferably at least 99.5%. As used herein, the term "purity" in the context of histidine refers to chemical purity of histidine as understood in the art, e.g., as described in The Merck Index, 13$^{th}$ ed., O'Neil et al. ed. (Merck & Co., 2001).

The pH of the formulation generally should not be equal to the isoelectric point of the particular antibody (including antibody fragment thereof) to be used in the formulation (e.g., the isoelectric point of 4D4, 4D4 H2-1 D11, 4D4com-XF-9, 4D4com-2F9, 7F3, 71A10, 7F3 22D3, 7F3com-2H2, 7F3com-3H5, or 7F3com-3D4 ranges from 8.65 to 8.89) and may range from about 5.0 to about 7.0, preferably about 5.5 to about 6.5, more preferably about 5.8 to about 6.2, and most preferably about 6.0.

In addition to histidine and an antibody (including antibody fragment thereof) that immunospecifically binds to an IL-9 polypeptide, the formulations of the present invention may further comprise glycine at a concentration of less than 150 mM, less than 100 mM, less than 75 mM, less than 50 mM, less than 25 mM, less than 10 mM, less than 5.0 mM, or less than 2.0 mM. In a specific embodiment, the formulations of the present invention further comprise glycine at a concentration of 1 mM to 150 mM, 1 mM to 100 mM, 1 mM to 75 mM, 1 mM to 50 mM, 1 mM to 25 mM, 1 mM to 10 mM, 1 mM to 5.0 mM, or 1 mM to 2.0 mM. The amount of glycine in the formulation should not cause a significant buffering effect so that antibody precipitation at its isoelectric point can be avoided. Glycine may be also used in a form of pharmaceutically acceptable salt, such as hydrochloride, hydrobromide, sulfate, acetate, etc. The purity of glycine should be at least 98%, preferably at least 99%, and most preferably 99.5%. As used herein, the term "purity" in the context of glycine refers to chemical purity of glycine as understood in the art, e.g., as described in The Merck Index, 13$^{th}$ ed., O'Neil et al. ed. (Merck & Co., 2001). In a specific embodiment, glycine is not included in the formulations of the present invention.

Optionally, the formulations of the present invention may further comprise other excipients, such as saccharides (e.g., sucrose, mannose, trehalose, etc.), and polyols (e.g., mannitol, sorbitol, etc.). In one embodiment, the other excipient is a saccharide. In a specific embodiment, the saccharide is sucrose, which is at a concentration ranging from between about 1% to about 20%, preferably about 5% to about 15%, and more preferably about 8% to 10% of the formulation. In another embodiment, the saccharide is sucrose, which is at a concentration of 1%, 3%, 5%, 8%, 10%, 15%, or 20% of the formulation. In another embodiment, an excipient is a polyol. Preferably, however, the liquid formulations of the present invention do not contain mannitol. In a specific embodiment, the polyol is polysorbate (e.g., Tween 20), which is at a concentration ranging from between about 0.001% to about 1%, preferably, about 0.01% to about 0.1% of the formulation. In a specific embodiment, the polyol is polysorbate (e.g., Tween 20), which is at a concentration of 0.001%, 0.005%, 0.01%, 0.02%, 0.05%, 0.08%, 0.1%, 0.5%, or 1% of the formulation.

The liquid formulations of the present invention exhibit stability at the temperature range of 38° C.-42° C. for at least 15 days and, in some embodiments, not more than 25 days, at the temperature range of 20° C.-24° C. for at least 6 months, at the temperature range of 2° C.-8° C. (in particular, at 4° C.) for at least 6 months, at least 1 year, at least 1.5 years, at least 2 years, at least 2.5 years, at least 3 years or at least 4 years, and at the temperature of −20° C. for at least 2 years, at least 3 years, at least 4 years, or at least 5 years, as assessed by high performance size exclusion chromatography (HPSEC). Namely, the liquid formulations of the present invention have low to undetectable levels of aggregation and/or fragmentation, as defined herein, after the storage for the defined periods as set forth above. Preferably, no more than 5%, no more than 4%, no more than 3%, no more than 2%, no more than 1%, and most preferably no more than 0.5% of the antibody (including antibody fragment thereof) forms an aggregate as measured by HPSEC, after the storage for the defined periods as set forth above. Furthermore, liquid formulations of the present invention exhibit almost no loss in biological activities of the antibody (including antibody fragment thereof) during the prolonged storage under the condition described above, as assessed by various immunological assays including, for example, enzyme-linked immunosorbent assay (ELISA) and radioimmunoassay to measure the ability of the antibody (including antibody fragment thereof) to immunospecifically bind to an IL-9 polypeptide. The liquid formulations of the present invention retain after the storage for the above-defined periods more than 80%, more than 85%, more than 90%, more than 95%, more than 98%, more than 99%, or more than 99.5% of the initial biological activities (e.g., the ability to bind to an IL-9 polypeptide) of the formulation prior to the storage. In some embodiments, the liquid formulations of the present invention retain after the storage for the above-defined periods at least 80%, at least 85%, at least 90%, at least 95%, at least 98%, at least 99%, or at least 99.5% of the biological activity (e.g., the ability to bind to an IL-9 polypeptide) compared to a reference antibody representing the antibody prior to the storage.

The liquid formulations of the present invention can be prepared as unit dosage forms. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of an antibody or antibody fragment that immunospecifically binds to an IL-9 polypeptide ranging from about 15 mg/ml to about 300 mg/ml, about 50 mg/ml to about 300 mg/ml, about 75 mg/ml to about 300 mg/ml, about 95 mg/ml to about 300 mg/ml, about 100 mg/ml to about 300 mg/ml, about 150 mg/ml to about 300 mg/ml, about 200 mg/ml to about 300 mg/ml, about 100 mg/ml to about 200 mg/ml, about 100 mg/ml to about 150 mg/ml, or about 100 mg/ml to about 175 mg/ml. If necessary, these preparations can be adjusted to a desired concentration by adding a sterile diluent to each vial.

The invention encompasses stable liquid formulations comprising a single antibody (including antibody fragment thereof) that immunospecifically binds to an IL-9 polypeptide. The invention also encompasses stable liquid formulations comprising two or more antibodies (including antibody fragments thereof) that immunospecifically bind to an IL-9 polypeptide. In a specific embodiment, a stable liquid formulation of the invention comprises 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or a fragment thereof that immunospecifically binds to an IL-9 polypeptide. In another embodiment, a stable liquid formulation of the invention comprises two or more antibodies (including antibody fragments thereof) that immunospecifically bind to an IL-9 polypeptide, wherein one of the antibodies (including antibody fragments thereof) is 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof. In an alternative embodiment, a stable liquid formulation of the invention comprises two or more antibodies (including antibody fragments thereof) that immunospecifically bind to an IL-9 polypeptide, with the proviso that the antibodies (including antibody fragments thereof) do not include 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof.

5.1.1. IL-9 Antibodies

The present invention provides formulations of antibodies that immunospecifically bind to an IL-9 polypeptide (preferably, a human IL-9 polypeptide). In particular, the invention provides for the formulations of the following antibodies that immunospecifically bind to an IL-9 polypeptide: 4D4 or an antigen-binding fragment thereof, 4D4 H2-1 D11 or an antigen-binding fragment thereof, 4D4com-XF-9 or an antigen-binding fragment thereof, 4D4com-2F9 or an antigen-binding fragment thereof, 7F3 or an antigen-binding fragment thereof, 71A10 or an antigen-binding fragment thereof, 7F3 22D3 or an antigen-binding fragment thereof, 7F3com-2H2 or an antigen-binding fragment thereof, 7F3com-3H5 or an antigen-binding fragment thereof, and 7F3com-3D4 or an antigen-binding fragment thereof. In a preferred embodiment, an antibody that immunospecifically binds to an IL-9 polypeptide is 7F3com-2H2 or an antigen-binding fragment thereof (e.g., one or more CDRs of 7F3com-2H2). The constant regions for 4D4, 4D4 H2-1 D11, 4D4com-XF-9, 4D4com-2F9, 71A10, 7F3 22D3, 7F3com, 7F3com-2H2, 7F3com-3H5, and 7F3com-3D4 are identical to the constant regions of palizvizumab (MedImmune, Inc.) IgG$_1$ (see U.S. Pat. No. 5,824,307, issued Oct. 20, 1998).

The present invention provides formulations of antibodies that immunospecifically bind an IL-9 polypeptide, said antibodies comprising a VH domain having an amino acid sequence of the VH domain of 4D4 (FIG. 1A; SEQ ID NO.: 7), 4D4 H2-1 D11 (FIG. 2A; SEQ ID NO.: 9), 4D4com-XF-9 (FIG. 3A; SEQ ID NO.: 15), 4D4com-2F9 (FIG. 4A; SEQ ID NO.: 17), 7F3 (FIG. 5A; SEQ ID NO.: 21), 71A10 (FIG. 6A; SEQ ID NO.: 23), 7F3 22D3 (FIG. 7A; SEQ ID NO.: 21), 7F3com-2H2 (FIG. 8A; SEQ ID NO.: 27), 7F3com-3H5 (FIG. 10A; SEQ ID NO.: 29), or 7F3com-3D4 (FIG. 11A; SEQ ID NO.: 31). In a preferred embodiment, an antibody that immunospecifically binds to an IL-9 polypeptide comprises a VH domain having an amino acid sequence of the VH domain of 7F3com-2H2 (FIG. 8A; SEQ ID NO: 27).

The present invention provides formulations of antibodies that immunospecifically bind to an IL-9 polypeptide, said antibodies comprising a VH CDR having an amino acid sequence of any one of the VH CDRs listed in Table 1, supra. In particular, the invention provides antibodies that immunospecifically bind to an IL-9 polypeptide, said antibodies comprising (or alternatively, consisting of) one, two, three, four, five or more VH CDRs having an amino acid sequence of any of the VH CDRs listed in Table 1, infra. In one embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26. In another embodiment, an antibody that immunospecifically binds to an IL-9 polypeptide comprises a VH CDR2 having the amino acid sequence of SEQ ID NO.: 2 or SEQ ID NO.: 10. In another embodiment, an antibody that immunospecifically binds to an IL-9 polypeptide comprises a VH CDR3 having the amino acid sequence of SEQ ID NO.: 3 or SEQ ID NO.: 12. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26 and a VH CDR2 having the amino acid sequence of SEQ ID NO.: 2 or SEQ ID NO.: 10. In another embodiment, an antibody that immunospecifically binds to an IL-9 polypeptide comprises a VH CDR1 having the amino acid sequence of SEQ ID NO.: 1, SEQ ID NO.: 1, SEQ ID NO.: 19, or SEQ ID NO.: 26 and a VH CDR3 having the amino acid sequence of SEQ ID NO.: 3 or SEQ ID NO.: 12. In another embodiment, an antibody that immunospecifically binds to an IL-9 polypeptide comprises a VH CDR2 having the amino acid sequence of SEQ ID NO.: 2 or SEQ ID NO.: 10 and a VH CDR3 having the amino acid sequence of SEQ ID NO.: 3 or SEQ ID NO.: 12. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26, a VH CDR2 having the amino acid sequence of SEQ ID NO.: 2 or SEQ ID NO.: 10, and a VH CDR3 having the amino acid sequence of SEQ ID NO.: 3 or SEQ ID NO.: 12.

The present invention provides formulations of antibodies that immunospecifically bind to an IL-9 polypeptide, said antibodies comprising a VL domain having an amino acid sequence of the VL domain for 4D4 (FIG. 1B; SEQ ID NO.: 8), 4D4 H2-1 D11 (FIG. 2B; SEQ ID NO.: 8), 4D4com-XF-9 (FIG. 3B; SEQ ID NO.: 16), 4D4com-2F9 (FIG. 4B; SEQ ID NO.: 18), 7F3 (FIG. 5B; SEQ ID NO.: 22), 71A10 (FIG. 6B; SEQ ID NO.: 24), 7F3 22D3 (FIG. 7B; SEQ ID NO.: 25), 7F3com-2H2 (FIG. 8B; SEQ ID NO.: 28), 7F3com-3H5 (FIG. 10B; SEQ ID NO.: 30), or 7F3com-3D4 (FIG. 11B; SEQ ID NO.: 32). In a preferred embodiment, an antibody that immunospecifically binds to an IL-9 polypeptide comprises a VL domain having an amino acid sequence of the VL domain for 7F3com-2H2 (FIG. 8B; SEQ ID NO.: 28).

The present invention also provides formulations of antibodies that immunospecifically bind to an IL-9 polypeptide, said antibodies comprising a VL CDR having an amino acid sequence of any one of the VL CDRs listed in Table 1, supra. In particular, the invention provides antibodies that immunospecifically bind to an IL-9 polypeptide, said antibodies comprising (or alternatively, consisting of) one, two, three or more VL CDRs having an amino acid sequence of any of the VL CDRs listed in Table 1, infra. In one embodiment, an antibody that immunospecifically binds to an IL-9 polypeptide comprises a VL CDR1 having the amino acid sequence of SEQ ID NO.: 4 or SEQ ID NO.: 13. In another embodiment, an antibody that immunospecifically binds to an IL-9 polypeptide comprises a VL CDR2 having the amino acid sequence of SEQ ID NO.: 5 or SEQ ID NO.: 14. In another embodiment, an antibody that immunospecifically binds to an IL-9 polypeptide comprises a VL CDR3 having the amino acid sequence of SEQ ID NO.: 6 or SEQ ID NO.: 20. In another embodiment, an antibody of that immunospecifically binds to an IL-9 polypeptide comprises a VL CDR1 having the amino acid sequence of SEQ ID NO.: 4 or SEQ ID NO.: 13 and a VL CDR2 having the amino acid sequence of SEQ ID NO.: 5 or SEQ ID NO.: 14. In another embodiment of an antibody that immunospecifically binds to an IL-9 polypeptide comprises a VL CDR1 having the amino acid sequence of SEQ ID NO.: 4 or SEQ ID NO.: 13 and a VL CDR3 having the amino acid sequence of SEQ ID NO.: 6 or SEQ ID NO.: 20. In another embodiment, an antibody that immunospecifically binds to an IL-9 polypeptide comprises a VL CDR2 having the amino acid sequence of SEQ ID NO.: 5 or SEQ ID NO.: 14 and a VL CDR3 having the amino acid sequence of SEQ ID NO.: 6 or SEQ ID NO.: 20. In another embodiment, an antibody that immunospecifically binds to an IL-9 polypeptide comprises a VL CDR1 having the amino acid sequence of SEQ ID NO.: 4 or SEQ ID NO.: 13, a VL CDR2 having the amino acid sequence of SEQ ID NO.: 5 or SEQ ID NO.: 14, and a VL CDR3 having the amino acid sequence of SEQ ID NO.: 6 or SEQ ID NO.:20, being a part of the antibody.

The present invention provides formulations of antibodies that immunospecifically bind to an IL-9 polypeptide, said antibodies comprising a VH domain disclosed herein combined with a VL domain disclosed herein, or other VL domain (e.g., a VL domain disclosed in U.S. provisional application Ser. No. 60/371,683, filed Apr. 12, 2002 and U.S. provisional application Ser. No. 60/371,728, filed Apr. 12, 2002, each of which is incorporated herein by reference in its entirety). The present invention also provides antibodies that immunospecifically bind to an IL-9 polypeptide, said antibodies comprising a VL domain disclosed herein combined with a VH domain disclosed herein, or other VH domain (e.g., a VH domain disclosed in U.S. provisional application Ser. No. 60/371,683, filed Apr. 12, 2002 and U.S. provisional application Ser. No. 60/371,728, filed Apr. 12, 2002, both of which are incorporated by reference herein in their entireties).

The present invention provides formulations of antibodies that immunospecifically bind to an IL-9 polypeptide, said antibodies comprising (or alternatively, consisting of) a VH CDR listed in Table 1, supra and a VL CDR disclosed in U.S. provisional application Ser. No. 60/371,683, filed Apr. 12, 2002 and U.S. provisional application Ser. No. 60/371,728, filed Apr. 12, 2002. The present invention also provides antibodies that immunospecifically bind to an IL-9 polypeptide, said antibodies comprising (or alternatively, consisting of) a VL CDR listed in Table 1, supra and a VH CDR disclosed in U.S. provisional application Ser. No. 60/371,683, filed Apr. 12, 2002 and U.S. provisional application Ser. No. 60/371, 728, filed Apr. 12, 2002. The invention further provides antibodies that immunospecifically bind to an IL-9 polypeptide, said antibodies comprising combinations of VH CDRs and VL CDRs described herein and disclosed in U.S. provisional application Ser. No. 60/371,683, filed Apr. 12, 2002 and U.S. provisional application Ser. No. 60/371,728, filed Apr. 12, 2002.

The present invention provides formulations of antibodies that immunospecifically bind to an IL-9 polypeptide, said antibodies comprising one or more VH CDRs and one or more VL CDRs listed in Table 1, supra. In particular, the invention provides an antibody that immunospecifically binds to an IL-9 polypeptide, said antibody comprising (or alternatively, consisting of) a VH CDR1 and a VL CDR1; a VH CDR1 and a VL CDR2; a VH CDR1 and a VL CDR3; a VH CDR2 and a VL CCDR1; V DR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2 and a VL CDR1; a VH CDR1, a VH CDR2, a VH CDR3 and a VL CDR2; a VH CDR1, a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR3, a VL CDR1 and a VL CDR2; a VH CDR3, a VL CDR1 and a VL CDR3; a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs listed in Table 1, supra.

In one embodiment, an antibody that immunospecifically binds to an IL-9 polypeptide comprises a VH CDR1 having the amino acid sequence of SEQ ID NO.: 1, SEQ ID NO.: 1, SEQ ID NO.: 19, or SEQ ID NO.: 26 and a VL CDR1 having the amino acid sequence of SEQ ID NO.: 4 or SEQ ID NO.: 13. In another embodiment, an antibody that immunospecifically binds to an IL-9 polypeptide comprises a VH CDR1 having the amino acid sequence of SEQ ID NO.: 1, SEQ ID NO.: 1, SEQ ID NO.: 19, or SEQ ID NO.: 26 and a VL CDR2 having the amino acid sequence of SEQ ID NO.: 5 or SEQ ID NO.: 14. In another embodiment, an antibody that immunospecifically binds to an IL-9 polypeptide comprises a VH CDR1 having the amino acid sequence of SEQ ID NO.: 1, SEQ ID NO.: 1, SEQ ID NO.: 19, or SEQ ID NO.: 26 and a VL CDR3 having an amino acid sequence of SEQ ID NO.: 6 or SEQ ID NO.: 20.

In one embodiment, an antibody that immunospecifically binds to an IL-9 polypeptide comprises a VH CDR2 having the amino acid sequence of SEQ ID NO.: 2 or SEQ ID NO.: 10 and a VL CDR1 having the amino acid sequence of SEQ ID NO.: 4 or SEQ ID NO.: 13. In another embodiment, an antibody that immunospecifically binds to an IL-9 polypeptide comprises a VH CDR2 having the amino acid sequence of SEQ ID NO.: 2 or SEQ ID NO.: 10 and a VL CDR2 having the amino acid sequence of SEQ ID NO.: 5 or SEQ ID NO.: 14. In another embodiment, an antibody that immunospecifically binds to an IL-9 polypeptide comprises a VH CDR2 having the amino acid sequence of SEQ ID NO.: 2 or SEQ ID NO.: 10 and a VL CDR3 having an amino acid sequence of SEQ ID NO.: 6 or SEQ ID NO.: 20.

In one embodiment, an antibody that immunospecifically binds to an IL-9 polypeptide comprises a VH CDR3 having the amino acid sequence of SEQ ID NO.: 3 or SEQ ID NO.: 12 and a VL CDR1 having the amino acid sequence of SEQ ID NO.: 4 or SEQ ID NO.: 13. In another embodiment, an antibody that immunospecifically binds to an IL-9 polypeptide comprises a VH CDR3 having the amino acid sequence of SEQ ID NO.: 3 or SEQ ID NO.: 12 and a VL CDR2 having the amino acid sequence of SEQ ID NO.: 5 or SEQ ID NO.: 14. In another embodiment, an antibody that immunospecifically binds to an IL-9 polypeptide comprises a VH CDR3 having the amino acid sequence of SEQ ID NO.: 3 or SEQ ID NO.: 12 and a VL CDR3 having an amino acid sequence of SEQ ID NO.: 6 or SEQ ID NO.: 20.

The present invention provides formulations of antibodies that immunospecifically bind to an IL-9 polypeptide, said antibodies comprising derivatives of the VH domains, VH CDRs, VL domains, or VL CDRs described herein that immunospecifically bind to an IL-9 polypeptide. Standard techniques known to those of skill in the art can be used to introduce mutations (e.g., deletions, additions, and/or substitutions) in the nucleotide sequence encoding an antibody of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues (i.e., amino acid residues which are not critical for the antibody to immunospecifically bind to an IL-9 polypeptide). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody can be expressed and the activity of the antibody can be determined.

The present invention provides for formulations of antibodies that immunospecifically bind to an IL-9 polypeptide, said antibodies comprising the amino acid sequence of 4D4, 4D4 H2-1 D11, 4D4com-XF-9, 4D4com-2F9, 7F3, 71A10, 7F3 22D3, 7F3com-2H2, 7F3com-3H5, or 7F3com-3D4 with one or more amino acid residue substitutions in the variable light (VL) domain and/or variable heavy (VH) domain. The present invention also provides for antibodies that immunospecifically bind to an IL-9 polypeptide, said antibodies comprising the amino acid sequence of 4D4, 4D4 H2-1 D11, 4D4com-XF-9, 4D4com-2F9, 7F3, 71A10, 7F3 22D3, 7F3com-2H2, 7F3com-3H5, or 7F3com-3D4 with one or more amino acid residue substitutions in one or more VL CDRs and/or one or more VH CDRs. The present invention also provides for antibodies that immunospecifically bind to an IL-9 polypeptide, said antibodies comprising the amino acid sequence of 4D4, 4D4 H2-1 D11, 4D4com-XF-9, 4D4com-2F9, 7F3, 71A10, 7F3 22D3, 7F3com-2H2, 7F3com-3H5, or 7F3com-3D4, or a VH and/or VL domain thereof with one or more amino acid residue substitutions in one or more VH frameworks and/or one or more VL frameworks. The antibody generated by introducing substitutions in the VH domain, VH CDRs, VL domain VL CDRs and/or frameworks of 4D4, 4D4 H2-1 D11, 4D4com-XF-9, 4D4com-2F9, 7F3, 71A10, 7F3 22D3, 7F3com-2H2, 7F3com-3H5, or 7F3com-3D4 can be tested in vitro and/or in vivo, for example, for its ability to bind to an IL-9 polypeptide, or for its ability to inhibit or reduce IL-9 mediated cell proliferation, or for its ability to prevent, treat and/or ameliorate an autoimmune disorder, an inflammatory disorder, a proliferative disorder or a respiratory infection, or a symptom thereof.

In a specific embodiment, an antibody that immunospecifically binds to an IL-9 polypeptide comprises a nucleotide sequence that hybridizes to the nucleotide sequence encoding 4D4, 4D4 H2-1 D11, 4D4com-XF-9, 4D4com-2F9, 7F3, 71A10, 7F3 22D3, 7F3com-2H2, 7F3com-3H5 or 7F3com-3D4, or an antigen-binding fragment thereof under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. 1, Green Publishing Associates, Inc. and John Wiley & Sons, Inc., New York at pages 6.3.1-6.3.6 and 2.10.3).

In another embodiment, an antibody that immunospecifically binds to an IL-9 polypeptide comprises an amino acid sequence of a VH domain or an amino acid sequence a VL domain encoded by a nucleotide sequence that hybridizes to the nucleotide sequence encoding the VH or VL domains of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 under stringent conditions described herein or under other stringent hybridization conditions which are known to those of skill in the art. In another embodiment, an antibody that immunospecifically binds to an IL-9 polypeptide comprises an amino acid sequence of a VH domain and an amino acid sequence of a VL domain encoded by a nucleotide sequence that hybridizes to the nucleotide sequence encoding the VH and VL domains of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 under stringent conditions described herein or under other stringent hybridization conditions which are known to those of skill in the art. In another embodiment, an antibody that immunospecifically binds to an IL-9 polypeptide comprises an amino acid sequence of a VH CDR or an amino acid sequence of a VL CDR encoded by a nucleotide sequence that hybridizes to the nucleotide sequence encoding any one of the VH CDRs or VL CDRs listed in Table 1, supra under stringent conditions described herein or under other stringent hybridization conditions which are known to those of skill in the art. In another embodiment, an antibody that immunospecifically binds to an IL-9 polypeptide comprises an amino acid sequence of a VH CDR and an amino acid sequence of a VL CDR encoded by nucleotide sequences that hybridize to the nucleotide sequences encoding any one of the VH CDRs listed in Table 1, supra, and any one of the VL CDRs listed Table 1, supra, under stringent conditions described herein or under other stringent hybridization conditions which are known to those of skill in the art.

In a specific embodiment, an antibody that immunospecifically binds to an IL-9 polypeptide comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, or an antigen-binding fragment thereof. In another embodiment, an antibody that immunospecifically binds to an IL-9 polypeptide comprises an amino acid sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the VH domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4. In another embodiment, an antibody that immunospecifically binds to an IL-9 polypeptide comprises an amino acid sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the VL domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide comprises an amino acid sequence of one or more VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in Table 1, supra. In another embodiment, an antibody that immunospecifically binds to an IL-9 polypeptide comprises an amino acid sequence of one or more VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of one of the VL CDRs listed in Table 1, supra.

The present invention encompasses formulations of antibodies that compete with an antibody described herein for binding to an IL-9 polypeptide. In particular, the present invention encompasses antibodies that compete with 4D4, 4D4 H2-1 D11, 4D4com-XF-9, 4D4com-2F9, 7F3, 71A10, 7F3 22D3, 7F3com-2H2, 7F3com-3H5 or 7F3com-3D4 or an antigen-binding fragment thereof for binding to the IL-9 polypeptide. In a specific embodiment, the invention encompasses an antibody that reduces the binding of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in the competition assay described herein or competition assays well known in the art. In another embodiment, the invention encompasses formulations of an antibody that reduces binding of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay. In a preferred embodiment, an ELISA competition assay may be performed in the following manner: recombinant IL-9 is prepared in PBS at a concentration of 10 µg/ml. 100 µl of this solution is added to each well of an ELISA 98-well microtiter plate and incubated overnight at 4-8° C. The ELISA plate is washed with PBS supplemented with 0.1% Tween to remove excess recombinant IL-9. Non-specific protein-protein interactions are blocked by adding 100 µl of bovine serum albumin (BSA) prepared in PBS to a final concentration of 1%. After one hour at room temperature, the ELISA plate is washed. Unlabeled competing antibodies are prepared in blocking solution at concentrations ranging from 1 µg/ml to 0.01 µg/ml. Control wells contain either blocking solution only or control antibodies at concentrations ranging from 1 µg/ml to 0.01 µg/ml. Test antibody (e.g., 7F3com-2H2) labeled with horseradish peroxidase is added to competing antibody dilutions at a fixed final concentration of 1 µg/ml. 100 µl of test and competing antibody mixtures are added to the ELISA wells in triplicate and the plate is incubated for 1 hour at room temperature. Residual unbound antibody is washed away. Bound test antibody is detected by adding 100 µl of horseradish peroxidase substrate to each well. The plate is incubated for 30 min. at room temperature, and absorbance is read using an automated plate reader. The average of triplicate wells is calculated. Antibodies which compete well with the test antibody reduce the measured absorbance compared with control wells. In another preferred embodiment, the invention encompasses an antibody that reduces the binding of 7F3com-2H2 to an IL-9 polypeptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay (described above).

In another embodiment, the invention encompasses formulations of an antibody that reduces the binding of an antibody comprising (alternatively, consisting of) an antigen-binding fragment (e.g., a VH domain, a VH CDR, a VL domain or a VL CDR) of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in a competition assay described herein or well-known to one of skill in the art. In another embodiment, the invention encompasses an antibody that reduces the binding of an antibody comprising (alternatively, consisting of) an antigen-binding fragment (e.g., a VH domain, VL domain, a VH CDR, or a VL CDR) of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay. In a preferred embodiment, the invention encompasses an antibody that reduces the binding of an antibody comprising (alternatively, consisting of) an antigen-binding fragment of 7F3com-2H2 to an IL-9 polypeptide by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay.

The present invention encompasses formulations of polypeptides or proteins comprising (alternatively, consisting of) VH domains that compete with the VH domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4 for binding to an IL-9 polypeptide. The present invention also encompasses formulations of polypeptides or proteins comprising (alternatively, consisting of) VL domains that compete with a VL domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 for binding to an IL-9 polypeptide.

The present invention encompasses formulations of polypeptides or proteins comprising (alternatively, consisting of) VH CDRs that compete with a VH CDR listed in Table 1, supra, for binding to an IL-9 polypeptide. The present invention also encompasses polypeptides or proteins comprising (alternatively consisting of) VL CDRs that compete with a VL CDR listed in Table 1, supra for binding to an IL-9 polypeptide.

The antibodies that immunospecifically bind to an IL-9 polypeptide include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The present invention also provides formulations of antibodies that immunospecifically bind to an IL-9 polypeptide, said antibodies comprising a framework region known to those of skill in the art (e.g., a human or non-human framework). The framework regions may be naturally occurring or consensus framework regions. Preferably, the fragment region of an antibody of the invention is human (see, e.g., Chothia et al., 1998, J. Mol. Biol. 278:457-479 for a listing of human framework regions, which is incorporated herein by reference in its entirety).

The present invention encompasses formulations of antibodies that immunospecifically bind to an IL-9 polypeptide, said antibodies comprising the amino acid sequence of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 with mutations (e.g., one or more amino acid substitutions) in the framework regions. In certain embodiments, antibodies that immunospecifically bind to an IL-9 polypeptide comprise the amino acid sequence of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 with one or more amino acid residue substitutions in the framework regions of the VH and/or VL domains. Preferably, the amino acid substitutions in the framework region improve binding of the antibody to an IL-9 polypeptide.

In a specific embodiment, formulations of antibodies that immunospecifically bind to an IL-9 polypeptide comprise the amino acid sequence of one or more of the CDRs of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, a VH framework region 1 having the amino acid sequence of QVQLVQSGAEVKKPGASVKVSCKAS (SEQ ID NO.: 33) or QVQLVQSGAEVKKPGSSVKVSCKAS (SEQ ID NO.: 37), a VH framework region 2 having the amino acid sequence of WVRQAPGQGLEWMG (SEQ ID NO.: 34), a VH framework region 3 region having the amino acid sequence of RVTMTRDTSTSTVYM ELSSLRSED-TAVYYCAR (SEQ ID.: 35) or RVTITADEST-STAYMELSSLRSED TAVYYCAR (SEQ ID NO.: 38), and a VH framework region 4 having the amino acid sequence of WGQGTLVTVSS (SEQ ID NO.: 36). In another embodiment, antibodies that immunospecifically bind to an IL-9 polypeptide comprise the amino acid sequence of one or more of the CDRs of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, a VL framework region 1 having the amino acid sequence of DIQMTQSPSSLSAS-VGDRVTITC (SEQ ID NO.: 39), a VL framework region 2 having the amino acid sequence of WYQQKPGKAPKLLIY (SEQ ID NO.: 40), a VL framework region 3 region having the amino acid sequence of GVPSRFSGSGSGTDFTLTISS-LQPEDFATYYC (SEQ ID NO.: 41), and a VL framework region 4 region having the amino acid sequence of FGGGT-KVEIK (SEQ ID NO.: 42). In yet another embodiment, antibodies that immunospecifically bind to an IL-9 polypeptide comprise the amino acid sequence of one or more of the CDRs of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, a VH framework region 1 having the amino acid sequence of SEQ ID NO.: 33 or SEQ ID NO.: 37, a VH framework region 2 having the amino acid sequence of SEQ ID NO.: 34, a VH framework region 3 having the amino acid sequence of SEQ ID NO.: 35 or 38, a VH framework region 4 having the amino acid sequence of SEQ ID NO.: 36, a VL framework region 1 having the amino acid sequence of SEQ ID NO.: 39, a VL framework region 2 having the amino acid sequence of SEQ ID NO.: 40, a VL framework region 3 having the amino acid sequence of SEQ ID NO.: 41, and a VL framework region 4 having the amino acid sequence of SEQ ID NO.: 42.

The present invention also encompasses formulations of antibodies that immunospecifically bind to an IL-9 polypeptide, said antibodies comprising the amino acid sequence of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 with mutations (e.g., one or more amino acid residue substitutions) in the variable and framework regions. Preferably, the amino acid substitutions in the variable and framework regions improve binding of the antibody to an IL-9 polypeptide.

The present invention also provides formulations of antibodies of the invention that comprise constant regions known to those of skill in the art. Preferably, the constant regions of an antibody of the invention or fragment thereof are human.

The invention encompasses formulations of antibodies that immunospecifically bind to an IL-9 polypeptide expressed by an immune cell such as an activated T cell or a mast cell. The invention also encompasses antibodies that immunospecifically bind to an IL-9 polypeptide and modulate an activity or function of T cells, B cells, mast cells, neutrophils, and/or eosinophils. The invention further encompasses antibodies that immunospecifically bind to an IL-9 polypeptide and inhibit or reduce the infiltration of inflammatory cells into a tissue, joint, or organ of a subject and/or inhibit or reduce epithelial cell hyperplasia.

The invention encompasses formulations of antibodies that immunospecifically bind to an IL-9 polypeptide found in the milieu, i.e., not bound to an IL-9R or a subunit thereof. The invention also encompasses antibodies that immunospecifically bind to an IL-9 polypeptide bound to a soluble IL-9Ra subunit. The invention further encompasses antibodies that immunospecifically bind to an IL-9 polypeptide bound to a cellular membrane-bound IL-9R or a subunit thereof.

In one embodiment, an antibody that immunospecifically binds to an IL-9 polypeptide inhibits and/or reduces the interaction between the IL-9 polypeptide and the IL-9R or a subunit thereof by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS or an IgG control antibody in an in vivo and/or in vitro assay described herein or well-known to one of skill in the art (e.g., an immunoassay such as an ELISA). In an alternative embodiment, an antibody that immunospecifically binds to an IL-9 polypeptide does not inhibit the interaction between an IL-9 polypeptide and the IL-9R or a subunit thereof relative to a control such as PBS or an IgG control antibody in an in vivo and/or in vitro assay described herein or well-known to one of skill in the art (e.g., an immunoassay such as an ELISA). In another embodiment, an antibody that immunospecifically binds to an IL-9 polypeptide inhibits the interaction between the IL-9 polypeptide and the IL-9R by less than 20%, less than 15%, less than 10%, or less than 5% relative to a control such as PBS or an IgG control antibody using, for example, an immunoassay such as an ELISA.

In one embodiment, antibodies that immunospecifically bind to an IL-9 polypeptide inhibit or reduce the interaction between the IL-9 polypeptide and the IL-9R or one or more subunits thereof by at least 25%, preferably, at least 30%, at least 35%, at least 45%, at least 50%, at least 55%, at least 60%, at least 65%, at least 70%, at least 75%, at least 80%, at least 85%, at least 90%, at least 95%, or at least 98% relative to a control such as phosphate buffered saline ("PBS") or an IgG control antibody in an in vivo and/or in vitro assay described herein or well-known to one of skill in the art (e.g., a cell proliferation assay using an IL-9 dependent cell line such as an IL-9 dependent mouse T cell line expressing the human IL-9R). In an alternative embodiment, antibodies that immunospecifically bind to an IL-9 polypeptide do not inhibit the interaction between an IL-9 polypeptide and the IL-9R or one or more subunits thereof relative to a control such as PBS or an IgG control antibody in an in vivo and/or in vitro assay described herein or well-known to one of skill in the art (e.g., a cell proliferation assay using an IL-9 dependent cell line such as an IL-9 dependent mouse T cell line expressing the human IL-9R). In another embodiment, antibodies that immunospecifically bind to an IL-9 polypeptide inhibit the interaction between the IL-9 polypeptide and the IL-9R or one or more subunits thereof by less than 20%, less than 15%, less than 10%, or less than 5% relative to a control such as PBS or an IgG control antibody in vivo and/or in vitro assay described herein or well-known to one of skill in the art, (e.g., a cell proliferation assay using an IL-9 dependent cell line such as an IL-9 dependent mouse T cell line expressing the human IL-9R).

The present invention encompasses formulations of antibodies that immunospecifically bind to an IL-9 polypeptide and do not induce or reduce cytokine expression and/or release relative to a control such as PBS or an IgG control antibody in an in vivo and/or in vitro assay described herein or well-known to one of skill in the art. In one embodiment, antibodies that immunospecifically bind to an IL-9 polypeptide and do not induce an increase in the concentration cytokines such as, e.g., IFN-γ, IL-2, IL-4, IL-5, IL-6, IL-7, IL-10, IL-12, IL-15, and IL-23 in the serum of a subject administered such an antibody relative to the concentration of such cytokines in the serum of a subject administered a ctrol such as PBS or an IgG control antibody. In an alternative embodiment, antibodies that immunospecifically bind to an IL-9 polypeptide induce cytokine expression and/or release relative to a control such as PBS or an IgG control antibody in an in vitro and/or in vivo assay described herein or well-known to one of skill in the art. In a specific embodiment, an antibody that immunospecifically binds to an IL-9 polypeptide induces an increase in the concentration of cytokines such as, e.g., IFN-γ, IL-2, IL-12, and IL-15 in the serum of a subject administered such an antibody relative to the concentration of such cytokines in the serum of a subject administered a control such as PBS or an IgG control antibody. In another specific embodiment, an antibody that immunospecifically binds to an IL-9 polypeptide induces an increase in the concentration of cytokines produced by Th1 cells, such as IFN-γ and IL-12, in a subject administered such an antibody relative to the concentration of such cytokines in the serum of a subject administered a control such as PBS or an IgG control antibody. In another specific embodiment, an antibody that immunospecifically binds to an IL-9 polypeptide induces a decrease in the concentration of cytokines such as, e.g., IL-4, IL-5, IL-10, IL-13, and IL-23 in the serum of a subject administered such an antibody relative to the concentration of such cytokines in the serum of a subject administered a control such as PBS or an IgG control antibody. In another specific embodiment, an antibody that immunospecifically binds to an IL-9 polypeptide induces a decrease in the concentration of cytokines produced by mast cells, such as TNF-α, IL-4, and IL-13, in the serum of a subject administered such an antibody relative to the concentration of such cytokines in the serum of a subject administered a control such as PBS or an IgG control antibody. In yet another specific embodiment, an antibody that immunospecifically binds to an IL-9 polypeptide induces a decrease in the concentration of cytokines produced by Th2 cells, such as IL-4, IL-5, IL-13, and IL-10, in the serum of a subject administered such an antibody relative to the concentration of such cytokines in the serum of a subject administered a control such as PBS or an IgG control antibody. Serum concentrations of a cytokine can be measured by any technique well-known to one of skill in the art such as, e.g., ELISA or Western blot assay.

In one embodiment, antibodies that immunospecifically bind to an IL-9 polypeptide reduce and/or inhibit proliferation of inflammatory cells (e.g., mast cells, T cells, B cells, macrophages, neutrophils, basophils, and/or eosinophils) by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art (e.g., a trypan blue assay or $^3$H-thymidine assay). In another embodiment, antibodies that immunospecifically bind to an IL-9 polypeptide reduce and/or inhibit infiltration of inflammatory cells into the upper and/or lower respiratory tracts by at least at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art. In yet another embodiment, antibodies that immunospecifically bind to an IL-9 polypeptide reduce and/or inhibit infiltration of inflammatory cells into the upper and/or respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well known in the art and reduce and/or inhibit proliferation of inflammatory cells by at least by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art (e.g., a trypan blue assay or $^3$H-thymidine assay).

In certain embodiments, antibodies that immunospecifically bind to an IL-9 polypeptide reduce mast cell degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art (see, e.g., Windmiller and Backer, 2003, *J. Biol. Chem.* 278:11874-78 for examples of mast cell degranulation assays). In other embodiments, antibodies that immunospecifically bind to an IL-9 polypeptide inhibit and/or reduce mast cell activation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art. In other embodiments, antibodies that immunospecifically bind to an IL-9 polypeptide inhibit and/or reduce the expression and/or release of products of mast cell activation and/or degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or an IgG control antibody in an in vivo and/or in vitro assay described herein or well-known to one of skill in the art.

In a specific embodiment, antibodies that immunospecifically bind to an IL-9 polypeptide inhibit and/or reduce the expression, activity, serum concentration, and/or release of mast cell proteases, such as chymase and tryptase, by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art. In a preferred embodiment, mast cell activity may be measured by culturing primary mast cells or a mast cell line in vitro in the presence of 10 ng/ml of IL-9. Baseline levels of protease (e.g., chymase and tryptase) and leukotriene are determined in the supernatant by commercially available ELISA kits. The ability of antibodies to modulate protease or leukotriene levels is assessed by adding an IL-9-reactive antibody or control antibody directly to cell cultures at a concentration of 1 µg/ml. Protease and leukotriene levels are assessed at 24 and 36 hour timepoints. In another specific embodiment, antibodies that immunospecifically bind to an IL-9 polypeptide inhibit and/or reduce the expression, activity, serum concentration, and/or release of mast cell leukotrienes, such as C4, D4, and E4 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In another specific embodiment, antibodies that immunospecifically bind to an IL-9 polypeptide inhibit and/or reduce the expression, activity, serum concentration, and/or release of mast cell cytokines, such as TNF-α, IL-4, and IL-13 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., an ELISA or Western blot assay).

In other embodiments, antibodies that immunospecifically bind to an IL-9 polypeptide inhibit and/or reduce mast cell infiltration by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known in the art. In other embodiments, antibodies that immunospecifically bind to an IL-9 polypeptide inhibit and/or reduce mast cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce mast cell infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vitro and/or in vivo assay described herein or well-known in the art and inhibit and/or reduce mast cell proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In a preferred embodiment, reductions in mast cell infiltration may be measured in vivo by sensitizing animals to ovalbumin. Briefly, 100 µg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On days 29, 30 and 31, animals are exposed to ovalbumin without adjuvant by aerosol delivery, or alternatively, by intrasal instillation of 100 μl of a 1 μg/ml solution prepared in PBS. On day 31, 6 hours after the last ovalbumin challenge, animals are euthanized and lung tissue is fixed by perfusion with formalin. Mast cell infiltration is assessed histologically by counting mast cells per field in lung epithelial tissue sections. Using this experimental design, mast cell precursors may be differentiated from mast cells in lung epithelium by assessing (for example) whether metachromatic granules are present, and/or by immunohistochemistry using differentiation-dependent cell surface markers (e.g., FcepsilonRI).

In other embodiments, antibodies that immunospecifically bind to an IL-9 polypeptide inhibit and/or reduce infiltration of mast cell precursors in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known in the art. In other embodiments, antibodies that immunospecifically bind to an IL-9 polypeptide inhibit and/or reduce proliferation of mast cell precursors by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce infiltration of mast cell precursors into the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known in the art and inhibit and/or reduce proliferation of mast cell precursors at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In a preferred embodiment, mast cell precursor infiltration may be measured in vivo by the mast cell infiltration assay described supra.

In certain embodiments, antibodies that immunospecifically bind to an IL-9 polypeptide mediate depletion of peripheral blood T-cells by inducing an increase in apoptosis of T-cells, particularly Th2 cells. In a preferred embodiment, Th2 T lymphocyte depletion may be measured in vivo by sensitizing animals with ovalbumin. Briefly, 100 μg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On day 28, animals receive a 100 μg boost of ovalbumin protein without adjuvant intravenously. Two days following the intravenous boost, the animals are euthanized. Spleen cells are recovered and analyzed by flow cytometry. Splenic Th2 T lymphocytes, identifiable by cytoplasmic staining for IL-4, should be reduced in animals receiving an IL-9 neutralizing antibody compared with the control antibody recipients. In another embodiment, antibodies that immunospecifically bind to an IL-9 polypeptide mediate inhibit and/or reduce Th1 and Th2 differentiation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., FACS). In certain embodiments, antibodies that immunospecifically bind to an IL-9 polypeptide inhibit and/or reduce T cell infiltration, particularly Th2 cell infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay well-known to one of skill in the art. In other embodiments, antibodies that immunospecifically bind to an IL-9 polypeptide inhibits and/or reduce T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce T cell infiltration, particularly Th2 cell infiltration, in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, inhibit and/or reduce T cell proliferation, particularly Th2 cell proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, and/or increases apoptosis of T cells relative to a control such as PBS or a control IgG antibody in an in vivo and/or in vitro assay described herein or well-known to one of skill in the art.

In certain embodiments, antibodies that immunospecifically bind to an IL-9 polypeptide reduce macrophage infiltration by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay well-known to one of skill in the art. In a preferred embodiment, reductions in macrophage infiltration may be measured in vivo by sensitizing animals to ovalbumin. Briefly, 100 μg of ovalbumin complexed with aluminum adjuvant is administered subcutaneously on days 1 and 21. Throughout the three-week sensitization procedure, animals are administered IL-9 reactive antibody or control antibody at 10 mg/kg dose every 5 to 7 days. On days 29, 30 and 31, animals are exposed to ovalbumin without adjuvant by aerosol delivery, or alternatively, by intrasal instillation of 100 μl of a 1 μg/ml solution prepared in PBS. On day 31, 6 hours after the last ovalbumin challenge, animals are euthanized and lung tissue is fixed by perfusion with formalin. Macrophage infiltration is assessed by immunocytochemistry by counting CD14 positive cells per field in lung tissue sections. In other embodiments, antibodies that immunospecifically bind to an IL-9 polypeptide inhibit and/or reduce macrophage proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce macrophage infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibit and/or reduce macrophage proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art.

In certain embodiments, antibodies that immunospecifically bind to an IL-9 polypeptide reduce B cell infiltration by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art. In a preferred embodiment, reductions in B lymphocyte infiltration may be measured in vivo by systemically sensitizing animals to ovalbumin. Briefly, 100 µg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On days 29, 30 and 31, animals are exposed to ovalbumin without adjuvant by aerosol delivery, or alternatively, by intrasal instillation of 100 µl of a 1 µg/ml solution prepared in PBS. On day 31, 6 hours after the last ovalbumin challenge, animals are euthanized and lung tissue is fixed by perfusion with formalin. B lymphocyte infiltration is assessed by immunocytochemistry by counting CD19 positive cells per field in lung tissue sections. In other embodiments, antibodies that immunospecifically bind to an IL-9 polypeptide inhibit and/or reduce B cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce B cell infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibits and/or reduces B cell proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art.

In certain embodiments, antibodies that immunospecifically bind to an IL-9 polypeptide reduce eosinophil infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art (see, e.g., Li et al., 2000, *Am. J. Respir. Cell Mol. Biol.* 25:644-51).

In other embodiments, antibodies that immunospecifically bind to an IL-9 polypeptide inhibit and/or reduce eosinophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein (see Section 5.6) or well known to one of skill in the art (e.g., a trypan blue assay, FACS or $^3$H thymidine assay). In yet other embodiments, antibodies that immunospecifically bind to an IL-9 polypeptide inhibit and/or reduce eosinophil infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibits and/or reduces eosinophil proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art.

In other embodiments, antibodies that immunospecifically bind to an IL-9 polypeptide reduce neutrophil infiltration by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art. In other embodiments, antibodies that immunospecifically bind to an IL-9 polypeptide inhibit and/or reduce neutrophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assays described herein or well-known to one of skill in the art (e.g., a trypan blue assay, FACS or $^3$H thymidine assay). In yet other embodiments, antibodies that immunospecifically bind to an IL-9 polypeptide inhibit and/or reduce neutrophil infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibits and/or reduces neutrophil proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art.

In a preferred embodiment, an antibody that immunospecifically binds to an IL-9 polypeptide neutralizes or inhibits IL-9 mediated biological effects including, but not limited to inflammatory cell recruitment, epithelia hyperplasia, mucin production of epithelial cells, and mast cell activation, degranulation, proliferation, and/or infiltration.

In a specific embodiment, an antibody that immunospecifically binds to an IL-9 polypeptide acts synergistically with a proteinaceous agent (e.g., a peptide, polypeptide, or protein (including an antibody)) and/or a non-proteinaceous agent that antagonizes the expression, function, and/or activity of IgE to reduce or inhibit the activation, degranulation, proliferation, and/or infiltration of mast cells by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assays described herein or well known to one of skill in the art.

In another embodiment, an antibody that immunospecifically binds to an IL-9 polypeptide acts synergistically with a proteinaceous agent (e.g., a peptide, polypeptide, protein (including an antibody)) and/or a non-proteinaceous agent that antagonizes the expression, function, and/or activity of a mast cell protease to reduce or inhibit the activation, degranulation, proliferation, and/or infiltration of mast cells by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art.

In another embodiment, an antibody that immunospecifically binds to an IL-9 polypeptide acts synergistically with a proteinaceous agent (e.g., a peptide, polypeptide, and protein (including an antibody)) or a non-proteinaceous agent that antagonizes the expression, function, and/or activity of a stem cell factor to reduce or inhibit to reduce or inhibit the activation, degranulation, proliferation, and/or infiltration of mast cells by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In a preferred embodiment, primary mast cells or a mast cell line is cultured in vitro in the presence of 1 ng/ml IL-9 plus 1 ng/ml stem cell factor. Baseline levels of protease (e.g., chymase and tryptase) and leukotriene are determined in the supernatant by commercially available ELISA kits. The ability of antibodies to modulate protease or leukotriene levels is assessed by adding IL-9 reactive antibody or control antibody directly to cell cultures at a concentration of 1 μg/ml. Protease and leukotriene levels are assessed at 24 and 36 hour time points.

The formulations of antibodies of the present invention that immunospecifically bind to an IL-9 polypeptide may be monospecific, bispecific, trispecific or of greater multispecificity. Multispecific antibodies may be specific for different epitopes of an IL-9 polypeptide or may be specific for both an IL-9 polypeptide as well as for a heterologous epitope, such as a heterologous polypeptide or solid support material. See, e.g., International publications WO 93/17715, WO 92/08802, WO 91/00360, and WO 92/05793; Tutt, et al., J. Immunol. 147:60-69(1991); U.S. Pat. Nos. 4,474,893, 4,714,681, 4,925,648, 5,573,920, and 5,601,819; and Kostelny et al., J. Immunol. 148:1547-1553 (1992).

The present invention provides for antibodies that have a high binding affinity for an IL-9 polypeptide. In a specific embodiment, an antibody that immunospecifically binds to an IL-9 polypeptide has an association rate constant or $k_{on}$ rate

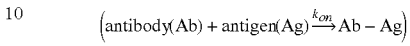

of at least $10^5$ $M^{-1}s^{-1}$, at least $1.5\times10^5$ $M^{-1}s^{-1}$, at least $2\times10^5$ $M^{-1}s^{-1}$, at least $2.5\times10^5$ $M^{-1}s^{-1}$, at least $5\times10^5$ $M^{-1}s^{-1}$, at least $10^6 M^{-1}s^{-1}$, at least $5\times10^6 M^{-1}s^{-1}$, at least $10^7$ $M^{-1}s^{-1}$, at least $5\times10^7$ $M^{-1}s^{-1}$, or at least $10^8$ $M^{-1}s^{-1}$, or $10^5$-$10^8 M^{-1}s^-$, $1.5\times10^5 M^{-1}s^{-1}$, $1\times10^7 M^{-1}s^{-1}$, $2\times10^5$-$1\times10^6 M^{-1}s^{-1}$, or $4.5\times10^5\times10^7 M^{-1}s^{-1}$. In a preferred embodiment, an antibody that immunospecifically binds to an IL-9 polypeptide has a $k_{on}$ of at least $2\times10^5$ $M^{-1}s^{-1}$, at least $2.5\times10^5$ $M^{-1}s^{-1}$, at least $5\times10^5$ $M^{-1}s^{-1}$, at least $10^6 M^{-1}s^{-1}$, at least $5\times10^6 M^{-1}s^{-1}$, at least $10^7 M^{-1}s^{-1}$, at least $5\times10^7 M^{-1}s^{-1}$, or at least $10^8$ $M^{-1}$ $s^{-1}$ as determined by a BIAcore assay and the antibody neutralizes human IL-9 in the microneutralization assay as described herein. In a preferred embodiment, an antibody that immunospecifically binds to an IL-9 polypeptide has a $k_{on}$ of at most $10^8$ $M^{-1}s^{-1}$, at most $10^9$ $M^{-1}s^{-1}$, at most $10^{10}$ $M^{-1}s^{-1}$, at most $10^{11}$ $M^{-1}s^{-1}$, or at most $10^{12}$ $M^{-1}s^{-1}$ as determined by a BIAcore assay and the antibody neutralizes human IL-9 in the microneutralization assay as described herein. In accordance with these embodiments, such antibodies may comprise a VH domain and/or a VL domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4 or a VH CDR and/or a VL CDR of 4D4, 4D4 H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide has a $k_{off}$ rate

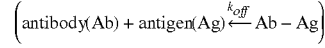

of less than $10^{-3}$ $s^{-1}$, less than $5\times10^{-3}$ $s^{-1}$, less than $10^4$ $s^{-1}$, less than $2\times10^4 s^{-1}$, less than $5\times10^4 s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7} s^{-1}$, less than $5\times10^{-7} s^{-1}$, less than $10^{-8} s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$, or $10^{-3}$-$10^{10}$ $s^{-1}$, $10^{-4}$-$10^{-8}$ $s^{-1}$, or $10^{-5}$-$10^{-8}$ $s^{-1}$. In a preferred embodiment, an antibody that immunospecifically binds to an IL-9 polypeptide has a $k_{off}$ of $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7} s^{-1}$, less than $5\times10^{-7} s^{-1}$, less than $10^{-8} s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$ as determined by a BIAcore assay and the antibody neutralizes human IL-9 in the microneutralization assay described herein. In another preferred embodiment, an antibody that immunospecifically binds to an IL-9 polypeptide has a $k_{off}$ of greater than $10^{-13}$ $s^{-1}$, greater than $10^{-12}$ $s^{-1}$, greater than $10^{-11}$ $s^{-1}$, greater than $10^{-10}$ $s^{-1}$, greater than $10^{-9}$ $s^{-1}$, or greater than $10^{-8}$ $s.^{-1}$. In accordance with these embodiments, such antibodies may comprise a VH domain and/or a VL domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, or a VH CDR and/or a VL CDR of 4D4, 4D4 H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide has an affinity constant or $K_a$ ($k_{on}/k_{off}$) of at least $10^2$ M$^{-1}$, at least $5\times10^2$ M$^{-1}$, at least $10^3$ M$^{-1}$, at least $5\times10^3$ M$^{-1}$, at least $10^4$ M$^{-1}$, at least $5\times10^4$ M$^{-1}$, at least $10^5$ M$^{-1}$, at least $5\times10^5$ M$^{-1}$, at least $10^6$ M$^{-1}$, at least $5\times10^6$ M$^{-1}$, at least $10^7$ M$^{-1}$, at least $5\times10^7$ M$^{-1}$, at least $10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$_{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$, or $10^2$–$5\times10^5$ M$^{-1}$, $10^4$–$1\times10^{10}$ M$^{-1}$, or $10^5$–$1\times10^8$ M$^{-1}$. In another embodiment, an antibody that immunospecifcaly binds to an IL-9 polypeptide has a $K_a$ of at most $10^{11}$ M$^{-1}$, at most $5\times10^{11}$M$^{-1}$, at most $10^{12}$ M$^{-1}$, at most $5\times10^{12}$ M$^{-1}$, at most $10^{13}$ M$^{-1}$, at most $5\times10^{13}$ M$^{-1}$, at most $10^{14}$ M$^{-1}$, or at most $5\times10^{14}$ M$^{-1}$. In another embodiment, an antibody that immunospecifically binds to an IL-9 polypeptide has a dissociation constant or $K_d$ ($k_{off}/k_{on}$) of less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{11}$ M, less than $5\times10^{11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M or $10^{-2}$ M–$5\times10^{-5}$ M, $10^{-6}$–$10^{-15}$ M, or $10^{-8}$–$10^{-14}$ M. In a preferred embodiment, an antibody that immunospecifically binds to an IL-9 polypeptide has a $K_d$ of less than $10^{-9}$ M, less than $5\times10^{-9}$ M, less than $10^{-10}$ M, less than $5\times10^{-10}$ M, less than $1\times10^{-11}$ M, less than $5\times10^{-11}$ M, less than $1\times10^{-12}$ M, less than $5\times10^{-12}$ M, less than $10^{-13}$ M, less than $5\times10^{-13}$ M or less than $1\times10^{-14}$ M, or $10^{-9}$ M–$10^{-14}$ M as determined by a BIAcore assay and the antibody neutralizes human IL-9 in the microneutralization assay described herein. In another preferred embodiment, an antibody that immunospecifically binds to an IL-9 polypeptide has a $K_d$ of greater than $10^{-9}$ M, greater than $5\times10^{-9}$ M, greater than $10^{-10}$ M, greater than $5\times10^{-10}$ M, greater than $10^{-1}$ M, greater than $5\times10^{-11}$ M, greater than $10^{-12}$ M, greater than $5\times10^{-12}$ M, greater than $6\times10^{-12}$ M, greater than $10^{-13}$ M, greater than $5\times10^{-13}$ M, greater than $10^{-14}$ M, greater than $5\times10^{-14}$ M or greater than $10^{-9}$ M–$10^{-14}$ M. In accordance with these embodiments, such antibodies may comprise a VH domain and/or a VL domain of 4D4, 4D4 H2-1 D11, 4D4com-XF-9, 4D4com-2F9, 7F3, 71A10, 7F3 22D3, 7F3com-2H2, 7F3com-3H5 or 7F3com-3D4, or a VH CDR and/or a VL CDR of 4D4, 4D4 H2-1 D11, 4D4com-XF-9, 4D4com-2F9, 7F3, 71A10, 7F3 22D3, 7F3com-2H2, 7F3com-3H5 or 7F3com-3D4.

In certain embodiments, formulations of the antibodies of the invention do not include antibodies known in the art that immunospecifically bind to an IL-9 polypeptide. Non-limiting examples of known antibodies that immunospecifically bind to an IL-9 polypeptide include 4D4, 4D4 H2-1 D11, 4D4com-XF-9, 4D4com-2F9, 7F3, 71A10, 7F3 22D3, 7F3com-2H2, 7F3com-3H5 or 7F3com-3D4.

In specific embodiments, formulations of antibodies of the invention bind antigenic epitope-bearing peptides and polypeptides of IL-9, and said antigenic epitope-bearing peptides and polypeptides comprise or consist of an amino acid sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50 contiguous amino acid residues, and, preferably, between about 15 to about 30 contiguous amino acids of IL-9 found in any species. Preferred polypeptides comprising immunogenic or antigenic epitopes are at least 8, at least 10, at least 15, at least 20, at least 25, at least at least 30, or at least 35 amino acid residues in length.

IL-9 epitope-bearing peptides, polypeptides, and fragments thereof may be produced by any conventional means. See, e.g., Houghten, R. A. (1985) "General method for the rapid solid-phase synthesis of large numbers of peptides: specificity of antigen-antibody interaction at the level of individual amino acids," Proc. Natl. Acad. Sci. USA 82:5 13 1-5 135; this "Simultaneous Multiple. Peptide Synthesis (SMPS)" process is further described in U.S. Pat. No. 4,631, 211 to Houghten et al. (1986).

The present invention provides formulations of peptides, polypeptides and/or proteins comprising one or more variable or hypervariable regions of the antibodies described herein. Preferably, peptides, polypeptides or proteins comprising one or more variable or hypervariable regions of antibodies of the invention further comprise a heterologous amino acid sequence. In certain embodiments, such a heterologous amino acid sequence comprises at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 75 contiguous amino acid residues, at least 100 contiguous amino acid residues or more contiguous amino acid residues. Such peptides, polypeptides and/or proteins may be referred to as fusion proteins.

In a specific embodiment, formulations of peptides, polypeptides or proteins comprising one or more variable or hypervariable regions of the antibodies of the invention are 10 amino acid residues, 15 amino acid residues, 20 amino acid residues, 25 amino acid residues, 30 amino acid residues, 35 amino acid residues, 40 amino acid residues, 45 amino acid residues, 50 amino acid residues, 75 amino acid residues, 100 amino acid residues, 125 amino acid residues, 150 amino acid residues or more amino acid residues in length. In certain embodiments, peptides, polypeptides, or proteins comprising one or more variable or hypervariable regions of an antibody of the invention immunospecifically bind to an IL-9 polypeptide. In other embodiments, peptides, polypeptides, or proteins comprising one or more variable or hypervariable regions of an antibody of the invention do not immunospecifically bind to an IL-9 polypeptide.

In a specific embodiment, the present invention provides formulations of peptides, polypeptides and/or proteins comprising a VH domain and/or VL domain of one of the antibodies described herein (see Table 1, supra). In a preferred embodiment, the present invention provides peptides, polypeptides and/or proteins comprising one or more CDRs having the amino acid sequence of any of the CDRs listed in Table 1, supra. In accordance with these embodiments, the peptides, polypeptides or proteins may further comprise a heterologous amino acid sequence.

Peptides, polypeptides or proteins comprising one or more variable or hypervariable regions have utility, e.g., in the production of anti-idiotypic antibodies which in turn may be used to prevent, treat, and/or ameliorate one or more symptoms associated with a disease or disorder (e.g., an autoimmune disorder, an inflammatory disorder, a proliferative disorder or an infection (preferably, a respiratory infection)). The anti-idiotypic antibodies produced can also be utilized in immunoassays, such as, e.g., ELISAs, for the detection of

5.1.1.1. Antibodies Having Increased Half-Lives That Immunospecifically Bind to an IL-9 Polypeptide The present invention provides for formulations of antibodies and antibody fragments that immunospecifically bind to an IL-9 polypeptide which have a extended half-life in vivo. In particular, the present invention provides formulations of antibodies and antibody fragments that immunospecifically bind to an IL-9 polypeptide which have a half-life in an animal, preferably a mammal and most preferably a human, of greater than 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibodies (e.g., monoclonal antibodies and single chain antibodies) or antibody fragments (e.g., Fab fragments) in vivo, for example, inert polymer molecules such as high molecular weight polyethyleneglycol (PEG) can be attached to the antibodies (including antibody fragments thereof) with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies (including antibody fragments thereof) can be tested for binding activity as well as for in vivo efficacy using methods known to those of skill in the art, for example, by immunoassays described herein.

Antibodies having an increased half-life in vivo can also be generated introducing one or more amino acid modifications (i.e., substitutions, insertions or deletions) into an IgG constant domain, or FcRn binding fragment thereof (preferably a Fc or hinge-Fc domain fragment). See, e.g., International Publication No. WO 98/23289; International Publication No. WO 97/34631; and U.S. Pat. No. 6,277,375, each of which is incorporated herein by reference in its entirety.

Further, antibodies (including antibody fragments thereof) can be conjugated to albumin in order to make the antibody (including antibody fragment thereof) more stable in vivo or have a longer half life in vivo. The techniques are well known in the art, see e.g., International Publication Nos. WO 93/15199, WO 93/15200, and WO 01/77137; and European Patent No. EP 413, 622, all of which are incorporated herein by reference.

5.1.1.2. Antibody Conjugates

The present invention provides formulations of antibodies (including antibody fragments thereof) that immunospecifically binds to an IL-9 polypeptide recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides formulations of fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. Preferably, the heterologous protein, polypeptide, or peptide that the antibody (including antibody fragments thereof) is fused to is useful for targeting the antibody to respiratory epithelial cells, mast cells, neutrophils, eosinophils, B cells, macrophages, or activated T cells. For example, an antibody that immunospecifically binds to a cell surface receptor expressed by a particular cell type (e.g., a respiratory epithelial cell, a mast cell, a neutrophil, an eosinophil, a B cell, a macrophage, or an activated T cell) may be fused or conjugated to an antibody (including antibody fragment thereof) of the invention. In a specific embodiment, an antibody that immunospecifically binds to an IL-9 polypeptide is fused or conjugated to an anti-stem cell factor or an anti-kit ligand. Methods for fusing or conjugating proteins, polypeptides, or peptides to an antibody (including antibody fragment thereof) are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references are incorporated herein by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al, 1999, J. Mol. Biol. 287:265-76; and Lorenzo and Blasco, 1998, Biotechniques 24(2):308-313 (each of these patents and publications are hereby incorporated by reference in its entirety). Antibodies (including antibody fragments thereof), or the encoded antibodies or fragments thereof, may be altered by being subjected to random mutagenesis by error-prone PCR, random nucleotide insertion or other methods prior to recombination. A polynucleotide encoding an antibody (including antibody fragment thereof) thereof that immunospecifically binds to an IL-9 polypeptide may be recombined with one or more components, motifs, sections, parts, domains, fragments, etc. of one or more heterologous molecules.

Moreover, the antibodies (including antibody fragments thereof) can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder (e.g., an autoimmune disorder, an inflammatory disorder, a proliferative disorder, or an infection (preferably, a respiratory infection)) as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cis-dichlorodiamine platinum (II) (DDP), and cisplatin); anthracyclines (e.g., daunorubicin (formerly daunomycin) and doxorubicin); antibiotics (e.g., dactinomycin (formerly actinomycin), bleomycin, mithranycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440, 974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-895 If; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (ZEVALIN®); tositumomab (BEXXAR®)) and pharmaceutically acceptable salts, solvates, clathrates, and prodrugs thereof.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, a-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma ("IFN-γ"), interleukin-1 ("IL-1"), interleukin-2 ("IL-2"), interleukin-5 ("IL-5"), interleukin-6 ("IL-6"), interleuking-7 ("IL-7"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid fibrinopeptides A and B from the α and β chains of fibrinogen, fibrin monomer). In a specific embodiment, an antibody that immunospecifically binds to an IL-9 polypeptide is conjugated with a leukotriene antagonist (e.g., montelukast, zafirlukast, pranlukast, and zyleuton).

Moreover, an antibody can be conjugated to therapeutic moieties such as a radioactive metal ion, such as alph-emiters such as $^{213}$Bi or macrocyclic chelators useful for conjugating radiometal ions, including but not limited to, $^{131}$In, $^{131}$L, $^{131}$y, $^{131}$Ho, $^{131}$Sm, to polypeptides or any of those listed supra. In certain embodiments, the macrocyclic chelator is 1,4,7,10-tetraazacyclododecane-N,N',N",N'''-tetraacetic acid (DOTA) which can be attached to the antibody via a linker molecule. Such linker molecules are commonly known in the art and described in Denardo et al., 1998, Clin Cancer Res. 4(10): 2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorp, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antibody that immunospecifically binds to an IL-9 polypeptide or fragment thereof should be chosen to achieve the desired prophylactic or therapeutic effect(s) for a particular disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, in a subject. A clinician or other medical personnel should consider the following when deciding on which therapeutic moiety or drug to conjugate to an antibody that immunospecifically binds to an IL-9 polypeptide or fragment thereof: the nature of the disease, the severity of the disease, and the condition of the subject.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The therapeutic moiety or drug conjugated to an antibody (including antibody fragment thereof) that immunospecifically binds to an IL-9 polypeptide should be chosen to achieve the desired prophylactic or therapeutic effect(s) for a particular disorder in a subject. A clinician or other medical personnel should consider the following when deciding on which therapeutic moiety or drug to conjugate to an antibody (including antibody fragment thereof) that immunospecifically binds to an IL-9 polypeptide: the nature of the disease, the severity of the disease, and the condition of the subject.

5.2. Method of Preparing the Antibody Formulations

The present invention provides methods for preparing liquid formulations of antibodies or derivatives, analogues, or fragments thereof that immunospecifically bind to an IL-9 polypeptide. FIG. 16 is a schematic diagram showing the outline for preparing purified anti-IL-9 antibodies. The methods for preparing liquid formulations of the present invention comprise: purifying the antibody (including antibody fragment thereof) from conditioned medium (either single lots or pooled lots of medium) and concentrating a fraction of the purified antibody (including antibody fragment thereof) to a final concentration of from about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 150 mg/ml, about 175 mg/ml, about 200 mg/ml, about 250 mg/ml, or about 300 mg/ml. Conditioned medium containing the antibody (including antibody fragment thereof) that immunospecifically binds to an IL-9 polypeptide is subjected to CUNO filtration and the filtered antibody is subjected to HS50 cation exchange chromatography. The fraction from the HS50 cation exchange chromatography is then subjected to rProtein A affinity chromatography followed by low pH treatment. Following low pH treatment, the antibody (including antibody fragment thereof) fraction is subject to super Q 650 anion exchange chromatography and then nanofiltration. The fraction of the antibody (including antibody fragment thereof) obtained after nanofiltration is then subjected to diafiltration to concentrate the antibody (including antibody fragment thereof) fraction into the formulation buffer using the same membrane. For a detailed description for preparation of the antibody formulations, see Section 6, infra.

The formulation buffer of the present invention comprises histidine at a concentration ranging from about 1 mM to about 100 mM, about 5 mM to about 50 mM, about 10 mM to about 30 mM, or about 10 mM to about 25 mM. In a specific embodiment, the formulation buffer of the present invention comprises histidine at a concentration of about 10 mM, about 12 mM, about 15 mM, about 20 mM or about 25 mM. The formulations may further comprise glycine at a concentration of less than 150 mM, less than 100 mM, less than 75 mM, less than 50 mM, less than 10 mM, less than 3.0 mM, or less than 2.0 mM. The amount of glycine in the formulation should not cause a significant buffering in order to avoid antibody precipitation at its isoelectric point. The pH of the formulation may range from about 5.0 to about 7.0, preferably about 5.5 to about 6.5, more preferably about 5.8 to about 6.2, and most preferably about 6.0. To obtain an appropriate pH for a particular antibody, it is preferable that histidine (and glycine, if added) is first dissolved in water to obtain a buffer solution with higher pH than the desired pH and then the pH is brought down to the desired level by adding HCl. This way, the formation of additional inorganic salts (e.g., formation of NaCl when, for example, histidine hydrochloride is used as histidine and pH is raised to a desired level by adding NaOH) can be avoided.

The liquid formulations of the present invention can be prepared as unit dosage forms by preparing a vial containing an aliquot of the liquid formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of an antibody (including antibody fragment thereof) that immunospecifically binds to an IL-9 polypeptide ranging from about 15 mg/ml to about 300 mg/ml. If necessary, these preparations can be adjusted to a desired concentration by adding a sterile diluent to each vial. In a preferred embodiment, the liquid formulations of the present invention are formulated into single dose vials as a sterile liquid that contains 10 mM histidine buffer at pH 6.0 and 150 mM sodium chloride. Each 1.0 mL of solution contains 100 mg of the antibody (including antibody fragment thereof), 1.6 mg of histidine and 8.9 mg of sodium chloride in water. During the manufacturing process, the pH of the formulation buffer is adjusted to 6.0 using hydrochloric acid. In a preferred embodiment, the antibody (including antibody fragment thereof) of the invention is supplied at 100 mg/ml in 3 cc USP Type I borosilicate amber vials (West Pharmaceutical Services—Part No. 6800-0675). The target fill volume is 1.2 mL.

The liquid formulations of the present invention may be sterilized by various sterilization methods, including sterile filtration, radiation, etc. In a most preferred embodiment, the difiltrated antibody formulation is filter-sterilized with a presterilized 0.2 micron filter. Sterilized liquid formulations of the present invention may be administered to a subject to prevent, treat or ameliorate a disease or disorder (e.g., a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection)) or one or more symptoms thereof.

Although the invention is directed to liquid non-lyophilized formulations, it should be noted for the purpose of equivalents that the formulations of the invention may be lyophilized if desired. Thus, the invention encompasses lyophilized forms of the formulations of the invention although such lyophilized formulations are not preferred.

5.3. Methods of Preparing Antibodies

The antibodies (including antibody fragments thereof) that immunospecifically bind to an antigen can be produced by any method known in the art for the synthesis of antibodies, in particular, by chemical synthesis or preferably, by recombinant expression techniques.

Polyclonal antibodies immunospecific for an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981), and Harlow et al., *Using Antibodies: A laboratory Manual*, Cold Spring Harbor Laboratory Press (1999) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilpatrack et al., 1997, *Hybridoma* 16:381-9, incorporated herein by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, 5,969,108, 6,33,187, 5,824,520, and 5,702,892; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human imuoglobulin. A humanized antibody comprises substantially all of at least one, and typically two, variable domains (Fab, Fab', $F(ab')_2$, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. Humanized antibody can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6): 805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119-25 (2002), Caldas et al., Protein Eng. 13(5):353-60 (2000), Morea et al., Methods 20(3):267-79 (2000), Baca et al., J. Biol. Chem. 272(16): 10678-84 (1997), Roguska et al., Protein Eng. 9(10):895-904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature 332:323, which are incorporated herein by reference in their entireties).

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that immunospecifically bind to an antigen (e.g., an IL-9 polypeptide) can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

5.3.1. Recombinant Expression of an Antibody

Recombinant expression of an antibody contained in a formulation of the invention (e.g., a heavy or light chain of an antibody of the invention or a fragment thereof or a single chain antibody of the invention) that immunospecifically binds to an IL-9 polypeptide requires construction of an expression vector containing a polynucleotide that encodes the antibody. Once a polynucleotide encoding an antibody molecule, heavy or light chain of an antibody, or fragment thereof (preferably, but not necessarily, containing the heavy or light chain variable domain) of the invention has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody (including antibody fragment thereof), or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or fragment thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies of the invention, derivative, analog, or fragment thereof which immunospecifically bind to an IL-9 polypeptide or fragments thereof is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT20 and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.4. Methods of Monitoring the Stability and Aggregation of Antibody Formulations There are various methods available for assessing the stability of protein formulations, including antibody formulations, based on the physical and chemical structures of the proteins as well as on their biological activities. For example, to study denaturation of proteins, methods such as charge-transfer absorption, thermal analysis, fluorescence spectroscopy, circular dichroism, NMR, and HPSEC, are available. See, for example, Wang et al., 1988, J. of Parenteral Science & Technology 42(Suppl):S4-S26.

The rCGE and HPSEC are the most common and simplest methods to assess the formation of protein aggregates, protein degradation, and protein fragmentation. Accordingly, the stability of the liquid formulations of the present invention may be assessed by these methods.

For example, the stability of the liquid formulations of the present invention may be evaluated by HPSEC or rCGE, wherein the percent area of the peaks represents the non-degraded antibody or non-degraded antibody fragments. In particular, approximately 250 μg of the antibody (including antibody fragment thereof) that immunospecifically binds to an IL-9 polypeptide (approximately 25 μl of a liquid formulation comprising 10 mg/ml said antibody or antibody fragment) is injected onto a TosoH Biosep TSK G3000SW$_{XL}$ column (7.8 mm×30 cm) fitted with a TSK SW×1 guard column (6.0 mm CX 4.0 cm). The antibody (including antibody fragment thereof) is eluted isocratically with 0.1 M disodium phosphate containing 0.1 M sodium sulfate and 0.05% sodium azide, at a flow rate of 0.8 to 1.0 ml/min. Eluted protein is detected using UV absorbance at 280 nm. 4D4, 4D4 H2-1 D11, 4D4com-XF-9, 4D4com-2F9, 7F3, 71A10, 7F3 22D3, 7F3com-2H2, 7F3com-3H5, or 7F3com-3D4 (or any other antibody that is in a formulation of the invention) reference standards are run in the assay as controls, and the results are reported as the area percent of the product monomer peak compared to all other peaks excluding the included volume peak observed at approximately 12 to 14 minutes. Peaks eluting earlier than the monomer peak are recorded as percent aggregate.

The liquid formulations of the present invention exhibit low to undetectable levels of aggregation as measured by HPSEC or rCGE, that is, no more than 5%, no more than 4%, no more than 3%, no more than 2%, no more than 1%, and most preferably no more than 0.5% aggregate by weight protein, and low to undetectable levels of fragmentation, that is, 80% or higher, 85% or higher, 90% or higher, 95% or higher, 98% or higher, or 99% or higher, or 99.5% or higher of the total peak area in the peak(s) representing intact antibodies (including antibody fragments thereof). In the case of SDS-PAGE, the density or the radioactivity of each band stained or labeled with radioisotope can be measured and the % density or % radioactivity of the band representing non-degraded antibodies (including antibody fragments thereof) can be obtained.

The stability of the liquid formulations of the present invention can be also assessed by any assays which measure the biological activity of the antibody in the formulation. The biological activities of antibodies include, but are not limited to, antigen-binding activity, complement-activation activity, Fc-receptor binding activity, and so forth. Antigen-binding activity of the antibodies (including antibody fragments thereof) can be measured by any method known to those skilled in the art, including but not limited to ELISA, radio-immunoassay, Western blot, and the like. Complement-activation activity can be measured by a C3a/C4a assay in the system where the antibody which immunospecifically binds to an IL-9 polypeptide is reacted in the presence of the complement components with the cells expressing the an IL-9 polypeptide. Also see Harlow et al., Antibodies: A Laboratory Manual, (Cold Spring Harbor Laboratory Press, 2nd ed. 1988) (incorporated by reference herein in its entirety). An ELISA based assay, e.g., may be used to compare the ability of an antibody (including antibody fragments thereof) to immunospecifically bind to an IL-9 polypeptide to 4D4, 4D4 H2-1 D11, 4D4com-XF-9, 4D4com-2F9, 7F3, 71A10, 7F3 22D3, 7F3com-2H2, 7F3com-3H5, or 7F3com-3D4 (or any other antibody that is in a formulation of the invention) reference standards. In this assay, referred to as the VnR Binding ELISA, plates are coated with an isolated IL-9 polypeptide and the binding signal of a set concentration of 4D4, 4D4 H2-1 D11, 4D4com-XF-9, 4D4com-2F9, 7F3, 71A10, 7F3 22D3, 7F3com-2H2, 7F3com-3H5, or 7F3com-3D4 reference standards is compared to the binding signal of the same concentration of a test antibody (including antibody fragment thereof).

The purity of the liquid antibody formulations of the invention may be measured by any method well-known to one of skill in the art such as, e.g., HPSEC. The sterility of the liquid antibody formulations may be assessed as follows: sterile soybean-casein digest medium and fluid thioglycollate medium are inoculated with a test liquid antibody formulation by filtering the liquid antibody formulation through a sterile filter having a nominal porosity of 0.45 μm. When using the Sterisure™ or Steritest™ method, each filter device is aseptically filled with approximately 100 ml of sterile soybean-casein digest medium or fluid thioglycollate medium. When using the conventional method, the challenged filter is aseptically transferred to 100 ml of sterile soybean-casein digest medium or fluid thioglycollate medium. The media are incubated at appropriate temperatures and observed three times over a 14 day period for evidence of bacterial or fungal growth.

5.5. Prophylactic and Therapeutic Utility of the Antibody Formulations

The present invention is also directed to antibody-based therapies which involve administering to a subject, preferably a human, the liquid antibody formulations (or "antibody formulations" or "liquid formulations") of the present invention for preventing, treating, managing or ameliorating a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof (see U.S. Provisional Appn. No. 60/477,801, filed Jun. 10, 2003, entitled "Methods of Preventing or Treating Respiratory Conditions," U.S. Provisional Appn. No. 60/462,307, filed Apr. 11, 2003, entitled "Methods of Preventing or Treating Respiratory Conditions" and a U.S. patent application Ser. No. 10/823,810 filed concurrently herewith on Apr. 12, 2004, entitled "Methods of Preventing or Treating Respiratory Conditions," which are all incorporated by reference herein in their entireties). The liquid formulations of the invention comprise an antibody (including antibody fragment thereof) at concentrations of from about 15 mg/ml to about 300 mg/ml in a solution containing histidine, which antibody (including antibody fragment thereof) immunospecifically binds to an IL-9 polypeptide. The liquid formulations of the invention may comprise a single antibody (including antibody fragment thereof) that immunospecifically binds to an IL-9 polypeptide (e.g., 4D4, 4D4 H2-1 D11, 4D4com-XF-9, 4D4com-2F9, 7F3, 71A10, 7F3 22D3, 7F3com-2H2, 7F3com-3H5, or 7F3com-3D4). The liquid formulations of the invention may also comprise two or more antibodies (including antibody fragments thereof) that immunospecifically bind to an IL-9 polypeptide. In a specific embodiment, antibodies (including antibody fragments thereof) included in such liquid formulations are 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or fragments thereof. In an alternative embodiment, antibodies (including antibody fragments thereof) included in such liquid formulations are not 4D4, 4D4 H2-1 D11, 4D4com-XF-9, 4D4com-2F9, 7F3, 71A10, 7F3 22D3, 7F3com-2H2, 7F3com-3H5, or 7F3com-3D4 or fragments thereof. In yet another embodiment, the liquid formulations of the invention comprise an antibody (including antibody fragment thereof) that immunospecifically binds to an IL-9 polypeptide, and the antibody (including antibody fragment thereof) is also conjugated to another moiety, including but not limited to, a heterologous protein, peptide or polypeptide, another antibody (including antibody fragment thereof), a marker sequence, a diagnostic agent, a therapeutic agent, a radioactive metal ion, and a solid support.

The liquid formulations of the present invention may be used locally or systemically in the body as a therapeutic. Particularly, the liquid formulations of the invention may be used in the prevention, treatment, management and amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. The formulations of the invention can be used to regulate the activity of cells expressing an IL-9R. In a specific embodiment, the formulations of the invention are used to regulate various activities of a body, including but not limited to, immune functions. The formulations of the present invention may also be advantageously utilized in combination with one or more other therapies (e.g., one or more other prophylactic or therapeutic agents), preferably therapies useful in the treatment, prevention, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. When one or more other therapies (e.g., prophylactic or therapeutic agents) are used, they can be administered separately, in any appropriate form and by any suitable route. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy (e.g., prophylactic or therapeutic agents) which is known to be useful, or which has been used or is currently being used for the prevention, management, treatment, or amelioration of one or more symptoms associated with a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), can be used in combination with the liquid antibody formulations of the present invention in accordance with the invention described herein. See, e.g., Gilman et al., *Goodman and Gilman's: The Pharmacological Basis of Therapeutics*, Tenth Ed., McGraw-Hill, New York, 2001; The *Merck Manual of Diagnosis and Therapy*, Berkow, M. D. et al. (eds.), 17th Ed., Merck Sharp & Dohme Research Laboratories, Rahway, N.J., 1999; and *Cecil Textbook of Medicine,* 20th Ed., Bennett and Plum (eds.), W.B. Saunders, Philadelphia, 1996 for information regarding therapies, in particular prophylactic or therapeutic agents, which have been or are currently being used for preventing, treating, managing, and/or ameliorating diseases or disorders associated with or characterized by aberrant expression and/or activity of an IL-9 polypeptide, diseases or disorders associated with or characterized by aberrant expression and/or activity of the IL-9R or one or more subunits thereof, autoimmune diseases, inflammatory diseases, proliferative diseases, or infections (preferably, respiratory infections), or one or more symptoms thereof. Examples of prophylactic and therapeutic agents include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

A liquid formulation of the invention may be administered to a mammal, preferably a human, concurrently with one or more other therapies (e.g., one or more other prophylactic or therapeutic agents), preferably therapies useful for the prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. The term "concurrently" is not limited to the administration of prophylactic or therapeutic agents/therapies at exactly the same time, but rather it is meant that a liquid formulation of the invention and the other agent/therapy are administered to a mammal in a sequence and within a time interval such that the antibody (including antibody fragment thereof) that immunospecifically binds to an IL-9 polypeptide contained in the liquid formulation can act together with the other agent/therapy to provide an increased benefit than if they were administered otherwise. For example, a liquid formulation of the invention and one or more other prophylactic or therapeutic agents useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, may be administered at the same time or sequentially in any order at different points in time; however, if not administered at the same time, they should be administered sufficiently close in time so as to provide the desired therapeutic or prophylactic effect.

In various embodiments, a liquid formulation of the invention and one or more other therapies (e.g., one or more other prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, a liquid formulation of the invention and one or more other therapies (e.g., one or more other prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered within the same patient visit. In other embodiments, a liquid formulation of the invention and one or more other therapies (e.g., one or more other prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered at about 2 to 4 days apart, at about 4 to 6 days apart, at about 1 week part, at about 1 to 2 weeks apart, or more than 2 weeks apart. In preferred embodiments, a liquid formulation of the invention and one or more other therapies (e.g., prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered in a time frame where both agents are still active. One skilled in the art would be able to determine such a time frame by determining the half-life of the administered agents.

In certain embodiments, a liquid formulation of the invention and one or more other therapies (e.g., one or more other prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, a liquid formulation of the invention and one or more other therapies (e.g., one or more other prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, liquid formulation of the invention and one or more other therapies (e.g., prophylactic or therapeutic agents), preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, are administered in metronomic dosing regimens, either by continuous infusion or frequent administration without extended rest periods. Such metronomic administration can involve dosing at constant intervals without rest periods. Typically the prophylactic or therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the prophylactic and therapeutic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months.

In one embodiment, a liquid formulation of the invention is administered in a dosing regimen that maintains the plasma concentration of the antibody (including antibody fragment thereof) immunospecific for an IL-9 polypeptide at a desirable level (e.g., about 0.1 to about 100 µg/ml), which continuously blocks the an IL-9R activity. In a specific embodiment, the plasma concentration of the antibody (including antibody fragment thereof) is maintained at 0.2 µg/ml, 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 35 µg/ml, 40 µg/ml, 45 µg/ml or 50 µg/ml. The plasma concentration that is desirable in a subject will vary depending on several factors, including but not limited to, the nature of the disease or disorder, the severity of the disease or disorder and the condition of the subject. Such dosing regimens are especially beneficial in prevention, treatment, management and amelioration of a chronic disease or disorder.

In one embodiment, a liquid formulation of the invention is administered to a subject with a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof using a dosing regimen that maintains the plasma concentration of the an antibody (including antibody fragment thereof) that immunospecifically binds to an IL-9 polypeptide at a level that blocks at least 40%, preferably at least 50%, at least 55%, at least 60%, at least 65%, at least 70%, at least 75%, at least 80%, at least 85%, at least 90% or at least 95% of IL-9R binding to an IL-9 polypeptide. In a specific embodiment, the plasma concentration of the an antibody (including antibody fragment thereof) that immunospecifically binds to an IL-9 polypeptide is maintained at about 0.1 µg/ml to about 100 µg/ml in a subject with a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof.

In some embodiments, a liquid formulation of the invention is administered intermittently to a subject, wherein the liquid formulation comprises an antibody (including antibody fragment thereof) conjugated to a moiety (e.g., a therapeutic agent or a toxin).

When used in combination with other therapies (e.g., prophylactic and/or therapeutic agents) useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, the liquid formulations of the invention and the other therapy can act additively or, more preferably, synergistically. The invention contemplates administration of a liquid formulation of the invention in combination with other therapies (e.g., prophylactic or therapeutic agents) preferably therapies useful for prevention, treatment, management or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof by the same or different routes of administration, e.g., oral and parenteral. In certain embodiments, when a liquid formulation of the invention is administered concurrently with one or more therapies (e.g., prophylactic or therapeutic agents) that potentially produce adverse side effects (including, but not limited to, toxicity), the therapies (e.g., prophylactic or therapeutic agents) can advantageously be administered at a dose that falls below the threshold that the adverse side effect is elicited.

5.5.1. Cancer Treatment

The liquid formulations of the invention may be administered to a subject in need thereof to prevent, treat, manage or ameliorate a cancer or one or more symptoms thereof. The liquid formulations of the invention may also be administered in combination with one or more other therapies, preferably therapies useful for the prevention, management or treatment of cancer (including, but not limited to the prophylactic or therapeutic agents listed in Section 5.5.1.1 hereinbelow) to a subject in need thereof to prevent, treat, manage or ameliorate a cancer or one or more symptoms thereof. In a specific embodiment, the invention provides a method of preventing, treating, managing or ameliorating cancer or one or more symptoms thereof, said method comprising administering to a subject in need thereof a dose of a prophylactically or therapeutically effective amount of a liquid formulation of the invention. In another embodiment, the invention provides a method of preventing, treating or ameliorating cancer or one or more symptoms thereof, said method comprising administering to a subject in need thereof a dose of a prophylactically or therapeutically effective amount of a liquid formulation of the invention and a dose of a prophylactically or therapeutically effective amount of one or more therapies (e.g., prophylactic or therapeutic agents other than antibodies (including antibody fragments thereof) that immunospecifically bind to an IL-9 polypeptide).

The liquid formulations of the invention may be used as a first, second, third or fourth line cancer treatment. The invention provides methods for treating or ameliorating one or more symptoms of a cancer in a subject refractory to conventional therapies for such a cancer, said methods comprising administering to said subject a dose of a prophylactically or therapeutically effective amount of a liquid formulation of the invention. A cancer may be determined to be refractory to a therapy means when at least some significant portion of the cancer cells are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

The invention provides methods for managing, treating or ameliorating cancer or one or more symptoms thereof in a subject refractory to existing single agent therapies for such a cancer, said methods comprising administering to said subject a dose of a prophylactically or therapeutically effective amount of a liquid formulation of the invention and a dose of a prophylactically or therapeutically effective amount of one or more therapies (e.g., prophylactic or therapeutic agents) other than antibodies (including antibody fragments thereof) that immunospecifically bind to an IL-9 polypeptide. The invention also provides methods for managing, treating or ameliorating cancer by administering a liquid formulation of the invention in combination with any other treatment (e.g., radiation therapy, chemotherapy or surgery) to patients who have proven refractory to other treatments but are no longer on these treatments. The invention also provides methods for the management or treatment of a patient having cancer and immunosuppressed by reason of having previously undergone other cancer therapies. The invention also provides alternative methods for the management, treatment or amelioration of cancer or one or more symptoms thereof, where chemotherapy, radiation therapy, hormonal therapy, and/or biological therapy/immunotherapy has proven or may prove too toxic, i.e., results in unacceptable or unbearable side effects, for the subject being treated. Further, the invention provides methods for preventing the recurrence of cancer in patients that have been treated and have no disease activity by administering a liquid formulation of the invention.

Cancers that can be treated by the methods encompassed by the invention include, but are not limited to, neoplasms, tumors, metastases, or any disease or disorder characterized by uncontrolled cell growth. The cancer may be a primary or metastatic cancer. The cancer may or may not express an IL-9R. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone cancer and connective tissue sarcomas such as but not limited to bone sarcoma, myeloma bone disease, osteosarcoma, chondrosarcoma, Ewing's sarcoma, Paget's disease of bone, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease), and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

5.5.1.1. Anti-Cancer Therapies

The present invention provides methods of preventing, managing, treating or ameliorating cancer or one or more symptoms thereof, said methods comprising administering to a subject in need thereof a liquid formulation of the invention and one or more therapies (e.g. prophylactic or therapeutic agents) other than antibodies (including antibody fragments thereof) that immunospecifically bind to an IL-9 polypeptide. Therapeutic or prophylactic agents include, but are not limited to, peptides, polypeptides, proteins, fusion proteins, nucleic acid molecules, small molecules, mimetic agents, synthetic drugs, inorganic molecules, and organic molecules. Any agent or therapy (e.g., chemotherapies, radiation therapies, hormonal therapies, and/or biological therapies/immunotherapies) which is known to be useful, or which has been used or is currently being used for the prevention, treatment, management or amelioration of cancer or one or more symptoms thereof can be used in combination with a liquid formulation of the invention in accordance with the invention described herein.

In certain embodiments, the anti-cancer agent is an immunomodulatory agent, such as a chemotherapeutic agent. In certain other embodiments, the anti-cancer agent is an immunomodulatory agent other than a chemotherapeutic agent. In other embodiments, the anti-cancer agent is not an immunomodulatory agent. In specific embodiments, the anti-cancer agent is an anti-angiogenic agent. In other embodiments, the anti-cancer agent is not an anti-angiogenic agent. In specific embodiments, the anti-cancer agent is an anti-inflammatory agent. In other embodiments, the anti-cancer agent is not an anti-inflammatory agent.

In particular embodiments, the anti-cancer agent is, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandomate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; EphA2 inhibitors (e.g., anti-EphA2 antibodies that result in the phosphorylation of EphA2 and the degration of EphA2 (see, U.S. Patent Application No. 60/418,213, which is incorporated herein by reference in its entirety); elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. U.S. 2002/0168360 A1, dated Nov. 14, 2002, entitled "Methods of Preventing or Treating Inflammatory or Autoimmune Disorders by Administering Integrin $\alpha_v\beta3$ Antagonists in Combination With Other Prophylactic or Therapeutic Agents"); vorozole; zanoterone; zeniplatin; zilascorb; and zinostatin stimalamer. In another preferred embodiment, an antibody derivative such as MT103, part of a class of antibody derivatives known as Bi-Specific T Cell Engagers (BiTE™; MedImmune, Inc.), may also be used in combination with one or more liquid formulations of the present invention.

Other examples of anti-cancer agents include, but are not limited to, angiogenesis inhibitors, topoisomerase inhibitors and immunomodulatory agents (such as chemotherapeutic agents and non-therapeutic immunomodulatory agents, including but not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., HERCEPTIN®).

The invention also encompasses administration of a liquid formulation of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

In specific embodiments, patients with breast cancer are administered a prophylactically or therapeutically effective amount of a liquid formulation of the invention in combination with the administration of a prophylactically or therapeutically effective amount of one or more other agents useful for breast cancer therapy including but not limited to: doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), Herceptin®, tamoxifen, the combination of tamoxifen and cytotoxic chemotherapy. In certain embodiments, patients with metastatic breast cancer are administered a prophylactically or therapeutically effective amount of one or more liquid formulations of the invention in combination with the administration of an effective amount of taxanes such as docetaxel and paclitaxel. In other embodiments, a prophylactically or therapeutically effective amount of a liquid formulation of the invention is administered in combination with the administration of a prophylactically or therapeutically effective amount of taxanes plus standard doxorubicin and cyclophosphamide for adjuvant treatment of node-positive, localized breast cancer.

In specific embodiments, patients with prostate cancer are administered a prophylactically or therapeutically effective amount of a liquid formulation of the invention in combination with the administration of a prophylactically or therapeutically effective amount of one or more other agents useful for prostate cancer therapy including but not limited to: external-beam radiation therapy, interstitial implantation of radioisotopes (i.e., $I^{125}$, palladium, Iridium), leuprolide or other LHRH agonists, non-steroidal antiandrogens (flutamide, nilutamide, bicalutamide), steroidal antiandrogens (cyproterone acetate), the combination of leuprolide and flutamide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxel, paclitaxel, estramustine/docetaxel, estramustine/etoposide, estramustine/vinblastine, and estramustine/paclitaxel. In specific embodiments, patients with ovarian cancer are administered a prophylactically or therapeutically effective amount of a liquid formulation of the invention in combination with a prophylactically or therapeutically effective amount of one or more other agents useful for ovarian cancer therapy including but not limited to: intraperitoneal radiation therapy, such as $p^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. It is contemplated that a prophylactically or therapeutically effective amount of a liquid formulation of the invention is administered in combination with the administration Taxol for patients with platinum-refractory disease. Included is the treatment of patients with refractory ovarian cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors. In specific embodiments, patients with bone sarcomas are administered a prophylactically or therapeutically effective amount of a liquid formulation of the invention in combination with a prophylactically or therapeutically effective amount of one or more other agents useful for bone sarcoma therapy including but not limited to: doxorubicin, ifosfamide, cisplatin, high-dose methotrexate, cyclophosphamide, etoposide, vincristine, dactinomycin, and surgery.

In specific embodiments, patients with tumor metastatic to bone are administered a prophylactically or therapeutically effective amount of a liquid formulation of the invention in combination with a prophylactically or therapeutically effective amount of one or more other agents useful for bone metastatic tumor therapy including but not limited to: agents or therapies used in treatment of underlying malignancy (non-limiting examples are hormone inhibitors for prostate or breast cancer metastasized to bone and surgery), radiotherapy (non-limiting examples are strontium 89 and samarium 153, which are bone-seeking radionuclides that can exert antitumor effects and relieve symptoms), and bisphosponates.

Cancer therapies and their dosages, routes of administration and recommended usage are known in the art and have been described in such literature as the *Physician's Desk Reference* (59$^{th}$ ed., 2005).

5.5.2. Proliferative Disorders

The liquid antibody formulations of the invention can be used to prevent, treat, manage, and/or ameliorate a proliferative disorder or one or more symptoms thereof. In a specific embodiment, the proliferative disorder is characterized by aberrant proliferation (e.g. uncontrolled proliferation or lack of proliferation) of cells that IL-9 mediates the growth of, including, but not limited to T cells, erythroid progenitors, B cells, mast cells, eosinophils, neutrophils, and fetal thymocytes.

The present invention provides methods for preventing, treating, managing, and/or ameliorating one or more symptoms of a non-cancerous disorder (i.e., a disorder that does not have the potential to metasasize) associated with IL-9 mediated cellular hyperproliferation, particularly of epithelial cells (e.g., as in asthma, COPD, lung fibrosis, bronchial hyperresponsiveness, psoriasis, lymphoproliferative disorder, and seborrheic dermatitis) and endothelial cells (e.g., as in restenosis, hyperproliferative vascular disease, Behcet's Syndrome, atherosclerosis, and macular degeneration), said methods comprising administering to a subject in need thereof an effective amount of one or more antibodies of the invention. The present invention also provides methods for preventing, managing, treating, and/or ameliorating a non-cancerous disorder associated with IL-9 mediated cellular hyperproliferation, said methods comprising of administering to a subject in need thereof an effective amount of one or more antibodies of the invention and an effective amount of one or more other therapies (e.g., one or more prophylactic or therapeutic agents) other than antibodies of the invention useful for the prevention, treatment, management, and/or amelioration of said disorder.

The invention provides methods for preventing, treating, managing, and/or ameliorating one or more symptoms of a non-cancerous disorder associated with IL-9 mediated cellular hyperproliferation in a subject refractory to conventional therapies for such disorder, said methods comprising administering to subject an effective amount of one or more antibodies, compositions, or combination therapies of the invention. In certain embodiments, a patient with a non-cancerous disorder associated with IL-9 mediated cellular hyperproliferation is refractory to a therapy when the hyperproliferation has not been eradicated and/or the symptoms have not been alleviated. The determination of whether a patient is refractory can be made either in vivo or in vitro by any method known in the art for assaying the effectiveness of a treatment of non-cancerous hyperproliferation disorders, using art-accepted meanings of "refractory" such a context. In various embodiments, a patient with a non-cancerous disorder associated with IL-9 mediated cellular hyperproliferation is refractory when the patient's levels of IL-9 remain abnormal and/or if cellular proliferation has not been decreased. The present invention also provides methods for preventing, managing, treating, and/or ameliorating a non-cancerous disorder associated with IL-9 mediated cellular hyperproliferation in a subject refractory to conventional therapies for such disorder, said methods comprising of administering to a subject in need thereof an effective amount of one or more antibody formulations of the invention and an effective amount of one or more other therapies (e.g., one or more prophylactic or therapeutic agents) other than antibody formulations of the invention useful for the prevention, treatment, management, and/or amelioration of said disorder.

In a specific embodiment, an effective amount of one or more antibodies of the invention is administered in combination with an effective amount of a liquid formulation of the invention containing an antibody (including antibody fragment thereof), (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4) to a subject at risk of or with a proliferative disorder. The liquid antibody formulations of the invention or combination therapies of the invention may be used as the first, second, third, fourth, or fifth therapy to prevent, manage, treat, and/or ameliorate a proliferative disorder or one or more symptom thereof. The invention also includes methods of preventing, treating, managing, and/or ameliorating a proliferative disorder or one or more symptoms thereof in a patient undergoing therapies for other disease or disorders. The invention encompasses methods of preventing, managing, treating, and/or ameliorating a proliferative disorder or one or more symptoms thereof in a patient before any adverse effects or intolerance to therapies other than antibodies of the invention develops. The invention also encompasses methods of preventing, managing, treating, and/or ameliorating a proliferative disorder or a symptom thereof in patients who are susceptible to adverse reactions to conventional therapies.

The invention encompasses methods for preventing, treating, managing, and/or ameliorating a proliferative disorder or a symptom thereof in a patient who has proven refractory to therapies other than antibodies, compositions, or combination therapies of the invention. In certain embodiments, a patient with a proliferative disorder is refractory to a therapy when proliferation disorders has not been eradicated and/or the symptoms have not been alleviated. The determination of whether a patient is refractory can be made either in vivo or in vitro by any method known in the art for assaying the effectiveness of a treatment of proliferative disorders, using art-accepted meanings of "refractory" such a context. In various embodiments, a patient with a proliferative disorder is refractory when the patient's levels of IL-9 remain abnormal and/or if cellular proliferation has not been decreased.

The present invention provides methods for preventing, treating, managing, and/or ameliorating a proliferative disorder or one or more symptoms thereof as an alternative to other conventional therapies. In specific embodiments, the patient being managed or treated in accordance with the methods of the invention is to other therapies or is susceptible to adverse reactions from such therapies. The patient may be a person with a suppressed immune system (e.g., post-operative patients, chemotherapy patients, and patients with immunodeficiency disease), a person with impaired renal or liver function, the elderly, children, infants, persons with neuropsychiatric disorders or those who take psychotropic drugs, persons with histories of seizures, or persons on medication that would negatively interact with conventional agents used to manage or treat a proliferative disorder.

Therapies and dosages, routes of administration, and recommended usage of therapies for preventing, treating, managing, and/or ameliorating proliferative disorders or one or more symptoms thereof are known in the art and have been described in such literature as the *Physician's Desk Reference* (59th ed., 2005).

5.5.3. Inflammatory Disorder Treatment

The liquid formulations of the invention may be administered to a subject in need thereof to prevent, manage, treat or ameliorate an inflammatory disorder (e.g., asthma) or one or more symptoms thereof. The liquid formulations of the invention may also be administered in combination with one or more other therapies, preferably therapies useful for the prevention, management, treatment or amelioration of an inflammatory disorder (including, but not limited to the prophylactic or therapeutic agents listed in Section 5.5.3.1 hereinbelow) to a subject in need thereof to prevent, manage, treat or ameliorate an inflammatory disorder or one or more symptoms thereof. In a specific embodiment, the invention provides a method of preventing, managing, treating or ameliorating an inflammatory disorder or one or more symptoms thereof, said method comprising administering to a subject in need thereof a dose of a prophylactically or therapeutically effective amount of a liquid formulation of the invention. In another embodiment, the invention provides a method of preventing, managing, treating or ameliorating an inflammatory disorder or one or more symptoms thereof, said method comprising administering to a subject in need thereof a dose of a prophylactically or therapeutically effective amount of a liquid formulation of the invention and a dose of a prophylactically or therapeutically effective amount of one or more therapies (e.g., prophylactic or therapeutic agents) other than antibodies (including antibody fragments thereof) that immunospecifically bind to an IL-9 polypeptide.

The invention provides methods for managing, treating or ameliorating one or more symptoms of an inflammatory disorder in a subject refractory to conventional therapies (e.g., methotrexate and a TNF-α antagonist (e.g., REMICADE™ or ENBREL™)) for such an inflammatory disorder, said methods comprising administering to said subject a dose of a prophylactically or therapeutically effective amount of a liquid formulation of the invention. The invention also provides methods for managing, treating or ameliorating one or more symptoms of an inflammatory disorder in a subject refractory to existing single agent therapies for such an inflammatory disorder, said methods comprising administering to said subject a dose of a prophylactically or therapeutically effective amount of a liquid formulation of the invention and a dose of a prophylactically or therapeutically effective amount of one or more therapies (e.g., prophylactic or therapeutic agents) other than antibodies (including antibody fragments thereof) that immunospecifically bind to an IL-9 polypeptide. The invention also provides methods for managing or treating an inflammatory disorder by administering a liquid formulation of the invention in combination with any other treatment to patients who have proven refractory to other treatments but are no longer on these treatments. The invention also provides alternative methods for the treatment of an inflammatory disorder where another therapy has proven or may prove too toxic, i.e., results in unacceptable or unbearable side effects, for the subject being treated. For example, the liquid formulations of the invention may be administered to a subject, wherein the subject is refractory to a TNF antagonist or methotrexate. Further, the invention provides methods for preventing the recurrence of an inflammatory disorder in patients that have been treated and have no disease activity by administering a liquid formulation of the invention.

Inflammatory disorders that can be treated by the methods encompassed by the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, osteoarthritis, spondyloarthropathies (e.g., psoriatic arthritis, ankylosing spondylitis, Reiter's Syndrome (reactive arthritis), inflammatory osteolysis, Wilson's disease and chronic inflammation resulting from chronic viral or bacteria infections. As described herein in Section 5.5.4.1, some autoimmune disorders are associated with an inflammatory condition.

Anti-inflammatory therapies and their dosages, routes of administration and recommended usage are known in the art and have been described in such literature as the *Physician's Desk Reference* (59th ed., 2005).

5.5.3.1. Anti-Inflammatory Therapies

The present invention provides methods of preventing, managing, treating or ameliorating an inflammatory disorder or one or more symptoms thereof, said methods comprising administering to a subject in need thereof a liquid formulation of the invention and one or more therapies (e.g., prophylactic or therapeutic agents other than antibodies (including antibody fragments thereof) that immunospecifically bind to an IL-9 polypeptide. Any agent or therapy which is known to be useful, or which has been used or is currently being used for the prevention, management, treatment or amelioration of an inflammatory disorder or one or more symptoms thereof can be used in combination with a liquid formulation of the invention in accordance with the invention described herein.

Any anti-inflammatory agent, including agents useful in therapies for inflammatory disorders, well-known to one of skill in the art can be used in the compositions and methods of the invention. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes (see Table 2, infra, for non-limiting examples of leukotriene and typical dosages of such agents)).

In a specific embodiment, an effective amount of one or more antibodies of the invention is administered in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3

Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin $\alpha_v\beta_3$ Antagonists in Combination With Other Prophylactic or Therapeutic Agents," and International Publication No. WO 03/075741 A2, dated Sep. 18, 2003, entitled, "Methods of Preventing or Treating Disorders by Administering an Integrin $\alpha v\beta_3$ Antagonist in Combination With an HMG-CoA Reductase Inhibitor or a Bisphosphonate," each of which is incorporated herewith by reference in its entirety) to a subject to prevent, treat, manage, and/or ameliorate an inflammatory disorder or one or more symptoms thereof. In another embodiment, an effective amount of one or more antibodies of the invention is administered in combination with an effective amount of siplizumab (MedImmune, Inc., International Publication No. WO 02/069904) to a subject to prevent, treat, manage, and/or ameliorate an inflammatory disorder or one or more symptoms thereof. In another embodiment, an effective amount of one or more antibodies of the invention is administered in combination with an effective amount of one or more EphA2 inhibitors (e.g., one or more anti-EphA2 antibodies (MedImmune, Inc.; International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Appn. No. 10/436,783; and U.S. Appn. No. 60/379,368, each of which is incorporated herewith by reference)) to a subject to prevent, treat, manage, and/or ameliorate an inflammatory disorder or one or more symptoms thereof. In yet another preferred embodiment, an effective amount of one or more antibodies of the invention is administered in combination with an effective amount of VITAXIN™, siplizumab, and/or EphA2 inhibitor to a subject to prevent, treat, manage, and/or ameliorate an inflammatory disorder or one or more symptoms thereof.

In one embodiment, an effective amount of one or more antibody formulations of the invention is administered in combination with a mast cell protease inhibitor to a subject at risk of or with an inflammatory disorder. In another embodiment, the mast cell protease inhibitor is a tryptase kinase inhibitor, such as, but not limited to GW-45, GW-58, and genisteine. In a specific embodiment, the mast cell protease inhibitor is phosphatidylinositide-3' (PI3)-kinase inhibitors, such as, but not limited to calphostin C. In another embodiment, the mast cell protease inhibitor is a protein kinase inhibitor such as, but not limited to staurosporine. In accordance with this embodiments, the mast cell protease inhibitor is preferably administered locally to the affected area.

Specific examples of immunomodulatory agents which can be administered in combination with a liquid formulation of the invention to a subject with an inflammatory disorder include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-$\alpha$ antibodies, anti-IL-1$\beta$ antibodies, anti-IL-6 antibodies, anti-IL-8 antibodies (e.g., ABX-IL-8 (Abgenix)), and anti-IL-12 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-a receptor or a fragment thereof, the extracellular domain of an IL-1$\beta$ receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, TNF-$\alpha$, TNF-$\beta$, interferon (IFN)-$\alpha$, IFN-$\beta$, IFN-$\gamma$, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-$\alpha$ antibodies, and anti-IFN-$\gamma$ antibodies).

Any TNF-$\alpha$ antagonist well-known to one of skill in the art can be used in the compositions and methods of the invention. Non-limiting examples of TNF-$\alpha$ antagonists which can be administered in combination with a liquid formulation of the invention to a subject with an inflammatory disorder include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-$\alpha$, nucleic acid molecules (e.g., antisense molecules or triple helices), organic molecules, inorganic molecules, and small molecules that blocks, reduces, inhibits or neutralizes the function, activity and/or expression of TNF-$\alpha$. In various embodiments, a TNF-$\alpha$ antagonist reduces the function, activity and/or expression of TNF-$\alpha$ by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS). Examples of antibodies that immunospecifically bind to TNF-$\alpha$ include, but are not limited to, infliximab (REMICADE™; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of antibodies that immunospecifically bind to TNF-$\alpha$ disclosed in the following U.S. Pat. Nos. in the compositions and methods of the invention: 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; each of which are herein incorporated by reference in their entirety. Examples of soluble TNF-$\alpha$ receptors include, but are not limited to, sTNF-R1 (Amgen), etanercept (ENBREL™; Immunex) and its rat homolog RENBREL™, soluble inhibitors of TNF-α derived from TNFrI, TNFrII (Kohno et al., 1990, Proc. Natl. Acad. Sci. USA 87:8331-8335), and TNF-α Inh (Seckinger et al, 1990, Proc. Natl. Acad. Sci. USA 87:5188-5192).

Other TNF-α antagonists encompassed by the invention include, but are not limited to, IL-10, which is known to block TNF-α production via interferon γ-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Serono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

Non-limiting examples of anti-inflammatory agents which can be administered in combination with a liquid formulation of the invention to a subject with an inflammatory disorder include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In specific embodiments, patients with osteoarthritis are administered a prophylactically or therapeutically effective amount of a liquid formulation of the invention in combination with other agents or therapies useful for osteoarthritis prevention, treatment, management or amelioration including but not limited to: analgesics (non-limiting examples are acetaminophen, in a dose up to 4000 mg/d; phenacetin; and tramadol, in a daily dose in the range of 200 to 300 mg); NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin. Low dose NSAIDs are preferred, e.g., ibuprofen at 1200 mg/d, naproxen at 500 mg/d. A gastroprotective agent, e.g., misoprostol, famotidine or omeprazole, is preferred to use concurrently with a NSAID); nonacetylated salicylates including but not limited to salsalate; cyclooxygenase (Cox)-2-specific inhibitors (CSIs), including but not limited to, celecoxib and rofecoxib; intra- or periarticular injection of a depot glucocorticoid preparation; intra-articular injection of hyaluronic acid; capsaicin cream; copious irrigation of the osteroarthritis knee to flush out fibrin, cartilage shards and other debris; and joint replacement surgery. The liquid formulations of the invention can also be used in combination with other nonpharmacologic measures in prevention, treatment, management and amelioration of osteoarthritis including but not limited to: reduction of joint loading (non-limiting examples are correction of poor posture, support for excessive lumbar lordosis, avoid excessive loading of the involved joint, avoid prolonged standing, kneeling and squatting); application of heat to the affected joint; aerobic exercise and other physical therapies.

In specific embodiments, patients with rheumatoid arthritis are administered a prophylactically or therapeutically effective amount of a liquid formulation of the invention in combination with other agents or therapies useful in prevention, treatment, management and amelioration of rheumatoid arthritis including but not limited to: NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin.); analgesics (non-limiting examples are acetaminophen, phenacetin and tramadol); CSIs including but not limited to, celecoxib and rofecoxib; glucocorticoids (preferably low-dose oral glucocorticoids, e.g., <7.5 mg/d prednisone, or monthly pulses with high-dose glucocorticoids, or intraarticular glucocorticoids); disease-modifying antirheumatic drugs (DMARDs) including but not limited to, methotrexate (preferably given intermittent low dose, e.g., 7.5-30 mg once weekly), gold compounds (e.g., gold salts), D-penicillamine, the antimalarials (e.g., chloroquine), and sulfasalazine; TNF-α neutralizing agents including but not limited to, etanercept and infliximab; immunosuppressive and cytotoxic agents (examples include but not limited to, azathioprine, leflunomide, cyclosporine, and cyclophosphamide), and surgery (examples include but not limited to, arthroplasties, total joint replacement, reconstructive hand surgery, open or arthroscopic synovectomy, and early tenosynovectomy of the wrist). The liquid formulations of the invention may also be used in combination with other measures in prevention, treatment, management and amelioration of the rheumatoid arthritis including but not limited to: rest, splinting to reduce unwanted motion of inflamed joint, exercise, used of a variety of orthotic and assistive devices, and other physical therapies. The liquid formulations of the invention may also be used in combination with some non-traditional approaches in prevention, treatment, management and amelioration of rheumatoid arthritis including but not limited to, diets (e.g., substituting omega-3 fatty acids such as eicosapentaenoic acid found in certain fish oils for dietary omega-6 essential fatty acids found in meat), vaccines, hormones and topical preparations.

In specific embodiments, patients with chronic obstructive pulmonary disease (COPD) are administered a prophylactically or therapeutically effective amount of a liquid formulation of the invention in combination with other agents or therapies useful in prevention, treatment, management and amelioration of COPD including but not limited to: bronchodilators including but not limited to, short- and long-acting $\beta_2$-adrenergic agonists (examples of short-acting $\beta_2$ agonist include but not limited to, albuterol, pirbuterol, terbutaline, and metaproterenol; examples of long-acting $\beta_2$ agonist include but not limited to, oral sustained-release albuterol and inhaled salmeterol), anticholinergics (examples include but not limited to ipratropium bromide), and theophylline and its derivatives (therapeutic range for theophylline is preferably 10-20 µg/mL); glucocorticoids; exogenous $\alpha_1$AT (e.g., $\alpha_1$AT derived from pooled human plasma administered intravenously in a weekly dose of 60 mg/kg); oxygen; lung transplantation; lung volume reduction surgery; endotracheal intubation, ventilation support; yearly influenza vaccine and pneumococcal vaccination with 23-valent polysaccharide; exercise; and smoking cessation.

In specific embodiments, patients with pulmonary fibrosis are administered a prophylactically or therapeutically effective amount of a liquid formulation of the invention in combination with an effective amount of one or more other agents useful for pulmonary fibrosis therapy including but not limited to: oxygen; corticosteroids (a non-limiting example is to administer daily prednisone beginning at 1-1.5 mg/kg/d (up to 100 mg/d) for six weeks and tapering slowly over 3-6 months to a minimum maintenance dose of 0.25 mg/kg/d); cytotoxic drugs (non-limiting examples are cyclophosphamide at 100-120 mg orally once daily, and azathioprine at 3 mg/kg up to 200 mg orally once daily); bronchodilators (non-limiting examples are short- and long-acting $\beta_2$-adrenergic agonists, anticholinergics, and theophylline and its derivatives); and antihistamines (non-limiting examples are diphenhydramine and doxylamine).

In specific embodiments, patients with asthma are administered a prophylactically or therapeutically effective amount of a liquid formulation of the invention in combination with an effective amount of one or more other agents useful for asthma therapy. Non-limiting examples of such agents include adrenergic stimulants (e.g., catecholamines (e.g., epinephrine, isoproterenol, and isoetharine), resorcinols (e.g., metaproterenol, terbutaline, and fenoterol), and saligenins (e.g., salbutamol)), adrenocorticoids, blucocorticoids, corticosteroids (e.g., beclomethadonse, budesonide, flunisolide, fluticasone, triamcinolone, methylprednisolone, prednisolone, and prednisone), other steroids, beta2-agonists (e.g., albtuerol, bitolterol, fenoterol, isoetharine, metaproterenol, pirbuterol, salbutamol, terbutaline, formoterol, salmeterol, and albutamol terbutaline), anti-cholinergics (e.g., ipratropium bromide and oxitropium bromide), IL-4 antagonists (including antibodies), IL-5 antagonists (including antibodies), IL-13 antagonists (including antibodies), PDE4-inhibitor, NF-Kappa-$\beta$ inhibitor, VLA-4 inhibitor, CpG, anti-CD23, selectin antagonists (TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine) (see Temkin et al., 2002 J Immunol 169(5):2662-2669; Vosseller et al., 1997 Mol. Biol. Cell 8(5): 909-922; and Nagai et al., 1995 Biochem Biophys Res Commun 208(2):576-581)), a C3 receptor antagonists (including antibodies), immunosuppressant agents (e.g., methotrexate and gold salts), mast cell modulators (e.g., cromolyn sodium (INTAL™) and nedocromil sodium (TILADE™)), and mucolytic agents (e.g., acetylcysteine)). In a specific embodiment, the anti-inflammatory agent is a leukotriene inhibitor (e.g., montelukast (SINGULAIR™), zafirlukast (ACCOLATE™), pranlukast (ONON™), or zileuton (ZYFLO™) (see Table 2)).

TABLE 2

Leukotriene Inhibitors for Asthma Therapy

| Leukotriene Modifier | Usual Daily Dosage |
|---|---|
| Montelukast (SINGULAIR ™) | 4 mg for 2-5 years old |
|  | 5 mg for 6 to 15 years old |
|  | 10 mg for 15 years and older |
| Zafirlukast (ACCOLATE ™) | 10 mg b.i.d. for 5 to 12 years old twice daily |
|  | 20 mg b.i.d. for 12 years or older twice daily |
| Pranlukast (ONON ™) | Only avialable in Asia |

TABLE 2-continued

Leukotriene Inhibitors for Asthma Therapy

| Leukotriene Modifier | Usual Daily Dosage |
|---|---|
| Zyleuton (ZYFLO ™) | 600 mg four times a day for 12 years and older |

In specific embodiments, patients with allergy are administered a prophylactically or therapeutically effective amount of a liquid formulation of the invention in combination with an effective amount of one or more other agents useful for allergy therapy. Non-limiting examples of such agents include antimediator drugs (e.g., antihistamine, see Table 3, infra for non-limiting examples of antihistamine and typical dosages of such agents), corticosteroids, decongestants, sympathomimetic drugs (e.g., $\alpha$-adrenergic and $\beta$-adrenergic drugs), TNX901 (Leung et al., 2003, N Engl J Med 348(11): 986-993), IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12): 696-704), HMK-12 and 6HD5 (see Miyajima et al., 2202 Int Arch Allergy Immuno 128(1):24-32), and mAB Hu-901 (see van Neerven et al., 2001 Int Arch Allergy Immuno 124(1-3):400), theophylline and its derivatives, glucocorticoids, and immunotherapies (e.g., repeated long-term injection of allergen, short course desensitization, and venom immunotherapy).

TABLE 3

$H_1$ Antihistamines

| Chemical class and representative drugs | Usual daily dosage |
|---|---|
| Ethanolamine | |
| Diphehydramine | 25-50 mg every 4-6 hours |
| Clemastine | 0.34-2.68 mg every 12 hours |
| Ethylenediamine | |
| Tripelennamine | 25-50 mg every 4-6 hours |
| Alkylamine | |
| Brompheniramine | 4 mg every 4-6 hours; or 8-12 mg of SR form every 8-12 hour |
| Chlorpheniramine | 4 mg every 4-6 hours; or 8-12 mg of SR form every 8-12 hour |
| Triprolidine (1.25 mg/5 ml) | 2.5 mg every 4-6 hours |
| Phenothiazine | |
| Promethazine | 25 mg at bedtime |
| Piperazine | |
| Hydroxyzine | 25 mg every 6-8 hours |
| Piperidines | |
| Astemizole (nonsedating) | 10 mg/d |
| Azatadine | 1-2 mg every 12 hours |
| Cetirzine | 10 mg/d |
| Cyproheptadine | 4 mg every 6-8 hour |
| Fexofenadine (nonsedating) | 60 mg every 12 hours |
| Loratidine (nonsedating) | 10 mg every 24 hours |

5.5.4. Autoimmune Disorder Treatment

The liquid formulations of the invention may be administered to a subject in need thereof to prevent, manage, treat or ameliorate an autoimmune disorder or one or more symptoms thereof. The liquid formulations of the invention may also be administered in combination with one or more other therapies, preferably therapies useful for the prevention, management or treatment of an autoimmune disorder (including, but not limited to the prophylactic or therapeutic agents listed in Section 5.5.4.1 hereinbelow) to a subject in need thereof to prevent, manage, treat or ameliorate an autoimmune disorder or one or more symptoms thereof. In a specific embodiment, the invention provides a method of preventing, managing, treating or ameliorating an autoimmune disorder or one or more symptoms thereof, said method comprising administering to a subject in need thereof a dose of a prophylactically or therapeutically effective amount of a liquid formulation of the invention. In another embodiment, the invention provides a method of preventing, managing, treating or ameliorating an autoimmune disorder or one or more symptoms thereof, said method comprising administering to a subject in need thereof a dose of a prophylactically or therapeutically effective amount of a liquid formulation of the invention and a dose of a prophylactically or therapeutically effective amount of one or more therapies (e.g., prophylactic or therapeutic agents) other than antibodies (including antibody fragments thereof) that immunospecifically bind to an IL-9 polypeptide.

The invention provides methods for managing, treating or ameliorating an autoimmune disorder or one or more symptoms thereof in a subject refractory to conventional therapies for such an autoimmune disorder, said methods comprising administering to said subject a dose of a prophylactically or therapeutically effective amount of a liquid formulation of the invention. The invention also provides methods for managing, treating or ameliorating an autoimmune disorder or one or more symptoms thereof in a subject refractory to existing single agent therapies for such an autoimmune disorder, said methods comprising administering to said subject a dose of a prophylactically or therapeutically effective amount of a liquid formulation of the invention and a dose of a prophylactically or therapeutically effective amount of one or more therapies (e.g., prophylactic or therapeutic agents) other than antibodies (including antibody fragments thereof) that immunospecifically bind to an IL-9 polypeptide. The invention also provides methods for managing, treating or ameliorating an autoimmune disorder or one or more symptoms thereof by administering a liquid formulation of the invention in combination with any other treatment to patients who have proven refractory to other treatments but are no longer on these treatments. The invention also provides alternative methods for the management or treatment of an autoimmune disorder where another therapy has proven or may prove too toxic, i.e., results in unacceptable or unbearable side effects, for the subject being treated. Particularly, the invention provides alternative methods for the management or treatment of an autoimmune disorder where the patient is refractory to other therapies. Further, the invention provides methods for preventing the recurrence of an autoimmune disorder in patients that have been treated and have no disease activity by administering a liquid formulation of the invention.

In autoimmune disorders, the immune system triggers an immune response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders that can be treated by the methods of the invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Autoimmune therapies and their dosages, routes of administration and recommended usage are known in the art and have been described in such literature as the *Physician's Desk Reference* (59th ed., 2005).

5.5.4.1. Autoimmune Disorder Therapies

The present invention provides methods of preventing, managing, treating or ameliorating an autoimmune disorder or one or more symptoms thereof, said methods comprising administering to a subject in need thereof a liquid formulation of the invention and one or more therapies (e.g., prophylactic or therapeutic agents) other than antibodies (including antibody fragments thereof) that immunospecifically bind to an IL-9 polypeptide. Any agent or therapy which is known to be useful, or which has been used or is currently being used for the prevention, management, treatment or amelioration of an autoimmune disorder or one or more symptoms thereof can be used in combination with a liquid formulation of the invention in accordance with the invention described herein. Examples of such agents include, but are not limited to, immunomodulatory agents, anti-inflammatory agents and TNF-α antagonists. Specific examples of immunomodulatory agents, anti-inflammatory agents and TNF-α antagonists which can be used in combination with a liquid formulation of the invention for the prevention, management, treatment or amelioration of an autoimmune disorder are disclosed herein above.

In specific embodiments, patients with multiple sclerosis (MS) are administered a prophylactically or therapeutically effective amount of a liquid formulation of the invention in combination with other agents or therapies useful in prevention, treatment, management and amelioration of MS including but not limited to: IFN-β1b (Betaseron) (e.g., 8.0 million international unites (MIU) is administered by subcutaneous injection every other day); IFN-β1a (Avonex) (e.g., 6.0 MIU is administered by intramuscular injection once every week); glatiramer acetate (Copaxone) (e.g., 20 mg is administered by subcutaneous injection every day); mitoxantrone (e.g., 12 mg/m$^2$ is administered by intravenous infusion every third month); azathioprine (e.g., 2-3 mg/kg body weight is administered orally each day); methotrexate (e.g., 7.5 mg is administered orally once each week); cyclophosphamide; intravenous immunoglobulin (e.g., 0.15-0.2 g/kg body weight administered monthly for up to 2 years); glucocorticoids; methylprednisolone (e.g., administered in bimonthly cycles at high doses); 2-chlorodeoxyadenosine (cladribine); baclofen (e.g., 15 to 80 mg/d in divided doses, or orally in higher doses up to 240 mg/d, or intrathecally via an indwelling catheter); cycloenzaprine hydrochloride (e.g., 5-10 mg bid or tid); clonazepam (e.g., 0.5 to 1.0 mg tid, including bedtime dose); clonidine hydrochloride (e.g., 0.1 to 0.2 mg tid, including a bedtime dose); carbamazepine (e.g., 100-1200 mg/d in divided, escalating doses); gabapentin (e.g., 300-3600 mg/d); dilantin (e.g., 300-400 mg/d); amitriptyline (e.g., 25-150 mg/d); baclofen (e.g., 10-80 mg/d); primidone (e.g., 125-250 mg bid or tid); ondansetron (e.g., 4 to 8 mg bid or tid); isoniazid (e.g., up to 1200 mg in divided doses); oxybutynin (e.g., 5 mg bid or tid); tolterodine (e.g., 1-2 mg bid); propantheline (e.g., 7.5 to 15 mg qid); bethanecol (e.g., 10-50 mg tid or qid); terazosin hydrochloride (e.g., 1-5 mg at bedtime); sildenafil citrate (e.g., 50-100 mg po prn); amantading (e.g., 100 mg bid); pemoline (e.g., 37.5 mg bid); high dose vitamins; calcium orotate; gancyclovir; antibiotic; and plasma exchange.

In specific embodiments, patients with psoriasis are administered a prophylactically or therapeutically effective amount of a liquid formulation of the invention in combination with other agents or therapies useful in prevention, treatment, management and amelioration of psoriasis including but not limited to: topical steroid cream or ointment; tar (examples including but not limited to, Estar, Psorigel, Fototar cream, and LCD 10% in Nutraderm lotion or mixed directly with triamcinolone 0.1% cream); occlusion; topical vitamin D analogue (a non-limiting example is calcipotriene ointment); ultraviolet light; PUVA (psoralen plus ultraviolet A); methotrexate (e.g., up to 25 mg once weekly or in divided doses every 12 hours for three doses once a week); synthetic retinoid (a non-limiting examples is etretinate, e.g., in dosage of 0.5-1 mg/kg/d); immunomodulatory therapy (a non-limiting example is cyclosporine); sulfasalazine (e.g., in dosages of 1 g three times daily).

In specific embodiments, patients with Crohn's disease are administered a prophylactically or therapeutically effective amount of a liquid formulation of the invention in combination with other agents or therapies useful in prevention, treatment, management and amelioration of Crohn's disease including but not limited to: antidiarrheals (e.g., loperamide 2-4 mg up to 4 times a day, diphenoxylate with atropine 1 tablet up to 4 times a day, tincture of opium 8-15 drops up to 4 times a day, cholestyramine 2-4 g or colestipol 5 g once or twice daily), antispasmodics (e.g., propantheline 15 mg, dicyclomine 10-20 mg, or hyoscyamine 0.125 mg given before meals), 5-aminosalicylic acid agents (e.g., sulfasalazine 1.5-2 g twice daily, mesalamine (ASACOL®) and its slow release form (PENTASA®), especially at high dosages, e.g., PENTASA® 1 g four times daily and ASACOL® 0.8-1.2 g four times daily), corticosteroids, immunomodulatory drugs (e.g., azathioprine (1-2 mg/kg), mercaptopurine (50-100 mg), cyclosporine, and methotrexate), antibiotics, TNF inhibitors (e.g., inflixmab (REMICADE®)), immunosuppressive agents (e.g., tacrolimus, mycophenolate mofetil, and thalidomide), anti-inflammatory cytokines (e.g., IL-10 and IL-11), nutritional therapies, enteral therapy with elemental diets (e.g., Vivonex for 4 weeks), and total parenteral nutrition.

In specific embodiments, patients with lupus erythematosus are administered a prophylactically or therapeutically effective amount of a liquid formulation of the invention in combination with other agents or therapies useful in prevention, treatment, management and amelioration of lupus erythematosus including but not limited to: antimalarials (including but not limited to, hydroxychloroquine); glucocorticoids (e.g., low dose, high dose, or high-dose intravenous pulse therapy can be used); immunosuppressive agents (including but not limited to, cyclophosphamide, chlorambucil, and azanthioprine); cytotoxic agents (including but not limited to methotrexate and mycophenolate mofetil); androgenic steroids (including but not limited to danazol); and anticoagulants (including but not limited to warfarin).

In a specific embodiment, an prophylactically or therapeutically effective amount of one or more liquid antibody formulations of the invention is administered in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin α$_v$β3 Antagonists in Combination With Other Prophylactic or Therapeutic Agents," and International Publication No. WO 03/075741 A2, dated Sep. 18, 2003, entitled, "Methods of Preventing or Treating Disorders by Administering an Integrin αvβ$_3$ Antagonist in Combination With an HMG-CoA Reductase Inhibitor or a Bisphosphonate," each of which is incorporated herewith by reference in its entirety) to a subject to prevent, treat, manage, and/or ameliorate an autoimmune disorder or one or more symptoms thereof. In another preferred embodiment, an effective amount of one or more antibodies of the invention is administered in combination with an effective amount of siplizumab (MedImmune, Inc., International Publication No. WO 02/069904) to a subject to prevent, treat, manage, and/or ameliorate an autoimmune disorder or one or more symptoms thereof. In another embodiment, an effective amount of one or more antibodies of the invention is administered in combination with an effective amount of one or more EphA2 inhibitors (e.g., one or more anti-EphA2 antibodies (MedImmune, Inc.; International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. application Ser. No. 10/436,783; and U.S. Appn. No. 60/379,368, each of which is incorporated herewith by reference)) to a subject to prevent, treat, manage, and/or ameliorate an autoimmune disorder or one or more symptoms thereof. In yet another embodiment, an effective amount of one or more antibodies of the invention is administered in combination with an effective amount of VITAXIN™, siplizumab, and/or EphA2 inhibitor to a subject to prevent, treat, manage, and/or ameliorate an autoimmune disorder or one or more symptoms thereof.

The antibody formulations of the invention or combination therapies of the invention may be used as the first, second, third, fourth, or fifth therapy to prevent, manage, treat, and/or ameliorate an autoimmune disorder or one or more symptom thereof. The invention also includes methods of preventing, treating, managing, and/or ameliorating an autoimmune disorder or one or more symptoms thereof in a patient undergoing therapies for other disease or disorders. The invention encompasses methods of preventing, managing, treating, and/or ameliorating an autoimmune disorder or one or more symptoms thereof in a patient before any adverse effects or intolerance to therapies other than antibodies of the invention develops. The invention also encompasses methods of preventing, treating, managing, and/or ameliorating an autoimmune disorder or a symptom thereof in refractory patients. The invention encompasses methods for preventing, treating, managing, and/or ameliorating a proliferative disorder or a symptom thereof in a patient who has proven refractory to therapies other than antibodies, compositions, or combination therapies of the invention. The determination of whether a patient is refractory can be made either in vivo or in vitro by any method known in the art for assaying the effectiveness of a treatment of autoimmune disorders, using art-accepted meanings of "refractory" such a context. In certain embodiments, a patent with an autoimmune disorder is refractory to a therapy when one or more symptoms of an autoimmune disorder is not prevented, managed, and/or alleviated. The invention also encompasses methods of preventing, managing, treating, and/or ameliorating an autoimmune disorder or a symptom thereof in patients who are susceptible to adverse reactions to conventional therapies.

The present invention encompasses methods for preventing, treating, managing, and/or ameliorating an autoimmune disorder or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from an infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a viral respiratory infection or one or more symptoms thereof.

Autoimmune therapies and their dosages, routes of administration and recommended usage are known in the art and have been described in such literature as the *Physician's Desk Reference* (59th ed., 2005).

5.5.5. Viral Infections

One or more antibody formulations of the invention can be administered to a subject to prevent, treat, manage, and/or ameliorate a viral infection or one or more symptoms thereof. One or more antibody formulations of the invention may be administered in combination with one or more other therapies (e.g., one or more prophylactic or therapeutic agents) other than antibody formulations of the invention useful for the prevention, treatment, management, or amelioration of a viral infection to a subject predisposed to or with a viral infection, preferably a respiratory viral infection. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an immunomodulatory agent that is immunospecific for a viral antigen. As used herein, the term "viral antigen" includes, but is not limited to, any viral peptide, polypeptide and protein (e.g., HIV gp120, HIV nef, RSV F glycoprotein, RSV G glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. Antibodies useful in this invention for treatment of a viral infectious disease include, but are not limited to, antibodies against antigens of pathogenic viruses, including as examples and not by limitation: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g., human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Specific examples of antibodies available useful for the treatment of a viral infectious disease include, but are not limited to, PRO542 (Progenics) which is a CD4 fusion antibody useful for the treatment of HIV infection; Ostavir (Protein Design Labs, Inc., CA) which is a human antibody useful for the treatment of hepatitis B virus; and Protovir (Protein Design Labs, Inc., CA) which is a humanized IgG1 antibody useful for the treatment of cytomegalovirus (CMV); and palivizumab (SYNAGIS®; MedImmune, Inc.; International Publication No. WO 02/43660) which is a humanized antibody useful for treatment of RSV.

In a specific embodiment, the anti-viral agents used in the compositions and methods of the invention inhibit or reduce a pulmonary or respiratory virus infection, inhibit or reduce the replication of a virus that causes a pulmonary or respiratory infection, or inhibit or reduce the spread of a virus that causes a pulmonary or respiratory infection to other cells or subjects. In another preferred embodiment, the anti-viral agents used in the compositions and methods of the invention inhibit or reduce infection by RSV, hMPV, or PIV, inhibit or reduce the replication of RSV, hMPV, or PIV, or inhibit or reduce the spread of RSV, hMPV, or PIV to other cells or subjects. Examples of such agents and methods of treatment of RSV, hMPV, and/or PIV infections include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. See U.S. Prov. Patent App. No. 60/398,475 filed Jul. 25, 2002, entitled "Methods of Treating and Preventing RSV, HMPV, and PIV Using Anti-RSV, Anti-HMPV, and Anti-PIV Antibodies," and U.S. patent application Ser. No. 10/371,122 filed Feb. 21, 2003, which are incorporated herein by reference in its entirety.

In preferred embodiments, the viral infection is RSV and the anti-viral antigen is an antibody that immunospecifically binds to an antigen of RSV. In certain embodiments, the anti-RSV-antigen antibody binds immunospecifically to an RSV antigen of the Group A of RSV. In other embodiments, the anti-RSV-antigen antibody binds immunospecifically to an RSV antigen of the Group B of RSV. In other embodiments, an antibody binds to an antigen of RSV of one Group and cross reacts with the analogous antigen of the other Group. In particular embodiments, the anti-RSV-antigen antibody binds immunospecifically to a RSV nucleoprotein, RSV phosphoprotein, RSV matrix protein, RSV small hydrophobic protein, RSV RNA-dependent RNA polymerase, RSV F protein, and/or RSV G protein. In additional specific embodiments, the anti-RSV-antigen antibody binds to allelic variants of a RSV nucleoprotein, a RSV nucleocapsid protein, a RSV phosphoprotein, a RSV matrix protein, a RSV attachment glycoprotein, a RSV fusion glycoprotein, a RSV nucleocapsid protein, a RSV matrix protein, a RSV small hydrophobic protein, a RSV RNA-dependent RNA polymerase, a RSV F protein, a RSV L protein, a RSV P protein, and/or a RSV G protein.

It should be recognized that antibodies that immunospecifically bind to a RSV antigen are known in the art. For example, SYNAGIS® (Palivizumab) is a humanized monoclonal antibody presently used for the prevention of RSV infection in pediatric patients. In a specific embodiment, an antibody to be used with the methods of the present invention is palivizumab or an antibody-binding fragment thereof (e.g., a fragment containing one or more complementarity determining regions (CDRs) and preferably, the variable domain of palivizumab). The amino acid sequence of palivizumab is disclosed, e.g., in Johnson et al., 1997, J. Infectious Disease 176:1215-1224, and U.S. Pat. No. 5,824,307 and International Application Publication No.: WO 02/43660, entitled "Methods of Administering/Dosing Anti-RSV Antibodies for Prophylaxis and Treatment", by Young et al., which are incorporated herein by reference in their entireties.

One or more antibodies or antigen-binding fragments thereof that bind immunospecifically to a RSV antigen comprise a Fc domain with a higher affinity for the FcRn receptor than the Fc domain of palivizumab can also be used in accordance with the invention. Such antibodies are described in U.S. patent application Ser. No. 10/020,354, filed Dec. 12, 2001, which is incorporated herein by reference in its entireties. Further, the anti-RSV-antigen antibody A4B4; P12f2 P12f4; P11d4; Ale9; A12a6; A13c4; A17d4; A4B4; 1X-493L1; FR H3-3F4; M3H9; Y10H6; DG; AFFF; AFFF (1); 6H8; L1-7E5; L2-15B10; A13a11; A1h5; A4B4(1); A4B4-F52S; or A4B4L1FR-S28R can be used in accordance with the invention. These antibodies are disclosed in International Application Publication No.: WO 02/43660, entitled "Methods of Administering/Dosing Anti-RSV Antibodies for Prophylaxis and Treatment", by Young et al., and U.S. Provisional Patent Application 60/398,475 filed Jul. 25, 2002, entitled "Methods of Treating and Preventing RSV, HMPV, and PIV Using Anti-RSV, Anti-HMPV, and Anti-PIV Antibodies" which are incorporated herein by reference in their In certain embodiments, the anti-RSV-antigen antibodies are the anti-RSV-antigen antibodies of or are prepared by the methods of U.S. application Ser. No. 09/724,531, filed Nov. 28, 2000; Ser. No. 09/996,288, filed Nov. 28, 2001; and Ser. No. 09/996,265, filed Nov. 28, 2001, all entitled "Methods of Administering/Dosing Anti-RSV Antibodies for Prophylaxis and Treatment", by Young et al., which are incorporated by reference herein in their entireties. Methods and composition for stabilized antibody formulations that can be used in the methods of the present invention are disclosed in U.S. Provisional Application Nos.: 60/388,921, filed Jun. 14, 2002, and 60/388,920, filed Jun. 14, 2002, which are incorporated by reference herein in their entireties.

Anti-viral therapies and their dosages, routes of administration and recommended usage are known in the art and have been described in such literature as the *Physician's Desk Reference* ($59^{th}$ ed., 2005). Additional information on respiratory viral infections is available in *Cecil Textbook of Medicine* (18th ed., 1988).

5.5.5.1. Therapies for Viral Infections

In a specific embodiment, the invention provides methods of preventing, treating, managing, and/or ameliorating a viral respiratory infection or one or more symptoms thereof, said method comprising administering to a subject in need thereof an effective amount of one or more antibody formulations of the invention. In another embodiment, the invention provides a method of preventing, treating, managing, and/or ameliorating a viral respiratory infection or one or more symptoms thereof, said method comprising administering to a subject in need thereof an effective amount of one or more antibody formulations of the invention and an effective amount of one or more therapies (e.g., one or more prophylactic or therapeutic agents) other the than antibody formulations of the invention.

In certain embodiments, an effective amount of one or more antibody formulations of the invention is administered in combination with an effective amount of one or more therapies (e.g., one or more prophylactic or therapeutic agents) currently being used, have been used, or are known to be useful in the prevention, management, treatment, and/or amelioration of a viral infection, preferably a viral respiratory infection, or one or more symptoms thereof to a subject in need thereof. Therapies for a viral infection, preferably a viral respiratory infection include, but are not limited to, anti-viral agents such as amantadine, oseltamivir, ribaviran, palivizumab (SYNAGIS™), and anamivir. In certain embodiments, an effective amount of one or more antibody formulations of the invention is administered in combination with one or more supportive measures to a subject in need thereof to prevent, manage, treat, and/or ameliorate a viral infection or one or more symptoms thereof. Non-limiting examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or antifungal therapy (i.e., to prevent or treat secondary bacterial infections).

Any type of viral infection or condition resulting from or associated with a viral infection (e.g., a respiratory condition)

can be prevented, treated, managed, and/or ameliorated in accordance with the methods of the invention, said methods comprising administering an effective amount of one or more antibody formulations of the invention alone or in combination with an effective amount of another therapy (e.g., a prophylactic or therapeutic agent other than antibody formulations of the invention). Examples of viruses which cause viral infections include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenavirues (e.g., lassa fever virus), paramyxoviruses (e.g., morbillivirus virus, human respiratory syncytial virus, mumps, hMPV, and pneumovirus), adenoviruses, bunyaviruses (e.g., hantavirus), comaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C and PIV), papovaviruses (e.g., papillomavirues), picomaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus). Biological responses to a viral infection include, but not limited to, elevated levels of IgE antibodies, increased proliferation and/or infiltration of T cells, increased proliferation and/or infiltration of B cells, epithelial hyperplasia, and mucin production. In a specific embodiment, the invention also provides methods of preventing, treating, managing, and/or ameliorating viral respiratory infections that are associated with or cause the common cold, viral pharyngitis, viral laryngitis, viral croup, viral bronchitis, influenza, parainfluenza viral diseases ("PIV") diseases (e.g., croup, bronchiolitis, bronchitis, pneumonia), respiratory syncytial virus ("RSV") diseases, metapneumavirus diseases, and adenovirus diseases (e.g., febrile respiratory disease, croup, bronchitis, pneumonia), said method comprising administering an effective amount of one or more antibody formulations of the invention alone or in combination with an effective amount of another therapy.

In a specific embodiment, influenza virus infections, PIV infections, hMPV infections, adenovirus infections, and/or RSV infections, or one or more of symptoms thereof are prevented, treated, managed, and/and/or ameliorated in accordance with the methods of the invention. In a specific embodiment, the invention provides methods for preventing, treating, managing, and/or ameliorating a RSV respiratory infection or one or more symptoms thereof, said methods comprising administering to a subject in need thereof an effective amount of one or more antibody formulations of the invention alone or in combination with one or more anti-viral agents such as, but not limited to, amantadine, rimantadine, oseltamivir, znamivir, ribaviran, RSV-IVIG (i.e., intravenous immune globulin infusion) (RESPIGAM™), and palivizumab (SYNAGIS™). In a specific embodiment, the invention provides methods for preventing, treating, managing, and/or ameliorating a PIV infection or one or more symptoms thereof, said methods comprising administering to a subject in need thereof an effective amount of one or more antibody formulations of the invention alone or in combination with an effective amount of one or more anti-viral agents such as, but not limited to, amantadine, rimantadine, oseltamivir, znamivir, ribaviran, and palivizumab (SYNAGIS™). In another specific embodiment, the invention provides methods for preventing, treating, managing, and/or ameliorating a hMPV infection or one or more symptoms thereof, said methods comprising of administering an effective amount of one or more antibody formulations of the invention alone or in combination with an effective amount of one or more anti-viral agents, such as, but not limited to, amantadine, rimantadine, oseltamivir, znamivir, ribaviran, and palivizumab (SYNAGIS™) to a subject in need thereof. In a specific embodiment, the invention provides methods for preventing, treating, managing, and/or ameliorating influenza, said methods comprising administering an effective amount of one or more antibody formulations of the invention alone or in combination with an effective amount of an anti-viral agent such as, but not limited to zanamivir (RELENZA®), oseltamivir (TAMIFLU®), rimantadine, and amantadine (SYMADINE®; SYMMETREL®) to a subject in need thereof.

The invention provides methods for preventing the development of asthma in a subject who suffers from or had suffered from a viral respiratory infection, said methods comprising adminsitering an effective amount of one or more antibody formulations of the invention alone or in combination with an effective amount of another therapy. In a specific embodiment, the subject is an infant born prematurely, an infant, or a child. In another specific embodiment, the subject suffered from or suffers from RSV infection.

In a specific embodiment, the invention provides methods for preventing, treating, managing, and/or ameliorating one or more secondary responses to a primary viral infection, said methods comprising of administering an effective amount of one or more antibody formulations of the invention alone or in combination with an effective amount of other therapies (e.g., other prophylactic or therapeutic agents). Examples of secondary responses to a primary viral infection, particularly a primary viral respiratory infection, include, but are not limited to, asthma-like responsiveness to mucosal stimula, elevated total respiratory resistance, increased susceptibility to secondary viral, bacterial, and fungal infections, and development of such conditions such as, but not limited to, pneumonia, croup, and febrile bronchitis.

In a specific embodiment, the invention provides methods of preventing, treating, managing, and/or ameliorating a viral infection or one or more symptoms thereof, said methods comprising administering to a subject in need thereof an effective amount of one or more antibody formulations of the invention in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin $\alpha_v\beta3$ Antagonists in Combination With Other Prophylactic or Therapeutic Agents," and International Publication No. WO 03/075741 A2, dated Sep. 18, 2003, entitled, "Methods of Preventing or Treating Disorders by Administering an Integrin $\alpha v\beta3$ Antagonist in Combination With an HMG-CoA Reductase Inhibitor or a Bisphosphonate," each of which is incorporated herewith by reference in its entirety). In another specific embodiment, the invention provides methods for preventing, treating, managing, and/or ameliorating a viral infection or one or more symptoms thereof, said methods comprising administering to a subject in need thereof an effective amount of one or more antibodies of the invention in combination with an effective amount of siplizumab (MedImmune, Inc., International Pub. No. WO 02/069904). In another embodiment, the invention provides methods for preventing, treating, managing, and/or ameliorating a viral infection or one or more symptoms thereof, said methods comprising administering to a subject in need thereof an effective amount of one or more antibodies of the invention in combination with an effective amount of one or more EphA2 inhibitors (e.g., one or more anti-EphA2 antibodies (MedImmune, Inc.; International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. application Ser. No. 10/436,783; and U.S. application Ser. No. 60/379,368, each of which is incorporated herewith by reference)). In yet another embodiment, the invention provides methods for preventing, treating, managing, and/or ameliorating a viral infection or one or more symptoms thereof, said methods comprising administering to a subject in need thereof an effective amount of one or more antibodies of the invention in combination with an effective amount of VITAXIN™, siplizumab, and/or EphA2.

In one embodiment, an effective amount of one or more antibody formulations of the invention is administered in combination with an effective amount of one or more anti-IgE antibodies to a subject to prevent, treat, manage, and/or ameliorate a viral infection or one or more symptoms thereof. In a specific embodiment, an effective amount of one or more antibody formulations of the invention is administered in combination with an effective amount of anti-IgE antibody TNX901 to a subject to prevent, treat, manage, and/or ameliorate a viral infection or one or more symptoms thereof. In a specific embodiment, an effective amount of one or more antibody formulations of the invention is administered in combination with an effective amount of anti-IgE antibody rhuMAb-E25 omalizumab to a subject to prevent, treat, manage, and/or ameliorate a viral infection or one or more symptoms thereof. In another embodiment, an effective amount of one or more antibody formulations of the invention is administered in combination with an effective amount of anti-IgE antibody HMK-12 to a subject to prevent, treat, manage, and/or ameliorate a viral infection or one or more symptoms thereof. In a specific embodiment, an effective amount of one or more antibody formulations of the invention is administered in combination with an effective amount of anti-IgE antibody 6HD5 to a subject to prevent, treat, manage, and/or ameliorate a viral infection or one or more symptoms thereof. In another embodiment, an effective amount of one or more antibody formulations of the invention is administered in combination with an effective amount of anti-IgE antibody MAb Hu-901 to a subject to prevent, treat, manage, and/or ameliorate a viral infection or one or more symptoms thereof.

The invention encompasses methods for preventing the development of viral infections, preferably viral respiratory infections, in a patient expected to suffer from a viral infection or at increased risk of such an infection, e.g., patients with suppressed immune systems (e.g., organ-transplant recipients, AIDS patients, patients undergoing chemotherapy, the elderly, infants born prematurely, infants, children, patients with carcinoma of the esophagus with obstruction, patients with tracheobronchial fistula, patients with neurological diseases (e.g., caused by stroke, amyotrophic lateral sclerosis, multiple sclerosis, and myopathies), and patients already suffering from a respiratory infection). The patients may or may not have been previously treated for a respiratory infection.

The antibody formulations of the invention or combination therapies of the invention may be used as the first, second, third, fourth, or fifth therapy to prevent, manage, treat, and/or ameliorate a viral infection, preferably a viral respiratory infection, or one or more symptom thereof. The invention also includes methods of preventing, treating, managing, and/or ameliorating a viral infection, preferably a viral respiratory infection, or one or more symptoms thereof in a patient undergoing therapies for other diseases or disorders associated with or characterized by aberrant expression and/or activity of an IL-9 polypeptide, diseases or disorders associated with or characterized by aberrant expression and/or activity of the IL-9R or one or more subunits thereof, autoimmune diseases, inflammatory diseases, proliferative diseases, or infections (preferably, respiratory infections), or one or more symptoms thereof. The invention encompasses methods of preventing, managing, treating, and/or ameliorating a viral infection, preferably a viral respiratory infection, or one or more symptoms thereof in a patient before any adverse effects or intolerance to therapies other than antibody formulations of the invention develops. The invention also encompasses methods of preventing, treating, managing, and/or ameliorating a viral infection, preferably a viral respiratory infection, or a symptom thereof in refractory patients. In certain embodiments, a patient with a viral infection, preferably a viral respiratory infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral respiratory infection is refractory when viral replication has not decreased or has increased. The invention also encompasses methods of preventing the onset or reoccurrence of viral respiratory infections in patients at risk of developing such infections. The invention also encompasses methods of preventing, managing, treating, and/or ameliorating a viral infection, preferably a viral respiratory infection, or a symptom thereof in patients who are susceptible to adverse reactions to conventional therapies. The invention further encompasses methods for preventing, treating, managing, and/or ameliorating a viral infection, preferably a viral respiratory infection, for which no anti-viral therapy is available.

The invention encompasses methods for preventing, treating, managing, and/or ameliorating a viral infection, preferably a viral respiratory infection, or a symptom thereof in a patient who has proven refractory to therapies other than antibody formulations of the invention but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

The present invention encompasses methods for preventing, treating, managing, and/or ameliorating a viral infection, preferably a viral respiratory infection, or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, and/or ameliorate a viral infection or one or more symptoms thereof.

Viral infection therapies and their dosages, routes of administration and recommended usage are known in the art and have been described in such literature as the *Physician's Desk Reference* (59th ed., 2005).

5.5.6. Bacterial Infections

The invention provides a method of preventing, treating, managing, and/or ameliorating a bacterial infection or one or more symptoms thereof, said method comprising administering to a subject in need thereof an effective amount of one or more antibody formulations of the invention. In another embodiment, the invention provides a method of preventing, treating, managing, and/or ameliorating a bacterial infection or one or more symptoms thereof, said method comprising administering to a subject in need thereof an effective amount of a one or more antibody formulations of the invention and an effective amount of one or more therapies (e.g., one or more prophylactic or therapeutic agents), other than antibody formulations of the invention. Anti-bacterial agents and therapies well known to one of skill in the art for the prevention, treatment, management, or amelioration of bacterial infections can be used in the compositions and methods of the invention. Non-limiting examples of anti-bacterial agents include proteins, polypeptides, peptides, fusion proteins, antibodies, nucleic acid molecules, organic molecules, inorganic molecules, and small molecules that inhibit or reduce a bacterial infection, inhibit or reduce the replication of bacteria, or inhibit or reduce the spread of bacteria to other subjects. In particular, examples of anti-bacterial agents include, but are not limited to, penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In a preferred embodiment, the anti-bacterial agent is an agent that inhibits or reduces a pulmonary or respiratory bacterial infection, inhibits or reduces the replication of a bacteria that causes a pulmonary or respiratory infection, or inhibits or reduces the spread of a bacteria that causes a pulmonary or respiratory infection to other subjects. In cases in which the pulmonary or respiratory bacterial infection is a mycoplasma infection (e.g., pharyngitis, tracheobronchitis, and pneumonia), the anti-bacterial agent is preferably a tetracycline, erythromycin, or spectinomycin. In cases in which the pulmonary or respiratory bacterial infection is pneumonia caused by an aerobic gram negative *bacilli* (GNB), the anti-bacterial agent is preferably penicillin, first second, or third generation cephalosporin (e.g., cefaclor, cefadroxil, cephalexin, or cephazolin), erythomycin, clindamycin, an aminoglycoside (e.g., gentamicin, tobramycin, or amikacine), or a monolactam (e.g., aztreonam). In cases in which the pulmonary or respiratory bacterial infection is tuberculosis, the anti-bacterial agent is preferably, rifampcin, isonaizid, pyranzinamide, ethambutol, and streptomycin. In cases in which the respiratory infection is recurrent aspiration pneumonia, the anti-bacterial agent is preferably penicillin, an aminoglycoside, or a second or third generation cephalosporin.

5.5.6.1. Therapies for Bacterial Infections

Any type of bacterial infection or condition resulting from or associated with a bacterial infection (e.g., a respiratory infection) can be prevented, treated, managed, and/or ameliorated in accordance with the methods of invention. Examples of bacteria which cause bacterial infections include, but not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, Edwardsiella, *Enterobacter aerogenes, Erwinia* species, *Escherichia coli, Hafnia* species, *Klebsiella* species, *Morganella* species, *Proteus vulgaris, Providencia, Salmonella* species, *Serratia marcescens,* and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae,* and *Streptococcus pneumoniae*), Vampirovibr Helicobacter family, and Vampirovibrio family.

In a specific embodiment, the invention provides methods for preventing, treating, managing, and/or ameliorating a bacterial respiratory infection or one or more symptoms thereof, said method comprising administering to a subject in need thereof an effective amount of one or more antibody formulations of the invention. In another embodiment, the invention provides a method of preventing, treating, managing, and/or ameliorating a bacterial respiratory infection or one or more symptoms thereof, said method comprising administering to a subject in need thereof an effective amount of a one or more antibody formulations of the invention and an effective amount of one or more therapies (e.g., prophylactic or therapeutic agents), other than antibody formulations of the invention.

In certain embodiments, the invention provides methods to prevent, treat, manage, and/or ameliorate a bacterial infection, preferably a bacterial respiratory infection, or one or more of the symptoms, said methods comprising administering to a subject in need thereof one or more antibody formulations of the invention in combination with and effective amount of one or more therapies (e.g., one or more prophylactic or therapeutic agents), other than antibody formulations of the invention, used to prevent, treat, manage, and/or ameliorate bacterial infections. Therapies for bacterial infections, particularly, bacterial respiratory infections include, but are not limited to, anti-bacterial agents (e.g., aminoglycosides (e.g., gentamicin, tobramycin, amikacin, netilimicin) aztreonam, celphalosporins (e.g., cefaclor, cefadroxil, cephalexin, cephazolin), clindamycin, erythromycin, penicillin (e.g., penicillin V, crystalline penicillin G, procaine penicillin G), spectinomycin, and tetracycline (e.g., chlortetracycline, doxycycline, oxytetracyine)) and supportive respiratory therapy, such as supplemental and mechanical ventilation. In certain embodiments, one or more antibody formulations of the invention are administered in combination with one or more supportive measures to a subject in need thereof to prevent, manage, treat, and/or ameliorate a bacterial infection or one or more symptoms thereof. Non-limiting examples of supportive measures include humidification of air by ultrasonic nebulizer, aerolized racemic epinephrine, oral dexamethasone, intravenous fluids, intubation, fever reducers (e.g., ibuprofen, acetometaphin), and more preferably, antibiotic or anti-viral therapy (i.e., to prevent or treat secondary infections).

The invention provides methods for preventing, managing, treating, and/or ameliorating a biological response to a bacterial infection, preferably a bacterial respiratory infection, such as, but not limited to, elevated levels of IgE antibodies, mast cell proliferation, degranulation, and/or infiltration, increased proliferation and/or infiltration of B cells, and increased proliferation and/or infiltration of T cells, said methods comprising administering to a subject in need thereof an effective amount of one or more antibody formulations of the invention alone or in combination with an effective amount one or more therapies (e.g. a prophylactic or therapeutic agent) other than antibody formulations of the invention. The invention also provides methods of preventing, treating, managing, and/or ameliorating respiratory conditions caused by or associated with bacterial infections, preferably bacterial respiratory infections, such as, but not limited to, pneumonococcal pneumonia, pneumonia caused by aerobic gram-negative bacilli, recurrent aspiration pneumonia, legionellosis, streptococcal disease, infections caused by *Hemophilus*, whooping cough, meningitis, or tuberculosis, said methods comprising administering to a subject in need thereof an effective amount of one or more antibody formulations of the invention alone or in combination with an effective amount of another therapy.

In a specific embodiment, the methods of the invention are utilized to prevent, treat, manage, and/or ameliorate a bacterial respiratory infection caused by *Pneumonococcus, Mycobacteria*, aerobic gram-negative *bacilli, Streptococcus*, or *Hemophilus* or one or more symptoms thereof, said method comprising administering to a subject in need thereof of an effective amount of one or more antibody formulations of the invention alone or in combination with an effective amount of one or more other therapies (e.g., one or more prophylactic or therapeutic agents) other than antibody formulations of the invention.

In a specific embodiment, the invention provides methods for preventing, treating, managing, and/or ameliorating one or more secondary conditions or responses to a primary bacterial infection, preferably a primary bacterial respiratory infection, said method comprising administering to a subject in need thereof an effective amount of one or more antibody formulations of the invention alone or in combination with an effective amount of other therapies (e.g., other prophylactic or therapeutic agents). Examples of secondary conditions or responses to a primary bacterial infection, particularly a bacterial respiratory infection, include, but are not limited to, asthma-like responsiveness to mucosal stimula, elevated total respiratory resistance, increased susceptibility to secondary viral, bacterial, and fungal infections, and development of such conditions such as, but not limited to, pneumonia, croup, and febrile bronchitits.

In a specific embodiment, the methods of the invention are used to prevent, manage, treat, and/or ameliorate a bacterial infection, preferably a bacterial respiratory infection, or one or more symptoms thereof, said methods comprising administering to a subject in need thereof an effective amount of one or more antibodies of the invention in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin $\alpha_v\beta3$ Antagonists in Combination With Other Prophylactic or Therapeutic Agents," and International Publication No. WO 03/075741 A2, dated Sep. 18, 2003, entitled, "Methods of Preventing or Treating Disorders by Administering an Integrin $\alpha v\beta3$ Antagonist in Combination With an HMG-CoA Reductase Inhibitor or a Bisphosphonate," each of which is incorporated herewith by reference in its entirety). In another specific embodiment, the methods of the invention are used to prevent, manage, treat, and/or ameliorate a bacterial infection, preferably a bacterial respiratory infection, or one or more symptoms thereof, said methods comprising administering to a subject in need thereof an effective amount of one or more antibodies of the invention in combination with an effective amount of siplizumab (MedImmune, Inc., International Pub. No. WO 02/069904). In another embodiment, the methods of the invention are used to prevent, manage, treat, and/or ameliorate a bacterial infection, preferably a bacterial respiratory infection, or one or more symptoms thereof, said methods comprising administering to a subject in need thereof an effective amount of one or more antibodies of the invention in combination with an effective amount of one or more EphA2 inhibitors (e.g., one or more anti-EphA2 antibodies (MedImmune, Inc.; International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Application Ser. No. 10/436,783; and U.S. Appn. No. 60/379,368, each of which is incorporated herewith by reference)). In yet another embodiment, the invention provides methods of preventing, treating, managing, and/or ameliorating a bacterial infection, preferably a bacterial respiratory infection, or one or more symptoms thereof, said methods comprising administering an effective amount of one or more antibodies of the invention in combination with an effective amount of VITAXIN™, siplizumab, and/or EphA2.

The invention encompasses methods for preventing the development of bacterial infections, preferably bacterial respiratory infections, in a patient expected to suffer from a bacterial respiratory infection or at increased risk of such an infection, e.g., patients with suppressed immune systems (e.g., organ-transplant recipients, AIDS patients, patients undergoing chemotherapy, the elderly, infants born prematurely, infants, children, patients with carcinoma of the esophagus with obstruction, patients with tracheobronchial fistula, patients with neurological diseases (e.g., caused by stroke, amyotrophic lateral sclerosis, multiple sclerosis, and myopathies), and patients already suffering from an infection, particularly a respiratory infection). The patients may or may not have been previously treated for an infection.

The antibody formulations of the invention or combination therapies of the invention may be used as the first, second, third, fourth, or fifth therapy to prevent, manage, treat, and/or ameliorate a bacterial infection, preferably a bacterial respiratory infection, or one or more symptom thereof. The invention also includes methods of preventing, treating, managing, and/or ameliorating a bacterial infection, preferably a bacterial respiratory infection, or one or more symptoms thereof in a patient undergoing therapies for other diseases or disorders. The invention encompasses methods of preventing, managing, treating, and/or ameliorating a bacterial infection, preferably a bacterial respiratory infection, or one or more symptoms thereof in a patient before any adverse effects or intolerance to therapies other than antibody formulations of the invention develops. The invention also encompasses methods of preventing, treating, managing, and/or ameliorating a bacterial infection, preferably a bacterial respiratory infection, or a symptom thereof in refractory patients. In certain embodiments, a patient with a bacterial respiratory infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a bacterial respiratory infection is refractory when bacterial replication has not decreased or has increased. The invention also encompasses methods of preventing the onset or reoccurrence of a bacterial infection, preferably a bacterial respiratory infection, in patients at risk of developing such infection. The invention also encompasses methods of preventing, managing, treating, and/or ameliorating a bacterial infection, preferably a bacterial respiratory infection, or a symptom thereof in patients who are susceptible to adverse reactions to conventional therapies. The invention further encompasses methods for preventing, treating, managing, and/or ameliorating bacterial infections, preferably bacterial respiratory infections, for which no anti-bacterial therapy is available.

The invention encompasses methods for preventing, treating, managing, and/or ameliorating a bacterial infection, preferably a bacterial respiratory infection, or a symptom thereof in a patient who has proven refractory to therapies other than antibody formulations of the invention, but are no longer on these therapies. In certain embodiments, the patients being managed or treated in accordance with the methods of this invention are patients already being treated with anti-inflammatory agents, antibiotics, anti-virals, anti-fungals, or other biological therapy/immunotherapy. Among these patients are refractory patients, patients who are too young for conventional therapies, and patients with reoccurring bacterial infections despite management or treatment with existing therapies.

The present invention encompasses methods for preventing, treating, managing, and/or ameliorating a bacterial infection, preferably a bacterial respiratory infection, or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, and/or ameliorate a bacterial infection, preferably a bacterial respiratory infection, or one or more symptoms thereof.

Bacterial infection therapies and their dosages, routes of administration and recommended usage are known in the art and have been described in such literature as the *Physician's Desk Reference* (59th ed., 2005).

5.5.7. Fungal Infections

Anti-fungal agents and therapies well known to one of skill in the art for prevention, management, treatment, and/or amelioration of a fungal infection or one or more symptoms thereof (e.g., a fungal respiratory infection) can be used in the compositions and methods of the invention. Non-limiting examples of anti-fungal agents include proteins, polypeptides, peptides, fusion proteins, antibodies, nucleic acid molecules, organic molecules, inorganic molecules, and small molecules that inhibit and/or reduce fungal infection, inhibit and/or reduce the replication of fungi, or inhibit and/or reduce the spread of fungi to other subjects. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B (FUNGIZONE®), amphotericin B lipid complex ("ABLC")(ABELCET®), amphotericin B colloidal dispersion ("ABCD")(AMPHOTEC®), liposomal amphotericin B (AMBISONE®)), potassium iodide (KI), pyrimidine (e.g., flucytosine (ANCOBON®)), and voriconazole (VFEND®). See, e.g., Table 4 for a list of specific anti-fungal agents and their recommended dosages.

TABLE 4

Anti-fungal Agents

| Anti-fungal Agent | Dosage |
| --- | --- |
| Amphotericin B | |
| ABELCET ® (lipid complex injection) | 5 mg/kg/day |
| AMBISOME ® (liposome for injection) | 3-5 mg/kg/day |
| AMPHOTEC ® (complex for injection) | 3-4 mg/kg/day |
| Caspofungin acetate (CANCIDAS ®) | 70 mg on day one followed by 50 mg/day |
| Fluconazole (DIFLUCAN ®) | up to 400 mg/day (adults) up to 12 mg/kg/day (children) |
| Itraconazole (SPORANOX ®) | 200-400 mg/day |
| Flucytosine (ANCOBON ®) | 50-150 mg/kg/day in divided dose every 6 hours |
| Liposomal nystatin | 1-4 mg/kg |
| Ketoconazole (NIZORAL ®) | 200 mg single daily dose up to 400 mg/day in two divided doses (adults) 3.3-6.6 mg/kg/day for children 2 years old and older |
| Voriconazole (VFEND ®) | 6 mg/kg i.v. loading dose every 12 hours for two doses, followed by maintenance dose of 4 mg/kg i.v. every 12 hours, then oral maintenance dose of 200-100 mg tablet |

In certain embodiments, the anti-fungal agent is an agent that inhibits or reduces a respiratory fungal infection, inhibits or reduces the replication of a fungus that causes a pulmonary or respiratory infection, or inhibits or reduces the spread of a fungus that causes a pulmonary or respiratory infection to other subjects. In cases in which the pulmonary or respiratory fungal infection is Blastomyces dermatitidis, the anti-fungal agent is preferably itraconazole, amphotericin B, fluconazole, or ketoconazole. In cases in which the pulmonary or respiratory fungal infection is pulmonary aspergilloma, the anti-fungal agent is preferably amphotericin B, liposomal amphotericin B, itraconazole, or fluconazole. In cases in which the pulmonary or respiratory fungal infection is histoplasmosis, the anti-fungal agent is preferably amphotericin B, itraconazole, fluconazole, or ketoconazole. In cases in which the pulmonary or respiratory fungal infection is coccidioidomycosis, the anti-fungal agent is preferably fluconazole or amphotericin B. In cases in which the pulmonary or respiratory fungal infection is cryptococcosis, the anti-fungal agent is preferably amphotericin B, fluconazole, or combination of the two agents. In cases in which the pulmonary or respiratory fungal infection is chromomycosis, the anti-fungal agent is preferably itraconazole, fluconazole, or flucytosine. In cases in which the pulmonary or respiratory fungal infection is mucormycosis, the anti-fungal agent is preferably amphotericin B or liposomal amphotericin B. In cases in which the pulmonary or respiratory fungal infection is pseudoallescheriasis, the anti-fungal agent is preferably itraconazole ore miconazole.

Anti-fungal therapies and their dosages, routes of administration, and recommended usage are known in the art and have been described in such literature as Dodds et al., 2000 Pharmacotherapy 20(11) 1335-1355, the *Physician's Desk Reference* (59th ed., 2005) and the *Merk Manual of Diagnosis and Therapy* (17th ed., 1999).

5.5.7.1. Anti-fungal Therapies

One or more antibody formulations of the invention can be administered according to methods of the invention to a subject to prevent, treat, manage, and/or ameliorate a fungal infection or one or more symptoms thereof. One or more antibody formulations of the invention may be also administered to a subject to treat, manage, and/or ameliorate a fungal infection and/or one or more symptoms thereof in combination with one or more other therapies (e.g., one or more prophylactic or therapeutic agents) other than antibody formulations of the invention which are useful for the prevention, treatment, management, or amelioration of a fungal infection or one or more symptoms thereof.

In a specific embodiment, the invention provides a method of preventing, treating, managing, and/or ameliorating a fungal infection or one or more symptoms thereof, said method comprising administering to a subject in need thereof an effective amount of one or more antibody formulations of the invention. In another embodiment, the invention provides a method of preventing, treating, managing, and/or ameliorating a fungal infection or one or more symptoms thereof, said method comprising administering to a subject in need thereof an effective amount of a one or more antibody formulations of the invention and an effective amount of one or more therapies (e.g., prophylactic or therapeutic agents), other than antibody formulations of the invention.

Any type of fungal infection or condition resulting from or associated with a fungal infection (e.g., a respiratory infection) can be prevented, treated, managed, and/or ameliorated in accordance with the methods of invention. Examples of fungus which cause fungal infections include, but not limited to, *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae,* and *Rhizopus microsporus*), *Saccharomyces* species, *Sporothrix schenckii, zygomycetes*, and classes such as *Zygomycetes, Ascomycetes*, the *Basidiomycetes, Deuteromycetes*, and *Oomycetes*.

In a specific embodiment, the invention provides a method of preventing, treating, managing, and/or ameliorating a fungal respiratory infection or one or more symptoms thereof, said method comprising administering to a subject in need thereof an effective amount of one or more antibody formulations of the invention. In another embodiment, the invention provides a method of preventing, treating, managing, and/or ameliorating a fungal respiratory infection or one or more symptoms thereof, said method comprising administering to a subject in need thereof an effective amount of one or more antibody formulations of the invention and an effective amount of one or more therapies (e.g., one or more prophylactic or therapeutic agents) other than antibody formulations of the invention.

In certain embodiments, an effective amount of one or more antibody formulations is administered in combination with an effective amount of one or more therapies (e.g., one or more prophylactic or therapeutic agents), other than antibody formulations of the invention, which are currently being used, have been used, or are known to be useful in the prevention, management, treatment, or amelioration of a fungal infection, preferably a fungal respiratory infection, to a subject in need thereof. Therapies for fungal infections include, but are not limited to, anti-fungal agents such as azole drugs e.g., miconazole, ketoconazole (NIZORAL®), caspofungin acetate (CANCIDAS®), imidazole, triazoles (e.g., fluconazole (DIFLUCAN®)), and itraconazole (SPORANOX®), polyene (e.g., nystatin, amphotericin B colloidal dispersion ("ABCD")(AMPHOTEC®), liposomal amphotericin B (AMBISONE®)), postassium iodide (KI), pyrimidine (e.g., flucytosine (ANCOBON®)), and voriconazole (VFEND®). In certain embodiments, an effective amount of one or more antibody formulations of the invention are administered in combination with one or more supportive measures to a subject in need thereof to prevent, manage, treat, and/or ameliorate a fungal infection or one or more symptoms thereof. Non-limiting examples of supportive measures include humidification of the air by an ultrasonic nebulizer, aerolized racemic epinephrine, oral desamethasone, intravenous fluids, intubation, fever reducers (e.g., ibuprofen and acetometaphin), and anti-viral or anti-bacterial therapy (i.e., to prevent or treat secondary viral or bacterial infections).

The invention also provides methods for preventing, managing, treating and/or ameliorating a biological response to a fungal respiratory infection such as, but not limited to, elevated levels of IgE antibodies, elevated nerve growth factor (NGF) levels, mast cell proliferation, degranulation, and/or infiltration, increased proliferation and/or infiltration of B cells, and increased proliferation and/or infiltration of T cells, said methods comprising administration of an effective amount of one or more antibody formulations that immunospecifically bind to an IL-9 polypeptide alone or in combination with one or more other therapies.

In a specific embodiment, the invention provides methods for preventing, treating, managing, and/or ameliorating one or more secondary conditions or responses to a primary fungal infection, preferably a primary fungal respiratory infection, said method comprising of administering to a subject in need thereof an effective amount of one or more antibody formulations of the invention alone or in combination with an effective amount of other therapies (e.g., other prophylactic or therapeutic agents) other than antibody formulations of the invention. Examples of secondary conditions or responses to a primary fungal infections, particularly primary fungal respiratory infection include, but are not limited to, asthma-like responsiveness to mucosal stimula, elevated total respiratory resistance, increased susceptibility to secondary viral, fungal, and fungal infections, and development of such conditions such as, but not limited to, pneumonia, croup, and febrile bronchitits.

In a specific embodiment, the invention provides methods to prevent, treat, manage, and/or ameliorate a fungal infection, preferably a fungal respiratory infection, or one or more symptoms thereof, said methods comprising administering to a subject in need thereof an effective amount of one or more antibodies of the invention in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin $\alpha_v\beta3$ Antagonists in Combination With Other Prophylactic or Therapeutic Agents," and International Publication No. WO 03/075741 A2, dated Sep. 18, 2003, entitled, "Methods of Preventing or Treating Disorders by Administering an Integrin $\alpha v\beta3$ Antagonist in Combination With an HMG-CoA Reductase Inhibitor or a Bisphosphonate," each of which is incorporated herewith by reference in its entirety) to a subject in need thereof. In another specific embodiment, the invention provides methods of preventing, treating, managing, and/or ameliorating a fungal respiratory infection or one or more symptoms thereof, said methods comprising administering to a subject in need thereof an effective amount of one or more antibodies of the invention in combination with an effective amount of siplizumab (MedImmune, Inc., International Pub. No. WO 02/069904) to a subject in need thereof. In another embodiment, the invention provides methods of preventing, treating, managing, and/or ameliorating a fungal respiratory infection or one or more symptoms thereof, said methods comprising administering an effective amount of one or more antibodies of the invention in combination with an effective amount of one or more EphA2 inhibitors (e.g., one or more anti-EphA2 antibodies (MedImmune, Inc.; International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. application Ser. No. 10/436,783; and U.S. Appn. No. 60/379,368, each of which is incorporated herewith by reference)) to a subject in need thereof. In yet another embodiment, the invention provides methods of preventing, treating, managing, and/or ameliorating a fungal infection, preferably a fungal respiratory infection, or one or more symptoms thereof, said methods comprising administering an effective amount of one or more antibodies of the invention in combination with an effective amount of VITAXIN™, siplizumab, and/or EphA2 to a subject in need thereof.

The invention encompasses methods for preventing the development of fungal respiratory infections in a patient expected to suffer from a fungal infection, preferably a fungal respiratory infection, or at increased risk of such an infection. Such subjects include, but are not limited to, patients with suppressed immune systems (e.g., patients organ-transplant recipients, AIDS patients, patients undergoing chemotherapy, patients with carcinoma of the esophagus with obstruction, patients with tracheobronchial fistula, patients with neurological diseases (e.g., caused by stroke, amyotorphic lateral sclerosis, multiple sclerosis, and myopathies), and patients already suffering from a respiratory condition, particularly a respiratory infection). In a specific embodiment, the patient suffers from bronchopulmonary dysplasia, congenital heart disease, cystic fibrosis, and/or acquired or congenital immunodeficiency. In another specific embodiment, the patient is an infant born prematurely, an infant, a child, an elderly human, or a human in a group home, nursing home, or some other type of institution. The invention also encompasses methods of preventing, managing, treating, and/or ameliorating a respiratory condition or one or more symptoms thereof in patients who are susceptible to adverse reactions to conventional therapies for respiratory conditions for which no therapies are available.

The antibody formulations of the invention or combination therapies of the invention may be used as the first, second, third, fourth, or fifth therapy to prevent, manage, treat, and/or ameliorate a fungal infection, preferably a fungal respiratory infection or one or more symptom thereof. The invention also includes methods of preventing, treating, managing, and/or ameliorating a fungal infection, preferably a fungal respiratory infection or one or more symptoms thereof in a patient undergoing therapies for other disease or disorders. The invention encompasses methods of preventing, managing, treating, and/or ameliorating a fungal infection, preferably a fungal respiratory infection or one or more symptoms thereof in a patient before any adverse effects or intolerance to therapies other antibody formulations of the invention develops. The invention also encompasses methods of preventing, treating, managing, and/or ameliorating a fungal infection, preferably a fungal respiratory infection or a symptom thereof in refractory patients. In certain embodiments, a patient with a fungal infection, preferably a fungal respiratory infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a fungal infection, preferably a fungal respiratory infection, is refractory when fungal replication has not decreased or has increased. The invention also encompasses methods of preventing the onset or reoccurrence of fungal infections, preferably fungal respiratory infections, in patients at risk of developing such infections. The invention also encompasses methods of preventing, managing, treating, and/or ameliorating a fungal infection, preferably a fungal respiratory infection, or a symptom thereof in patients who are susceptible to adverse reactions to conventional therapies. The invention further encompasses methods for preventing, treating, managing, and/or ameliorating fungal infections, preferably fungal respiratory infections, for which no anti-fungal therapy is available.

The invention encompasses methods for preventing, treating, managing, and/or ameliorating a fungal infection, preferably a fungal respiratory infection, or a symptom thereof in a patient who has proven refractory to therapies other than antibody formulations of the invention but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring fungal infections despite management or treatment with existing therapies.

The present invention provides methods for preventing, treating, managing, and/or ameliorating a fungal infection, preferably a fungal respiratory infection, or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, and/or ameliorate a fungal infection, preferably a fungal respiratory infection, or one or more symptoms thereof.

Fungal infection therapies and their dosages, routes of administration and recommended usage are known in the art and have been described in such literature as the *Physician's Desk Reference* (59th ed., 2005).

5.6. Methods of Administering the Antibody Formulations

The invention provides methods of treatment, management, prophylaxis, and amelioration of a disorder associated with or characterized by aberrant expression and/or activity of the IL-9R or one or more subunits thereof, autoimmune diseases, inflammatory diseases, proliferative diseases, or infections (preferably, respiratory infections), or one or more symptoms thereof by administrating to a subject of an effective amount of liquid formulations of the invention. Various delivery systems are known and can be used to administer a liquid formulation of the present invention or a prophylactic or therapeutic agent. Methods of administering antibody liquid formulations of the present invention or a therapy (e.g., a prophylactic or therapeutic agent) include, but are not limited to, parenteral administration (e.g., intradermal, intramuscular, intraperitoneal, intravenous and subcutaneous), epidural administration, topical administration, and mucosal administration (e.g., intranasal and oral routes). In a specific embodiment, liquid formulations of the present invention are administered intramuscularly, intravenously, or subcutaneously. In a preferred embodiment, the liquid formulations of the invention are administered subcutaneously. The formulations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a specific embodiment, the liquid formulations of the invention are administered intratumorally or at the site of inflammation.

In a specific embodiment, the antibody formulations of the invention comprise a pharmaceutically acceptable carrier. In a preferred embodiment, the pharmaceutically acceptable carrier is water for injection, USP, 5% dextrose in water (D5W) or saline.

Generally, the antibodies (including antibody fragments thereof) that immunospecifically bind to an IL-9 polypeptide contained in the liquid formulations of the invention are derived from a subject that is of the same species origin or species reactivity as recipient of the liquid formulations of the invention. Thus, in a preferred embodiment, liquid formulations of the invention comprising human or humanized antibodies that immunospecifically bind to an IL-9 polypeptide contained in the liquid formulations of the invention are administered to a human patient for therapy or prophylaxis.

The invention also provides that a liquid formulation of the present invention is packaged in a hermetically sealed container such as an ampoule or sachette indicating the quantity of antibody (including antibody fragment thereof). Preferably, the liquid formulations of the present invention are in a hermetically sealed container indicating the quantity and concentration of the antibody (including antibody fragment thereof). Preferably, the liquid formulation of the present invention is supplied in a hermetically sealed container and comprises at least 15 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 175 mg/ml, 200 mg/ml, 250 mg/ml, or 300 mg/ml of an antibody (including antibody fragment thereof) that immunospecifically binds to an IL-9 polypeptide, in a quantity of 1 ml, 2 ml, 3 ml, 4 ml, 5 ml, 6 ml, 7 ml, 8 ml, 9 ml, 10 ml, 15 ml, or 20 ml and, most preferably, 1.2 ml. In a specific embodiment of the invention, a liquid formulation of the invention is supplied in a hermetically sealed container and comprises at least 15 mg/ml, at least 20 mg/ml, at least 25 mg/ml, at least 50 mg/ml, at least 100 mg/ml, at least 150 mg/ml, at least 175 mg/ml, at least 200 mg/ml, at least 250 mg/ml or at least 300 mg/ml of an antibody (including antibody fragment thereof) that immunospecifically binds to an IL-9 polypeptide (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof) for intravenous injections, and at least 15 mg/ml, 20 mg/ml, 50 mg/ml, 80 mg/ml 100 mg/ml, 150 mg/ml, 175 mg/ml, 200 mg/ml, 250 mg/ml or 300 mg/ml an antibody (including antibody fragment thereof) that immunospecifically binds to an IL-9 polypeptide (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4 or a fragment thereof) for repeated subcutaneous administration. In a specific embodiment, an antibody formulation of the present invention may be produced by lyophilizing the aqueous antibody formulation. In a specific embodiment, the lyophilized antibody aqueous antibody solution may be reconstituted with a pharmaceutically acceptable carrier. In a specific embodiment, a pharmaceutically acceptable carrier is water for injection, USP, 5% dextrose in water (D5W) or saline.

The amount of a liquid formulation of the present invention which will be effective in the treatment, management, prevention or amelioration of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof can be determined by standard clinical techniques well-known in the art or described herein. The precise dose to be employed in the formulation will also depend on the route of administration, and the seriousness of the inflammatory disorder, autoimmune disorder or cancer, and should be decided according to the judgment of the practitioner and each patient's circumstances. Effective doses may be extrapolated from dose-response curves derived from in vitro or animal model test systems.

For formulations of the antibodies, proteins, polypeptides, peptides and fusion proteins encompassed by the invention, the dosage administered to a patient may be calculated using the patient's weight in kilograms (kg) multiplied by the dose to be administered in mg/kg. The required volume (in mL) to be given is then determined by taking the mg dose required divided by the concentration of the antibody formulation. The final calculated required volume will be obtained by pooling the contents of as many vials as are necessary into syringe(s) to administer the antibody formulation of the invention. The final calculated required volume will be obtained by pooling the contents of as many vials as are necessary into syringe(s) to administer the drug. A maximum volume of 2.0 mL of the antibody formulation can be injected per site. The dose (in mL) can be calculated using the following formula: Dose (mL)=[volunteer weight](kg)×[dose]mg/kg÷100 mg/mL of the antibody formulation. Generally, human antibodies have a longer half-life within the human body than antibodies from other species due to the immune response to the foreign polypeptides. Thus, lower dosages of human antibodies and less frequent administration is often possible. Further, the dosage, volume and frequency of administration of liquid formulations of the present invention may be reduced by increasing the concentration of an antibody (including antibody fragment thereof) in the formulations, increasing affinity and/or avidity of the antibody (including antibody fragment thereof), and/or increasing the half-life of the antibody (including antibody fragment thereof).

In a specific embodiment, the dosage administered to a patient will be calculated using the patient's weight in kilograms (kg) multiplied by the dose to be administered in mg/kg. The required volume (in mL) to be given is then determined by taking the mg dose required divided by the concentration of the antibody (including antibody fragment thereof) in the formulations (100 mg/mL). The final calculated required volume will be obtained by pooling the contents of as many vials as are necessary into syringe(s) to administer the drug. A maximum volume of 2.0 mL of antibody (including antibody fragment thereof) in the formulations can be injected per site.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In a specific embodiment, 0.1 to 20 mg/kg/week, preferably 1 to 15 mg/kg/week, more preferably 2 to 8 mg/kg/week, even more preferably 3 to 7 mg/kg/week, and most preferably 4 to 6 mg/kg/week of an antibody (including antibody fragment thereof) that immunospecifically binds to an IL-9 polypeptide (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4 or a fragment thereof) in a liquid formulation of the invention is administered to a subject with an inflammatory disorder, an autoimmune disorder or cancer. In another embodiment, a subject is administered one or more doses of a prophylactically or therapeutically effective amount of a liquid formulation of the invention, wherein the prophylactically or therapeutically effective amount is not the same for each dose.

In one embodiment, a liquid formulation of the invention is administered in a dosing regimen that maintains the plasma concentration of the antibody immunospecific for $\alpha_v\beta_3$ at a desirable level (e.g., about 0.1 to about 100 µg/ml), which continuously blocks the an IL-9 polypeptide activity. In a specific embodiment, the plasma concentration of the antibody is maintained at 0.2 µg/ml, 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 35 µg/ml, 40 µg/ml, 45 µg/ml or 50 µg/ml. The plasma concentration that is desirable in a subject will vary depending on several factors, including but not limited to, the nature of the disease or disorder, the severity of the disease or disorder and the condition of the subject. Such dosing regimens are especially beneficial in prevention, treatment, management and amelioration of a chronic disease or disorder.

In specific embodiments, a liquid formulation of the invention comprising a conjugated antibody (including antibody fragment thereof) immunospecific for an IL-9 polypeptide is administered intermittently. As used herein, "a conjugated antibody or antibody fragment" refers to an antibody (including antibody fragment thereof) that is conjugated or fused to another moiety, including but not limited to, a heterologous peptide, polypeptide, another antibody (including antibody fragment thereof), a marker sequence, a diagnostic agent, a therapeutic moiety, a therapeutic drug, a radioactive metal ion, a polymer, albumin, and a solid support.

In another embodiment, a subject, preferably a human, is administered one or more doses of a prophylactically or therapeutically effective amount of an antibody (including antibody fragment thereof) that immunospecifically binds to an IL-9 polypeptide (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4 or a fragment thereof) in a liquid formulation of the invention, wherein the dose of a prophylactically or therapeutically effective amount of the antibody (including antibody fragment thereof) in the liquid formulation of the invention administered to said subject is increased by, e.g., 0.01 µg/kg, 0.02 µg/kg, 0.04 µg/kg, 0.05 gg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 pg/kg, 75 µg/kg, 80 µg/kg, 85 µg/kg, 90 µg/kg, 95 µg/kg, 100 µg/kg, or 125 µg/kg, as treatment progresses.

In another embodiment, a subject, preferably a human, is administered one or more doses of a prophylactically or therapeutically effective amount of an antibody (including antibody fragment thereof) that immunospecifically binds to an IL-9 polypeptide (e.g., 4D4, 4D4H2-1 D11, 4D4com-XF-9, 4D4com-2F9, 7F3, 71A10, 7F3 22D3, 7F3com-2H2, 7F3com-3H5, or 7F3com-3D4 or a fragment thereof) in a liquid formulation of the invention, wherein the dose of a prophylactically or therapeutically effective amount of the antibody (including antibody fragment thereof) in the liquid formulation of the invention administered to said subject is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, or 125 µg/kg, as treatment progresses.

The dosages of prophylactic or therapeutically agents are described in the *Physicians' Desk Reference* (56th ed., 2002 and 57th ed., 2003).

5.7. Biological Assays

The antibodies (including antibody fragment thereof) of the liquid formulations of the invention may be characterized in a variety of ways well-known to one of skill in the art. In particular, antibodies (including antibody fragments thereof) of the liquid formulations of the invention may be assayed for the ability to immunospecifically bind to an IL-9 polypeptide.

Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Cwirla et al., 1990, Proc. Natl. Acad. Sci. USA 87:6378-6382; and Felici, 1991, J. Mol. Biol. 222:301-310) (each of these references is incorporated herein in its entirety by reference). Antibodies (including antibody fragments thereof) that have been identified to immunospecifically bind to an IL-9 polypeptide can then be assayed for their specificity and affinity for an IL-9 polypeptide.

The antibodies (including antibody fragments thereof) of the liquid formulations of the invention may be assayed for immunospecific binding to an IL-9 polypeptide and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. In a preferred embodiment, an ELISA may be performed by coating a high binding 96-well microtiter plate (Costar) with 2 µg/ml of rhu-IL-9 in PBS overnight. Following three washes with PBS, the plate is incubated with three-fold serial dilutions of Fab at 25° C. for 1 hour. Following another three washes of PBS, 1 µg/ml anti-human kappa-alkaline phosphatase-conjugate is added and the plate is incubated for 1 hour at 25° C. Following three washes with PBST, the alkaline phosphatase activity is determined in 50 µl/AMP/PPMP substrate. The reactions are stopped and the absorbance at 560 nm is determined with a VMAX microplate reader. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I) with the antibody of interest in the presence of increasing amounts of unlabeled antigen, and the detection of the antibody bound to the labeled antigen. The affinity of the antibody of the contained in a liquid formulation of the present invention or a fragment thereof for an IL-9 polypeptide and the binding off-rates can be determined from the data by scatchard plot analysis. Competition with a second antibody can also be determined using radioimmunoassays. In this case, an IL-9 polypeptide is incubated with an antibody of the present invention conjugated to a labeled compound (e.g., $^{3}$H or $^{125}$I) in the presence of increasing amounts of an unlabeled second antibody.

In a preferred embodiment, BIAcore kinetic analysis is used to determine the binding on and off rates of antibodies of the liquid formulations of the invention to an IL-9 polypeptide. BIAcore kinetic analysis comprises analyzing the binding and dissociation of an IL-9 polypeptide from chips with immobilized antibodies of the invention on their surface. A typical BIAcore kinetic study involves the injection of 250 µL of an antibody reagent (mab, Fab) at varying concentration in HBS buffer containing 0.005% Tween-20 over a sensor chip surface, onto which has been immobilized the antigen. The flow rate is maintained constant at 75 μL/min. Dissociation data is collected for 15 min. or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, $k_{on}$, and dissociation, $k_{off}$, the antigen is directly immobilized onto the sensor chip surface through the use of standard amine coupling chemistries, namely the EDCINHS method (EDC=N-diethylaminopropyl)-carbodiimide). Briefly, a 5-100 nM solution of the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The antibodies (including antibody fragments thereof) of the liquid formulations of the invention can also be assayed for their ability to inhibit the binding of IL-9 to its host cell receptor using techniques known to those of skill in the art. For example, cells expressing IL-9 receptor can be contacted with IL-9 in the presence or absence of an antibody (including antibody fragment thereof) of the liquid formulations of the invention and the ability of the antibody (including antibody fragment thereof) to inhibit IL-9's binding can measured by, for example, flow cytometry or a scintillation assay. IL-9 or the antibody (including antibody fragment thereof) contained in the liquid formulation of the invention can be labeled with a detectable compound such as a radioactive label (e.g., 32P, 35S, and 125I) or a fluorescent label (e.g., fluorescein isothiocyanate, rhodanine, phycoerythrin, phycocyanin, allophycocyanin, o-phthaldehyde and fluorescamine) to enable detection of an interaction between IL-9 and its host cell receptor. Alternatively, the ability of antibodies (including antibody fragment thereof) of the liquid formulations of the invention to inhibit IL-9 from binding to its receptor can be determined in cell-free assays. For example, an IL-9 polypeptide can be contacted with an antibody (including antibody fragment thereof) of the liquid formulations of the invention and the ability of the antibody (including antibody fragment thereof) to inhibit the IL-9 polypeptide from binding to its host cell receptor can be determined. Preferably, the antibody (including antibody fragment thereof) of the liquid formulations of the invention of the invention is immobilized on a solid support and an IL-9 polypeptide is labeled with a detectable compound. Alternatively, an IL-9 polypeptide is immobilized on a solid support and the antibody (including antibody fragment thereof) contained within a liquid formulation of the invention is labeled with a detectable compound. An IL-9 may be partially or completely purified (e.g., partially or completely free of other polypeptides) or part of a cell lysate. Further, an IL-9 polypeptide may be a fusion protein comprising IL-9, a derivative, analog or fragment thereof and a domain such as glutathionine-5-transferase. Alternatively, an IL-9 polypeptide can be biotinylated using techniques well known to those of skill in the art (e.g., biotinylation kit, Pierce Chemicals; Rockford, Ill.).

In a specific embodiment, the ability of antibodies (including antibody fragments thereof) of the liquid formulations of the invention to inhibit IL-9 from binding to its host cell receptor can be measured by cell proliferation assays. In a preferred embodiment, the murine TS1-RA3 T cell line expressing both human and murine IL-9Rα may be grown continuously in growth medium (DMEM) containing rhuIL-9 (25 ng/ml, R & D Systems). Upon withdrawal of rhuIL-9, TS 1-RA3 undergoes cell death in 18-24 hours. TS1-RA3 cells grown in RPMI 1640 (ATCC) medium supplemented with 10% FBS and 25 ng/ml rHu-IL9. Prior to the assay, the cells are washed with media containing no IL-9 and resuspended at $5\times10^5$ cells/ml in media containing 2 ng/ml rhuIL-9. The cells are distributed into a black clear bottom non-binding 96-well microtiter plate (100 μl cells/well) and 100 ml of serially diluted variant Fabs is then added to the plate. The plate is incubated at 72 hours at 37° C., 5% CO2. 20 μl/well of Alamar blue® is added, and the cells are incubated for an additional 4-5 hours. Cell metabolism is quantitated using a fluorimeter with excitation at 555 nm and emission at 590 nm.

5.7.1. In Vitro Studies

The antibodies, compositions, or combination therapies of the invention can be tested in vitro and/or in vivo for their ability to modulate the biological activity of immune cells (e.g., T cells, neutrophils, and mast cells), endothelial cells, and epithelial cells. The ability of an antibody, composition, or combination therapy of the invention to modulate the biological activity of immune cells (e.g., T cells, B cells, mast cells, macrophages, neutrophils, and eosinophils), endothelial cells, and epithelial cells can be assessed by: detecting the expression of antigens (e.g., activation of genes by IL-9, such as, but not limited to, mucin genes (e.g., MUC2, MUC5AC, MUC5B, and MUC6) and genes involved in lymphocyte activation (e.g., Lgamma-6A/E)); detecting the proliferation of immune cells, endothelia cells and/or epithelial cells; detecting the activation of signaling molecules (e.g., the phosphorylation of Stat2, the phosphorylation of JAK3, or the phosphorylation of the IL-9R); detecting the effector function of immune cells (e.g., T cells, B cells, mast cells, macrophages, neutrophils, and eosinophils), endothelial cells, and/or epithelial cells; or detecting the differentiation of immune cells, endothelial cells, and/or epithelial cells. Techniques known to those of skill in the art can be used for measuring these activities. For example, cellular proliferation can be assayed by 3H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and FACS analysis. The activation of signaling molecules can be assayed, for example, by kinase assays and electrophoretic shift assays (EMSAs). Mast cell degranulation can be assayed, for example by measuring serotonin (5-HT) release or histamine release with high-performance liquid chromatogoraphy (see, e.g., Taylor et al. 1995 Immunology 86(3): 427-433 and Kurosawa et al., 1998 Clin Exp Allergy 28(8): 1007-1012).

The antibodies, compositions, or combination therapies of the invention are preferably tested in vitro and then in vivo for the desired therapeutic or prophylactic activity prior to use in humans. For example, assays which can be used to determine whether administration of a specific pharmaceutical composition is indicated include cell culture assays in which a patient tissue sample is grown in culture and exposed to, or otherwise contacted with, a pharmaceutical composition, and the effect of such composition upon the tissue sample is observed. The tissue sample can be obtained by biopsy from the patient. This test allows the identification of the therapeutically most effective therapy (e.g., prophylactic or therapeutic agent) for each individual patient. In various specific embodiments, in vitro assays can be carried out with representative cells of cell types involved a disease or disorder associated with or characterized by aberrant expression and/or activity of an IL-9 polypeptide, a disease or disorder associated with or characterized by aberrant expression and/or activity of an IL-9R or one or more subunits thereof, an inflammatory disorder, an autoimmune disorder, a proliferative disorder, or an infection (preferably, a respiratory infection) to determine if a pharmaceutical composition of the invention has a desired effect upon such cell types.

The effect of an antibody, a composition, or a combination therapy of the invention on peripheral blood lymphocyte counts can be monitored/assessed using standard techniques known to one of skill in the art. Peripheral blood lymphocytes counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in subject can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen which is conjugated to FITC or phycoerythrin, and measuring the number of T-cells by FACS.

The methods of the invention for treating, managing, preventing, and/or ameliorating a viral respiratory infection or one or more symptoms thereof can be tested for their ability to inhibit viral replication or reduce viral load in in vitro assays. For example, viral replication can be assayed by a plaque assay such as described, e.g., by Johnson et al., 1997, Journal of Infectious Diseases 176:1215-1224 176:1215-1224. The antibodies, compositions, or combination therapies administered according to the methods of the invention can also be assayed for their ability to inhibit or downregulate the expression of viral polypeptides. Techniques known to those of skill in the art, including, but not limited to, western blot analysis, northern blot analysis, and RT-PCR can be used to measure the expression of viral polypeptides.

The methods of the invention for preventing, treating, managing, and/or ameliorating a respiratory infection or one or more symptoms thereof can be tested for activity against bacteria causing respiratory infections in in vitro assays well-known in the art. In vitro assays known in the art can also be used to test the existence or development of resistance of bacteria to a therapy (e.g., an antibody of the invention, other prophylactic or therapeutic agent, a combination thereof, or a composition thereof) of the invention. Such in vitro assays are described in Gales et al., 2002, Diag. Nicrobiol. Infect. Dis. 44(3):301-311; Hicks et al., 2002, Clin. Microbiol. Infect. 8(11): 753-757; and Nicholson et al., 2002, Diagn. Microbiol. Infect. Dis. 44(1): 101-107.

The therapies (e.g., an antibody of the liquid formulations of the invention alone or in combination with prophylactic or therapeutic agents, other than antibodies of the invention) of the invention for treating, managing, preventing, and/or ameliorating a respiratory infection or one or more symptoms thereof can be tested for anti-fungal activity against different species of fungus. Any of the standard anti-fungal assays well-known in the art can be used to assess the anti-fungal activity of a therapy. The anti-fungal effect on different species of fungus can be tested. The tests recommended by the National Committee for Clinical Laboratories (NCCLS) (See National Committee for Clinical Laboratories Standards. 1995, Proposed Standard M27T. Villanova, Pa., all of which is incorporated herein by reference in its entirety) and other methods known to those skilled in the art (Pfaller et al., 1993, Infectious Dis. Clin. N. Am. 7: 435-444) can be used to assess the anti-fungal effect of a therapy. The antifungal properties of a therapy may also be determined from a fungal lysis assay, as well as by other methods, including, inter alia, growth inhibition assays, fluorescence-based fungal viability assays, flow cytometry analyses, and other standard assays known to those skilled in the art.

For example, the anti-fungal activity of a therapy can be tested using macrodilution methods and/or microdilution methods using protocols well-known to those skilled in the art (see, e.g., Clancy et al., 1997 Journal of Clinical Microbiology, 35(11): 2878-82; Ryder et al., 1998, Antimicrobial Agents and Chemotherapy, 42(5): 1057-61; U.S. Pat. No. 5,521,153; U.S. Pat. No. 5,883,120, U.S. Pat. No. 5,521,169, all of which are incorporated by reference in their entirety). Briefly, a fungal strain is cultured in an appropriate liquid media, and grown at an appropriate temperature, depending on the particular fungal strain used for a determined amount of time, which is also depends on the particular fungal strain used. An innoculum is then prepared photometrically and the turbidity of the suspension is matched to that of a standard, e.g., a McFarland standard. The effect of a therapy on the turbidity of the inoculum is determined visually or spectrophotometrically. The minimal inhibitory concentration ("MIC") of the therapy is determined, which is defined as the lowest concentration of the lead compound which prevents visible growth of an inoculum as measured by determining the culture turbidity.

The anti-fungal activity of a therapy can also be determined utilizing colorimetric based assays well-known to one of skill in the art. One exemplary calorimetric assay that can be used to assess the anti-fungal activity of a therapy is described by Pfaller et al. (1994, Journal of Clinical Microbiology, 32(8): 1993-6, which is incorporated herein by reference in its entirety; also see Tiballi et al., 1995, Journal of Clinical Microbiology, 33(4): 915-7). This assay employs a colorimetric endpoint using an oxidation-reduction indicator (Alamar Biosciences, Inc., Sacramento Calif.).

The anti-fungal activity of a therapy can also be determined utilizing photometric assays well-known to one of skill in the art (see, e.g., Clancy et al., 1997 Journal of Clinical Microbiology, 35(11): 2878-82; Jahn et al., 1995, Journal of Clinical Microbiology, 33(3): 661-667, each of which is incorporated herein by reference in its entirety). This photometric assay is based on quantifying mitochondrial respiration by viable fungi through the reduction of 3-(4,5-dimethyl-2thiazolyl)-2,5,-diphenyl-2H-tetrazolium bromide (MTT) to formazan. MIC's determined by this assay are defined as the highest concentration of the test therapy associated with the first precipitous drop in optical density. In some embodiments, the therapy is assayed for anti-fungal activity using macrodilution, microdilution and MTT assays in parallel.

Further, any in vitro assays known to those skilled in the art can be used to evaluate the prophylactic and/or therapeutic utility of an antibody, a composition, a combination therapy disclosed herein for a respiratory infection or one or more symptoms thereof.

5.7.2. In Vivo Assays

The antibodies, compositions, or combination therapies of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapies (e.g., prophylactic and/or therapeutic agents), whether such therapies are administered separately or as an admixture, and the frequency of administration of the therapies.

Animal models for autoimmune disorders can also be used to assess the efficacy of an antibody, a composition, or a combination therapy of the invention. Animal models for autoimmune disorders such as type 1 diabetes, thyroid autoimmunity, systemic lupus erythematosus, and glomerulonephritis have been developed (Flanders et al., 1999, Autoimmunity 29:235-246; Krogh et al., 1999, Biochimie 81:511-515; Foster, 1999, Semin. Nephrol. 19:12-24).

Efficacy in preventing, treating, managing, and/or ameliorating an autoimmune disorder may be demonstrated, e.g., by detecting the ability of an antibody, a composition, or a combination therapy of the invention to reduce one or more symptoms of the autoimmune disorder, to reduce mean absolute lymphocyte counts, to decrease T cell activation, to decrease T cell proliferation, to reduce cytokine production, or to modulate one or more particular cytokine profiles. Efficacy in preventing or treating psoriasis may be demonstrated, e.g., by detecting the ability of an antibody, fragment thereof, or composition of the invention to reduce one or more symptoms of psoriasis, to reduce mean absolute lymphocyte counts, to reduce cytokine production, to modulate one or more particular cytokine profiles, to decrease scaling, to decrease erythema, to decrease plaque elevation, to decrease T cell activation in the dermis or epidermis of an affected area, to decrease T cell infiltration to the dermis or epidermis of an affected area, to reduce PASI, to improve the physician's global assessment score, or to improve quality of life.

Animal models for cancer can be used to assess the efficacy of an antibody, a composition, or a combination therapy of the invention. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23): 13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

The anti-inflammatory activity of an antibody, a composition, or a combination therapy of the invention can be determined by using various experimental animal models of inflammatory arthritis known in the art and described in Crofford L. J. and Wilder R. L., "Arthritis and Autoimmunity in Animals," in Arthritis and Allied Conditions: A Textbook of Rheumatology, McCarty (eds.), Chapter 30 (Lee and Febiger, 1993). Experimental and spontaneous animal models of inflammatory arthritis and autoimmune rheumatic diseases can also be used to assess the anti-inflammatory activity of the antibodies, compositions, or combination therapies of invention.

The anti-inflammatory activity of an antibody, a composition, or a combination therapy of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test therapies (e.g., prophylactic or therapeutic agents) is expressed as the percent inhibition of the increase in hind paw weight of the test group relative to the vehicle dosed control group.

In a specific embodiment of the invention where the experimental animal model used is adjuvant-induced arthritis rat model, body weight can be measured relative to a control group to determine the anti-inflammatory activity of an antibody, a composition, a combination therapy of the invention.

Animal models for allergies and asthma are known in the art, such as constant-flow inflation with end-inspiratory occlusion described in Ewart et al., 1995 J Appi Physiol 79(2):560-566 and other assays described in, e.g., Komai et al., 2003 Br J Pharmacol 138(5): 912-920; Kenyon et al., 2003 Toxicol Appl Pharmacol 186(2): 90-100; Path et al., 2002 Am J Resp & Critical Care Med 166(6): 818-826; Martins et al., 1990 Crit Care Med 19:515-519; Nicolaides et al., 1997 Proc Natl Acad Sci USA 94:13175-13180; McLane et al., 1998 19:713-720; and Temann et al., 1998 J Exp Med 188(7): 1307-1320. For example, the murine adoptive transfer model is an animal model used to assess the efficacy an antibody, a composition, or a combination therapy of the invention for the prevention, treatment, management, and/or asthma include. In the murine adoptive transfer model, aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 1861737-1747). Airway hypersensitivity can be induced in mice by ovalbumin (Tomkinson et al., 2001, J. Immunol. 166:5792-5800) or *Schistosoma mansoni* egg antigen (Tesciuba et al., 2001, J. Immunol. 167:1996-2003).

Efficacy in preventing or treating an inflammatory disorder may be demonstrated, e.g., by detecting the ability of an antibody, a composition, or a combination therapy of the invention to reduce one or more symptoms of the inflammatory disorder, to decrease T cell activation, to decrease T cell proliferation, to modulate one or more cytokine profiles, to reduce cytokine production, to reduce inflammation of a joint, organ or tissue or to improve quality of life.

Changes in inflammatory disease activity may also be assessed through tender and swollen joint counts, patient and physician global scores for pain and disease activity, and the ESR/CRP. Progression of structural joint damage may be assessed by quantitative scoring of X-rays of hands, wrists, and feet (Sharp method). Changes in functional status in humans with inflammatory disorders may be evaluated using the Health Assessment Questionnaire (HAQ), and quality of life changes are assessed with the SF.

The efficacy of an antibody, a composition, or a combination therapy of the invention in preventing, treating, managing, and/or ameliorating Type I allergic reaction may be assessed by its ability to induce anti-IgE antibodies that inhibit IgE from binding to is receptor on mast cells or basophils in vitro. IgE levels can be assayed by immunoassays, gel electrophoresis followed by visualization, radioimmunosorbent test (RIST), radioallergosorbent test (RAST), or any other method known to those skilled in the art.

Animal models for viral infections can also be used to assess the efficacy of an antibody, a composition, or a combination therapy of the invention. Animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("FIV"), HTLV type 1 infection, human rotaviruses, and genital herpes have been developed (see, e.g., Hayashi et al., 2002, Histol Histopathol 17(4):1293-310; Arico et al., 2002, J Interferon Cytokine Res 22(11):1081-8; Flano et al., 2002, Immunol Res 25(3):201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:201-19; Phillips et al., 2000, J Psychopharmacol. 14(3): 244-50; Kazanji, 2000, AIDS Res Hum Retroviruses. 16(16): 1741-6; Saif et al., 1996, Arch Virol Suppl. 12:153-61; and Hsiung et al., 1984, Rev Infect Dis. 6(1):33-50).

Animal models for viral respiratory infections such as, but not limited to, PIV (see, e.g., Shephard et al., 2003 Res Vet Sci 74(2): 187-190; Ottolini et al., 2002 J Infect Dis 186(12): 1713-1717), RSV (see, e.g., Culley et al., 2002 J Exp Med 196(10): 1381-1386; and Curtis et al., 2002 Exp Biol Med 227(9): 799-802). In a specific embodiment, cotton rats are administered an antibody of the invention, a composition, or a combination therapy according to the methods of the invention, challenged with $10^5$ pfu of RSV, and four or more days later the rats are sacrificed and RSV titer and anti-RSV antibody serum titer is determined. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the formulation is the dosage of the formulation that can be administered to a human for the treatment, prevention or amelioration of one or more symptoms associated with RSV infection. Further, in accordance with this embodiment, the tissues (e.g., the lung tissues) from the sacrificed rats can be examined for histological changes.

The antibodies, compositions, or combination therapies of the invention can be tested for their ability to decrease the time course of viral infection. The antibodies, compositions, or combination therapies of the invention can also be tested for their ability to increase the survival period of humans suffering from a viral infection by at least 25%, preferably at least 50%, at least 60%, at least 75%, at least 85%, at least 95%, or at least 99%. Further, antibodies, compositions, or combination therapies of the invention can be tested for their ability reduce the hospitalization period of humans suffering from viral infection by at least 60%, preferably at least 75%, at least 85%, at least 95%, or at least 99%. Techniques known to those of skill in the art can be used to analyze the function of the antibodies, compositions, or combination therapies of the invention in vivo.

Animal models for bacterial infections can also be used to assess the efficacy of an antibody, a composition, or a combination therapy of the invention. Animal models for bacterial infections such as *H. pylori*-infection, genital mycoplasmosis, primary sclerosing cholangitis, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia coli* infections, and *Mycoplasma pneumoniae* infections have been developed (see, e.g., Sugiyama et al., 2002, J Gastroenterol. 37 Suppl 13:6-9; Brown et al., 2001, Am J Reprod Immunol. 46(3):232-41; Vierling, 2001, Best Pract Res Clin Gastroenterol. 15(4):591-610; Klose, 2000, Trends Microbiol. 8(4):189-91; Stotland et al., 2000, Pediatr Pulmonol. 30(5):413-24; Brieland et al., 2000, Immunopharmacology 48(3):249-52; Lee, 2000, Baillieres Best Pract Res Clin Gastroenterol. 14(1):75-96; Koedel & Pfister, 1999, Infect Dis Clin North Am. 13(3):549-77; Nedrud, 1999, FEMS Immunol Med Microbiol. 24(2):243-50; Prellner et al., 1999, Microb Drug Resist. 5(1):73-82; Vriesendorp, 1997, J Infect Dis. 176 Suppl 2:S164-8; Shetty & Antia, 1996, Indian J Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit Rev Microbiol. 16(3):181-234; Scheld, 1987, J Antimicrob Chemother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2):291-301; Smith, 1976, Ciba Found Symp. (42):45-72, and Taylor-Robinson, 1976, Infection. 4(1 Suppl):4-8).

The antibodies, compositions, or combination therapies of the invention can be tested for their ability to decrease the time course of bacterial infection, preferably bacterial respiratory infection by at least 25%, preferably at least 50%, at least 60%, at least 75%, at least 85%, at least 95%, or at least 99%. The antibodies, compositions, or combination therapies of the invention can also be tested for their ability to increase the survival period of humans suffering from a bacterial infection by at least 25%, preferably at least 50%, at least 60%, at least 75%, at least 85%, at least 95%, or at least 99%. Further, the antibodies, compositions, or combination therapies administered according to the methods of the invention can be tested for their ability reduce the hospitalization period of humans suffering from bacterial infection, preferably a bacterial respiratory infection, by at least 60%, preferably at least 75%, at least 85%, at least 95%, or at least 99%. Techniques known to those of skill in the art can be used to analyze the function of the Antibodies of the invention, compositions, or combination therapies of the invention in vivo.

The efficacy of the antibodies, compositions, or combination therapies of the invention for the prevention, management, treatment, or amelioration of a fungal infection can be assessed in animal models for such infections. Animal models for fungal infections such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis have been developed (see, e.g., Arendrup et al., 2002, Infection 30(5):286-91; Kamei, 2001, Mycopathologia 152(1):5-13; Guhad et al., 2000, FEMS Microbiol Lett. 192(1):27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al., 1999, Microb Pathog. 27(3):123-31; Beers et al., 1999, J Lab Clin Med. 133(5):423-33; Najvar et al., 1999, Antimicrob Agents Chemother.43(2):413-4; Williams et al., 1988, J Infect Dis. 178(4):1217-21; Yoshida, 1988, Kansenshogaku Zasshi. 1998 June;72(6):621-30; Alexandrakis et al., 1998, Br J Ophthalmol. 82(3):306-11; Chakrabarti et al., 1997, J Med Vet Mycol. 35(4):295-7; Martin et al., 1997, Antimicrob Agents Chemother. 41(1):13-6; Chu et al., 1996, Avian Dis. 40(3): 715-9; Fidel et al., 1996, J Infect Dis. 173(2):425-31; Cole et al., 1995, FEMS Microbiol Lett. 15;126(2):177-80; Pollock et al., 1995, Nat Genet. 9(2):202-9; Uchida et al., 1994, Jpn J. Antibiot. 47(10):1407-12;: Maebashi et al., 1994, J Med Vet Mycol. 32(5):349-59; Jensen & Schonheyder, 1993, J Exp Anim Sci. 35(4):155-60; Gokaslan & Anaissie, 1992, Infect Immun. 60(8):3339-44; Kurup et al., 1992, J. Immunol. 148 (12):3783-8; Singh et al., 1990, Mycopathologia. 112(3): 127-37; Salkowski & Balish, 1990, Infect Immun. 58(10): 3300-6; Ahmad et al., 1986, Am J Kidney Dis. 7(2):153-6; Alture-Werber E, Edberg S C, 1985, Mycopathologia. 89(2): 69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6). Animal models for fungal respiratory infections such as *Candida albicans, Aspergillus fumigatus*, invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13): 1281-1290; Kurup et al., 2002 Int Arch Allergy Immunol 129(2):129-137; Hori et al., 2002 Eur J Immuno 32(5): 1282-1291; Rivera et al., 2002 J Immuno 168(7): 3419-3427; Vassallo et al., 2001, Am J Respir Cell Mol Biol 25(2): 203-211; Wilder et al., 2002 Am J Respir Cell Mol Biol 26(3): 304-314; Yonezawa et al., 2000 J Infect Chemother 6(3): 155-161; Cacciapuoti et al., 2000 Antimicrob Agents Chemother 44(8): 2017-2022; and Honda et al., 1998 Mycopathologia 144(3):141-146).

The antibodies, compositions, or combination therapies of the invention can be tested for their ability to decrease the time course of fungal respiratory infection by at least 25%, preferably at least 50%, at least 60%, at least 75%, at least 85%, at least 95%, or at least 99%. The antibodies, compositions, or combination therapies of the invention can also be tested for their ability to increase the survival period of humans suffering from a fungal respiratory infection by at least 25%, preferably at least 50%, at least 60%, at least 75%, at least 85%, at least 95%, or at least 99%. Further, antibodies, compositions, or combination therapies administered according to the methods of the invention can be tested for their ability reduce the hospitalization period of humans suffering from fungal respiratory infection by at least 60%, preferably at least 75%, at least 85%, at least 95%, or at least 99%. Techniques known to those of skill in the art can be used to analyze the function of the antibodies, compositions, or combination therapies of the invention in vivo.

Further, any assays known to those skilled in the art can be used to evaluate the prophylactic and/or therapeutic utility of an antibody, a composition, a combination therapy disclosed herein for prevention, treatment, management, and/or amelioration of disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof.

5.7.3. Toxicity Assays

The toxicity and/or efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Further, any assays known to those skilled in the art can be used to evaluate the prophylactic and/or therapeutic utility of an antibody, a composition, a combination therapy disclosed herein for a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an

5.8. Diagnostic Uses of Antibody Formulations

Antibodies (including molecules comprising, or alternatively consisting of, antibody fragments or variants thereof) of the liquid formulations of the invention that immunospecifically bind to an IL-9 polypeptide can be used for diagnostic purposes to detect, diagnose, prognose, or monitor a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. The invention provides for the detection of aberrant expression of IL-9 comprising: (a) assaying the expression of IL-9 in a biological sample from an individual using one or more antibodies of the liquid formulations of the invention that immunospecifically binds to an IL-9 polypeptide; and (b) comparing the level of IL-9 with a standard level of IL-9, e.g., in normal biological samples, whereby an increase or decrease in the assayed level of IL-9 compared to the standard level of IL-9 is indicative of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In specific embodiments, aberrant expression level of IL-9 is indicative of an autoimmune disorder or a disease or condition associated therewith. In another specific embodiment, an aberrant expression level of IL-9 is indicative of an inflammatory disorder or a disease or condition associated therewith, such as asthma. In preferred embodiments, an aberrant expression level of IL-9 is indicative of a respiratory infection, such as, but not limited to RSV, PVI, or hMPV.

In preferred embodiments, the labeled antibodies of the liquid formulations of the invention that immunospecifically bind to IL-9 are used for diagnostic purposes to detect, diagnose, prognose, or monitor a respiratory infection, preferably RSV infection, PIV infection, or hMPV. The invention provides methods for the detection of a respiratory infection, comprising: (a) assaying the expression of IL-9 in cells or a tissue sample of a subject using one or more antibodies that immunospecifically bind to IL-9; and (b) comparing the level of IL-9 with a control level, e.g., levels in normal tissue samples not infected, whereby an increase in the assayed level of IL-9 compared to the control level of IL-9 is indicative of a respiratory infection.

Antibodies of the liquid formulations of the invention can be used to assay IL-9 levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of IL-9 in an animal, preferably a mammal, and most preferably a human. In one embodiment, diagnosis comprises: a) administering (for example, parenterally, subcutaneously, or intraperitoneally) to a subject an effective amount of a labeled antibody (including molecules comprising, or alternatively consisting of, antibody fragments or variants thereof) of the liquid formulations of the invention that immunospecifically binds to an IL-9 polypeptide; b) waiting for a time interval following the administering for permitting the labeled antibody to preferentially concentrate at sites in the subject where IL-9 is expressed (and for unbound labeled molecule to be cleared to background level); c) determining background level; and d) detecting the labeled antibody in the subject, such that detection of labeled antibody (including antibody fragment thereof) above the background level and above or below the level observed in a person without the disease or disorder indicates that the subject has a particular disease or disorder associated with aberrant expression of IL-9. Background level can be determined by various methods including, comparing the amount of labeled molecule detected to a standard value previously determined for a particular system. Aberrant expression of IL-9 can occur particularly in lymphoid and myeloid cell types. A more definitive diagnosis of respiratory infection may allow health professionals to employ preventive measures or aggressive treatment earlier and thereby prevent the development or further progression of the infection.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds, Masson Publishing Inc. (1982). Depending on several variables, including the type of label used and the mode of administration, the time interval following the administration for permitting the labeled molecule to preferentially concentrate at sites in the subject and for unbound labeled molecule to be cleared to background level is 6 to 48 hours, 6 to 24 hours, or 6 to 12 hours. In another embodiment the time interval following administration is 5 to 20 days or 5 to 10 days.

In an embodiment, monitoring of the disease or disorder is carried out by repeating the method for diagnosing the disease or disorder, for example, one month after initial diagnosis, six months after initial diagnosis, one year after initial diagnosis, etc.

Presence of the labeled IL-9 antibody can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the IL-9 antibody is labeled with a radioisotope and is detected in the patient using a radiation responsive surgical instrument (Thurston et al., U.S. Pat. No. 5,441,050). In another embodiment, the IL-9 antibody is labeled with a fluorescent compound and is detected in the patient using a fluorescence responsive scanning instrument. In another embodiment, the IL-9 antibody is labeled with a positron emitting metal and is detected in the patient using positron emission-tomography. In yet another embodiment, the IL-9 antibody is labeled with a paramagnetic label and is detected in a patient using magnetic resonance imaging (MRI).

The antibodies of the invention (including molecules comprising, or alternatively consisting of, antibody fragments or variants thereof) may be utilized for immunophenotyping of cell lines and biological samples by their IL-9 expression or IL-9 receptor expression. Various techniques can be utilized using the antibodies, fragments, or variants of the liquid formulations of the invention to screen for cellular populations (that express IL-9 and/or IL-9 receptor, particularly immune cells, i.e., T and B lymphocytes, mast cells, eosinophils, macrophages, neutrophils and epithelial cells or IL-9 receptor, and include magnetic separation using antibody-coated magnetic beads, "panning" with antibody attached to a solid matrix (i.e., plate), and flow cytometry (see, e.g., U.S. Pat. No. 5,985,660; and Morrison et al., Cell, 96:737-49 (1999)).

These techniques allow for the screening of particular populations of cells, such as might be found with hematological malignancies (i.e., minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

5.9. Kits

The invention provides a pharmaceutical pack or kit comprising one or more containers filled with a liquid formulation of the invention. In a specific embodiment, the liquid formulations of the invention comprise antibodies (including antibody fragments thereof) recombinantly fused or chemically conjugated to another moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support. The invention also provides a pharmaceutical pack or kit comprising in one or more first containers a liquid formulation of the invention and in one or more second containers one or more other prophylactic or therapeutic agents useful for the prevention, management or treatment of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof. In a preferred embodiment, the liquid formulations of the invention are formulated in single dose vials as a sterile liquid containing 10 mM histidine buffer at pH 6.0 and 150 mM sodium chloride. Each 1.0 mL of solution contains 100 mg of an IL-9 antibody (including antibody fragment thereof), 1.6 mg of histidine and 8.9 mg of sodium chloride. During the manufacturing process, the pH of the formulation buffer is adjusted to 6.0 using hydrochloric acid. The formulations of the invention may be supplied in 3 cc USP Type I borosilicate amber vials (West Pharmaceutical Serices—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises a liquid formulation of the invention, in one or more containers. In another embodiment, a kit comprises a liquid formulation of the invention, in one or more containers, and one or more other prophylactic or therapeutic agents useful for the prevention, management or treatment of a disease or disorder associated with or characterized by aberrant expression and/or activity of an IL-9 polypeptide, a disease or disorder associated with or characterized by aberrant expression and/or activity of the IL-9R or one or more subunits thereof, an autoimmune disease, an inflammatory disease, a proliferative disease, or an infection (preferably, a respiratory infection), or one or more symptoms thereof, in one or more other containers. In a specific embodiment, the antibodies (including antibody fragments thereof) included in said liquid formulations is 4D4, 4D4H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment. In an alternative embodiment, the antibody (including antibody fragment thereof) included in said liquid formulations is not 4D4, 4D4H2-1 D11, 4D4com-XF-9, 4D4com-2F9, 7F3, 71A10, 7F3 22D3, 7F3com-2H2, 7F3com-3H5, or 7F3com-3D4 or an antigen-binding fragment thereof. Preferably, the kit further comprises instructions for preventing, treating, managing or ameliorating a disorder (e.g., using the liquid formulations of the invention alone or in combination with another prophylactic or therapeutic agent), as well as side effects and dosage information for method of administration.

5.10. Articles of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient, e.g., an antibody of the invention that immunospecifically binds to an IL-9 polypeptide, is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, intransal, or topical delivery.

In a preferred embodiment, the unit dosage form is suitable for intravenous, intramuscular, intranasal, oral, topical or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, total lymphocyte, mast cell counts, T cell counts, IgE production, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a liquid formulation containing an antibody that immunospecifically binds to IL-9 and wherein said packaging material includes instruction means which indicate that said antibody can be used to prevent, manage, treat, and/or ameliorate one or more symptoms associated with a disorder associated with aberrant expression and/or activity of an IL-9 polypeptide, a disorder associated with aberrant expression and/or activity of an IL-9R or one or more subunits thereof, an autoimmune disorder, an inflammatory disorder, a proliferative disorder, an infection (preferably, a respiratory infection), or one or more symptoms thereof by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a liquid formulation containing an antibody that immunospecifically binds to an IL-9 polypeptide and the other pharmaceutical agent comprises a second, different antibody that immunospecifically binds to an IL-9 polypeptide, and wherein said packaging material includes instruction means which indicate that said agents can be used to treat, prevent and/or ameliorate a disorder associated with aberrant expression and/or activity of an IL-9 polypeptide, a disorder associated with aberrant expression and/or activity of an IL-9R or one or more subunits thereof, an autoimmune disorder, an inflammatory disorder, a proliferative disorder, an infection (preferably, a respiratory infection), or one or more symptoms thereof by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a liquid formulation containing an antibody that immunospecifically binds to an IL-9 polypeptide and the other pharmaceutical agent comprises a prophylactic or therapeutic agent other than an antibody that immunospecifically binds to an IL-9 polypeptide, and wherein said packaging material includes instruction means which indicate that said agents can be used to treat, prevent and/or ameliorate one or more symptoms associated with a disorder associated with aberrant expression and/or activity of an IL-9 polypeptide, a disorder associated with aberrant expression and/or activity of an IL-9R or one or more subunits thereof, an autoimmune disorder, an inflammatory disorder, a proliferative disorder, an infection (preferably, a respiratory infection), or one or more symptoms thereof by administering specific doses and using specific dosing regimens as described herein.

The present invention provides that the adverse effects that may be reduced or avoided by the methods of the invention are indicated in informational material enclosed in an article of manufacture for use in preventing, treating and/or ameliorating one or more symptoms associated with an autoimmune disorder, an inflammatory disorder or an infection. Adverse effects that may be reduced or avoided by the methods of the invention include, but are not limited to, vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, and vasodilatation. Since antibodies of the invention that immunospecifically bind to an IL-9 polypeptide may be immunosuppressive, prolonged immunosuppression may increase the risk of infection, including opportunistic infections. Prolonged and sustained immunosuppression may also result in an increased risk of developing certain types of cancer.

Further, the information material enclosed in an article of manufacture for use in preventing, treating, managing, and/or ameliorating disorder characterized by aberrant expression and/or activity of an IL-9 polypeptide, a disorder characterized by aberrant expression and/or activity of an IL-9R or one or more subunits thereof, an inflammatory disorder, an autoimmune disorder, a proliferative disorder, or an infection (preferably, a respiratory infection) or one or more symptoms thereof can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens-Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

6. EXAMPLES

6.1. Antibody Purification and Antibody Formulation

The following section describes a method for purifying antibodies to be used in the formulations of the invention (see FIG. 16).

6.1.1. Buffer Components and Equipment

Buffers, process solutions and cleaning solutions are prepared with water for injection (WFI). Buffers are tested for bioburden and endotoxin.

Buffers and Process Solutions
0.1 M citric acid
10 mM sodium citrate, 80 mM NaCl, pH 4.6
25 mM sodium phosphate, pH 6.5
20 mM Tris-HCl, 40 mM NaCl, pH 7.5
0.5 M sodium phosphate, pH 6.5
5 mM sodium phosphate, 40 mM NaCl, pH 6.5
50 mM Glycine-HCl, 30 mM NaCl, pH 2.5
50 mM Glycine-HC, pH 2.35
1.0 M Tris base
Cleaning and Storage Solutions
Water for Injection (WFI)
1.0 N NaOH
0.1 N NaOH
20% (v/v) ethanol
0.5 N NaOH, 400 ppm sodium hypochlorite
Formulation Buffers
10 mM Histidine, 150 mM NaCl, pH 6.0
4 M sodium chloride
Equipment (Substitutions with Equivalent Performing Materials are Acceptable)
300 kg scale
Conductivity meter Stir plate
pH meter
Vessels: Appropriately sized Stedim™ bags, buffer tanks, PETG Bottles
Watson Marlow 1700 peristaltic pump
Wedgewood UV, pH, conductivity unit
Amersham Pharmacia chromatography controller
Packed POROS HS50 cation exchange gel
Packed Pharmacia rProtein A affinity gel
Packed POROS HQ anion exchange gel
Sterile, depyrogenated silicone tubing
Integritest Filter Integrity Tester II
Sterile Asahi Planova 20 N membrane viral removal filter
Millipore 0.2 micron Durapore filter
Millipore Multimedia filter
CUNO 60LP, 10/60 SP filter
CUNO filter housing
Class 100 hood

6.1.2. Purification and Formulation of the Antibodies

FIG. 16 outlines the process steps for the purification and formulation of the antibodies (including antibody fragments thereof) of the invention. The purification process comprises three chromatography steps, a nanofiltration step, a low pH treatment step, and formulation. These steps are designed to remove host cell proteins, DNA and cell culture components such as BSA and transferrin. In addition, the process includes steps to control bioburden and endotoxin and to remove and inactivate viruses.

6.1.2.1. Conditioned Medium (Steps 1 to 6)

Conditioned medium from a single cell culture lot or pooled from multiple cell culture lots is purified as a single lot. The combination of multiple cell culture lots into one purification lot is performed in order to utilize downstream processing steps sized for a single lot size and to decrease the number of purification lots. For example, because the working volumes of 130 L and 250 L cell culture bioreactors are approximately 100 L and 200 L, respectively, these two cell culture lots could be pooled and run as one 300 L purification lot. Process product samples are analyzed for DNA using a PicoGreen or a quantitative PCR assay to detect DNA. Protein concentration is determined either by a Protein A bindable HPLC assay or by UV absorbance at 280 nm. Product-containing process streams are monitored for endotoxin and bioburden. Column effluents are monitored for endotoxin. A description of each step is summarized below.

6.1.2.2. Conditioned Medium Adjustment and Filtration (Step 7)

The conditioned medium is adjusted to pH 4.6±0.2 with 0.1 M citric acid. The adjusted conditioned medium is then filtered using a CUNO filter in-line with a Millipore 0.2 micron Durapore filter.

6.1.2.3. Cation Exchange Chromatography Step (Step 8)

The adjusted and filtered conditioned medium is loaded onto a cation exchange column that has been equilibrated with 10 mM sodium phosphate, 80 mM sodium chloride, pH 4.6. The bound antibody is washed using the same buffer. The column is then washed with 25 mM sodium phosphate pH 6.5 to remove process impurities, especially BSA. The product is eluted using 20 mM Tris-HCl buffer, 40 mM NaCl, pH 7.5. Following elution of the product, the column is cleaned with 1.0 N NaOH and stored in 0.1 N NaOH at room temperature.

6.1.2.4. rProtein A Chromatograph (Step 9)

The cation exchange product is loaded directly onto a rProtein A column equilibrated with 20 mM Tris-HCl buffer, 40 mM NaCl, pH 7.5. Following loading, the column is washed with the equilibration buffer, and the product is eluted with 50 mM glycine, 30 mM NaCl, pH 3.2. The rProtein A product is neutralized to pH 6.5±0.2 with 1.0 M Tris base. This chromatography step removes additional process-related impurities. At the end of the step, the column is washed with equilibration buffer, cleaned with 0.1 N NaOH, washed with equilibration buffer and stored in 20% (v/v) ethanol at room temperature.

6.1.2.5. Anion Exchange Chromatography (Step 10)

This chromatographic step is the final step designed to remove any trace levels of process-related impurities. The column is equilibrated with 0.5 M sodium phosphate, pH 6.5 followed by equilibration with 5 mM sodium phosphate, 40 mM sodium chloride, pH 6.5. Under these conditions, the neutralized rProtein A product is loaded onto the equilibrated anion exchange column, and under these conditions, the product is recovered in the non-bound fraction and the process-related impurities are retained in the column. The column is cleaned with 1.0 N NaOH and stored in 0.1 N NaOH at room temperature.

6.1.2.6. Nanofiltration (Step 11)

The anion exchange product is filtered through a sterile Planova™ 20 N membrane (pore size=20 nm) that is prepared by flushing first with WFI and then with 5 mM sodium phosphate, 40 mM sodium chloride pH 6.5. After the product is filtered, the filter is chased with a small volume of 5 mM sodium phosphate, 40 mM sodium chloride, pH 6.5 to maximize product recovery. After filtration the nanofilter is integrity tested.

6.1.2.7. Low pH Treatment (Step 12)

The pH of the nanofiltered product is adjusted to 3.4±0.1 with 50 mM glycine, pH 2.35 and held at this pH for 30±10 minutes. After low pH treatment, the product pH is adjusted to 6.5±0.2 with 1.0 M Tris base.

6.1.2.8. Formulation of Anti-IL-9 Antibodies

Sodium chloride (150 mM) is added to the antibody purified as in steps 1-12 above using a 4 M NaCl stock solution. It is then 0.2 micron filtered and concentrated to 20 g/L using tangential flow filtration with a 30 kDa membrane. The product is then diafiltered into the formulation buffer (10 mM Histidine, 150 mM NaCl, pH 6.0), using a minimum of five buffer exchanges. The product is then concentrated to 100 g/L and filtered through a 1.2/0.2 micron membrane into sterile Stedim® storage bags.

6.2. Monitoring Antibody Stability and Aggregation of Antibody Formulations

6.2.1. Reference Standard Stability

The stability of the 7F3com-2H2 Reference Standard (purified as in Section 6.1 above) was tested. Following low pH treatment, the antibody composition was adjusted to pH 6.5, concentrated to 11 mg/ml by tangential flow filtration, buffer exchanged into 10 mM Histidine pH 6.0 buffer and filtered through a 0.22 micron filter yielding an anti-IL-9 antibody Reference Standard at a protein concentration of 11.3 mg/ml.

The following stability-indicating tests were used to assess the stability of the anti-IL-9 antibody Reference Standard: appearance, native isoelectric focusing (IEF), reducing and non-reducing gel electrophoresis, HPSEC, IL-9 binding ELISA, and protein concentration by $A_{280}$. These assays represent the primary identity, purity, and potency tests and are capable of detecting aggregates, proteolytic degradation, and loss of potency.

Tests were done at −70° C., 2-8° C., 38-42° C., or after three freeze-thaw cycles. The −70° C. stability condition was chosen because reference standards are typically stored at this temperature. The three freeze-thaw cycle study was done to determine the robustness of the Reference Standard material stored at −70° C. in the event of inadvertent thawing and to assess if there is any adverse effect with repeated freeze/thaw cycles. The 2-8° C. condition was chosen to evaluate possible alternative storage conditions. The 38-42° C. accelerated temperature condition was chosen to demonstrate that the chosen assays are stability-indicating and to monitor the stability of the molecule under stress conditions.

Table 5, infra, shows the stability testing results for the 7F3com-2H2 Reference Standard. All test results for the 2-8° C. and the 3× freeze-thaw conditions listed in the table were within specifications. Unsatisfactory percent purity results were obtained for the two and three-month time points of condition D. After 3-month storage at 38-42° C., the percent purity by HPSEC dropped to 93.6%. The non-reduced gel electrophoresis profile at the same condition at the two and three-month time points was not consistent when compared to the initial Reference Standard profile. The isoelectric focusing (IEF) profile for the two and three-month time point at 38-42° C. was not consistent when compared to the initial Reference Standard (stored at −70° C.) due to the presence of a new acidic band that is not seen in the Reference Standard.

TABLE 5

Stability Results for the 7F3com-2H2 Reference Standard

| Condition Description | Time point (month) | Total Protein (A280) (mg/ml) | IEF (non-reduced) (Pass/Fail) | Gel electrophoresis (reduced) (Pass/Fail) | Gel electrophoresis (reduced) (% Purity) | Gel electrophoresis (non-reduced) (Pass/Fail) | HPSEC (% Purity) | HPSEC (% Aggregate) | Appearance (Pass/Fail) | IL-9 Binding ELISA Parallelism | IL-9 Binding ELISA (ED50) |
|---|---|---|---|---|---|---|---|---|---|---|---|
| Condition A: −70° C. | 0 | 11.3 | Pass | Pass | 98.8 | Pass | 99.5 | 0.5 | Pass | Pass | 15.2 |
| Condition A: −70° C. | 3 | 10.9 | Pass | Pass | 98.4 | Pass | 99.5 | 0.5 | Pass | Pass | 8.7 |
| Condition B: 2-8° C. | 0 | 11.3 | Pass | Pass | 98.8 | Pass | 99.5 | 0.5 | Pass | Pass | 15.2 |
| Condition B: 2-8° C. | 1 | 11.0 | Pass | Pass | 98.6 | Pass | 99.5 | 0.5 | Pass | Pass | 15.0 |
| Condition B: 2-8° C. | 2 | 10.5 | Pass | Pass | 98.2 | Pass | 99.4 | 0.6 | Pass | Pass | 19.5 |
| Condition B: 2-8° C. | 3 | 11.0 | Pass | Pass | 98.8 | Pass | 99.3 | 0.6 | Pass | Pass | 8.9 |
| Condition D: 38-42° C. | 0 | 11.3 | Pass | Pass | 98.8 | Pass | 99.5 | 0.5 | Pass | Pass | 15.2 |
| Condition D: 38-42° C. | 1 | 11.7 | Pass | Pass | 98.6 | Pass | 96.7 | 1.2 | Pass | Pass | 12.2 |
| Condition D: 38-42° C. | 2 | 11.4 | Fail | Pass | 97.6 | Fail | 94.7 | 1.4 | Pass | Pass | 18.2 |
| Condition D: 38-42° C. | 3 | 11.4 | Fail | Pass | 97.4 | Fail | 93.6 | 1.7 | Pass | Pass | 19.6 |
| Condition E: 3X Freeze/Thaw | 0 | 11.1 | Pass | Pass | 98.8 | Pass | 99.4 | 0.6 | Pass | Pass | 11.0 |

Shaded boxes indicate out of specifications (OOS) results.

6.2.2. Antibody Formulation Stability

The stability of the 7F3com-2H2 antibody formulation (described in Section 6.1) is also monitored by the same stability-indicating assays used to evaluate the stability of the 7F3com-2H2 Reference Standard. These assays are performed at intervals indicated in Table 6, infra.

TABLE 6

Stability Testing Plan for the 7F3com-2H2 Antibody Formulation

| Condition | Time (months) | | | | | | | | | | | | |
|---|---|---|---|---|---|---|---|---|---|---|---|---|---|
| | 0 | 0.25 | 0.50 | 0.75 | 1 | 1.5 | 2 | 3 | 6 | 9 | 12 | 18 | 24 | 36 |
| B (2-8° C.) | X | X | X | X | X | X | X | X | X | X | X | X | X | X |

X = assays are performed at this time point;

The 2-8° C. condition was chosen because the 7F3com-2H2 antibody composition in the purification process is adjusted to pH 6.5, and stored at this temperature prior to formulation, concentration, and fill. The storage time is not anticipated to exceed 12 months; however, the stability is continually monitored for at least 36 months in the event that prolonged storage at 2-8° C. is needed.

Table 7, infra, shows the stability testing results obtained for the 7F3com-2H2 antibody formulation. The 2-8° C. storage condition samples met specifications through the three-month time point.

6.3.2.1. Container Closure System

The antibody formulations are supplied at 100 mg/ml in 3 cc USP Type I borosilicate amber vials. The target fill volume is 1.2 mL, which represents a 20% overage and meets USP guidelines. A description of each component of the container closure system is listed below.

Vials

West Pharmaceutical Services—Part # 6800-0675 (Manufacturer: Schott) 3 cc, 13 mm amber serum/lyo, USP/EP Type I Borosilicate, blowback (Purform)

TABLE 7

Stability Results for the 7F3com-2H2 Antibody Formulation

| Condition | Time point | Total Protein (A280) | IEF (non-reduced) | Gel electrophoresis (reduced) | | Gel electrophoresis (non-reduced) | HPSEC | | Appearance | IL-9 Binding ELISA | |
|---|---|---|---|---|---|---|---|---|---|---|---|
| Description | (month) | (mg/ml) | (Pass/Fail) | (Pass/Fail) | (% Purity) | (Pass/Fail) | (% Purity) | (% Aggregate) | (Pass/Fail) | Parallelism | (ED50) |
| Condition B: 2-8° C. | 0 | 2.3 | Pass | Pass | 98.5 | Pass | 99.5 | 0.5 | Pass | Pass | 15.5 |
| Condition B: 2-8° C. | 0.25 | 2.4 | Pass | Pass | 97.7 | Pass | 99.5 | 0.5 | Pass | Pass | 10.8 |
| Condition B: 2-8° C. | 0.50 | 2.6 | Pass | Pass | 98.2 | Pass | 99.2 | 0.5 | Pass | Pass | 28.0 |
| Condition B: 2-8° C. | 0.75 | 2.3 | Pass | Pass | 98.1 | Pass | 99.5 | 0.5 | Pass | Pass | 26.4 |
| Condition B: 2-8° C. | 1 | 2.3 | Pass | Pass | 99.7 | Pass | 99.5 | 0.5 | Pass | Pass | 10.2 |
| Condition B: 2-8° C. | 1.5 | 2.4 | Pass | Pass | 98.0 | Pass | 99.5 | 0.5 | Pass | Pass | 16.7 |
| Condition B: 2-8° C. | 2 | 2.4 | Pass | Pass | 98.5 | Pass | 99.4 | 0.6 | Pass | Pass | 20.3 |
| Condition B: 2-8° C. | 3 | 2.4 | Pass | Pass | 98.2 | Pass | 99.5 | 0.5 | Pass | Pass | 11.0 |

6.3. Compositions and Formulations of Antibodies

6.3.1. Description and Composition

F3com-2H2 antibodies are formulated in single dose vials as a sterile liquid containing 10 mM histidine buffer at pH 6.0 and 150 mM sodium chloride. Each 1.0 mL of solution contains 100 mg of protein, 1.6 mg of histidine and 8.9 mg of sodium chloride in water for injection. During the manufacturing process, the pH of the formulation buffer is adjusted to pH 6.0 using hydrochloric acid.

6.3.2. Formulation Development

Formulation studies were designed to evaluate chemical and physical properties that influence protein stability and solubility. The goal was to determine the most suitable conditions for long-term storage of the product. Studies were divided into three main areas: preformulation, concentration and stability. Preformulation biophysical studies, such as differential scanning calorimetry, were used to evaluate the effects of temperature and pH on the secondary and tertiary structure of the protein. Concentration studies were undertaken to provide information on native protein-protein interactions during a concentration step, and the impact of high concentration on long-term storage. Solution pH studies were designed to examine buffers over a physiologically useful pH range in order to achieve optimal solubility of the protein at high concentration. Based on data generated, a formulation of 7F3com-2H2 at 100 mg/mL concentration in 10 mM histidine, pH 6.0 that contains 150 mM NaCl was developed as providing optimal stability and solubility.

Stoppers

West Pharmaceutical Services—Part # 1012-4635, 13 mm 4432/50 gray chlorobutyl, Teflon-coated, Westar RS Silicone level 3

Overseals

West Pharmaceutical Services, 13 mm Flip-Off TruEdge

6.4. Stability Testing of Vialed Antibody Formulations

The 7F3com-2H2 liquid formulation was vialed at a concentration of 100 mg/mL in 10 mM Histidine-HCl, 150 mM sodium chloride, pH 6.0 buffer and tested for stability. Vials were stored at 2-8° C. (condition B), 20-24° C. (condition C) and 38-42° C. (condition D). For this study, appearance, protein concentration by $A_{280}$, reducing and non-reducing gel electrophoresis, native IEF, IL-9 binding ELISA, and HPSEC were evaluated on the upright vial condition. Time points for each condition are listed in Table 8, infra.

TABLE 8

Stability Testing Plan for Vialed 7F3com-2H2 Formulation

| Condition | Time (Months) | | | | | | | | | | | | |
|---|---|---|---|---|---|---|---|---|---|---|---|---|---|
| | 0 | 0.5 | 0.75 | 1 | 1.5 | 2 | 3 | 6 | 9 | 12 | 18 | 24 | 36 |
| B (2-8° C.) | X | X | X | X | X | X | X | X | X | X | X | X | X |
| C (20-24° C.) | X | X | X | X | X | X | X | X | NP | NP | NP | NP | NP |

TABLE 8-continued

Stability Testing Plan for Vialed 7F3com-2H2 Formulation

| Condi- | Time (Months) | | | | | | | | | | | | |
|---|---|---|---|---|---|---|---|---|---|---|---|---|---|
| tion | 0 | 0.5 | 0.75 | 1 | 1.5 | 2 | 3 | 6 | 9 | 12 | 18 | 24 | 36 |
| D (38-42° C.) | X | X | X | | X | X | X | X | X | NP | NP | NP | NP | NP |

X = testing preformed at this time point;
NP—test not performed at this time point.
* = upright vials.

Test results for the initial time point through the three-month time points for all three conditions are listed Table 9, infra. The vialed product was stable for at least three months when stored at 2-8° C. and 20-24° C. storage temperatures. No discernible changes in stability assays were seen after two weeks of storage at the 38-42° C. condition. After three weeks of storage at the elevated temperature of 38-42° C., the percent purity determined by the HPSEC method dropped to 94.9%. Unsatisfactory percent purity results were obtained for the three weeks, one-month, one and a half-month, two-month, and three-month time points of condition D. The chromatographic profile showed both aggregate and lower molecular weight degradation products. In addition, the non-reducing gel electrophoresis profile for the one-month, one and a half-month, two-month, and three-month time points of condition D was not consistent when compared to the Reference Standard due to the presence of small peaks that are not seen in the Reference Standard profile. The IEF profile for the one and half-month, two-month, and three-month time points at 38-42° C. was not consistent when compared to the Reference Standard due to the presence of a new acidic band that is not seen in the Reference Standard. These data indicate there is a sufficient stability of 7F3com-2H2 at the recommended storage temperature.

TABLE 9

Stability Results for Vialed 7F3com-2H2 Antibody Formulation

| Condition Description | Time point (month) | Total Protein (A280) (mg/ml) | IEF (non-reduced) (Pass/Fail) | Bioanalyzer (reduced) (Pass/Fail) | Bioanalyzer (reduced) (% Purity) | Bioanalyzer (non-reduced) (Pass/Fail) | HPSEC (% Purity) | HPSEC (% Aggregate) | Appearance (Pass/Fail) | IL-9 Binding ELISA Parallelism | IL-9 Binding ELISA (ED50) |
|---|---|---|---|---|---|---|---|---|---|---|---|
| Condition B: 2-8° C., upright | 0 | 111 | Pass | Pass | 98.9 | Pass | 99.1 | 0.9 | Pass | NP | NP |
| Condition B: 2-8° C., upright | 0.5 | 111 | Pass | Pass | 99.1 | Pass | 99.2 | 0.8 | Pass | Pass | 12.6 |
| Condition B: 2-8° C., upright | 0.75 | NP | NP | NP | NP | NP | 99.1 | 0.9 | NP | NP | NP |
| Condition B: 2-8° C., upright | 1 | 98.7 | Pass | Pass | 98.3 | Pass | 99.1 | 0.9 | Pass | Pass | 9.5 |
| Condition B: 2-8° C., upright | 1.5 | 110 | Pass | Pass | 97.7 | Pass | 99.1 | 0.9 | Pass | Pass | 14.9 |
| Condition B: 2-8° C., upright | 2 | 103 | Pass | Pass | 99.5 | Pass | 99.0 | 1.0 | Pass | Pass | 12.4 |
| Condition B: 2-8° C., upright | 3 | 110 | Pass | Pass | 99.3 | Pass | 98.8 | 1.1 | Pass | Pass | 9.4 |
| Condition C: 20-24° C., upright | 0 | 111 | Pass | Pass | 98.9 | Pass | 99.1 | 0.9 | Pass | NP | NP |
| Condition C: 20-24° C., upright | 0.5 | 109 | Pass | Pass | 98.9 | Pass | 98.5 | 1.2 | Pass | Pass | 13.2 |
| Condition C: 20-24° C., upright | 0.75 | NP | NP | NP | NP | NP | 98.4 | 1.4 | NP | NP | NP |
| Condition C: 20-24° C., upright | 1 | 103 | Pass | Pass | 99.0 | Pass | 98.3 | 1.5 | Pass | Pass | 9.3 |

TABLE 9-continued

Stability Results for Vialed 7F3com-2H2 Antibody Formulation

| Condition | Time (mo) | | | | | | | | | | |
|---|---|---|---|---|---|---|---|---|---|---|---|
| Condition C: 20-24° C., upright | 1.5 | 111 | Pass | Pass | 98.0 | Pass | 98.2 | 1.6 | Pass | Pass | 13.7 |
| Condition C: 20-24° C., upright | 2 | 109 | Pass | Pass | 99.0 | Pass | 98.0 | 1.8 | Pass | Pass | 9.7 |
| Condition C: 20-24° C., upright | 3 | 110 | Pass | Pass | 99.3 | Pass | 96.7 | 2.0 | Pass | Pass | 10.2 |
| Condition D: 38-44° C., upright | 0 | 111 | Pass | Pass | 98.9 | Pass | 99.1 | 0.9 | Pass | NP | NP |
| Condition D: 38-44° C., upright | 0.5 | 103 | Pass | Pass | 98.8 | Pass | 97.5 | 2.2 | Pass | Pass | 14.9 |
| Condition D: 38-44° C., upright | 0.75 | NP | NP | NP | NP | NP | 94.9 | 2.9 | NP | NP | NP |
| Condition D: 38-44° C., upright | 1 | 101 | Pass | Pass | 96.2 | Fail | 94.3 | 3.2 | Pass | Pass | 11.3 |
| Condition D: 38-44° C., upright | 1.5 | 111 | Fail | Pass | 98.7 | Fail | 92.4 | 3.6 | Pass | Pass | 15.7 |
| Condition D: 38-44° C., upright | 2 | 109 | Fail | Pass | 96.3 | Fail | 91.5 | 4.3 | Pass | Pass | 13.1 |
| Condition D: 38-44° C., upright | 3 | 110 | Fail | Pass | 95.9 | Fail | 89.6 | 5.3 | Pass | Pass | 16.4 |

A second lot of the 7F3com-2H2 antibody formulation was vialed at a concentration of 100 mg/mL in 10 mM Histidine-HCl, 150 mM sodium chloride, pH 6.0 buffer and placed on a stability protocol. The stability plan for 7F3com-2H2 antibody formulation is outlined in Table 10, infra. The stability-indicating assays chosen are reducing and non-reducing gel electrophoresis, native IEF, IL-9 binding ELISA, and HPSEC. The general assays of A280 and appearance are also be performed. Container/closure integrity testing are conducted at 0, 6, 12, 24, and 36-month time points for condition B, and at 0, and 6-month time points for condition C. This test may also be performed on vials for condition D at 0 and 3-month time points. All tests for condition B are performed only on the inverted vial condition. The upright vial orientation are used for the accelerated temperature conditions (C and D).

TABLE 10

Stability Testing Plan for Vialed Antibody Formulations

| Condition | Time (Months) | | | | | | | | | |
|---|---|---|---|---|---|---|---|---|---|---|
| | 0 | 1 | 2 | 3 | 6 | 9 | 12 | 18 | 24 | 36 |
| B inverted vial, (2-8° C.) | X | NP | NP | X | X | X | X | X | X | X |
| B upright vial, (2-8° C.) | NP | NP | NP | NP | NP | NP | NP | NP | NP | NP |
| C inverted vial (20-24° C.) | X | X | X | X | X | NP | NP | NP | NP | NP |
| D upright vial (38-42° C.) | X | X | X | X | NP | NP | NP | NP | NP | NP |

*The upright vial orientation is analyzed in the event of a stability failure at condition B (2-8° C.) for the inverted vial orientation. Container/closure integrity testing is performed on inverted vials from condition B & C at the 0, 6, 12, 24, and 36-month time points only, and at the 0 and 3-month time points for condition D.
X = testing performed at this time point;
NP = test not performed at this time point.

7. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed:

1. A sterile antibody formulation comprising an aqueous carrier, between 1 mM and 100 mM of histidine, and 50 mg/ml or higher of an antibody or antibody fragment that immunospecifically binds to an interleukin-9 polypeptide, wherein the antibody or antibody fragment comprises a VH domain comprising the amino acid sequence of SEQ ID NO:27 and a VL domain comprising the amino acid sequence of SEQ ID NO:28.

2. A pharmaceutical unit dosage form suitable for parenteral administration to a human which comprises an antibody formulation of claim 1 in a suitable container.

3. The pharmaceutical unit dosage form of claim 2, wherein the antibody formulation is administered intravenously, subcutaneously, or intramuscularly.

4. A pharmaceutical unit dosage form suitable for aerosol administration to a human which comprises an antibody formulation of claim 1 in a suitable container.

5. The pharmaceutical unit dosage of claim 4, wherein the antibody formulation is suitable for intranasal administration.

6. An antibody formulation which is produced by lyophilizing the aqueous antibody formulation of claim 1.

7. A hermetically sealed container containing the formulation of claim 1.

8. A hermetically sealed container containing the formulation of claim 6.

9. The hermetically sealed container of claim 8 having sufficient volume for reconstitution with a pharmaceutically acceptable carrier.

10. The hermetically sealed container of claim 9, wherein said carrier is water for injection, 5% dextrose in water or saline.

11. The hermetically sealed container of claim 10, wherein said container maintains a sterile environment and allows reconstitution of the formulation without loss of sterility.

12. A kit comprising in one or more containers the antibody formulation of claim 1, and instructions for use of the formulation, wherein said formulation is substantially free of surfactant.

13. The kit of claim 12, wherein the aqueous carrier is distilled water.

14. The kit of claim 12, wherein the formulation is produced by lyophilizing the aqueous antibody formulation.

15. The kit of claim 12, wherein the antibody or antibody fragment is at a concentration of 95 mg/ml.

16. The formulation of claim 1, comprising NaCl.

17. The formulation of claim 16, wherein the NaCl is at a concentration in the range from about 100 mM to about 200 mM.

18. The formulation of claim 17, wherein the NaCl is at a concentration of 150 mM.

19. The formulation of claim 1, wherein said formulation is substantially free of surfactants, sugars, sugar alcohols, and amino acids other than histidine.

20. The formulation of claim 19, wherein said amino acids other than histidine have a pKa value of less than 5 or above 7.

21. The formulation of claim 1, wherein the aqueous carrier is distilled water.

22. The formulation of claim 1 further comprising glycine at a concentration in the range from about 1 to about 10 mM.

23. The formulation of claim 1, wherein the histidine is at a concentration in the range from about 5 to about 25 mM.

24. The formulation of claim 23, wherein the histidine is at a concentration of 10 mM.

25. The formulation of claim 1, wherein the formulation has a pH in the range between 5.0 and 7.0.

26. The formulation of 25, wherein said formulation has a pH of 6.0.

27. The formulation of claim 1 further comprising an excipient.

28. The formulation of claim 27, wherein the excipient is a saccharide.

29. The formulation of claim 27, wherein the excipient is a polyol.

30. The formulation of claim 1, wherein the antibody or antibody fragment is at a concentration of at least 95 mg/ml.

31. The formulation of claim 30, wherein the antibody or antibody fragment is at a concentration of at least 100 mg/ml.

32. The formulation of claim 31, wherein the antibody or antibody fragment is at a concentration of at least 150 mg/ml.

33. The formulation of claim 1, wherein the antibody or antibody fragment that immunospecifically binds to an interleukin-9 polypeptide is stable during storage at 40° C. for at least 15 days as determined by high performance size exclusion chromatography (HPSEC).

34. The formulation of claim 1, wherein the antibody or antibody fragment that immunospecifically binds to an interleukin-9 polypeptide is stable during storage at about ambient temperature for at least 6 months as determined by HPSEC.

35. The formulation of claim 1, wherein the antibody or antibody fragment that immunospecifically binds to an interleukin-9 polypeptide is stable during storage at 4° C. for at least 1.5 years as determined by HPSEC.

36. The formulation of claim 33, wherein less than 5% of the antibody or antibody fragment forms an aggregate during the storage as measured by HPSEC.

37. The formulation of claim 34, wherein less than 5% of the antibody or antibody fragment forms an aggregate during the storage as measured by HPSEC.

38. The formulation of claim 35, wherein less than 5% of the antibody or antibody fragment forms an aggregate during the storage as measured by HPSEC.

39. The formulation of claim 36, wherein less than 2% of the antibody or antibody fragment forms an aggregate during the storage as measured by HPSEC.

40. The formulation of claim 37, wherein less than 2% of the antibody or antibody fragment forms an aggregate during the storage as measured by HPSEC.

41. The formulation of claim 38, wherein less than 2% of the antibody or antibody fragment forms an aggregate during the storage as measured by HPSEC.

42. The formulation of claim 39, wherein less than 1% of the antibody or antibody fragment forms an aggregate during the storage as measured by HPSEC.

43. The formulation of claim 40, wherein less than 1% of the antibody or antibody fragment forms an aggregate during the storage as measured by HPSEC.

44. The formulation of claim 41, wherein less than 1% of the antibody or antibody fragment forms an aggregate during the storage as measured by HPSEC.

45. The formulation of claim 33, wherein the antibody or antibody fragment retains at least 80% of binding ability to an interleukin-9 polypeptide compared to a reference antibody representing the antibody prior to the storage.

46. The formulation of claim 34, wherein the antibody or antibody fragment retains at least 80% of binding ability to an interleukin-9 polypeptide compared to a reference antibody representing the antibody prior to the storage.

47. The formulation of claim 35, wherein the antibody or antibody fragment retains at least 80% of binding ability to an interleukin-9 polypeptide compared to a reference antibody representing the antibody prior to the storage.

48. The formulation of claim 45, wherein the antibody or antibody fragment retains at least 85% of binding ability to an interleukin-9 polypeptide compared to the reference antibody.

49. The formulation of claim 46, wherein the antibody or antibody fragment retains at least 85% of binding ability to an interleukin-9 polypeptide compared to the reference antibody.

50. The formulation of claim 47, wherein the antibody or antibody fragment retains at least 85% of binding ability to an interleukin-9 polypeptide compared to the reference antibody.

51. The formulation of claim 48, wherein the antibody or antibody fragment retains at least 90% of binding ability to an interleukin-9 polypeptide compared to the reference antibody.

52. The formulation of claim 49, wherein the antibody or antibody fragment retains at least 90% of binding ability to an interleukin-9 polypeptide compared to the reference antibody.

53. The formulation of claim 50, wherein the antibody or antibody fragment retains at least 90% of binding ability to an interleukin-9 polypeptide compared to the reference antibody.

54. The formulation of claim 51, wherein the antibody or antibody fragment retains at least 95% of binding ability to an interleukin-9 polypeptide compared to the reference antibody.

55. The formulation of claim 52, wherein the antibody or antibody fragment retains at least 95% of binding ability to an interleukin-9 polypeptide compared to the reference antibody.

56. The formulation of claim 53, wherein the antibody or antibody fragment retains at least 95% of binding ability to an interleukin-9 polypeptide compared to the reference antibody.

57. The formulation of claim 30, wherein the histidine is at a concentration of 10 mM and wherein the aqueous carrier is distilled water, and wherein the formulation further comprises NaCl at a concentration of 150 mM.

58. The formulation of claim 57, wherein the antibody or antibody fragment that immunospecifically binds to an interleukin-9 polypeptide is stable during storage at 40° C. for at least 15 days as determined by high performance size exclusion chromatography (HPSEC).

59. The formulation of claim 57, wherein the antibody or antibody fragment that immunospecifically binds to an interleukin-9 polypeptide is stable during storage at 4° C. for at least 1.5 years as determined by HPSEC.

60. The formulation of claim 57, wherein less than 5% of the antibody or antibody fragment forms an aggregate during the storage as measured by HPSEC.

61. The formulation of claim 57, wherein the antibody or antibody fragment retains at least 80% of binding ability to an interleukin-9 polypeptide compared to a reference antibody representing the antibody prior to the storage.

62. A sterile antibody formulation comprising an aqueous carrier, between 1 mM and 100 mM of histidine, and 50 mg/ml or higher of an antibody or antibody fragment that immunospecifically binds to an interleukin-9 polypeptide, wherein the antibody or antibody fragment comprises:
a) a VH CDR1 comprising the amino acid sequence of SEQ ID NO:26,
b) a VH CDR2 comprising the amino acid sequence of SEQ ID NO:61,
c) a VH CDR3 comprising the amino acid sequence of SEQ ID NO:3,
d) a VL CDR1 comprising the amino acid sequence of SEQ ID NO:62,
e) a VL CDR2 comprising the amino acid sequence of SEQ ID NO:63, and
f) a VL CDR3 comprising the amino acid sequence of SEQ ID NO:20.

63. The formulation of claim 62, further comprising NaCl.

64. The formulation of claim 63, wherein the NaCl is at a concentration of about 100 mM to about 200 mM.

65. The formulation of claim 64, wherein the NaCl is at a concentration of 150 mM.

66. The formulation of claim 62 further comprising glycine at a concentration of about 1 to about 10 mM.

67. The formulation of claim 62, wherein the histidine is at concentration of about 5 to about 25 mM.

68. The formulation of claim 67, wherein the histidine is at a concentration of 10 mM.

69. The formulation of claim 62, wherein said formulation is substantially free of surfactants, sugars, sugar alcohols, and amino acids other than histidine.

70. The formulation of claim 69, wherein said amino acids other than histidine have a pKa value of less than 5 or above 7.

71. The formulation of claim 62, wherein the aqueous carrier is distilled water.

72. The formulation of claim 62, wherein the formulation has a pH in the range between 5.0 and 7.0.

73. The formulation of claim 72, wherein said formulation has a pH of 6.0.

74. The formulation of claim 62, wherein the antibody or antibody fragment is at a concentration of at least 95 mg/ml.

75. The formulation of claim 74, wherein the antibody or antibody fragment is at a concentration of at least 100 mg/ml.

76. The formulation of claim 75, wherein the antibody or antibody fragment is at a concentration of at least 150 mg/mi.

77. The formulation of claim 74, wherein the histidine is at a concentration of 10 mM and wherein the aqueous carrier is distilled water, and wherein the formulation further comprises NaCl at a concentration of 150 mM.

78. The formulation of claim 77, wherein the antibody or antibody fragment that immunospecifically binds to an interleukin-9 polypeptide is stable during storage at 40° C. for at least 15 days as determined by high performance size exclusion chromatography (HPSEC).

79. The formulation of claim 77, wherein the antibody or antibody fragment that immunospecifically binds to an interleukin-9 polypeptide is stable during storage at 4° C. for at least 1.5 years as determined by HPSEC.

80. The formulation of claim 77, wherein less than 5% of the antibody or antibody fragment forms an aggregate during the storage as measured by HPSEC.

81. The formulation of claim 77, wherein the antibody or antibody fragment retains at least 80% of binding ability to an interleukin-9 polypeptide compared to a reference antibody representing the antibody prior to the storage.

* * * * *